(12) United States Patent
Hoveyda et al.

(10) Patent No.: US 9,328,061 B2
(45) Date of Patent: May 3, 2016

(54) SIMPLE ORGANIC MOLECULES AS CATALYSTS FOR PRACTICAL AND EFFICIENT ENANTIOSELECTIVE SYNTHESIS OF AMINES AND ALCOHOLS

(71) Applicant: Trustees of Boston College, Chestnut Hill, MA (US)

(72) Inventors: Amir H. Hoveyda, Lincoln, MA (US); Daniel L. Silverio, Chestnut Hill, MA (US); Tatiana Pilyugina, Waltham, MA (US); Sebastian Torker, Brighton, MA (US); Daniel Robbins, Boston, MA (US)

(73) Assignee: Trustees of Boston College, Chestnut Hill, MA (US)

( * ) Notice: Subject to any disclaimer, the term of this patent is extended or adjusted under 35 U.S.C. 154(b) by 0 days.

(21) Appl. No.: 14/382,053

(22) PCT Filed: Mar. 1, 2013

(86) PCT No.: PCT/US2013/028731
§ 371 (c)(1),
(2) Date: Aug. 29, 2014

(87) PCT Pub. No.: WO2013/131043
PCT Pub. Date: Sep. 6, 2013

(65) Prior Publication Data
US 2015/0057451 A1     Feb. 26, 2015

Related U.S. Application Data

(60) Provisional application No. 61/605,582, filed on Mar. 1, 2012.

(51) Int. Cl.
| | | |
|---|---|---|
| C07C 237/06 | (2006.01) | |
| C07C 229/04 | (2006.01) | |
| C07D 295/185 | (2006.01) | |
| C07C 227/10 | (2006.01) | |
| C07C 229/14 | (2006.01) | |
| C07C 251/24 | (2006.01) | |
| C07F 9/6539 | (2006.01) | |
| C07F 9/36 | (2006.01) | |
| C07C 41/30 | (2006.01) | |
| C07C 29/38 | (2006.01) | |
| C07C 67/343 | (2006.01) | |
| C07F 7/08 | (2006.01) | |
| C07C 229/08 | (2006.01) | |
| C07D 207/06 | (2006.01) | |
| C07F 9/50 | (2006.01) | |

(52) U.S. Cl.
CPC ............ *C07C 237/06* (2013.01); *C07C 29/38* (2013.01); *C07C 41/30* (2013.01); *C07C 67/343* (2013.01); *C07C 227/10* (2013.01); *C07C 229/08* (2013.01); *C07C 229/14* (2013.01); *C07C 251/24* (2013.01); *C07D 207/06* (2013.01); *C07D 295/185* (2013.01); *C07F 7/0812* (2013.01); *C07F 7/0818* (2013.01); *C07F 9/36* (2013.01); *C07F 9/5022* (2013.01); *C07F 9/6539* (2013.01); *C07B 2200/07* (2013.01); *C07C 229/04* (2013.01)

(58) Field of Classification Search
CPC .... C07F 9/6539; C07F 9/65062; C07F 9/653; A01N 57/08; A01N 57/16; C07C 237/06; C07C 229/04; C07D 207/06; C07D 295/185
USPC ..................................... 548/119, 540; 564/12
See application file for complete search history.

(56) References Cited

U.S. PATENT DOCUMENTS

2007/0066646 A1*    3/2007    Clauzel ................ A61K 31/165
                                                            514/310

OTHER PUBLICATIONS

Akullian, L., M. Snapper, and A. Hoveyda "Three-Component Enantioselective Synthesis of Propargylamines through Zr-Catalyzed Additions of Alkyl Zinc Reagents to Alkynylimines" Angew. Chem. Int. Ed. 2003, 42: pp. 4244-4247.*
Akullian, L.C. et al., Asymmetric Synthesis of Acyclic Amines Through Zr- and Hf-Catalyzed Enantioselective Alkylzinc Reagents to Imines, Adv. Synth. Catal., 347: 417-425 (2005).
Aydin, J. et al., Synthesis and catalytic application of chiral 1,1'-bi-2-napthol and biphenanthrol-based pincer complexes: Selective allylation of sulfonimines and allyl stannane and allyltrifluoroborate, J. Org. Chem., 72: 4689-4697 (2007).
Barnett, D. S. et al., The mechanism and an improved asymmetric allylboration of ketones catalyzed by chiral biphenols, Angew. Chem. Int. Edn, 48: 8679-8682 (2009).
Borzilleri, R. M. et al., A novel application of a Pd(0)-catalyzed nucleophilic substitution reaction to the regio- and stereoselective synthesis of lactam analogues of the epothilone natural products, J. Am. Chem. Soc. 122, 8890-8897 (2000).
Brown, H. C. & Jadhav, P. K. Asymmetric carbon—carbon bond formation via B-allyldiisopinocamphenylborance. Simple synthesis of secondary homoallylic alcohols with excellent enantiomeric purities, J. Am. Chem. Soc., 105: 2092-2093 (1983).
Cao, Z. et al., A Hg(ClO4)2-3H2O catalyzed Sakurai-Hosomi allylation of isatins and isatin ketoimines using allyltrimethylsilane, J. Org. Lett., 13: 6398-6401 (2011).
Chakrabarti, A. et al., Indium(I)-catalyzed asymmetric allylation, crotylation, and a-chloroallylation of hydrazones with rare constitutional and high configurational selectivities, Angew. Chem. Int. Edn., 49: 1838-1841 (2010).

(Continued)

*Primary Examiner* — Alicia L Otton
*Assistant Examiner* — Sagar Patel
(74) *Attorney, Agent, or Firm* — HoustonHogle, Esq.

(57) ABSTRACT

The present invention provides organic molecules and methods thereof for reactions between organoboron reagents and double bonds, such as imines or carbonyls, to stereoselectively provide chiral products including amines and alcohols, entities useful for the preparation of biologically active molecules.

5 Claims, 9 Drawing Sheets

(56) References Cited

OTHER PUBLICATIONS

Chen, M. Z. et al., Preparation of stereodefined homoallylic amines from the reductive cross-coupling of allylic alcohols with imines, J. Org. Chem., 75: 8048-8059 (2010).
Cogan, D.A. et al., Asymmetric synthesis of chiral amines by highly diastereoselective 1,2-additions of organometallic reagents to N-tert-butanesulfinyl imines, Tetrahedron, 55: 8883-8904 (1999).
Cook, G. R., Maity, B. C. & Kargbo, R. Highly diastereoselective indium-mediated allylation of chiral hydrazones, Org. Lett., 6: 1741-1743 (2004).
Corberan, R. et al., NHC—Cu-catalyzed enantioselective hydroboration of acyclic and exocyclic 1,1-disubstituted aryl alkenes, Angew. Chem., Int. Ed., 50: 7079-7082 (2011).
Coste, A. et al., TMC-95A-D and analogues: Chemistry and biology, Comp. Rend. Chemie., 11: 1544-1573 (2008).
Cote, A. et al., Catalytic asymmetric addition of diorganozinc reagents to N-phosphinoylalkylimines, Proc. Natl. Acad. Sci., 101: 5405-5410 (2004).
Cravotto, G. et al. Convolutamydine A: the first authenticated absolute configuration and enantioselective synthesis. Tetrahedron Asymm. 17, 3070-3074 (2006).
Desrosiers, J-N. et al., Preparation of Enantiomerically Enriched (1S)-1-Phenylpropan-1-Amine Hydrochloride by a Catalytic Addition of Diorganozinc Reagents to Imines, Org. Syn., 83: 5-17 (2006).
Ding, H. and Friestad, G. K. Trifluoroacetyl-activated nitrogen—nitrogen bond cleavage of hydrazines by samarium(II) iodide, Org. Lett., 6: 637-640 (2004).
Fandrick, K.R., et al., Mild and general zinc-alkoxide-catalyzed allylations of ketones with allyl pinacol boronates, Org. Lett., 12: 3748-3751 (2010).
Ferraris, D. et al. Catalytic, enantioselective alkylation of a-imino esters: The synthesis of nonnatural a-amino acid derivatives, J. Am. Chem. Soc., 124: 67-77 (2002).
Friestad, G. K. et al., Dual activation in asymmetric allylsilane addition to chiral N-acylhydrazones: Method development, mechanistic studies, and elaboration of homoallylic amine adducts, J. Org. Chem., 71: 281-289 (2006).
Fu, P. et al., Catalytic asymmetric alkylations of ketoimines. Enantioselective synthesis of N-substituted quaternary carbon stereogenic centers by Zr-catalyzed additions of dialkylzinc reagents to aryl-, alkyl-, and trifluoroalkyl-substituted ketoimines, J. Am. Chem. Soc., 130: 5530-5541 (2008).
Fujita, M. et al., Zn-catalyzed asymmetric allylation for the synthesis of optically active allylglycine derivatives. Regio- and stereoselective formal a-addition of allylboronates to hydrazono esters, J. Am. Chem. Soc., 130: 2914-2915 (2008).
González-Gómez, J. C. et al., Stereoselective a-aminoallylation of aldehydes with chiral tert-butanesulfamides and allyl bromides, J. Org. Chem., 75: 6308-6311 (2010).
Guzman-Martinez, A. & Hoveyda, A. H. Enantioselective synthesis of allylboronates bearing a tertiary or quaternary B-substituted stereogenic carbon by NHC—Cu-catalyzed substitution reactions, J. Am. Chem. Soc., 132: 10634-10637 (2010).
Hagmann, W.K. The Many Roles for Fluorine in Medicinal Chemistry, Journal of Medicinal Chemistry, 51(15): 4359-4369 (2008).
Hamada, T. et al., Catalytic asymmetric allylation of hydrazono esters in aqueous media by using ZnF2-chiral diamine, Angew. Chem. Int. Edn., 42: 3927-3930 (2003).
Hanhan, N. V. et al., Catalytic asymmetric synthesis of 3-hydroxy-2-oxindoles, Angew. Chem. Int. Edn. 49: 744-747 (2010).
Ishikura, M. and Yamada, K., Simple indole alkaloids and those with a nonrearranged monoterpenoid unit, Nat. Prod. Rep. 26: 803-852 (2009).
Ito, H. et al., Copper-catalyzed enantioselective substitution of allylic carbonates with diboron: An efficient route to optically active a-chiral allylboronates, J. Am. Chem. Soc., 129: 14856-14857 (2007).
Itoh, J. et al., Enantioselective allylation, crotylation, and reverse prenylation of substituted isatins: Iridium-catalyzed C—C bond-forming transfer hydrogenation. Angew. Chem. Int. Edn., 48: 6313-6316 (2009).

Itoh, T. et al., Asymmetric aldol reaction of acetaldehyde and isatin derivatives for the total syntheses of ent-convolutamydine E and CPC-1 and a half fragment of madindoline A and B, Org. Lett., 11: 3854-3857 (2009).
Jennings, W. B. and Lovely, C. J., The titanium tetrachloride induced synthesis of N-phosphinoylimines and N-sulphonylimines directly from aromatic aldehydes, Tetrahedron, 47: 5561-5568 (1991).
Kargo, R. et al., Readily accessible, modular, and tunable BINOL 3,3'-perfluoroalkylsulfones: Highly efficient catalysts for enantioselective In-mediated imine allylation, J. Am. Chem. Soc., 129: 3846-3847 (2007).
Karimi, A. R. and Sedaghatpour, F., Novel mono- and bis(spiro-2-amino-4H-pyrans): alum-catalyzed reaction of 4-hydroxycoumarin and malononitrile with isatins, quinones, or ninhydrin, Synthesis, 10: 1731-1735 (2010).
Kattuboina, A. et al., Chiral N-phosphoyl imine chemistry: Asymmetric 1,2-additions of allylmagnesium bromides, Tetrahedron Lett., 49: 3722-3724 (2008).
Kim, S. J. and Jang, D. O., Indium-mediated catalytic enantioselective allylation of N-benzohydrazones using a protonated chiral amine, J. Am. Chem. Soc., 132: 12168-12169 (2010).
Kinnaird, J.W.A. et al., Strained Silacycles in Organic Synthesis: A new reagent for the enantioselective allylation of aldehydes, J. Am. Chem. Soc., 124: 7920-7921 (2002).
Kobayashi, S. et al., Catalytic enantioselective formation of C—C bonds by addition to imines and hydrazones: A ten-year update, Chem. Rev., 111: 2626-2704 (2011).
Kobayashi, S. et al., Neutral coordinate-organocatalysts in organic synthesis: Allylation of acylhydrazones with allyltrichlorosilanes, Adv. Synth. Catal., 346: 1023-1034 (2004).
Kowalcyk, J.J. et al., Phenolic Replacements for Cysteine in Farnesyl Transferase Inhibitors Based on CVFM, Bioorg. Med. Chem. Lett., 5: 3073-3078 (1995).
Kulkarni, N. A. et al., On the scope of diastereoselective allylation of various chiral glyoxylic oxime ethers with allyltributylstannane in the presence of a Lewis acid and triallylaluminum, Tetrahedron, 63: 7816-7822 (2007).
Laschat, S. and Kunz, H., Carbohydrates as chiral templates: Diastereoselective synthesis of N-glycosyl-N-homoallylamines and b-amino acids from imines, J. Org. Chem., 56: 5883-5889 (1991).
Leighton, J. L. Powerful and versatile silicon Lewis acids for asymmetric chemical synthesis, Aldrichimica Acta 43: 3-12 (2010).
Liu, M. et al., Dramatic lithium chloride effect on the reaction stereocontrol in Zn-mediated asymmetric cinnamylation: Highly practical synthesis of b-aryl homoallylic amines, Chem. Commun., 46: 8460-8462 (2010).
Lou, S. et al., Asymmetric allylboration of acyl imines catalyzed by chiral diols, J. Am. Chem. Soc., 129: 15398-15404 (2007).
Lovering, F. et al., Escape from flatland: Increasing saturation as an approach to improving clinical success, J. Med. Chem., 52: 6752-6756 (2009).
Lysenko, I. L. et al., Stereoselective cross-coupling between allylic alcohols and aldimines, Org. Lett., 11: 3132-3134 (2009).
Müller, K. et al., Fluorine in Pharmaceuticals: Looking Beyond Intuition, Science, 317: 1181-1886 (2007).
Nakamura, E. and Sato, K. Managing the scarcity of chemical elements, Nature Mat. 10, 158-161 (2011).
Naodovic, M. et al., Enantioselective Ag-catalyzed allylation of aldimines, Eur. J. Org. Chem., 5129-5131 (2009).
Nowrouzi, F. et al., Allylation and crotylation of ketones and aldehydes using potassium organotrifluoroborate salts under Lewis acid and montmorillonite K10 catalyzed conditions, Org. Lett., 11(12): 2631-2634 (2009).
Panek, J. S. & Jain, N. F. Direct amino-crotylsilylation of achiral acetals and aldehydes: Asymmetric synthesis of homoallylic amines and functionalized pyrrolidines, J. Org. Chem., 59: 2674-2675 (1994).
Paton, R. S. et al., Mechanistic insights into the catalytic asymmetric allylboration of ketones: Brønsted or Lewis acid activation?, Org. Lett., 11: 37-40 (2009).
Peddibhotla, S., 3-Substituted-3-hydroxy-2-oxindole, an emerging new scaffold for drug discovery with potential anti-cancer and other biological activities, Curr. Bioact. Compd., 5: 20-38 (2009).

(56) References Cited

OTHER PUBLICATIONS

Peng, Z. et al., Diastereoselective synthesis of homoallylic alcohols with adjacent tertiary and quaternary centers by using functionalized allylic aluminum reagents, Angew. Chem. Int. Ed., 49: 8516 (2010).

Porter, A.R. et al., Enantioselective Synthesis of Arylamines Through Zr-Catalyzed Addition of Dialkylzincs to Imines. Reaction Development by Screening of Parallel Libraries, J. Am. Chem. Soc., 123: 984-985 (2001).

Puentes, C. O. and Kouznetsov, V. Recent advancements in the homoallylaime chemistry, J. Heterocyclic Chem., 39: 595-614 (2002).

Raducan, M. et al., Palladium-catalyzed synthesis and isolation of functionalized allylboronic acids: selective, direct allylboration of ketones, Angew. Chem. Int. Ed., 51: 13050-13053 (2012).

Ramachandran, P. V. and Burghardt, T. E. Recent developments in the chiral synthesis of homoallylic amines via organoboranes, Pure Appl. Chem., 78: 1397-1406 (2006).

Ramandhar, T. R. and Batey, R. A. Allylation of imines and their derivatives with organoboron reagents: Stereocontrolled synthesis of homoallylic amines, Synthesis, 9: 1321-1346 (2011).

Ren, H. et al., Highly diastereoselective synthesis of homoallylic alcohols bearing adjacent quaternary centers using substituted allylic zinc reagents, J. Am. Chem. Soc., 129: 5376-5377 (2007).

Ruiz-Sanchis, P. et al., Structure, bioactivity and synthesis of natural products with hexahydropyrrolo[2,3-b]indole, Chem. Eur. J., 17: 1388-1408 (2011).

Sano, D. et al., Catalytic asymmetric hydroxylation of oxindoles by molecular oxygen using a phase-transfer catalyst, Org. Lett., 10: 1593-1595 (2008).

Schneider, U. et al., Catalytic use of indium(0) for carbon—carbon bond transformations in water: general catalytic allylations of ketones with allylboronates, J. Am. Chem. Soc., 130: 13824-13825 (2008).

Sieber, J. D. et al., Asymmetric Ni-catalyzed conjugate allylation of activated enones, J. Am. Chem. Soc., 130: 4978-4983 (2008).

Silverio, D.L. et al., Simple organic molecules as catalysts for enantioselective synthesis of amines and alcohols, Natues, 494: 216-221 (2013).

Sirasani, G. and Andrade, R. B., Total synthesis of (−)-leuconicine A and B, Org. Lett., 13: 4736-4737 (2011).

Sisko, J. et al., α-Tosylbenzyl isocyanide, Org. Syn., 77: 198 (2000).

Sugimoto, Y. et al., Diastereoselective allylation of a chiral imine with allylzinc reagents: Diastereoselective synthesis of a novel broad spectrum carbapenem, Synlett, 11: 1747-1750 (2001).

Suh, Y-g. et al. Expedient synthesis of chiral homoallylamines via N,O-acetal TMS ethers and its application, Org. Lett., 13: 5920-5923 (2011).

Sun, X.-W. et al., Room-temperature highly diastereoselective Zn-mediated allylation of chiral N-tert-butanesulfinyl imines: Remarkable reaction condition controlled stereoselectivity reversal, Org. Lett., 8: 4979-4982 (2006).

Takahashi, M. et al., Complex allylation by the direct cross-coupling of imines with unactivated allylic alcohols, Angew. Chem. Int. Ed., 48: 3648-3652 (2009).

Takeda, T. et al., Highly diastereoselective construction of acyclic systems with two adjacent quaternary stereocenters by allylation of ketones, Angew. Chem. Int. Ed., 51: 7263-7266 (2012).

Tan, K. L. and Jacobsen, E. N. Indium-mediated asymmetric allylation of acylhydrazones using a chiral urea catalyst, Angew. Chem. Int. Edn., 46: 1315-1317 (2007).

Thayer, A., Chiral catalysts, Chem. Eng. News, 83: 40-48 (2005).

Tian, L. et al., Synthesis and two-photon optical characterization of D-O-D type Schiff bases, 127: 423-430 (2007).

Trost, B. M. and Frederiksen, M. U., Palladium-catalyzed asymmetric allylation of prochiral nucleophiles: synthesis of 3-allyl-3-aryl oxindoles, Angew. Chem., Int. Ed., 44: 308-310 (2005).

Vieira, E. M. et al., A robust, efficient and highly enantioselective method for synthesis of homopropargyl amines, Angew. Chem. Int. Edn, 51: 6618-6621 (2012).

Vieira, E. M. et al., Enantioselective synthesis of homoallylic amines through reactions of (pinacolato)allylborons with aryl-, heteroaryl-, alkyl-, or alkene-substituted aldimines catalyzed by chiral C1-symmetric NHC—Cu complexes, J. Am. Chem. Soc., 133: 3332-3335 (2011).

Vilaivan, T. et al., Indium-mediated asymmetric Barbier-type allylation of aldimines in alcoholic solvents: Synthesis of optically active homoallylic amines, J. Org. Chem., 70: 3464-3471 (2005).

Wada, R. et al., Catalytic enantioselective allylation of ketoimines, J. Am. Chem. Soc., 128: 7687-7691 (2006).

Wadamoto, M. Stereochemical Studies of Ag-Catalyzed Hosomi-Sakurai Reaction Using Chiral Silanes, Eur. J. Org. Chem., 5132-5133 (2009).

Weinreb, S. M. & Orr, R. K. N-Phosphinoylimines: An emerging class of reactive intermediates for stereoselective organic synthesis. Synthesis 8, 1205-1227 (2005).

Wen, J. et al., Asymmetric pinacol coupling reaction catalyzed by dipeptide-type Schiff bases, J. Mol. Cat. A: Chem, 245: 242-247 (2006).

Xie, W. et al., Total synthesis of cyclic tetrapeptide FR235222, a potent immunosuppressant that inhibits mammalian histone deacetylases, Org. Lett., 7: 2775-2777 (2005).

Yamada, K. The First Catalytic Asymmetric Nitro-Mannich-Type Reaction Promoted by a New Heterobimetallic Complex, Angew. Chem., Int. Ed., 38: 3504-3506 (1999).

Yamaguchi, A. et al., Direct catalytic asymmetric Mannich-type reactions of isomerizable aliphatic imines: chemoselective enolate formation from a hyfroxyketone by a Zn-catalyst, Tetrahedron Lett., 47: 3985-3989 (2006).

Yamamoto, D. et al., Design, synthesis, and biological activities of madindoline analogues, Bioorg. Med. Chem. Lett., 16: 2807-2811 (2006).

Yanada, R. et al., Diastereoselective Barbier-type and palladium-mediated allylation of optically active aldimine with allylindium reagents, J. Org. Chem., 66: 7516-7518 (2001).

Yang, D. and Micalizio, G. C. Convergent and stereodivergent synthesis of complex 1-aza-7-oxabicyclo[2.2.1]heptenes, J. Am. Chem. Soc., 133: 9216-9219 (2011).

Yus, M., et al., Catalytic enantioselective allylation of carbonyl compounds and imines, Chem. Rev., 111: 7774-7854 (2011).

Zhang, P. et al., Ni- and Pd-catalyzed synthesis of substituted and functionalized allylic boronates, Org. Lett., 14: 1416-1419 (2012).

\* cited by examiner

SIMPLE ORGANIC MOLECULES AS CATALYSTS FOR PRACTICAL AND EFFICIENT ENANTIOSELECTIVE SYNTHESIS OF AMINES AND ALCOHOLS

CROSS-REFERENCE TO RELATED APPLICATIONS

The present application is a U.S. national phase application under 35 U.S.C. 371 of International PCT Application No. PCT/US2013/028731, filed Mar. 1, 2013, which claims priority to U.S. Provisional Application No. 61/605,582, filed Mar. 1, 2012, the entirety of each of which is incorporated herein by reference.

STATEMENT REGARDING FEDERALLY SPONSORED RESEARCH OR DEVELOPMENT

This invention was made with the support under the following government contract: GM 57212, awarded by the National Institute of Health. The US government has certain rights in the invention.

FIELD OF THE INVENTION

The present invention generally relates to synthesis of amines and alcohols.

BACKGROUND

Discovery of catalysts that promote efficient and enantioselective transformations that deliver high value organic molecules is crucial to future advances in the life sciences. For decades, chemists have searched for catalysts that are easily accessible and simple in architecture yet serve as the reliable engine that turns a large number of reaction cycles to generate products within a handful of hours. Catalytic reactions that do not tax our non-renewable resources and do not require expensive reagents, and long hours or recourse to strictly inert conditions are in high demand but scarce.

For nearly half a century, chemists have searched for catalysts that initiate reactions that afford valuable chiral molecules and preferentially afford one product enantiomer (Jacobsen, E. N.; Pfaltz, A. & Yamamoto, H. (eds) *Comprehensive Asymmetric Catalysis* (Springer, Berlin, 1999)). The importance of ease of access to the large variety of enantiomerically pure organic molecules in biology and medicine, whether discovered in nature or a laboratory, and their derivatives, as well as the inherent economic advantages of a catalytic process has served as the impetus for such longstanding activity (Thayer, A. Chiral catalysts. *Chem. Eng. News* 83, 40-48 (2005)). Robust reagents that are easily available and devoid of exceedingly toxic metals (e.g., tin or chromium), product isolation and purification conditions that are not severe (e.g., strong reductants or oxidants) and/or costly, are now considered the hallmarks of a desirable transformation. Low catalyst loadings (e.g., ≤1.0 mol %), short reaction times (e.g., ≤8 hours) and the feasibility of reaction at ambient temperature and with a broad range of substrate classes without resorting to rigorous techniques for exclusion of air and moisture are further distinguishing features. Additionally, if transformations generate minimal waste, do not require halogenated solvents, can be promoted by small-molecule catalysts (e.g., ≤350 g/mol$^{-1}$) that are prepared and purified easily and inexpensively in bulk, and which are stable to air and moisture and do not contain rare and/or precious elements (Nakamura, E. & Sato, K. Managing the scarcity of chemical elements. *Nature Mat.* 10, 158-161 (2011)), then the transformation belongs to a scarce category. A catalytic method that furnishes sought-after organic molecules and satisfies a portion of the above standards is valuable, but rarely a set of transformations, particularly one that affords a CC bond, meets the large majority of such constraints.

Many biologically active molecules contain one or more nitrogen-substituted carbon stereogenic centers (Kobayashi, S.; Mori, Y.; Fossey, J. S. & Salter, M. M. Catalytic enantioselective formation of CC bonds by addition to imines and hydrazones: A ten-year update. *Chem. Rev.* 111, 2626-2704 (2011); Yus, M.; González-Gómez, J. C. & Foubelo, F. Catalytic enantioselective allylation of carbonyl compounds and imines *Chem. Rev.* 111, 7774-7854 (2011); and Puentes, C. O. & Kouznetsov, V. Recent advancements in the homoallylaime chemistry. *J. Heterocyclic Chem.* 39, 595-614 (2002)). In this context, an efficient route for synthesis of enantiomerically enriched homoallylic amines is of great consequence, since the alkene unit resides within such entities or can be readily manipulated to furnish a notable array of desirable N-containing molecules. Catalytic enantioselective addition of an allyl group to an imine, a direct approach for preparation of enantiomerically enriched homoallylic amines, has thus been the subject of substantial scrutiny. Although a number of innovative strategies have been introduced, a catalytic enantioselective method that possesses most of the abovementioned attributes remains absent. Several approaches require the intermediacy of allylindiums (Kim, S. J. & Jong, D. O. Indium-mediated catalytic enantioselective allylation of N-benzohydrazones using a protonated chiral amine. *J. Am. Chem. Soc.* 132, 12168-12169 (2010)), prepared in situ from allyl halides and the costly metal, which, at times, must be added in stoichiometric amounts or more (up to 3.0 equivalents; Tan, K. L. & Jacobsen, E. N. Indium-mediated asymmetric allylation of acylhydrazones using a chiral urea catalyst. *Angew. Chem. Int. Edn* 46, 1315-1317 (2007); Kargo, R.; Takahashi, Y.; Bhor, S.; Cook, G. R.; Lloyd-Jones & G. C.; Shepperson, I. R. Readily accessible, modular, and tunable BINOL 3,3'-perfluoroalkylsulfones: Highly efficient catalysts for enantioselective In-mediated imine allylation. *J. Am. Chem. Soc.* 129, 3846-3847 (2007)); other protocols entail the use of rare elements (e.g., Pd or Ir salts). Additionally, the following drawbacks are frequently encountered: difficult-to-access or expensive chiral ligands (Wada, R.; Shibuguchi, T.; Makino, S.; Oisaki, K.; Kanai, M. & Shibasaki, M. Catalytic enantioselective allylation of ketoimines *J. Am. Chem. Soc.* 126, 7687-7691 (2006)), relatively high catalyst loadings (e.g., ≥10 mol %, Lou, S.; Moquist, P. N. & Schaus, S. E. Asymmetric allylboration of acyl imines catalyzed by chiral diols. *J. Am. Chem. Soc.* 129, 15398-15404 (2007)), long reaction times (e.g., 12 hours, Chakrabarti, A.; Konishi, H.; Yamaguchi, M.; Schneider, U. & Kobayashi, S. Indium(I)-catalyzed asymmetric allylation, crotylation, and α-chloroallylation of hydrazones with rare constitutional and high configurational selectivities. *Angew. Chem. Int. Edn* 49, 1838-1841 (2010)), low or elevated temperatures (e.g., −50 or 100° C.; Vieira, E. M.; Snapper, M. L. & Hoveyda, A. H. Enantioselective synthesis of homoallylic amines through reactions of (pinacolato)allylborons with aryl-, heteroaryl-, alkyl-, or alkene-substituted aldimines catalyzed by chiral $C_1$-symmetric NHC—Cu complexes. *J. Am. Chem. Soc.* 133, 3332-3335 (2011); Naodovic, M.; Wadamoto, M. & Yamamoto, H. Enantioselective Ag-catalyzed allylation of aldimines. *Eur. J. Org. Chem.* 2009, 5129-5131 (2009)), necessity for highly activated aldimines (e.g., glyoxylate derived; Ferraris, D.; Young, B.; Cox, C.; Dudding, T.; Drury, W. J.; Ryzhkov, L.; Taggi, A. E. and Lectka, T. Catalytic, enantioselective alkylation of α-imino esters: The synthesis of normatural α-amino acid derivatives. *J. Am. Chem. Soc.* 124, 67-77 (2002); Hamada, T.; Manabe, K. & Kobayashi, S. *Angew. Chem. Int. Edn* 42, 3927-3930 (2003)), narrow substrate range (e.g., low yield and/or e.r. when alkyl-substituted), imine protecting groups removal of which demands pricey reagents (e.g., $SmI_2$; Fujita, M.; Nagano, T.; Schneider, U.; Hamada, T. & Kobayashi, S. Zn-catalyzed asymmetric allylation for the synthesis of optically active allylglycine derivatives. Regio- and Stereoselective formal addition of allylboronates to hydrazono esters. *J. Am. Chem. Soc.* 130, 2914-2915 (2008)) or harsh conditions (e.g., strong alkylating (Ding, H. & Friestad, G. K. Trifluoroacetyl-activated nitrogen-nitrogen bond cleavage of hydrazines by samarium(II) iodide. *Org. Lett.* 6, 637-640 (2004)) or reducing agent (Lou, S.; Moquist, P. N. & Schaus, S. E. Asymmetric allylboration of acyl imines catalyzed by chiral diols. *J. Am. Chem. Soc.* 129, 15398-15404 (2007))), the need for allyltins (Aydin, J.; Kumar, S.; Sayah, M. J.; Wallner, O. A. & Szabó, K. J. Synthesis and catalytic application of chiral 1,1'-bi-2-napthol and biphenanthrol-based pincer complexes: Selective allylation of sulfonimines and allyl stannane and allyltrifluoroborate. *J. Org. Chem.* 72, 4689-4697 (2007)) or moisture-sensitive allyl-containing agents (Lou, S.; Moquist, P. N. & Schaus, S. E. Asymmetric allylboration of acyl imines catalyzed by chiral diols. *J. Am. Chem. Soc.* 129, 15398-15404 (2007)). The corresponding additions to ketones represent an equally important class of transformations, and a particularly noteworthy group of substrates in this regard are isatins (Ruiz-Sanchis, P.; Savina, S. A.; Albericio, F. & Álvarez, M. Structure, bioactivity and synthesis of natural products with hexahydropyrrolo[2,3-b]indole. *Chem. Eur. J.* 17, 1388-1408 (2011)). Such reactions offer access to enantiomerically enriched 3-hydroxy-2-indoles, which are imbedded within several alkaloids of substantial biological significance (Ishikura, M. & Yamada, K. Simple indole alkaloids and those with a nonrearranged monoterpenoid unit. *Nat. Prod. Rep.* 26, 803-852 (2009)). There is evidence that the absolute configuration of the tertiary hydroxyl unit impacts biological activity (Peddibhotla, S. 3-Substituted-3-hydroxy-2-oxindole, an emerging new scaffold for drug discovery with potential anti-cancer and other biological activites. *Curr. Bioact. Compd.* 5, 20-38 (2009)). Nevertheless, only a small number of reports address catalytic enantioselective allyl additions to isatins, and similar limitations, including the need for allyltins and precious metal salts (Itoh, J., Han, S. B. & Krische, M. J. Enantioselective allylation, crotylation, and reverse prenylation of substituted isatins: Iridium-catalyzed CC bond-forming transfer hydrogenation. *Angew. Chem. Int. Edn* 48, 6313-6316 (2009)), moderate selectivities, and difficult-to-prepare catalysts exist here as well.

Previous research, dominated by reactions involving exceptionally nucleophilic and thus sensitive allylmetal intermediates requires rigorously anhydrous and/or oxygen-free conditions (Vieira, E. M.; Snapper, M. L. & Hoveyda, A. H. Enantioselective synthesis of homoallylic amines through reactions of (pinacolato)allylborons with aryl-, heteroaryl-, alkyl-, or alkene-substituted aldimines catalyzed by chiral $C_1$-symmetric NHC Cu complexes. *J. Am. Chem. Soc.* 133, 3332-3335 (2011)). Furthermore, with substituted allylmetal intermediates, high diastereoselectivity is either not observed (Tan, K. L. & Jacobsen, E. N. Indium-mediated asymmetric allylation of acylhydrazones using a chiral urea catalyst. *Angew. Chem. Int. Edn* 46, 1315-1317 (2007); Vieira, E. M.; Snapper, M. L. & Hoveyda, A. H. Enantioselective synthesis of homoallylic amines through reactions of (pinacolato)allylborons with aryl-, heteroaryl-, alkyl-, or alkene-substituted aldimines catalyzed by chiral $C_1$-symmetric NHCCu complexes. *J. Am. Chem. Soc.* 133, 3332-3335 (2011)), or only one of the two possible diastereomers can be accessed (Itoh, J., Han, S. B. & Krische, M. J. Enantioselective allylation, crotylation, and reverse prenylation of substituted isatins: Iridium-catalyzed CC bond-forming transfer hydrogenation. *Angew. Chem. Int. Edn* 48, 6313-6316 (2009)). One example of a catalytic "all-boron" allyl addition protocol proceeds less readily, requiring higher catalyst amounts and longer reaction times, than when an allylmetal is involved (e.g., 15 mol % loading and 36 hours). Similar to cases that proceed via an allylmetal, reactions with the latter metal-free catalyst and E- or Z-disubstituted allylborons deliver the same product diastereomers (Lou, S.; Moquist, P. N. & Schaus, S. E. Asymmetric allylboration of acyl imines catalyzed by chiral diols. *J. Am. Chem. Soc.* 129, 15398-15404 (2007)).

SUMMARY

Figure 1A:
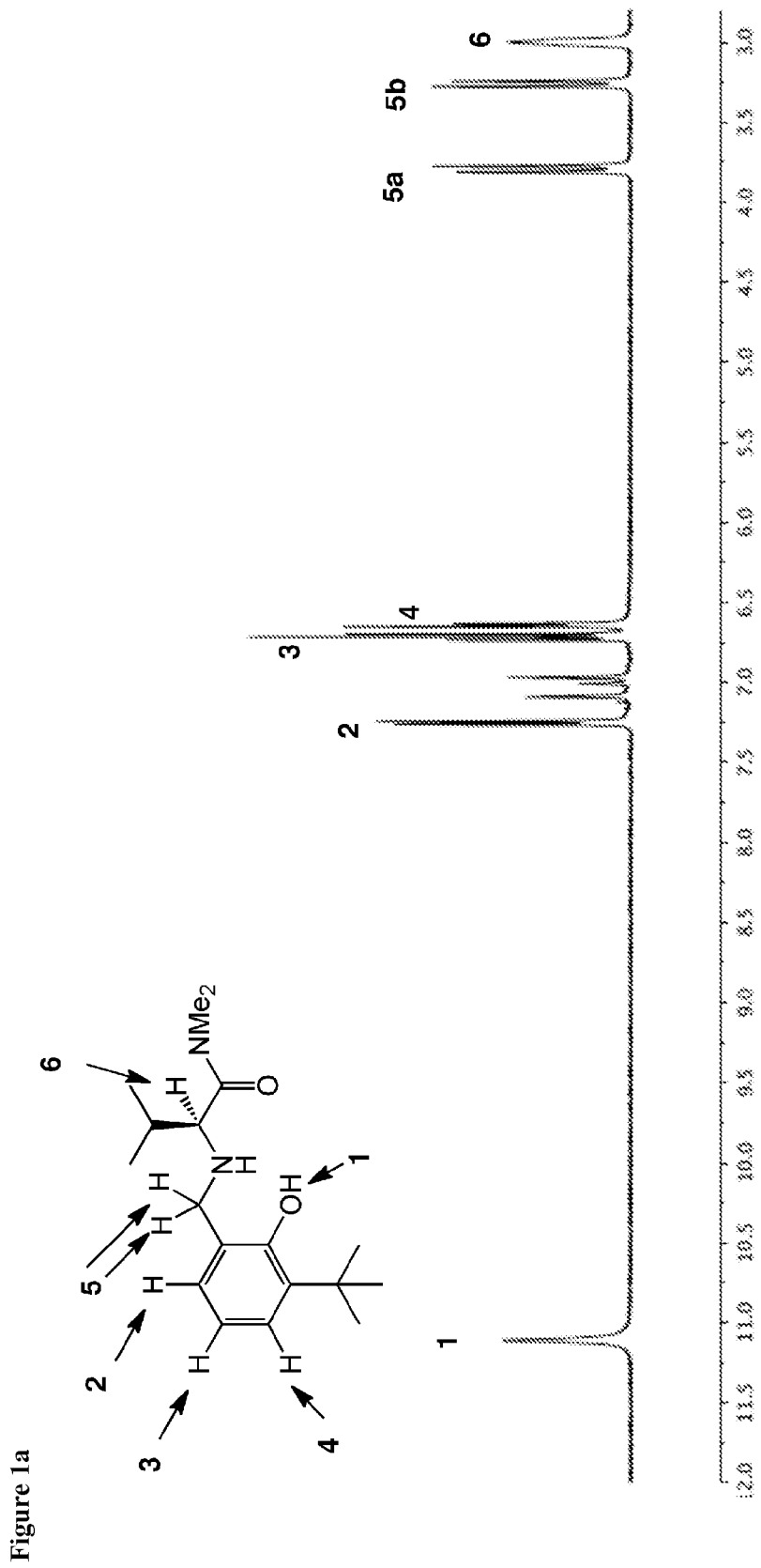
FIG. 1. Spectra of $^1H$ NMR of 2g for Investrigation of the Effect of Allyboronate 1a and MeOH on the Phenoxide of Aminophenol 2g. (a) Spectrum 1; (b) Spectrum 2; (c) Spectrum 3; (d) Spectrum 4; and (e) Spectrum 5.

In some embodiments, the present invention provides novel methods for the synthesis of alcohols and amines. In some embodiments, such methods are stereoselective. In some embodiments, a provided method is enantioselective. In some embodiments, a provided method is diastereoselective. In some embodiments, a provided method is both enantioselective and diastereoselective. In some embodiments, the product, i.e., the alcohol or the amine, has a double or triple bond between the atoms at the 3' and 4' positions, wherein the carbon atom to which the hydroxyl or amino group is attached is designated as 1'. In some embodiments, such a product is a homoallylic amine. In some embodiments, such a product is a homoallylic alcohol. In some embodiments, such a product is a homopropargyl alcohol. In some other embodiments, such a product is a homopropargyl amine.

In some embodiments, the present invention provides a method for synthesis of an amine or alcohol, comprising reacting an organoboron reagent and an imine or carbonyl compound with a compound of formula I:

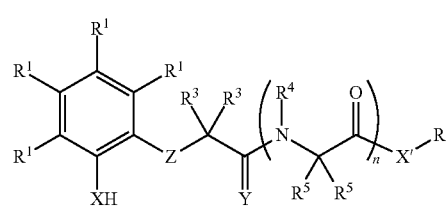

wherein each variable is independently described in detail, infra. In some embodiments, a provided method is stereoselective.

In some embodiments, the present invention provides new methods for synthesis of homoallylic amines and alcohols. In some embodiments, the present invention provides new methods for stereoselective synthesis of homoallylic amines and alcohols. In some embodiments, the present invention provides a compound of formula I:

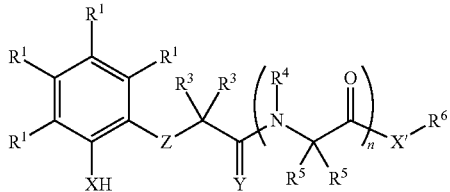

I wherein each variable is independently described in detail, infra. In some embodiments, the present invention provides a method for synthesis of a homoallylic amine or alcohol comprising reacting an allylboron reagent and an imine or carbonyl compound with a compound of formula I:

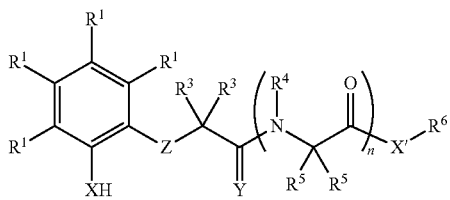

I wherein the variables are described in detail, infra.

DETAILED DESCRIPTION OF CERTAIN EMBODIMENTS

1. General Description of Certain Embodiments of the Invention

In some embodiments, the present invention provides methods for the synthesis of homoallylic amines and alcohols with high efficiency and stereoselectivity, in some embodiments, delivering over 98% yield, up to 96:4 enantiomeric ratio, in four hours at 22° C. Utility is demonstrated by applications to preparation of homoallylic amines or alcohols, entities used in the preparation of biologically active molecules.

In some embodiments, the present invention provides a compound of formula I:

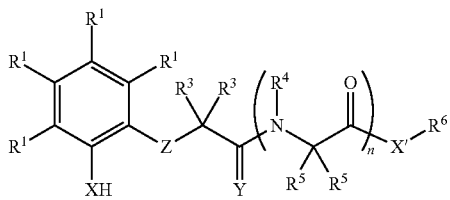

I wherein:

n is 0-10;

each $R^1$ is independently R, halogen, —OR, —N(R)$_2$, —SR, —NO$_2$, —SOR, —SO$_2$R, —Si(R)$_3$, or —C(O)L;

X is —O—, —NR—, —S—, or —Se—;

X' is —O—, —NR$^6$—, —S—, or —Se—;

Z is —C(R$^2$)$_2$—NR—, —C(R$^2$)=N—, or —C(=Y)—NR—;

Y is =O, =S, or =NR;

each of $R^2$, $R^3$, $R^4$, $R^5$ and $R^6$ is independently R, —OR, —N(R)$_2$, —SR, or —C(O)L;

L is R, halogen, —OR, —N(R)$_2$, or —SR;

each R is independently hydrogen or R';

each R' is independently an optionally substituted group selected from $C_{1-12}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; or:

two R' groups on the same nitrogen atom are optionally taken together with the nitrogen atom to form an optionally substituted 3-8 membered, saturated, partially unsaturated, or aryl ring having 1-4 heteroatoms independently selected from nitrogen, oxygen, or sulfur; or two R' groups on the same carbon atom are optionally taken together with their intervening atoms to form an optionally substituted 3-8 membered saturated or partially unsaturated spirocycle ring having 0-4 heteroatoms independently selected from nitrogen, oxygen, or sulfur, or two R' groups on adjacent atoms are optionally taken together with their intervening atoms form an optionally substituted 3-8 membered, saturated, partially unsaturated, or aryl ring having 0-4 heteroatoms independently selected from nitrogen, oxygen, or sulfur.

In some embodiments, the present invention provides a compound of formula I having the structure of:

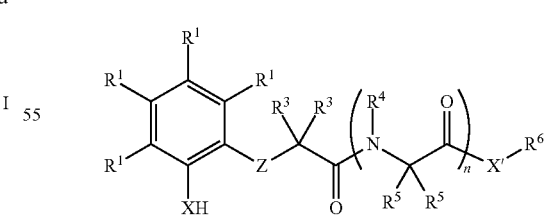

wherein each variable is independently as defined above and described herein.

In some embodiments, the present invention provides a method comprising: reacting an organoboron reagent with a compound comprising a double bond with a compound of formula I:

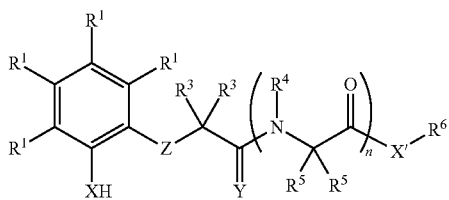

I wherein the double bond is converted into a single bond through the addition of an organic group of the organoboron reagent. In some embodiments, the present invention provides a method comprising:

reacting an organoboron reagent with a compound comprising a double bond with a compound of formula I having the structure of:

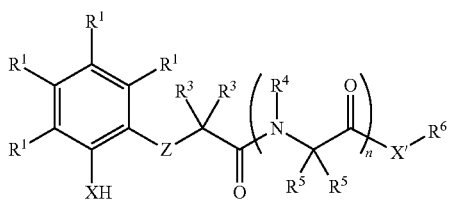

wherein the double bond is converted into a single bond through the addition an organic group of the organoboron reagent.

In some embodiments, the present invention provides a method for synthesis of a homoallylic amine or alcohol comprising reacting an allylboron reagent and an imine or carbonyl compound with a compound of formula I:

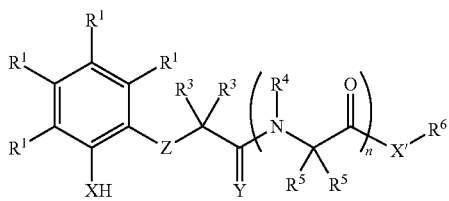

I wherein:
n is 0-10;
each R' is independently R, halogen, —OR, —N(R)$_2$, —SR, —NO$_2$, —SOR, —SO$_2$R, —Si(R)$_3$, or —C(O)L;
X is —O—, —NR—, —S—, or —Se—;
X' is —O—, —NR$^6$—, —S—, or —Se—;
Z is —C(R$^2$)$_2$—NR—, —C(R$^2$)=N—, or —C(=Y)—NR—;
Y is =O, =S, or =NR;
each of R$^2$, R$^3$, R$^4$, R$^5$ and R$^6$ is independently R, —OR, —N(R)$_2$, —SR, or —C(O)L;
L is R, halogen, —OR, —N(R)$_2$, or —SR;
each R is independently hydrogen or R'; and
each R' is independently an optionally substituted group selected from C$_{1-12}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; or:

two R' groups on the same nitrogen atom are optionally taken together with the nitrogen atom to form an optionally substituted 3-8 membered, saturated, partially unsaturated, or aryl ring having 1-4 heteroatoms independently selected from nitrogen, oxygen, or sulfur; or two R' groups on the same carbon atom are optionally taken together with their intervening atoms to form an optionally substituted 3-8 membered saturated or partially unsaturated spirocycle ring having 0-4 heteroatoms independently selected from nitrogen, oxygen, or sulfur, or two R' groups on adjacent atoms are optionally taken together with their intervening atoms form an optionally substituted 3-8 membered, saturated, partially unsaturated, or aryl ring having 0-4 heteroatoms independently selected from nitrogen, oxygen, or sulfur.

In some embodiments, the present invention provides a method for synthesis of a homoallylic amine or alcohol comprising reacting an allylboron reagent and an imine or carbonyl compound with a compound of formula I having the structure of

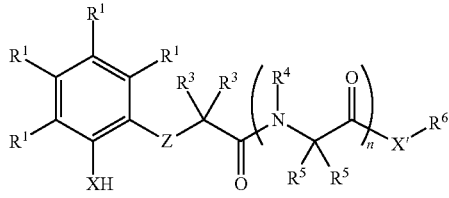

wherein each variable is independently as defined above and described herein.

2. Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon, bicyclic hydrocarbon, or tricyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-30 aliphatic carbon atoms. In some embodiments, aliphatic groups contain 1-20 aliphatic carbon atoms. In other embodiments, aliphatic groups contain 1-10 aliphatic carbon atoms. In still other embodiments, aliphatic groups contain 1-5 aliphatic carbon atoms, and in yet other embodiments, aliphatic groups contain 1, 2, 3, or 4 aliphatic carbon atoms. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "cycloaliphatic," as used herein, refers to saturated or partially unsaturated cyclic aliphatic monocyclic, bicyclic, or polycyclic ring systems, as described herein, having from 3 to 14 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, norbornyl, adamantyl, and cyclooctadienyl. In some embodiments, the cycloalkyl has 3-6 carbons. The terms "cycloaliphatic," may also include aliphatic rings that are fused to one or more aromatic or nonaromatic rings, such as decahydronaphthyl or tetrahydronaphthyl, where the radical or point of attachment is on the aliphatic ring. In some embodiments, a carbocyclic group is bicyclic. In some embodiments, a carbocyclic group is tricyclic. In some embodiments, a carbocyclic group is polycyclic. In some embodiments, "cycloaliphatic" (or "carbocycle" or "cycloalkyl") refers to a monocyclic $C_3$-$C_6$ hydrocarbon, or a $C_8$-$C_{10}$ bicyclic hydrocarbon that is completely saturated or that contains one or more units of unsaturation, but which is not aromatic, that has a single point of attachment to the rest of the molecule, or a $C_9$-$C_{16}$ tricyclic hydrocarbon that is completely saturated or that contains one or more units of unsaturation, but which is not aromatic, that has a single point of attachment to the rest of the molecule.

As used herein, the term "alkyl" is given its ordinary meaning in the art and may include saturated aliphatic groups, including straight-chain alkyl groups, branched-chain alkyl groups, cycloalkyl(alicyclic) groups, alkyl substituted cycloalkyl groups, and cycloalkyl substituted alkyl groups. In certain embodiments, a straight chain or branched chain alkyl has about 1-20 carbon atoms in its backbone (e.g., $C_1$-$C_{20}$ for straight chain, $C_2$-$C_{20}$ for branched chain), and alternatively, about 1-10. In some embodiments, a cycloalkyl ring has from about 3-10 carbon atoms in their ring structure where such rings are monocyclic or bicyclic, and alternatively about 5, 6 or 7 carbons in the ring structure. In some embodiments, an alkyl group may be a lower alkyl group, wherein a lower alkyl group comprises 1-4 carbon atoms (e.g., $C_1$-$C_4$ for straight chain lower alkyls).

As used herein, the term "alkenyl" refers to an alkyl group, as defined herein, having one or more double bonds.

As used herein, the term "alkynyl" refers to an alkyl group, as defined herein, having one or more triple bonds.

The term "heteroalkyl" is given its ordinary meaning in the art and refers to alkyl groups as described herein in which one or more carbon atoms is replaced with a heteroatom (e.g., oxygen, nitrogen, sulfur, and the like). Examples of heteroalkyl groups include, but are not limited to, alkoxy, poly (ethylene glycol)-, alkyl-substituted amino, tetrahydrofuranyl, piperidinyl, morpholinyl, etc.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, binaphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms (i.e., monocyclic or bicyclic), in some embodiments 5, 6, 9, or 10 ring atoms. In some embodiments, such rings have 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. In some embodiments, a heteroaryl is a heterobiaryl group, such as bipyridyl and the like. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1, 4-oxazin-3(4H)-one. A heteroaryl group may be monocyclic, bicyclic, tricyclic, tetracyclic, and/or otherwise polycyclic The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be monocyclic, bicyclic, tricyclic, tetracyclic, and/or otherwise polycyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or, a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

The term "halogen" means F, Cl, Br, or I.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —(CH$_2$)$_{0-4}$SR°; —(CH$_2$)$_{0-4}$S(O)R°; —(CH$_2$)$_{0-4}$S(O)$_2$R°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$Ph, which may be substituted with R°; —(CH$_2$)$_{0-4}$O(CH$_2$)$_{0-1}$Ph which may be substituted with R°; —CH═CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)RO$_2$; —OP(O)RO$_2$; —OP(O)(OR°)$_2$; —PR°$_2$; —OPR°$_2$; —SiR°$_3$; —OSiR°$_3$; —(C$_{1-4}$ straight or branched alkylene)O—N(R°)$_2$; or —(C$_{1-4}$ straight or branched alkylene)C(O)O—N(R°)$_2$; wherein each R° may be substituted as defined below and is independently hydrogen, C$_{1-6}$aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-6 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R•, -(haloR•), —(CH$_2$)$_{0-2}$OH, —(CH$_2$)$_{0-2}$OR•, —(CH$_2$)$_{0-2}$CH(OR•)$_2$; —O(haloR•), —CN, —N$_3$, —(CH$_2$)$_{0-2}$C(O)R•, —(CH$_2$)$_{0-2}$C(O)OH, —(CH$_2$)$_{0-2}$C(O)OR•, —(CH$_2$)$_{0-2}$SR•, —(CH$_2$)$_{0-2}$SH, —(CH$_2$)$_{0-2}$NH$_2$, —(CH$_2$)$_{0-2}$NHR•, —(CH$_2$)$_{0-2}$NR•$_2$, —NO$_2$, —SiR•$_3$, —OSiR•$_3$, —C(O)SR•, —(C$_{1-4}$ straight or branched alkylene)C(O)OR•, or —SSR• wherein each R• is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include ═O and ═S.

Suitable divalent substituents on a saturated carbon atom of an "optionally substituted" group include the following: ═O, ═S, ═NNR*$_2$, ═NNHC(O)R*, ═NNHC(O)OR*, ═NNHS(O)$_2$R*, ═NR*, ═NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R•, -(haloR•), —OH, —OR•, —O(haloR•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†$_2$, —C(O)R†, —C(O)OR†, C(O)C(O)R†, —C(O)CH$_2$C(O)R†, —S(O)$_2$R†, —S(O)$_2$NR†$_2$, —C(S)NR†$_2$, —C(NH)NR†$_2$, or —N(Rt)S(O)$_2$R†; wherein each R† is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R† , taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R˙, -(haloR˙), —OH, —OR˙, —O(haloR˙), —CN, —C(O)OH, —C(O)OR˙, —NH$_2$, —NHR˙, —NR˙$_2$, or —NO$_2$, wherein each R' is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "chiral" is given its ordinary meaning in the art and refers to a molecule that is not superimposable with its mirror image, wherein the resulting nonsuperimposable mirror images are known as "enantiomers" and are labeled as either an (R) enantiomer or an (S) enantiomer. Typically, chiral molecules lack a plane of symmetry.

The term "achiral" is given its ordinary meaning in the art and refers to a molecule that is superimposable with its mirror image. Typically, achiral molecules possess a plane of symmetry.

As used herein, a "nitrogen-containing ligand" may be any species comprising a nitrogen atom. In some cases, the nitrogen atom may bind to the metal atom. In some cases, the nitrogen-containing ligand may bind the metal center via a different atom. In some cases, the nitrogen atom may be a ring atom of a heteroaryl or heteroalkyl group. In some cases, the nitrogen atom may be a substituted amine group. It should be understood that, in catalyst precursors described herein, the nitrogen-containing ligand may have sufficiently ionic character to coordinate a metal center, such as a Mo or W metal center. Examples of nitrogen-containing ligands include, but are not limited to, pyrrolyl, pyrazolyl, pyridinyl, pyrazinyl, pyrimidinyl, imidazolyl, triazolyl, tetrazolyl, oxazolyl, isoxazolyl, thiazolyl, isothiazolyl, indolyl, indazolyl, carbazolyl, morpholinyl, piperidinyl, oxazinyl, substituted derivatives thereof, and the like. For example, the nitrogen-containing ligand may be pyrrolide or 2,5-dimethylpyrrolide. The nitrogen-containing ligand may be selected to interact with an oxygen-containing ligand such that the oxygen-containing ligand can readily replace the nitrogen-containing ligand in a precatalyst to generate a catalyst. In cases where the catalyst composition may be generated in situ in order to carry out a chemical reaction, the first, nitrogen-containing ligand may be selected such that, upon replacement by an oxygen-containing ligand, the nitrogen-containing ligands or protonated versions thereof do not interfere with the chemical reaction. In some embodiments, the nitrogen-containing ligand may be chiral and the precatalyst may be provided as a racemic mixture or a purified stereoisomer.

The phrase "protecting group," as used herein, refers to temporary substituents which protect a potentially reactive functional group from undesired chemical transformations. Examples of such protecting groups include esters of carboxylic acids, silyl ethers of alcohols, and acetals and ketals of aldehydes and ketones, respectively. A "Si protecting group" is a protecting group comprising a Si atom, such as Si-trialkyl (e.g., trimethylsilyl, tributylsilyl, t-butyldimethylsilyl), Si-triaryl, Si-alkyl-diphenyl (e.g., t-butyldiphenylsilyl), or Si-aryl-dialkyl (e.g., Si-phenyldialkyl). Generally, a Si protecting group is attached to an oxygen atom. The field of protecting group chemistry has been reviewed (Greene, T. W.; Wuts, P. G. M. Protective Groups in Organic Synthesis, 2nd ed.; Wiley: New York, 1991). Such protecting groups (and associated protected moieties) are described in detail below.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{11}$C- or $^{13}$C- or $^{14}$C-enriched carbon are within the scope of this invention. Such compounds are useful, for example, as analytical tools or probes in biological assays.

Protected hydroxyl groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Examples of suitably protected hydroxyl groups further include, but are not limited to, esters, carbonates, sulfonates allyl ethers, ethers, silyl ethers, alkyl ethers, arylalkyl ethers, and alkoxyalkyl ethers. Examples of suitable esters include formates, acetates, proprionates, pentanoates, crotonates, and benzoates. Specific examples of suitable esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetate), crotonate, 4-methoxy-crotonate, benzoate, p-benzylbenzoate, 2,4,6-trimethylbenzoate. Examples of suitable carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, and other trialkylsilyl ethers. Examples of suitable alkyl ethers include methyl, benzyl, p-methoxybenzyl, 3,4-dimethoxybenzyl, trityl, t-butyl, and allyl ether, or derivatives thereof. Alkoxyalkyl ethers include acetals such as methoxymethyl, methylthiomethyl, (2-methoxyethoxy) methyl, benzyloxymethyl, beta-(trimethylsilyl)ethoxymethyl, and tetrahydropyran-2-yl ether. Examples of suitable arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

Protected amines are well known in the art and include those described in detail in Greene (1999). Suitable monoprotected amines further include, but are not limited to, aralkylamines, carbamates, allyl amines, amides, and the like. Examples of suitable mono-protected amino moieties include t-butyloxycarbonylamino (—NHBOC), ethyloxycarbonylamino, methyloxycarbonylamino, trichloroethyloxycarbonylamino, allyloxycarbonylamino (—NHAlloc), benzyloxocarbonylamino (—NHCBZ), allylamino, benzylamino (—NHBn), fluorenylmethylcarbonyl (—NHFmoc), formamido, acetamido, chloroacetamido, dichloroacetamido, trichloroacetamido, phenylacetamido, trifluoroacetamido, benzamido, t-butyldiphenylsilyl, and the like. Suitable di-protected amines include amines that are substituted with two substituents independently selected from those described above as mono-protected amines, and further include cyclic imides, such as phthalimide, maleimide, succinimide, and the like. Suitable di-protected amines also include pyrroles and the like, 2,2,5,5-tetramethyl-[1,2,5]azadisilolidine and the like, and azide.

Protected aldehydes are well known in the art and include those described in detail in Greene (1999). Suitable protected aldehydes further include, but are not limited to, acyclic acetals, cyclic acetals, hydrazones, imines, and the like. Examples of such groups include dimethyl acetal, diethyl acetal, diisopropyl acetal, dibenzyl acetal, bis(2-nitrobenzyl) acetal, 1,3-dioxanes, 1,3-dioxolanes, semicarbazones, and derivatives thereof.

Protected carboxylic acids are well known in the art and include those described in detail in Greene (1999). Suitable protected carboxylic acids further include, but are not limited to, optionally substituted $C_{1-6}$ aliphatic esters, optionally substituted aryl esters, silyl esters, activated esters, amides, hydrazides, and the like. Examples of such ester groups include methyl, ethyl, propyl, isopropyl, butyl, isobutyl, benzyl, and phenyl ester, wherein each group is optionally substituted. Additional suitable protected carboxylic acids include oxazolines and ortho esters.

Protected thiols are well known in the art and include those described in detail in Greene (1999). Suitable protected thiols further include, but are not limited to, disulfides, thioethers, silyl thioethers, thioesters, thiocarbonates, and thiocarbamates, and the like. Examples of such groups include, but are not limited to, alkyl thioethers, benzyl and substituted benzyl thioethers, triphenylmethyl thioethers, and trichloroethoxycarbonyl thioester, to name but a few.

Unless otherwise designated, the term "homoallylic amine" means a molecule that has a non-substituted, mono- or di-substituted amino group at the homoallylic position of a homoallylic moiety within the molecule; and the term "homoallylic alcohol" means a molecule that has a hydroxyl group at the homoallylic position of a homoallylic moiety within the molecule. Unless otherwise designated, an allyl-boron reagent means a compound that has a boron atom at the allylic position of an allyl moiety within the molecule. Exemplary allylic moiety is $CH_2\!=\!CH\!-\!CH_2\!-$, wherein the saturated carbon is the allylic carbon, and wherein each hydrogen can be independently optionally substituted by another atom within the molecule. Exemplary homoallylic moiety is $CH_2\!=\!CH\!-\!CH_2\!-\!CH_2\!-$, wherein the saturated carbon directly connected to the double bond is the allylic carbon and the other saturated carbon is the homoallylic carbon, and wherein each hydrogen can be independently optionally substituted by another atom within the molecule. In some embodiments, the amino group of the homoallylic amine is substituted with phosphinoyl. In some embodiments, the amino group of the homoallylic amine is substituted with $-P(O)R°_2$. In some embodiments, the amino group of the homoallylic amine is substituted with $-P(O)Ph_2$.

3. Description of Certain Embodiments of the Invention

As generally defined above, the present invention provides a compound of formula I:

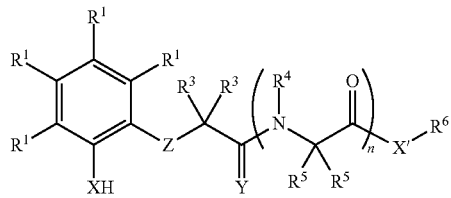

I wherein:
n is 0-10;
each $R^1$ is independently R, halogen, $-OR$, $-N(R)_2$, $-SR$, $-NO_2$, $-SOR$, $-SO_2R$, $-Si(R)_3$, or $-C(O)L$;

X is $-O-$, $-NR-$, $-S-$, or $-Se-$;
X' is $-O-$, $-NR^6-$, $-S-$, or $-Se-$;
Z is $-C(R^2)_2-NR-$, $-C(R^2)=N-$, or $-C(\!=\!Y)-NR-$;
Y is $=O$, $=S$, or $=NR$;
each of $R^2$, $R^3$, $R^4$, $R^5$ and $R^6$ is independently R, $-OR$, $-N(R)_2$, $-SR$, or $-C(O)L$;
L is R, halogen, $-OR$, $-N(R)_2$, or $-SR$;
each R is independently hydrogen or R'; and
each R' is independently an optionally substituted group selected from $C_{1-12}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; or:

two R' groups on the same nitrogen atom are optionally taken together with the nitrogen atom to form an optionally substituted 3-8 membered, saturated, partially unsaturated, or aryl ring having 1-4 heteroatoms independently selected from nitrogen, oxygen, or sulfur; or two R' groups on the same carbon atom are optionally taken together with their intervening atoms to form an optionally substituted 3-8 membered saturated or partially unsaturated spirocycle ring having 0-4 heteroatoms independently selected from nitrogen, oxygen, or sulfur, or two R' groups on adjacent atoms are optionally taken together with their intervening atoms form an optionally substituted 3-8 membered, saturated, partially unsaturated, or aryl ring having 0-4 heteroatoms independently selected from nitrogen, oxygen, or sulfur.

In some embodiments, the present invention provides a compound of formula I having the structure of:

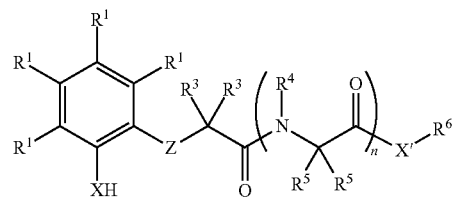

wherein each variable is independently as defined above and described herein.

As generally defined above, n is 0-10. In some embodiments, n is 0. In some embodiments, n is 1-10. In some embodiments, n is 1.

As generally defined above, each R' is independently R, halogen, $-OR$, $-N(R)_2$, $-SR$, $-NO_2$, $-SOR$, $-SO_2R$, $-Si(R)_3$, or $-C(O)L$, wherein each of R and L is independently as defined above and described herein. In some embodiments, each R' is independently R, halogen, $-OR$, $-N(R)_2$, $-SR$, $-NO_2$, $-SOR$, $-SO_2R$, or $-C(O)L$, wherein each of R and L is independently as defined above and described herein. In some embodiments, $R^1$ is R, wherein R is as defined above and described herein. In some embodiments, $R^1$ is hydrogen. In some embodiments, $R^1$ is optionally substituted $C_{1-12}$ aliphatic. In some embodiments, $R^1$ is optionally substituted $C_{1-12}$ alkyl. In some embodiments, $R^1$ is tert-butyl. In some embodiments, $R^1$ is —Si(R)$_3$, wherein each of R is independently as defined above and described herein. In some embodiments, $R^1$ is —Si(R')$_3$, wherein each of R' is independently as defined above and described herein. In some embodiments, $R^1$ is —Si(R')$_3$, wherein each of R' is independently optionally substituted phenyl. In some embodiments, $R^1$ is —Si(R')$_3$, wherein each of R' is independently phenyl. In some embodiments, $R^1$ is —SiPh$_3$. In some embodiments, the R' at o position of —XH is optionally substituted $C_{1-12}$ alkyl and each other R' is hydrogen. In some embodiments, the $R^1$ at o position of —XH is R' or —Si(R')$_3$ and each other $R^1$ is hydrogen. In some embodiments, the $R^1$ at o position of —XH is R', and each other $R^1$ is hydrogen. In some embodiments, the $R^1$ at o position of —XH is —Si(R')$_3$, and each other $R^1$ is hydrogen. In some embodiments, the $R^1$ at o position of —XH is —SiPh$_3$ and each other $R^1$ is hydrogen. In some embodiments, the $R^1$ at o position of —XH is tert-butyl and each other $R^1$ is hydrogen. In some embodiments, each $R^1$ is hydrogen. In some embodiments, each $R^1$ is hydrogen, and the carbon atom to which $R^1$ is attached is optionally substituted.

In some embodiments, each $R^1$ is independently R, halogen, —OR, —N(R)$_2$, —SR, —NO$_2$, —SOR', —SO$_2$R', or —C(O)L, wherein each of R, R' and L is independently as defined above and described herein.

As generally defined above, X is —O—, —NR—, —S—, or —Se—, wherein R is as defined above and described herein. In some embodiments, X is —O—, —NH—, —S—, or —Se—. In some embodiments, X is —O—.

As generally defined above, X' is —O—, —NR$^6$—, —S—, or —Se—, wherein $R^6$ is as defined above and described herein. In some embodiments, X' is —O—. In some embodiments, X' is —NR$^6$—, wherein $R^6$ is as defined above and described herein.

As generally defined above, Z is —C(R$^2$)$_2$—NR—, —C(R$^2$)=N—, or —C(=Y)—NR—, wherein each of R$^2$, R and Y is independently as defined above and described herein. In some embodiments, Z is —C(R$^2$)$_2$—NH—, —CH=N—, or —C(=Y)—NH—, wherein each of R$^2$ and Y is independently as defined above and described herein. In some embodiments, Z is —C(R$^2$)$_2$—NH—, wherein R$^2$ is as defined above and described herein. In some embodiments, Z is —CH$_2$—NH—. In some embodiments, Z is —CH=N—. In some embodiments, Z is —C(=Y)—NH—, wherein Y is as defined above and described herein. In some embodiments, Z is —C(O)—NH—.

As generally defined above, Y is =O, =S, or =NR, wherein R is as defined above and described herein. In some embodiments, Y is =O, =S, or =NR', wherein R' is as defined above and described herein. In some embodiments, Y is =O. In some embodiments, Y is =S. In some embodiments, Y is =NR, wherein R is as defined above and described herein. In some embodiments, Y is =NR', wherein R' is as defined above and described herein.

As generally defined above, each of R$^2$, R$^3$, R$^4$, R$^5$ and R$^6$ is independently R, —OR, —N(R)$_2$, —SR, or —C(O)L, wherein each of R and L is independently as defined above and described herein. In some embodiments, each of R$^2$, R$^3$, R$^4$, R$^5$ and R$^6$ is independently R, —OR', —NR'$_2$, —SR, or —C(O)L, wherein each of R, R' and L is independently as defined above and described herein.

In some embodiments, each R$^2$ is independently R, —OR, —N(R)$_2$, —SR, or —C(O)L, wherein each of R and L is independently as defined above and described herein. In some embodiments, R$^2$ is R, wherein R is as defined above and described herein. In some embodiments, R$^2$ is hydrogen. In some embodiments, each R$^2$ is hydrogen.

In some embodiments, each R$^3$ is independently R, —OR, —N(R)$_2$, —SR, or —C(O)L, wherein each of R and L is independently as defined above and described herein. In some embodiments, R$^3$ is R, wherein R is as defined above and described herein. In some embodiments, R$^3$ is hydrogen. In some embodiments, R$^3$ is an optionally substituted $C_{1-12}$ aliphatic. In some embodiments, R$^3$ is an optionally substituted $C_{1-12}$ alkyl. In some embodiments, R$^3$ is isopropyl. In some embodiments, R$^3$ is tert-butyl. In some embodiments, one R$^3$ is hydrogen and the other is R'. In some embodiments, one R$^3$ is hydrogen and the other is optionally substituted $C_{1-12}$ aliphatic. In some embodiments, one R$^3$ is hydrogen and the other is optionally substituted $C_{1-12}$ alkyl. In some embodiments, one R$^3$ is hydrogen and the other is isopropyl. In some embodiments, one R$^3$ is hydrogen and the other is tert-butyl.

In some embodiments, R$^4$ is independently R, —OR, —N(R)$_2$, —SR, or —C(O)L, wherein each of R and L is independently as defined above and described herein. In some embodiments, R$^4$ is hydrogen. In some embodiments, R$^4$ is R', wherein R' is as defined above and described herein.

In some embodiments, each R$^5$ is independently R, —OR, —N(R)$_2$, —SR, or —C(O)L, wherein each of R and L is independently as defined above and described herein. In some embodiments, R$^5$ is R, wherein R is as defined above and described herein. In some embodiments, R$^5$ is hydrogen. In some embodiments, R$^5$ is R', wherein R' is as defined above and described herein. In some embodiments, R$^5$ is an optionally substituted $C_{1-12}$ aliphatic. In some embodiments, R$^5$ is an optionally substituted $C_{1-12}$ alkyl. In some embodiments, R$^5$ is isopropyl. In some embodiments, R$^5$ is tert-butyl. In some embodiments, one R$^5$ is hydrogen and the other is R', wherein R' is as defined above and described herein. In some embodiments, one R$^5$ is hydrogen and the other is optionally substituted $C_{1-12}$ alkyl. In some embodiments, one R$^5$ is hydrogen and the other is isopropyl. In some embodiments, one R$^5$ is hydrogen and the other is tert-butyl.

In some embodiments, each R$^6$ is independently R, —OR, —N(R)$_2$, —SR, or —C(O)L, wherein each of R and L is independently as defined above and described herein. In some embodiments, R$^6$ is R, wherein R is as defined above and described herein. In some embodiments, R$^6$ is hydrogen. In some embodiments, R$^6$ is R', wherein R' is as defined above and described herein. In some embodiments, R$^6$ is an optionally substituted $C_{1-12}$ aliphatic. In some embodiments, R$^6$ is an optionally substituted $C_{1-12}$ alkyl. In some embodiments, R$^6$ is methyl. In some embodiments, R$^6$ is isopropyl. In some embodiments, R$^6$ is n-butyl. In some embodiments, R$^6$ is tert-butyl. In some embodiments, R$^6$ is optionally substituted phenyl. In some embodiments, R$^6$ is unsubstituted phenyl. In some embodiments, R$^6$ is substituted phenyl. In some embodiments, one R$^6$ is hydrogen and the other is phenyl. In some embodiments, for two R$^6$ attached to the same atom, one R$^6$ is hydrogen and the other is R, wherein R is as defined above and described herein. In some embodiments, for two R$^6$ attached to the same atom, one R$^6$ is hydrogen and the other is R', wherein R' is as defined above and described herein. In some embodiments, one R$^6$ is hydrogen and the other is optionally substituted phenyl. In some embodiments, one R$^6$ is hydrogen and the other is optionally substituted $C_{1-12}$ aliphatic. In some embodiments, one R$^6$ is hydrogen and the other is optionally substituted $C_{1-12}$ alkyl. In some embodiments, one R$^6$ is hydrogen and the other is optionally substituted $C_{1-12}$ alkyl. In some embodiments, one R$^6$ is hydrogen and the other is methyl. In some embodiments, one R⁶ is hydrogen and the other is isopropyl. In some embodiments, one R⁶ is hydrogen and the other is n-butyl. In some embodiments, one R⁶ is hydrogen and the other is tert-butyl. In some embodiments, for two R⁶ connected to the same atom, each R⁶ is independently R', wherein R' is as defined above and described herein. In some embodiments, for two R⁶ connected to the same atom, each R⁶ is independently optionally substituted $C_{1-12}$ aliphatic. In some embodiments, for two R⁶ connected to the same atom, each R⁶ is independently optionally substituted $C_{1-12}$ alkyl. In some embodiments, both R⁶ are methyl.

In some embodiments, —X'R⁶ is —N(R)₂, wherein each R⁶ is independently as defined above and described herein. In some embodiments, —X'R⁶ is —N(R)₂, wherein each R is independently as defined above and described herein. In some embodiments, —X'R⁶ is —N(R')₂, wherein each R' is independently as defined above and described herein. In some embodiments, —X'R⁶ is —N(R')₂, wherein the two R' are taken together with the nitrogen atom to form an optionally substituted 3-8 membered, saturated, partially unsaturated, or aryl ring having 1-4 heteroatoms independently selected from nitrogen, oxygen, or sulfur. In some embodiments, —X'R⁶ is —N(R')₂, wherein the two R' are taken together with the nitrogen atom to form an optionally substituted 3-8 membered saturated ring having 1-4 heteroatoms independently selected from nitrogen, oxygen, or sulfur. In some embodiments, —X'R⁶ is —N(R')₂, wherein the two R' are taken together with the nitrogen atom to form an optionally substituted 3-8 membered saturated ring having 1-4 nitrogen atoms. In some embodiments, —X'R⁶ is —N(R')₂, wherein the two R' are taken together with the nitrogen atom to form an optionally substituted 3-8 membered saturated ring having one nitrogen atom. In some embodiments, —X'R⁶ is —N(R')₂, wherein the two R' are taken together with the nitrogen atom to form an optionally substituted 5- or 6-membered saturated ring having one nitrogen atom. In some embodiments, —X'R⁶ is —N(R')₂, wherein the two R' are taken together with the nitrogen atom to form an optionally substituted 5-membered saturated ring having one nitrogen atom. In some embodiments, —X'R⁶ is —N(R')₂, wherein the two R' are taken together with the nitrogen atom to form an optionally substituted 6-membered saturated ring having one nitrogen atom. In some embodiments, —X'R⁶ is optionally substituted

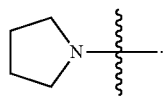

In some embodiments, —X'R⁶ is

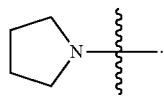

In some embodiments, —X'R⁶ is —OR⁶, wherein R⁶ is as defined above and described herein. In some embodiments, —X'R⁶ is —OR, wherein R is as defined above and described herein. In some embodiments, —X'R⁶ is —OR', wherein R' is as defined above and described herein. In some embodiments, —X'R⁶ is —OR', wherein R' is optionally substituted $C_{1-12}$ aliphatic. In some embodiments, —X'R⁶ is —OR', wherein R' is optionally substituted $C_{1-12}$ alkyl. In some embodiments, —X'R⁶ is —OR', wherein R' is optionally substituted ethyl.

As generally defined above, L is R, halogen, —OR, —N(R)₂, or —SR, wherein R is as defined above and described herein. In some embodiments, L is R, wherein R is as defined above and described herein. In some embodiments, L is hydrogen. In some embodiments, L is R', wherein R' is as defined above and described herein.

As generally defined above, each R is independently hydrogen or R', wherein R' is as defined above and described herein. In some embodiments, R is hydrogen. In some embodiments, R is R', wherein R' is as defined above and described herein.

As generally defined above, each R' is independently an optionally substituted group selected from $C_{1-12}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; or:

two R' groups on the same nitrogen atom are optionally taken together with the nitrogen atom to form an optionally substituted 3-8 membered, saturated, partially unsaturated, or aryl ring having 1-4 heteroatoms independently selected from nitrogen, oxygen, or sulfur, or two R' groups on the same carbon atom are optionally taken together with their intervening atoms to form an optionally substituted 3-8 membered saturated or partially unsaturated spirocycle ring having 0-4 heteroatoms independently selected from nitrogen, oxygen, or sulfur; or two R' groups on adjacent atoms are optionally taken together with their intervening atoms form an optionally substituted 3-8 membered, saturated, partially unsaturated, or aryl ring having 0-4 heteroatoms independently selected from nitrogen, oxygen, or sulfur.

In some embodiments, R' is an optionally substituted group selected from $C_{1-12}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur. In some embodiments, R' is an optionally substituted group selected from phenyl, an 8-10 membered bicyclic aryl ring, a 5-6 membered monocyclic heteroaryl ring having 1-4 heteroatoms independently selected from nitrogen, oxygen, or sulfur, or an 8-10 membered bicyclic heteroaryl ring having 1-5 heteroatoms independently selected from nitrogen, oxygen, or sulfur. In some embodiments, R' is an optionally substituted $C_{1-12}$ aliphatic. In some embodiments, R' is phenyl. In some embodiments, R' is an optionally substituted 3-7 membered saturated or partially unsaturated carbocyclic ring. In some embodiments, R' is an optionally substituted 8-10 membered bicyclic saturated, partially unsaturated or aryl ring. In some embodiments, R' is an optionally substituted 5-6 membered monocyclic heteroaryl ring having 1-4 heteroatoms independently selected from nitrogen, oxygen, or sulfur. In some embodiments, R' is an optionally substituted 4-7 membered saturated or partially unsaturated heterocyclic ring having 1-3 heteroatoms independently selected from nitrogen, oxygen, or sulfur. In some embodiments, R' is an optionally substituted 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur. In some embodiments, R' is an optionally substituted $C_{1-12}$ alkyl. In some embodiments, R' is methyl. In some embodiments, R' is ethyl. In some embodiments, R' is propyl. In some embodiments, R' is isopropyl. In some embodiments, R' is butyl. In some embodiments, R' is n-butyl. In some embodiments, R' is t-butyl. In some embodiments, R' is benzyl. In some embodiments, R' is phenyl. In some embodiments, R' is cyclopropyl, cyclobutyl, cyclopentyl or cyclohexyl. In some embodiments, R' is cyclohexyl. In some embodiments, R' is optionally substituted allyl. In some embodiments, R' is optionally substituted allyl, wherein the allylic carbon is optionally substituted. In some embodiments, R' is optionally substituted allyl, wherein the allylic carbon is unsubstituted. In some embodiments, R' is optionally substituted allyl, wherein the allylic carbon is substituted. In some embodiments, R' is allyl optionally substituted at C3, wherein the allylic carbon is designated as C1 (—C1-C2═C3). In some embodiments, R' allyl unsubstituted at C3, wherein the allylic carbon is designated as C1. In some embodiments, R' allyl substituted at C3, wherein the allylic carbon is designated as C1. In some embodiments, R' allyl substituted at C3, wherein the allylic carbon is designated as C1, and one substituent at C3 is optionally substituted $C_{1-9}$ aliphatic. In some embodiments, R' is optionally substituted allenyl. In some embodiments, R' is optionally substituted propargyl.

In some embodiments, two R' groups on the same nitrogen atom are optionally taken together with the nitrogen atom to form an optionally substituted 3-8 membered, saturated, partially unsaturated, or aryl ring having 1-4 heteroatoms independently selected from nitrogen, oxygen, or sulfur.

In some embodiments, two R' groups on the same carbon atom are optionally taken together with their intervening atoms to form an optionally substituted 3-8 membered saturated or partially unsaturated spirocycle ring having 0-4 heteroatoms independently selected from nitrogen, oxygen, or sulfur.

In some embodiments, two R' groups on adjacent atoms are optionally taken together with their intervening atoms form an optionally substituted 3-8 membered, saturated, partially unsaturated, or aryl ring having 0-4 heteroatoms independently selected from nitrogen, oxygen, or sulfur.

In some embodiments:
n is 0-10;
each R' is independently R, halogen, —OR, —N(R)$_2$, —SR, —NO$_2$, —SOR', —SO$_2$R', —Si(R)$_3$, or —C(O)L;
X is —O—, —NR—, —S—, or —Se—;
Z is —C(R$^2$)$_2$—NR—, —C(R$^2$)═N—, or —C(═Y)—NR—;
Y is ═O, ═S, or ═NR';
X' is —NR$^6$—;

each of R$^2$, R$^3$, R$^4$, R$^6$ and R$^6$ is independently R, —OR', —NR'$_2$, —SR', or —C(O)L; and each of L, R and R' is independently as defined above and described herein.

In some embodiments:
n is 0-10;
each R' is independently R, halogen, —OR, —N(R)$_2$, —SR, —NO$_2$, —SOR', —SO$_2$R', or —C(O)L;
X is —O—, —NR—, —S—, or —Se—;
Z is —C(R$^2$)$_2$—NR—, —C(R$^2$)═N—, or —C(═Y)—NR—;
Y is ═O, ═S, or ═NR';
X' is —NR$^6$—;
each of R$^2$, R$^3$, R$^4$, R$^6$ and R$^6$ is independently R, —OR', —NR'$_2$, —SR', or —C(O)L; and each of L, R and R' is independently as defined above and described herein.

In some embodiments, the present invention provides a compound of formula I having the structure of formula I':

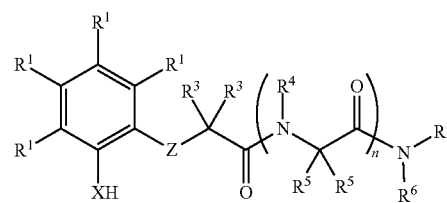

wherein:
n is 0-10;
each R$^1$ is independently R, halogen, —OR, —N(R)$_2$, —SR, —NO$_2$, —SOR', —SO$_2$R', —Si(R)$_3$, or —C(O)L;
X is —O—, —NR—, —S—, or —Se—;
Z is —C(R$^2$)$_2$—NH—, —CH═N—, or —C(═Y)—NH—;
Y is ═O, ═S, or ═NR';
each of R$^2$, R$^3$, R$^4$, R$^6$ and R$^6$ is independently R, —OR', —NR'$_2$, —SR', or —C(O)L; and
each of L, R and R' is independently as defined above and described herein. In some embodiments.

In some embodiments, the present invention provides a compound of formula I having the structure of formula I":

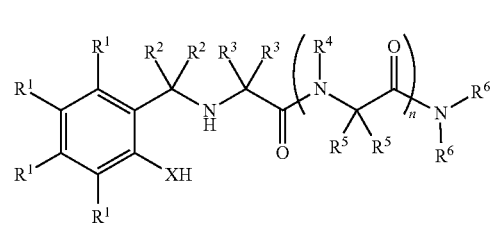

wherein:
n is 0-10;
each R$^1$ is independently R, halogen, —OR, —N(R)$_2$, —SR, —NO$_2$, —SOR', —SO$_2$R', —Si(R)$_3$, or —C(O)L;
X is —O—, —NR—, —S—, or —Se—;
each of R$^2$, R$^3$, R$^4$, R$^6$ and R$^6$ is independently R, —OR', —NR'$_2$, —SR', or —C(O)L; and
each of L, R and R' is independently as defined above and described herein.

In some embodiments, each R' is independently R, halogen, —OR, —N(R)$_2$, —SR, —NO$_2$, —SOR', —SO$_2$R', or —C(O)L; and each of R$^2$, R$^3$ and R$^6$ is independently R, —OR', —NR'$_2$, —SR', or —C(O)L; wherein each of L, R and R' is independently as defined above and described herein. In some embodiments, each R' is independently R, halogen, —OR, —N(R)₂, —SR, —NO₂, —SOR', —SO₂R', or —C(O)L, wherein each of L, R and R' is independently as defined above and described herein. In some embodiments, each of R², R³ and R⁶ is independently R, —OR', —NR'₂, —SR, or —C(O)L; wherein each of L, R and R' is independently as defined above and described herein.

In some embodiments, the present invention provides a compound of formula I having the structure of formula I-a:

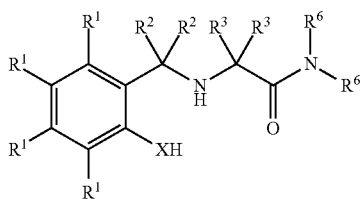

I-a wherein:
each R¹ is independently R, halogen, —OR, —N(R)₂, —SR, —NO₂, —SOR', —SO₂R', —Si(R)₃, or —C(O)L;
X is —O—, —NR—, —S—, or —Se—;
each of R², R³ and R⁶ is independently R, —OR', —NR'₂, —SR, or —C(O)L; and
each of L, R and R' is independently as defined above and described herein.

In some embodiments, the present invention provides a compound of formula I having the structure of formula I-b:

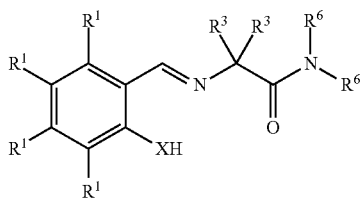

I-b wherein:
each R¹ is independently R, halogen, —OR, —N(R)₂, —SR, —NO₂, —SOR', —SO₂R', —Si(R)₃, or —C(O)L;
X is —O—, —NR—, —S—, or —Se—;
each of R³ and R⁶ is independently R, —OR', —NR'₂, —SR', or —C(O)L; and
each of L, R and R' is independently as defined above and described herein.

In some embodiments, the present invention provides a compound of formula I having the structure of formula I-c:

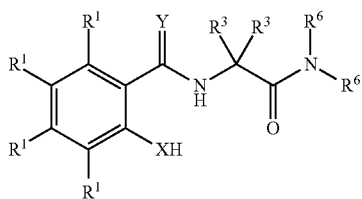

I-c wherein:
each R¹ is independently R, halogen, —OR, —N(R)₂, —SR, —NO₂, —SOR', —SO₂R', —Si(R)₃, or —C(O)L;

X is —O—, —NR—, —S—, or —Se—;
Y is =O, =S, or =NR';
each of R³ and R⁶ is independently R, —OR', —NR'₂, —SR, or —C(O)L; and
each of L, R and R' is independently as defined above and described herein.

Exemplary compounds of formula I are depicted below:

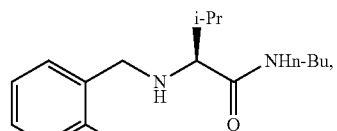

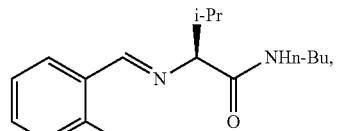

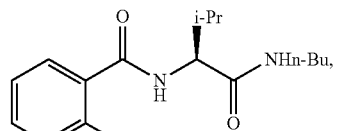

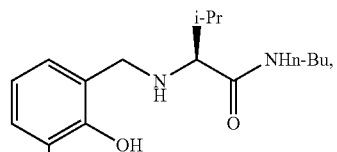

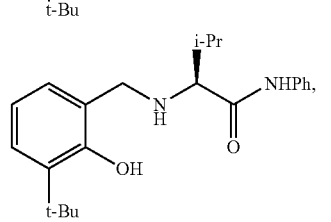

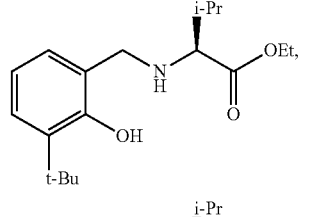

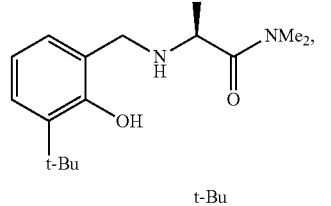

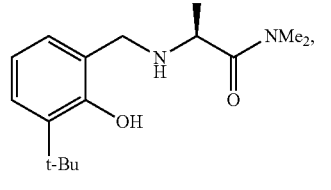

-continued

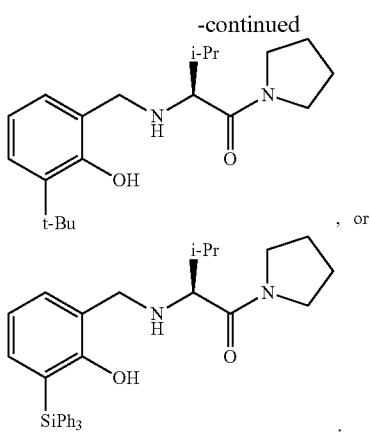, or

In some embodiments, methods of the present invention are useful in the synthesis of alcohols or amines. In some embodiments, methods of the present invention are useful in the stereoselective synthesis of alcohols or amines. In some embodiments, methods of the present invention are useful in the synthesis of homoallylic amines and alcohols. In some embodiments, methods of the present invention are useful in the stereoselective synthesis of homoallylic amines and alcohols.

In some embodiments, the present invention provides a method comprising: reacting an organoboron reagent with a compound comprising a double bond with a compound of formula I:

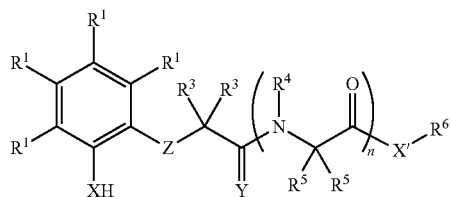

I wherein the double bond is converted into a single bond through the addition of an organic group of the organoboron reagent. In some embodiments, the present invention provides a method comprising:
reacting an organoboron reagent with a compound comprising a double bond with a compound of formula I having the structure of:

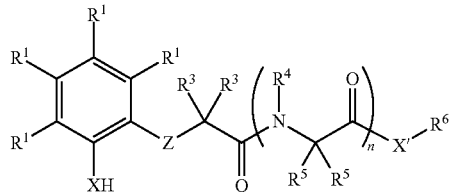

wherein the double bond is converted into a single bond through the addition of an organic group of the organoboron reagent.

In some embodiments, the double bond is a C=O double bond. In some embodiments, the double bond is a C=N double bond. In some embodiments, the double bond is a C=S double bond. In some embodiments, the double bond is a C=C double bond. An atom of the double bond can be bonded to various groups, including but not limited to halogen, a nitrogen-containing group (optionally through the nitrogen atom), a phosphorous-containing group (optionally through the phosphorous atom), chalcogen-containing group (optionally through the chalcogen atom), hydrogen, or an optionally substituted aliphatic, aryl, heteroaryl, or heterocycle group. In some embodiments, the two groups bonded to the same atom of the double bond are different, and each is independently selected from halogen, a nitrogen-containing group (optionally through the nitrogen atom), a phosphorous-containing group (optionally through the phosphorous atom), chalcogen-containing group (optionally through the chalcogen atom), hydrogen, or an optionally substituted aliphatic, aryl, heteroaryl, or heterocycle group. In some embodiments, the two groups bonded to the same atom of the double bond are different, and one group is selected from halogen, a nitrogen-containing group (optionally through the nitrogen atom), a phosphorous-containing group (optionally through the phosphorous atom), chalcogen-containing group (optionally through the chalcogen atom), hydrogen, or an optionally substituted aliphatic, aryl, heteroaryl, or heterocycle group, and the other is selected from halogen, a nitrogen-containing group (optionally through the nitrogen atom), a phosphorous-containing group (optionally through the phosphorous atom), chalcogen-containing group (optionally through the chalcogen atom), hydrogen, or an optionally substituted aliphatic, aryl, heteroaryl, or heterocycle group comprising one or more fluorine atoms. In some embodiments, one atom of the double bond is a member of a mono-, bi- or polycyclic ring system. In some embodiments, both atoms of the double bond are members of a mono-, bi- or polycyclic ring system.

In some embodiments, the double bond is a C=N double bond or C=O double bond, and the compound comprising a double bond is an imine or carbonyl compound. In some embodiments, the present invention provides a method for synthesis of an amine or alcohol, comprising reacting an organoboron reagent and an imine or carbonyl compound with a compound of formula I:

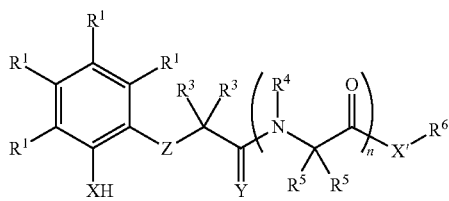

I wherein:
n is 0-10;
each $R^1$ is independently R, halogen, —OR, —N(R)$_2$, —SR, —NO$_2$, —SOR, —SO$_2$R, —Si(R)$_3$, or —C(O)L;
X is —O—, —NR—, —S—, or —Se—;
X' is —O—, —NR$^6$—, —S—, or —Se—;
Z is —C(R$^2$)$_2$—NR—, —C(R$^2$)=N—, or —C(=Y)—NR—;
Y is =O, =S, or =NR;
each of $R^2$, $R^3$, $R^4$, $R^5$ and $R^6$ is independently R, —OR, —N(R)$_2$, —SR, or —C(O)L;
L is R, halogen, —OR, —N(R)$_2$, or —SR;
each R is independently hydrogen or R'; and
each R' is independently an optionally substituted group selected from C$_{1-12}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; or two R' groups on the same nitrogen atom are optionally taken together with the nitrogen atom to form an optionally substituted 3-8 membered, saturated, partially unsaturated, or aryl ring having 1-4 heteroatoms independently selected from nitrogen, oxygen, or sulfur; or two R' groups on the same carbon atom are optionally taken together with their intervening atoms to form an optionally substituted 3-8 membered saturated or partially unsaturated spirocycle ring having 0-4 heteroatoms independently selected from nitrogen, oxygen, or sulfur, or two R' groups on adjacent atoms are optionally taken together with their intervening atoms form an optionally substituted 3-8 membered, saturated, partially unsaturated, or aryl ring having 0-4 heteroatoms independently selected from nitrogen, oxygen, or sulfur.

In some embodiments, the present invention provides a method for synthesis of an amine or alcohol, comprising reacting an organoboron reagent and an imine or carbonyl compound with a compound of formula I having the structure of:

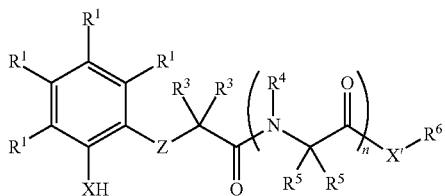

wherein each variable is independently as defined above and described herein.

In some embodiments, a provided method comprises the reaction between the organoboron reagent and the imine or carbonyl group in the imine or carbonyl compound.

In some embodiments, the product of a provided method is a substituted amine. In some embodiments, the amine is mono-, di-, or tri-substituted. In some embodiments, the amine is mono-substituted. In some embodiments, the amine is di-substituted. In some embodiments, the amine is tri-substituted. Suitable substituents are extensively described in the art and in the present application, including but not limited to optionally substituted aliphatic, carbocyclyl, aryl, heteroaryl and heterocyclyl groups and the combinations thereof. In some embodiments, each of the substituent is independently —R', wherein R' is as defined above and described herein. In some embodiments, one or more substituent is phosphinoyl. In some embodiments, one or more substituent is —PO(R$^8$)$_2$, wherein each R$^8$ is independently R'. In some embodiments, one or more substituent is —PO(R$^8$)$_2$, wherein each R$^8$ is independently optionally substituted phenyl. In some embodiments, one or more substituent is —PO(Ph)$_2$.

In some embodiments, the imine compound is a compound comprising a C=N double bond. In some embodiments, the imine compound is a compound comprising a C=N double bond, wherein the C=N double bond reacts with the organoboron reagent and is converted into a C—N single bond. In some embodiments, the imine compound is an aldimine. In some embodiments, the imine is a compound having the structure of formula III:

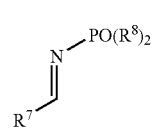

III wherein each of R$^7$ and R$^8$ is independently R', and R' is as defined above and described herein.

In some embodiments, the nitrogen atom of the imine group in the imine compound is bonded to an aromatic ring. In some embodiments, the nitrogen atom of the imine group in the imine compound is bonded to an aromatic ring, and the carbon atom of the imine group is bonded to a carbonyl group. In some embodiments, the nitrogen atom of the imine group in the imine compound is bonded to an aromatic ring, and the carbon atom of the imine group is bonded to a carbonyl group, wherein the carbonyl group is not a ketone or aldehyde group. In some embodiments, the nitrogen atom of the imine group in the imine compound is bonded to an aromatic ring, and the carbon atom of the imine group is bonded to the carbonyl carbon of an ester group. In some embodiments, the aromatic ring is optionally substituted or part of a larger moiety. In some embodiments, such an imine compound is N-substituted with an optionally substituted phenyl.

In some embodiments, the imine compound has the structure of R$^7$CH=NR$^8$, wherein each of R$^7$ and R$^8$ is independently as defined above and described herein. In some embodiments, the imine compound has the structure of R$^7$CH=NR$^8$, wherein R$^8$ is an optionally substituted group selected from phenyl, an 8-10 membered bicyclic aryl ring, a 5-6 membered monocyclic heteroaryl ring having 1-4 heteroatoms independently selected from nitrogen, oxygen, or sulfur, or an 8-10 membered bicyclic heteroaryl ring having 1-5 heteroatoms independently selected from nitrogen, oxygen, or sulfur, and R$^7$ is as defined above and described herein.

In some embodiments, R$^7$ is optionally substituted phenyl. In some embodiments, R$^7$ is phenyl. In some embodiments, R$^7$ is an optionally substituted C$_{1-12}$ aliphatic. In some embodiments, R$^7$ is an optionally substituted C$_{1-12}$ alkyl. In some embodiments, R$^7$ is an optionally substituted C$_{1-12}$ cycloalkyl. In some embodiments, R$^7$ is cyclohexyl. In some embodiments, R$^7$ is an optionally substituted 3-7 membered saturated or partially unsaturated carbocyclic ring. In some embodiments, R$^7$ is an optionally substituted 8-10 membered bicyclic saturated, partially unsaturated or aryl ring. In some embodiments, R$^7$ is an optionally substituted 5-6 membered monocyclic heteroaryl ring having 1-4 heteroatoms independently selected from nitrogen, oxygen, or sulfur. In some embodiments, R$^7$ is 2-furyl. In some embodiments, R$^7$ is an optionally substituted 4-7 membered saturated or partially unsaturated heterocyclic ring having 1-3 heteroatoms independently selected from nitrogen, oxygen, or sulfur. In some embodiments, R$^7$ is an optionally substituted 7-10 membered bicyclic saturated or partially unsaturated heterocyclic ring having 1-5 heteroatoms independently selected from nitrogen, oxygen, or sulfur. In some embodiments, $R^7$ is an optionally substituted 8-10 membered bicyclic heteroaryl ring having 1-5 heteroatoms independently selected from nitrogen, oxygen, or sulfur.

Exemplary $R^7$ groups are depicted below:

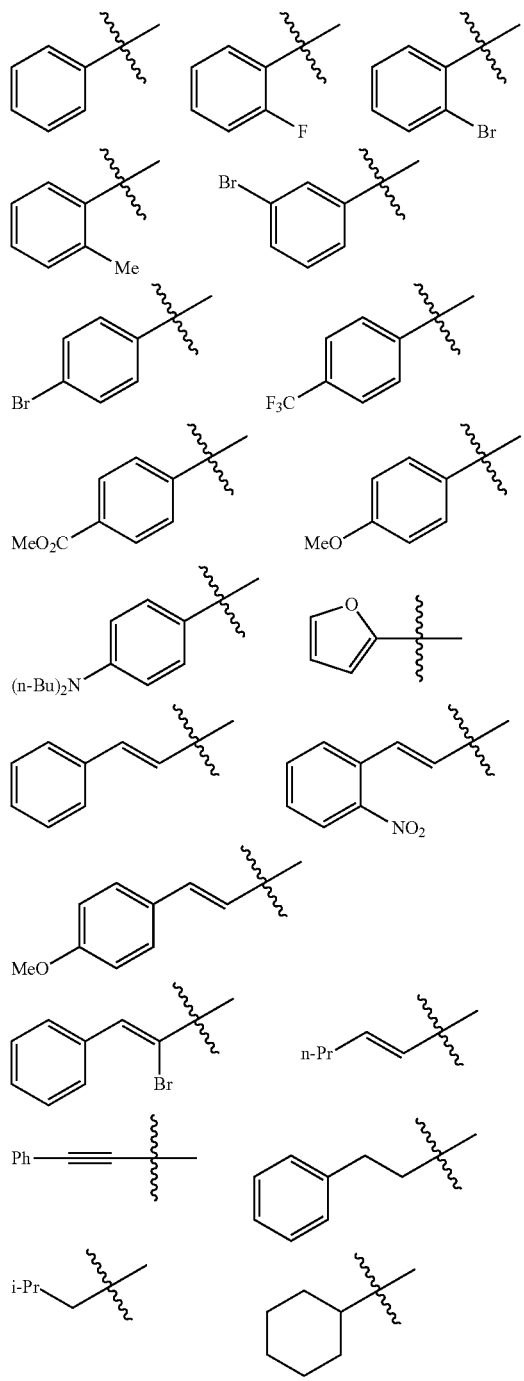

In some embodiments, $R^8$ is optionally substituted phenyl. In some embodiments, each $R^S$ is unsubstituted phenyl.

In some embodiments, the imine compound has the structure of formula IV:

$$R^9CH=NR \quad\quad IV$$

wherein $R^9$ is R or —$CO_2R$, and each of $R^S$ and R is independently as defined above and described herein. In some embodiments, $R^9$ is R' or —$CO_2R'$. In some embodiments, $R^9$ is R'. In some embodiments, $R^9$ is —$CO_2R'$. In some embodiments, $R^S$ is optionally substituted phenyl. In some embodiments, $R^9$ is —$CO_2R'$, and $R^8$ is an optionally substituted group selected from phenyl, an 8-10 membered bicyclic aryl ring, a 5-6 membered monocyclic heteroaryl ring having 1-4 heteroatoms independently selected from nitrogen, oxygen, or sulfur, or an 8-10 membered bicyclic heteroaryl ring having 1-5 heteroatoms independently selected from nitrogen, oxygen, or sulfur. In some embodiments, $R^9$ is —$CO_2R'$, and $R^8$ is optionally substituted phenyl.

Exemplary imine compounds are depicted below.

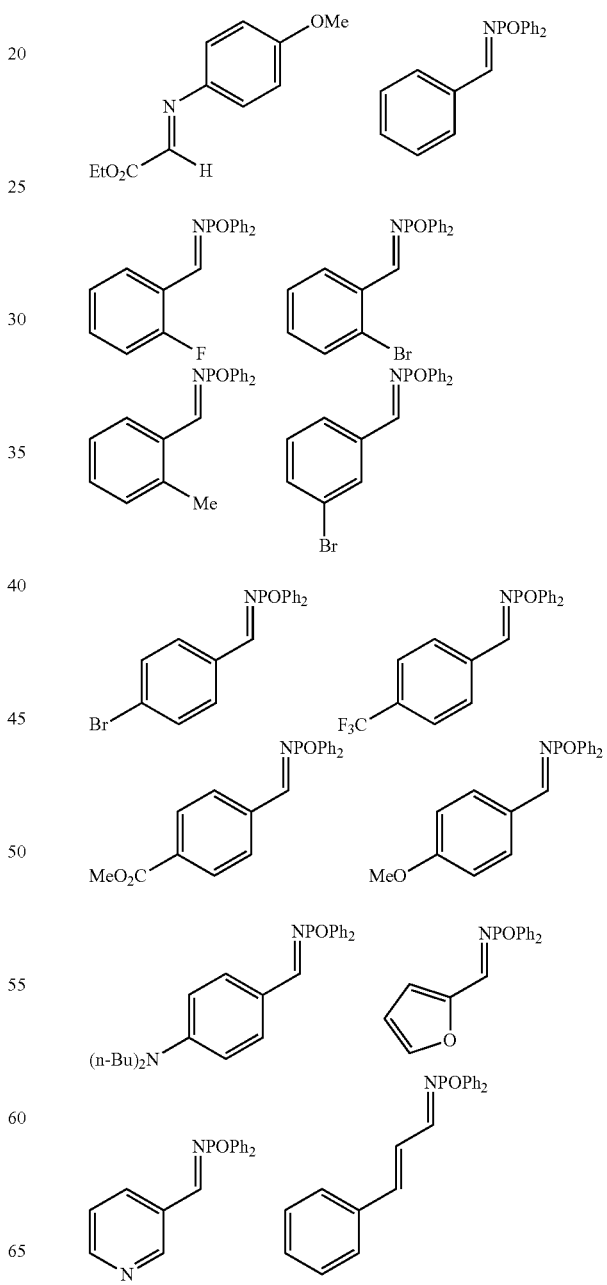

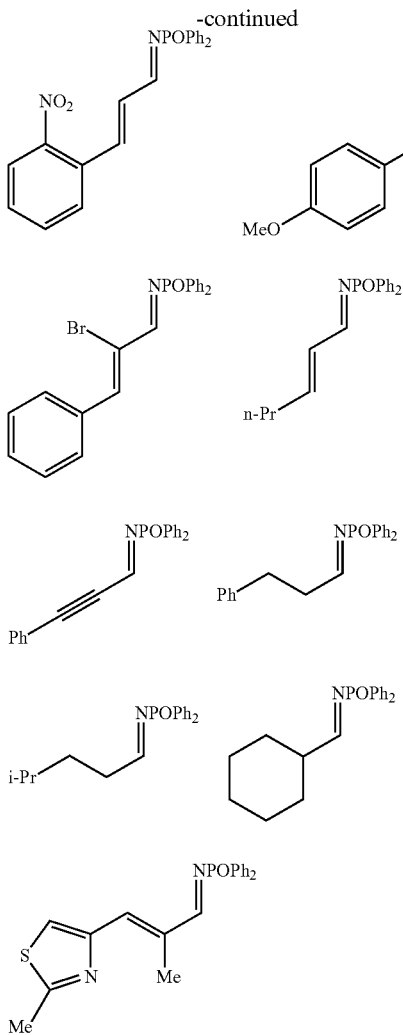

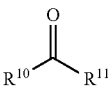

V wherein:

each of $R^{10}$ and $R^{11}$ is independently R' or —$C(R^{12})_2$R'; and
each $R^{12}$ is independently —F or R.

In some embodiments, $R^{10}$ and $R^{11}$ are different. In some embodiments, each of $R^{10}$ and $R^{11}$ is independently R'. In some embodiments, $R^{10}$ is an optionally substituted group selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur, and $R^{11}$ is optionally substituted $C_{1-12}$ aliphatic. In some embodiments, $R^{10}$ is an optionally substituted group selected from phenyl, an 8-10 membered bicyclic aryl ring, a 5-6 membered monocyclic heteroaryl ring having 1-4 heteroatoms independently selected from nitrogen, oxygen, or sulfur, or an 8-10 membered bicyclic heteroaryl ring having 1-5 heteroatoms independently selected from nitrogen, oxygen, or sulfur, and $R^{11}$ is optionally substituted $C_{1-12}$ aliphatic. In some embodiments, $R^{10}$ is an optionally substituted group selected from phenyl or an 8-10 membered bicyclic aryl ring, and $R^{11}$ is optionally substituted $C_{1-12}$ aliphatic. In some embodiments, $R^{10}$ is an optionally substituted group selected from phenyl or 10-membered bicyclic aryl ring, and $R^{11}$ is optionally substituted $C_{1-12}$ aliphatic. In some embodiments, $R^{10}$ is an optionally substituted phenyl or naphthyl, and $R^{11}$ is optionally substituted $C_{1-12}$ aliphatic. In some embodiments, $R^{10}$ is an optionally substituted phenyl or naphthyl, and $R^{11}$ is methyl. In some embodiments, at least one of $R^{10}$ and $R^{11}$ is —$C(R^{12})_2$R', wherein at least one $R^{12}$ is —F, and R' is as defined above and described herein. In some embodiments, at least one of $R^{10}$ and $R^{11}$ is R' optionally substituted with one or more —F. In some embodiments, $R^{10}$ is —$CF_3$ and $R^{11}$ is R'. In some embodiments, $R^{10}$ is —$CF_3$ and $R^{11}$ is optionally substituted phenyl. In some embodiments, $R^{10}$ is —$CF_3$ and $R^{11}$ is optionally substituted $C_{1-12}$ aliphatic. In some embodiments, $R^{10}$ is —$C(R^{12})_2$R', wherein at least one $R^{12}$ is —F, and $R^{11}$ is R'. In some embodiments, $R^{10}$ is —$C(R^{12})_2$R', wherein at least one $R^{12}$ is —F, and $R^{11}$ is optionally substituted phenyl. In some embodiments, $R^{10}$ is —$C(R^{12})_2$R', wherein at least one $R^{12}$ is —F, and $R^{11}$ is optionally substituted $C_{1-12}$ aliphatic. In some embodiments, $R^{10}$ is substituted phenyl with one or more —F, and $R^{11}$ is R'. In some embodiments, $R^{10}$ is substituted phenyl with one or more —F, and $R^{11}$ is optionally substituted $C_{1-12}$ aliphatic. In some embodiments, $R^{10}$ is substituted phenyl with one or more —F, and $R^{11}$ is unsubstituted $C_{1-12}$ aliphatic.

In some embodiments, the ketone is a cyclic ketone. In some embodiments, the ketone is an acyclic ketone.

In some embodiments, the carbonyl compound is a ketone (comprising a ketone group, a carbonyl group bonded to two carbon atoms). In some embodiments, the ketone carbonyl reacts with the organoboron reagent and the C=O double bond is converted to a C—O single bond. In some embodiments, the carbonyl compound is an asymmetric ketone, wherein the two moieties connected to the carbon atom of the C=O are not identical. In some embodiments, the carbonyl compound is an asymmetric ketone comprising one or more fluorine atoms. In some embodiments, the carbonyl compound is an asymmetric ketone comprising one or more fluorine atoms. In some embodiments, the carbonyl compound is an asymmetric ketone comprising one or more fluorine atoms at one of the α positions of the ketone group. Exemplary such ketones includes but are not limited to those having a —$CF_3$ or —$CF_2CF_3$ group bonded to the carbon atom of the ketone group. In some embodiments, the carbonyl compound is an asymmetric ketone wherein one group bonded to the carbon atom of the ketone group is an aromatic group optionally substituted with one or more fluorine atoms. In some embodiments, the carbonyl compound is an asymmetric ketone wherein one group bonded to the carbon atom of the ketone group is a phenyl group substituted with one or more —F. In some embodiments, the carbonyl compound has the structure of formula V:

Exemplary ketone compounds are depicted below.

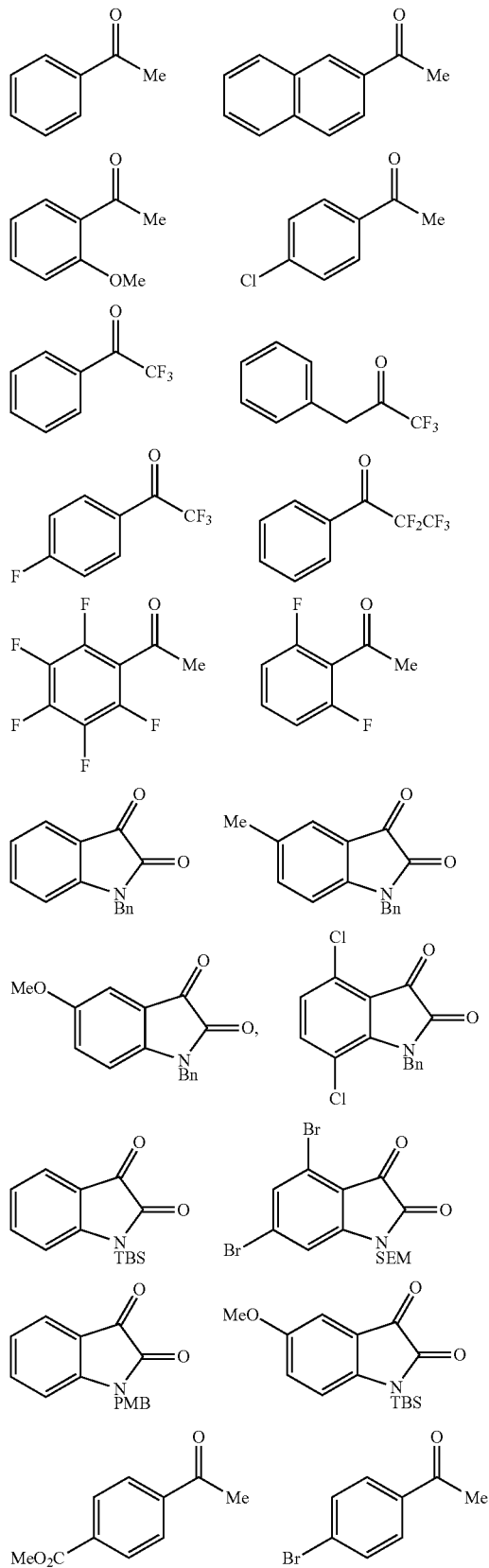

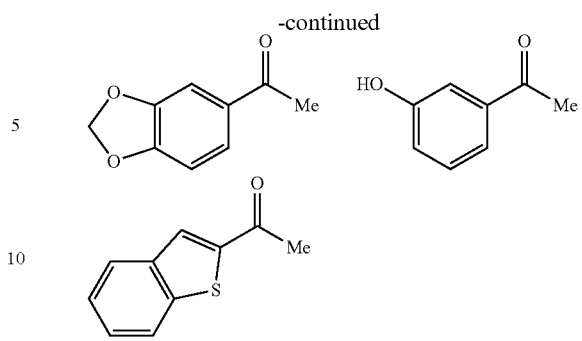

In some embodiments, the product of a provided method, e.g., an alcohol or amine, comprises a moiety:

$$C^1-C^2-C^3-C^4$$

wherein:
each of $C^1$, $C^2$, $C^3$ and $C^4$ is independently a carbon atom; $C^1$ is a carbon atom from the double bond; the chemical bond between $C^3$ and $C^4$ is a double or triple bond; and
each of the chemical bonds between $C^1$ and $C^2$ and $C^2$ and $C^3$ is independently a single or double bond.

In some embodiments, the compound comprising a double bond is an imine or carbonyl compound, and the product, i.e., the corresponding amine or alcohol, respectively, has a double or triple bond between $C^3$ and $C^4$, wherein the hydroxyl or amino group is attached to $C^1$. In some embodiments, the product of a provided method, e.g., the alcohol or amine, comprises a moiety:

$$C^1\text{-}C_2\text{-}C^3\text{-}C^4$$

wherein:
each of $C^1$, $C^2$, $C^3$ and $C^4$ is independently a carbon atom; $C^1$ is the carbon atom of the imine or carbonyl group;
the chemical bond $C^3$ and $C^4$, is a double or triple bond; and each of the chemical bonds between $C^1$ and $C^2$ and $C^2$ and $C^3$ is independently a single or double bond.

In some embodiments, the chemical bond between $C^1$ and $C^2$ is a single bond and the chemical bond between $C^2$ and $C^3$ is a single or a double bond. In some embodiments, the chemical bond between $C^1$ and $C^2$ is a single bond, the chemical bond between $C^2$ and $C^3$ is a single or a double bond, and the chemical bond between $C^3$ and $C^4$ is a double bond. Exemplary such $C^1-C^2-C^3-C^4$ moiety can be found in, for example but not limited to, a homoallylic (C—C—C=C) or homoallenyl (C—C=C=C) group. In some embodiments, the chemical bond between $C^2$ and $C^3$ is a single bond. In some embodiments, the chemical bond between $C^2$ and $C^3$ is a double bond. In some embodiments, the chemical bond between $C^1$ and $C^2$ is a single bond, the chemical bond between $C^2$ and $C^3$ is a double bond, and the chemical bond between $C^3$ and $C^4$ is a double bond. Exemplary such $C^1-C^2-C^3-C^4$ moiety can be found in, for example but not limited to, a homoallenyl group (C—C=C=C). In some embodiments, the chemical bond between $C^1$ and $C^2$ is a single bond, the chemical bond between $C^2$ and $C^3$ is a single bond, and the chemical bond between $C^3$ and $C^4$ is a triple bond. Exemplary such $C^1-C^2-C^3-C^4$ moiety can be found in, for example but not limited to, a homopropargyl group (C—C—C≡C).

In some embodiments, the product of a provided method is a homoallylic amine or alcohol. In some embodiments, the product of a provided method is a homoallylic amine. In some embodiments, the product of a provided method is a homoallylic alcohol. In some embodiments, the product of a provided method is a homoallenyl amine or alcohol. In some embodiments, the product of a provided method is a homoallenyl amine (N—C—C=C=C). In some embodiments, the product of a provided method is a homoallenyl alcohol (O—C—C=C=C). In some embodiments, the product of a provided method is a homopropargylic amine or alcohol. In some embodiments, the product of a provided method is a homopropargylic amine (N—C=C—C—C). In some embodiments, the product of a provided method is a homopropargylic alcohol (N—C—C—C=C).

Suitable organoboron reagents are extensively described in the art. In some embodiments, the organic group bonded to the boron atom is added to the double bond e.g., an imine or carbonyl group, in a provided method. In some embodiments, the organoboron reagent is unsaturated. In some embodiments, $C^1$ of the $C^1$—$C^2$—$C^3$—$C^4$ moiety in the product is from the imine or carbonyl group, and $C^2$—$C^3$—$C^4$ are from the organoboron reagent. In some embodiments, the boron atom is bond to $C^2$, and the organoboron reagent comprising the moiety of B—$C^2$—$C^3$—$C^4$, wherein:

B is boron;
each of $C^2$, $C^3$ and $C^4$ is independently a carbon atom;
the chemical bond between $C^3$ and $C^4$ is a double or triple bond; and
each of the chemical bonds between B and $C^2$ and $C^2$ and $C^3$ is independently a single or double bond.

In some embodiments, the chemical bond between B and $C^2$ is a single bond and the chemical bond between $C^2$ and $C^3$ is a single or double bond. In some embodiments, the chemical bond between B and $C^2$ is a single bond, the chemical bond between $C^2$ and $C^3$ is a single or a double bond, and the chemical bond between $C^3$ and $C^4$ is a double bond. In some embodiments, the chemical bond between $C^2$ and $C^3$ is a single bond. In some embodiments, the chemical bond between $C^2$ and $C^3$ is a double bond. In some embodiments, the chemical bond between B and $C^2$ is a single bond, the chemical bond between $C^2$ and $C^3$ is a single bond, and the chemical bond between $C^3$ and $C^4$ is a triple bond. Exemplary organoboron reagents include but not limited to allylboron (B—C—C=C), allenylboron (B—C=C=C) and propargylboron (B—C—C≡C) reagents.

The organic group bonded to boron can be added to the double bond, e.g., imine or carbonyl, through different positions. For an organoboron reagent comprising the moiety of B—$C^2$—$C^3$—$C^4$, the $C^2$—$C^3$—$C^4$ moiety can be added to the double bond, e.g., the imine or carbonyl, through each of $C^2$, $C^3$, and $C^4$. In some embodiments, the $C^2$—$C^3$—$C^4$ moiety is added through $C^2$, which is directly bonded to the boron atom (α selectivity). In some embodiments, the $C^2$—$C^3$—$C^4$ moiety is added through $C^4$, which is at the γ position relative to the boron atom (γ selectivity).

In some embodiments, the boron atom is attached to $C^4$ in the organoboron reagent, and the organoboron reagent comprising the moiety of B—$C^4$—$C^3$—$C^2$, wherein:
B is boron;
each of $C^2$, $C^3$ and $C^4$ is independently a carbon atom;
the chemical bond between $C^2$ and $C^3$ is a double or triple bond; and
each of the chemical bonds between B and $C^4$ and $C^4$ and $C^3$ is independently a single or double bond.

In some embodiments, the chemical bond between B and $C^4$ is a single bond and the chemical bond between $C^4$ and $C^3$ is a single or a double bond. In some embodiments, the chemical bond between B and $C^4$ is a single bond, the chemical bond between $C^4$ and $C^3$ is a single or a double bond, and the chemical bond between $C^3$ and $C^2$ is a double bond. In some embodiments, the chemical bond between $C^4$ and $C^3$ is a single bond. In some embodiments, the chemical bond between $C^4$ and $C^3$ is a double bond. In some embodiments, the chemical bond between B and $C^4$ is a single bond, the chemical bond between $C^4$ and $C^3$ is a single bond, and the chemical bond between $C^3$ and $C^2$ is a triple bond. Exemplary organoboron reagents include but not limited to allylboron (B—C—C=C), allenylboron (B—C=C=C) and propargylboron (B—C—C≡C) reagents.

In some embodiments, an organoboron reagent has the structure of:

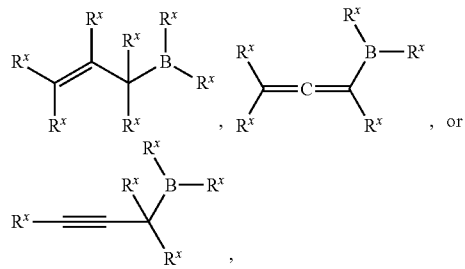

wherein each $R^x$ is independently an aryl, alkyl, alkynyl, alkenyl, heteroaryl, halogen, a nitrogen-containing group, a phosphorus-containing group, a chalcogen-containing group or hydrogen. In some embodiments, each $R^x$ is independently R, halogen, —N(R)$_2$, —N(R)N(R)C(O)R; —N(R)N(R)C(O)NR$_2$; —N(R)N(R)C(O)OR, —P(O)$_2$R; —P(O)(R)$_2$; —P(O)(OR)R; —P(O)(OR)$_2$; —OP(O)(R)$_2$; —OP(O)(OR)R; —OP(O)(OR)$_2$; —P(R)$_2$; —P(OR)R; —P(OR)$_2$; —OP(R)$_2$; —OP(OR)R; —OP(OR)$_2$, —OR, —SR, —S(O)$_2$R, —S(O)$_2$OR, —OS(O)$_2$OR, —S(O)$_2$N(R)$_2$, —S(O)R, —NRS(O)$_2$NR$_2$, —N(R)S(O)$_2$R, —SeR, —Se(O)$_2$R, —Se(O)$_2$OR, —OSe(O)$_2$OR, —Se(O)$_2$N(R)$_2$, —Se(O)R, —NRSe(O)$_2$NR$_2$, —N(R)Se(O)$_2$R, —TeR, or any suitable monovalent substituents described above, or:

two $R^x$ are taken together with their intervening atoms to form an optionally substituted 3-12 membered, saturated, partially unsaturated, or aryl ring having 0-6 heteroatoms independently selected from boron, nitrogen, oxygen, phosphorus, or sulfur;

wherein each R is independently as defined above and described herein.

In some embodiments, an organoboron reagent has the structure of B($R^3$)$_2$R, wherein:
each $R^{13}$ is independently R, —N(R)$_2$, or —OR, or
two $R^{13}$ are taken together with the boron atom to form an optionally substituted 3-12 membered, saturated or partially unsaturated, mono-, bi- or polycyclic ring having 0-4 heteroatoms independently selected from nitrogen, oxygen or sulfur in addition to the boron atom; and
each R is independently as defined above and described herein.

In some embodiments, the two $R^{13}$ groups are taken together with the boron atom to form an optionally substituted 5-membered ring having the structure of

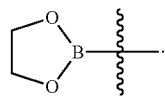

In some embodiments, the two $R^{13}$ groups are taken together with the boron atom to form a 5-membered ring having the structure of

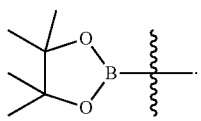

In some embodiments, $R^{13}$ is —OR, wherein R is as defined above and described herein. In some embodiments, $R^{13}$ is —OR', wherein R' is as defined above and described herein. In some embodiments, each of $R^{13}$ is —O-i-Pr. In some embodiments, $R^{13}$ is —N(R)$_2$. In some embodiments, $R^{13}$ is —N(R')$_2$.

In some embodiments, an organoboron reagent has the structure of B($R^{13}$)$_2$R, wherein R is R', and each of $R^{13}$ and R' is independently as defined above and described herein. In some embodiments, an organoboron reagent has the structure of B($R^{13}$)$_2$R, wherein R is an optionally substituted allyl, allenyl or propargyl group, and $R^{13}$ is as defined above and described herein. In some embodiments, R' is optionally substituted allyl, wherein the allylic carbon is unsubstituted. In some embodiments, R' is optionally substituted allyl, wherein the allylic carbon is substituted. In some embodiments, R' is allyl optionally substituted at C3, wherein the allylic carbon is designated as C1 (—C—C2═C3). In some embodiments, R' allyl unsubstituted at C3, wherein the allylic carbon is designated as C1. In some embodiments, R' allyl substituted at C3, wherein the allylic carbon is designated as C1. In some embodiments, R' allyl substituted at C3, wherein the allylic carbon is designated as C1, and one substituent at C3 is optionally substituted $C_{1-9}$ aliphatic. In some embodiments, R' is optionally substituted allenyl. In some embodiments, R' is optionally substituted propargyl. In some embodiments, an organoboron reagent is optionally substituted B($R^{13}$)$_2$(CH$_2$—CH═CH$_2$), B($R^{13}$)$_2$(CH═C═CH$_2$), or B($R^3$)$_2$(CH$_2$—C≡CH), wherein each $R^{13}$ is independently as defined above and described herein. In some embodiments, an organoboron reagent is B($R^{13}$)$_2$(CH$_2$—C≡CSiMe$_3$). In some embodiments, an organoboron reagent is

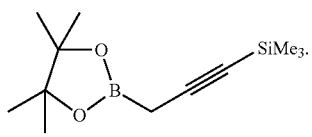 [SMILES: CC1(C)OB(CC#C[Si](C)(C)C)OC1(C)C]

In some embodiments, an organoboron reagent has the structure of B($R^{13}$)$_2$(C(R)$_2$—CR═C(R)$_2$), B($R^{13}$)$_2$(CR═C═C(R)$_2$), or B($R^{13}$)$_2$(C(R)$_2$—C≡CR), wherein:
each $R^{13}$ is independently R or —OR, or
two $R^{13}$ are taken together with the boron atom to form an optionally substituted 3-12 membered, saturated or partially unsaturated, mono-, bi- or polycyclic ring, in addition to the boron atom, having 0-4 heteroatoms independently selected from nitrogen, oxygen or sulfur; and
each R is independently as defined above and described herein. In some embodiments, an organoboron reagent has the structure of

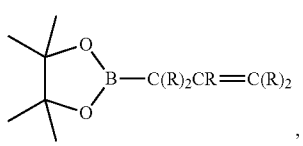

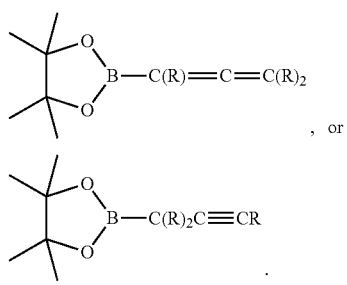

, or

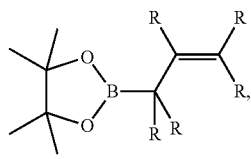

In some embodiments, the R groups within an organoboron reagent are the same. In some embodiments, the R groups within an organoboron reagent are different. In some embodiments, the two R groups at the allylic or propargyl position are the same. In some embodiments, the two R groups at the allylic or propargyl position are different. In some embodiments, one of the two R groups at the allylic or propargyl position is hydrogen, and the other is R'. In some embodiments, both of the R groups at the allylic or propargyl position are R'.

In some embodiments, the two allylic R group of B(OR)$_2$ (C(R)$_2$—CR═C(R)$_2$) are the same. In some embodiments, the two allylic R group of B(OR)$_2$(C(R)$_2$—CR═C(R)$_2$) are different.

In some embodiments, the allylboron reagent in the provided method is

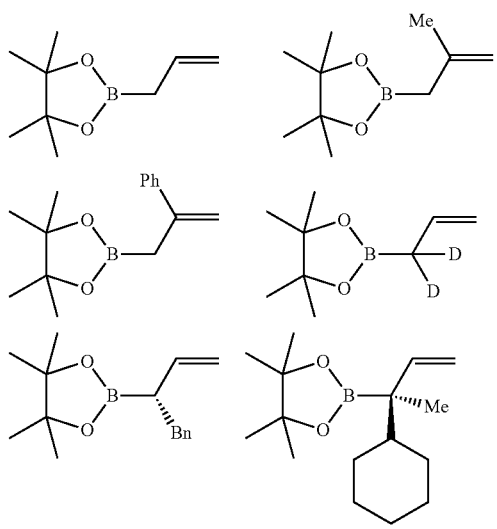

herein each R is independently as defined above and described herein.

Exemplary reagents are depicted below:

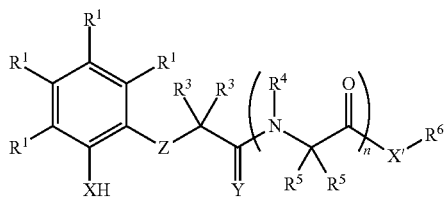

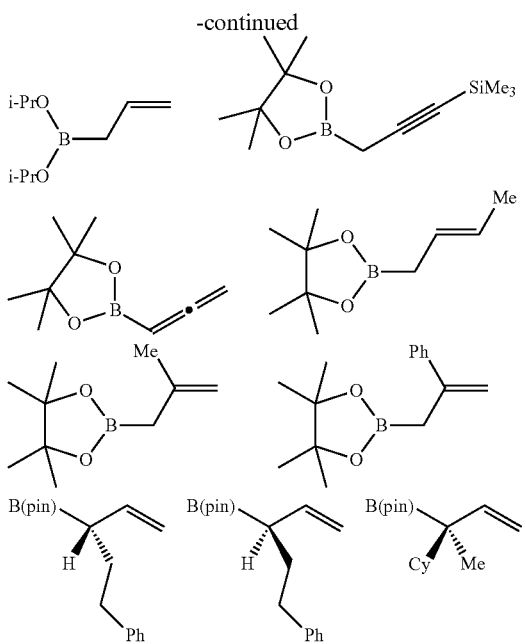

In some embodiments, the present invention provides a method for synthesis of a homoallylic, homoallenyl or homopropargyl amine or alcohol, comprising reacting an allylboron reagents and an amine or carbonyl compound with a compound of formula I:

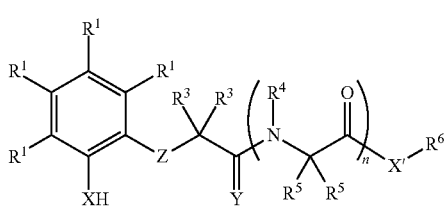

wherein each variable is independently as defined above and described herein. In some embodiments, the present invention provides a method for synthesis of a homoallylic, homoallenyl or homopropargyl amine or alcohol, comprising reacting an allylboron reagents and an amine or carbonyl compound with a compound having the structure of:

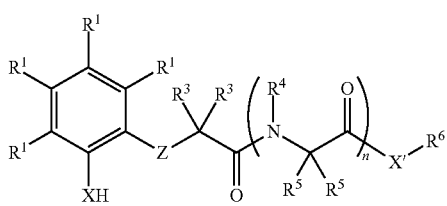

wherein each variable is independently as defined above and described herein.

In some embodiments, the present invention provides a method for synthesis of a homoallylic amine or alcohol comprising reacting an allylboron reagent and an imine or carbonyl compound with a compound of formula I:

I wherein:

n is 0-10;

each $R^1$ is independently R, halogen, —OR, —N(R)$_2$, —SR, —NO$_2$, —SOR, —SO$_2$R, —Si(R)$_3$, or —C(O)L;

X is —O—, —NR—, —S—, or —Se—;

X' is —O—, —NR$^6$—, —S—, or —Se—;

Z is —C(R$^2$)$_2$—NR—, —C(R$^2$)=N—, or —C(=Y)—NR—;

Y is =O, =S, or =NR;

each of $R^2$, $R^3$, $R^4$, $R^5$ and $R^6$ is independently R, —OR, —N(R)$_2$, —SR, or —C(O)L;

L is R, halogen, —OR, —N(R)$_2$, or —SR;

each R is independently hydrogen or R'; and each R' is independently an optionally substituted group selected from $C_{1-12}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; or two R' groups on the same nitrogen atom are optionally taken together with the nitrogen atom to form an optionally substituted 3-8 membered, saturated, partially unsaturated, or aryl ring having 1-4 heteroatoms independently selected from nitrogen, oxygen, or sulfur; or two R' groups on the same carbon atom are optionally taken together with their intervening atoms to form an optionally substituted 3-8 membered saturated or partially unsaturated spirocycle ring having 0-4 heteroatoms independently selected from nitrogen, oxygen, or sulfur, or two R' groups on adjacent atoms are optionally taken together with their intervening atoms form an optionally substituted 3-8 membered, saturated, partially unsaturated, or aryl ring having 0-4 heteroatoms independently selected from nitrogen, oxygen, or sulfur.

In some embodiments, the present invention provides a method for synthesis of a homoallylic amine or alcohol comprising reacting an allylboron reagent and an imine or carbonyl compound with a compound of formula I having the structure of:

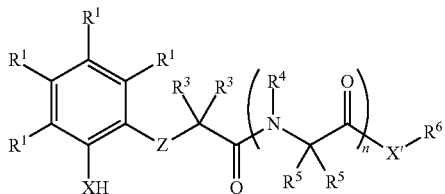

wherein each variable is independently as defined above and described herein.

In some embodiments, the present invention provides a method for synthesis of a homoallylic, homoallenyl or homopropargyl amine comprising reacting an imine and an organoboron reagent with a compound of formula I:

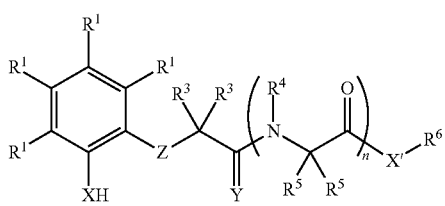

I wherein each variable is independently as defined above and described herein. In some embodiments, the present invention provides a method for synthesis of a homoallylic, homoallenyl or homopropargyl amine comprising reacting an imine and an organoboron reagent with a compound of formula I having the structure of:

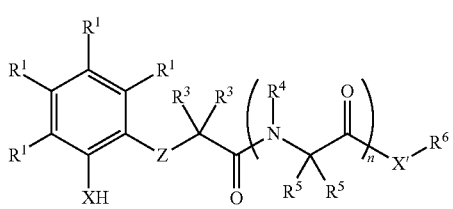

I wherein each variable is independently as defined above and described herein. In some embodiments, the present invention provides a method for synthesis of a homopropargyl amine, comprising reacting an imine and a propargylboron reagent with a compound of formula I. In some embodiments, the present invention provides a method for synthesis of a homoallenyl amine, comprising reacting an imine and an allenylboron reagent with a compound of formula I.

In some embodiments, the present invention provides a method for synthesis of a homoallylic amine comprising reacting an imine and an allylboron reagent with a compound of formula I:

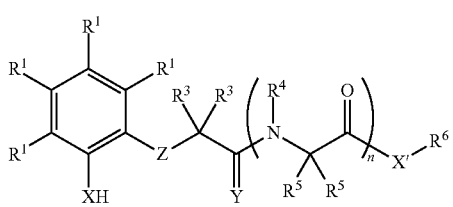

I wherein each variable is independently as defined above and described herein. In some embodiments, the present invention provides a method for synthesis of a homoallylic amine comprising reacting an imine and an allylboron reagent with a compound of formula I having the structure of:

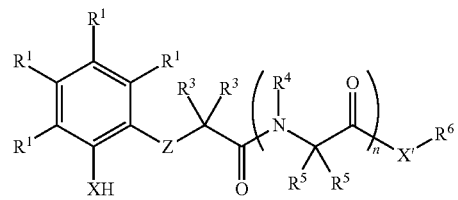

I wherein each variable is independently as defined above and described herein.

In some embodiments, the present invention provides a method for synthesis of a homoallylic alcohol comprising reacting a carbonyl compound and an allylboron reagent with a compound of formula I:

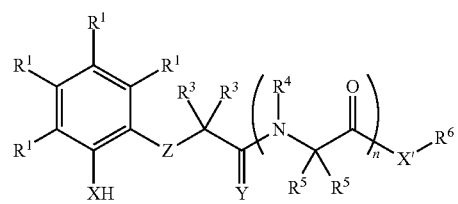

I wherein each variable is independently as defined above and described herein. In some embodiments, the present invention provides a method for synthesis of a homoallylic alcohol comprising reacting a carbonyl compound and an allylboron reagent with a compound of formula I having the structure of:

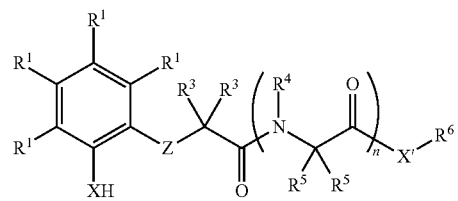

I wherein each variable is independently as defined above and described herein. In some embodiments, the present invention provides a method for synthesis of a homoallenyl alcohol, comprising reacting a carbonyl compound and an allenylboron reagent with a compound of formula I. In some embodiments, the present invention provides a method for synthesis of a homopropargyl alcohol, comprising reacting a carbonyl compound and a propargylboron reagent with a compound of formula I.

In some embodiments, the present invention provides a method for synthesis of a homoallylic alcohol comprising reacting a ketone and an allylboron reagent with a compound of formula I:

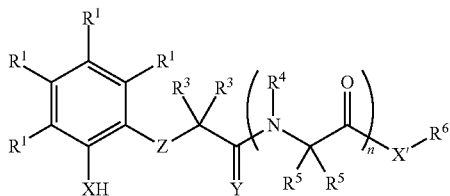

wherein each variable is independently as defined above and described herein. In some embodiments, the present invention provides a method for synthesis of a homoallylic alcohol comprising reacting a ketone and an allylboron reagent with a compound of formula I having the structure of:

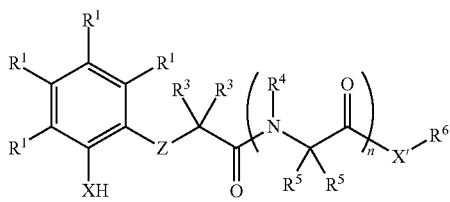

wherein each variable is independently as defined above and described herein. In some embodiments, the present invention provides a method for synthesis of a homoallenyl alcohol, comprising reacting a ketone and an allenylboron reagent with a compound of formula I. In some embodiments, the present invention provides a method for synthesis of a homopropargyl alcohol, comprising reacting a ketone and a propargylboron reagent with a compound of formula I. In some embodiments, the ketone in a provided method is an asymmetric ketone.

In some embodiments, the present invention provides a method for synthesis of a homoallylic alcohol comprising reacting an aldehyde and an allylboron reagent with a compound of formula I:

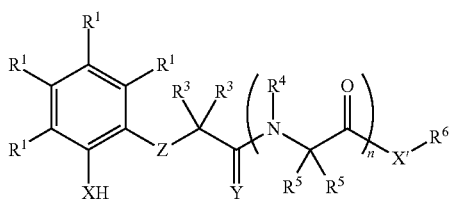

wherein each variable is independently as defined above and described herein. In some embodiments, the present invention provides a method for synthesis of a homoallylic alcohol comprising reacting an aldehyde and an allylboron reagent with a compound of formula I having the structure of:

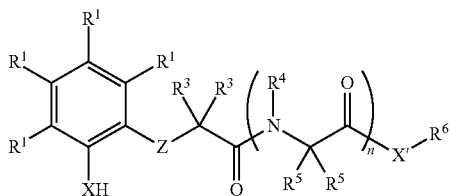

wherein each variable is independently as defined above and described herein. In some embodiments, the present invention provides a method for synthesis of a homoallenyl alcohol, comprising reacting an aldehyde and an allenylboron reagent with a compound of formula I. In some embodiments, the present invention provides a method for synthesis of a homopropargyl alcohol, comprising reacting an aldehyde and a propargylboron reagent with a compound of formula I.

In some embodiments, the present invention provides a method for synthesis of a homoallylic alcohol comprising reacting an optionally substituted isatin and an allylboron reagent with a compound of formula I:

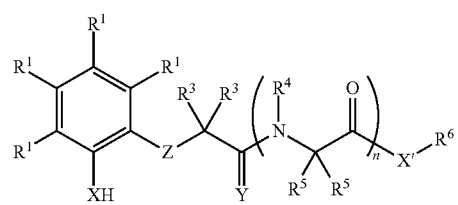

wherein each variable is independently as defined above and described herein. In some embodiments, the present invention provides a method for synthesis of a homoallylic alcohol comprising reacting an optionally substituted isatin and an allylboron reagent with a compound of formula I having the structure of:

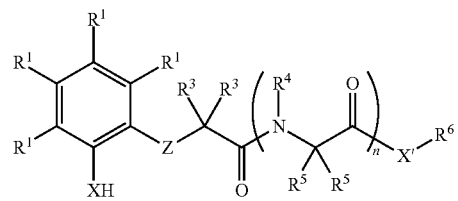

wherein each variable is independently as defined above and described herein. In some embodiments, the present invention provides a method for synthesis of a homoallenyl alcohol, comprising reacting an isatin and an allenylboron reagent with a compound of formula I. In some embodiments, the present invention provides a method for synthesis of a homopropargyl alcohol, comprising reacting an isatin and a propargylboron reagent with a compound of formula I. In some embodiments, the phenyl ring of the isatin in a provided method is optionally substituted.

In some embodiments, the present invention provides a method for synthesis of a homoallylic alcohol comprising reacting an optionally substituted isatin and an allylboron reagent with a compound of formula I:

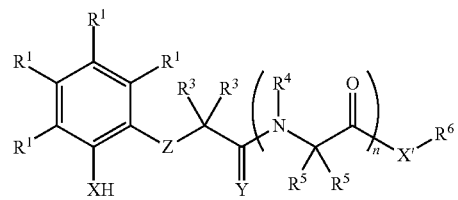

wherein each variable of formula I is independently as defined above and described herein, and wherein the phenyl ring of the isatin is optionally substituted. In some embodiments, the present invention provides a method for synthesis of a homoallylic alcohol comprising reacting an optionally substituted isatin and an allylboron reagent with a compound of formula I having the structure of:

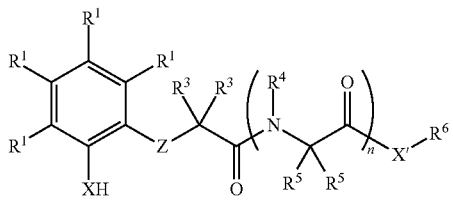

wherein each variable is independently as defined above and described herein, and wherein the phenyl ring of the isatin is optionally substituted.

Exemplary isatins are depicted below.

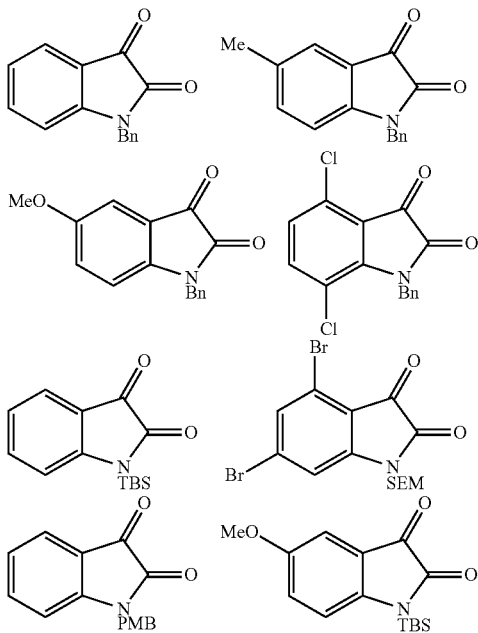

In some embodiments, the provided method comprises using a compound of formula I having the structure of formula I':

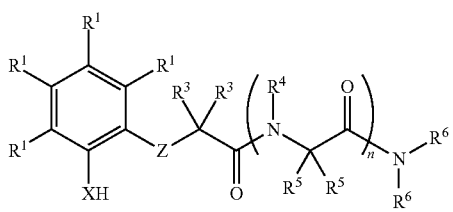

I' wherein:
n is 0-10;
each R' is independently R, halogen, —OR, —N(R)$_2$, —SR, —NO$_2$, —SOR', —SO$_2$R', —Si(R)$_3$, or —C(O)L;

X is —O—, —NR—, —S—, or —Se—;
Z is —C(R$^2$)—NH—, —CH=N—, or —C(=Y)—NH—;
Y is =O, =S, or =NR';
each of R$^2$, R$^3$, R$^4$, R$^6$ and R$^6$ is independently R, —OR', —NR'$_2$, —SR, or —C(O)L; and
each of L, R and R' is independently as defined above and described herein.

In some embodiments, the provided method comprises using a compound of formula I having the structure of formula I-a:

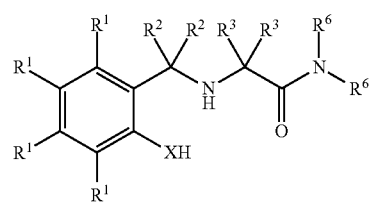

I-a wherein each of R$^1$, R$^2$, R$^3$, R$^6$ and X is independently as defined above and described herein.

In some embodiments, the provided method comprises using a compound of formula I having the structure of formula I-b:

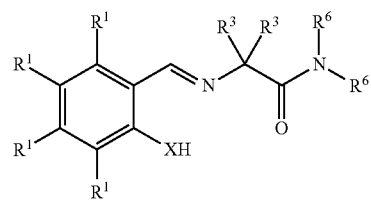

I-b wherein each of R$^1$, R$^3$, R$^6$ and X is independently as defined above and described herein.

In some embodiments, the provided method comprises using a compound of formula I having the structure of formula I-c:

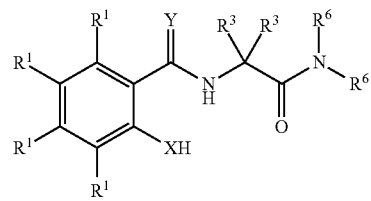

I-c wherein each of R$^1$, R$^3$, R$^6$, X and Y is independently as defined above and described herein.

In some embodiments, the present invention provides a method for synthesis of a homoallylic amine or alcohol comprising reacting an allylboron reagent and an imine or carbonyl compound with a compound of formula I:

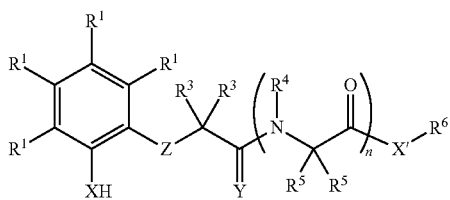

wherein the imine is of formula III:

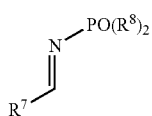

wherein each R⁷ and R⁸ is independently R', and each of $R^1$, X, Z, $R^3$, $R^4$, $R^5$, n, X', $R^6$ and R' is independently as defined above and described herein. In some embodiments, the present invention provides a method for synthesis of a homoallenyl amine, comprising reacting an imine and an allenylboron reagent with a compound of formula I, wherein the imine has the structure of formula III. In some embodiments, the present invention provides a method for synthesis of a homopropargyl amine, comprising reacting an imine and an propargylboron reagent with a compound of formula I, wherein the imine has the structure of formula III. In some embodiments, a compound of formula I has the structure of:

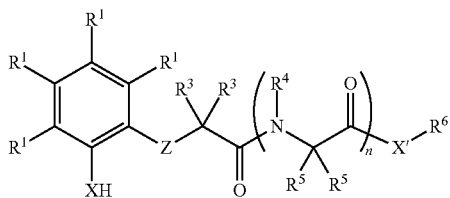

wherein each variable is independently as defined above and described herein.

In some embodiments, $R^7$ is optionally substituted phenyl. In some embodiments, $R^7$ is phenyl. In some embodiments, $R^7$ is an optionally substituted $C_{1-12}$ aliphatic. In some embodiments, $R^7$ is an optionally substituted $C_{1-12}$ alkyl. In some embodiments, $R^7$ is an optionally substituted $C_{1-12}$ cycloalkyl. In some embodiments, $R^7$ is cyclohexyl. In some embodiments, $R^7$ is an optionally substituted 3-7 membered saturated or partially unsaturated carbocyclic ring. In some embodiments, $R^7$ is an optionally substituted 8-10 membered bicyclic saturated, partially unsaturated or aryl ring. In some embodiments, $R^7$ is an optionally substituted 5-6 membered monocyclic heteroaryl ring having 1-4 heteroatoms independently selected from nitrogen, oxygen, or sulfur. In some embodiments, $R^7$ is 2-furyl. In some embodiments, $R^7$ is an optionally substituted 4-7 membered saturated or partially unsaturated heterocyclic ring having 1-3 heteroatoms independently selected from nitrogen, oxygen, or sulfur. In some embodiments, $R^7$ is an optionally substituted 7-10 membered bicyclic saturated or partially unsaturated heterocyclic ring having 1-5 heteroatoms independently selected from nitrogen, oxygen, or sulfur. In some embodiments, $R^7$ is an optionally substituted 8-10 membered bicyclic heteroaryl ring having 1-5 heteroatoms independently selected from nitrogen, oxygen, or sulfur.

Exemplary $R^7$ groups are depicted below:

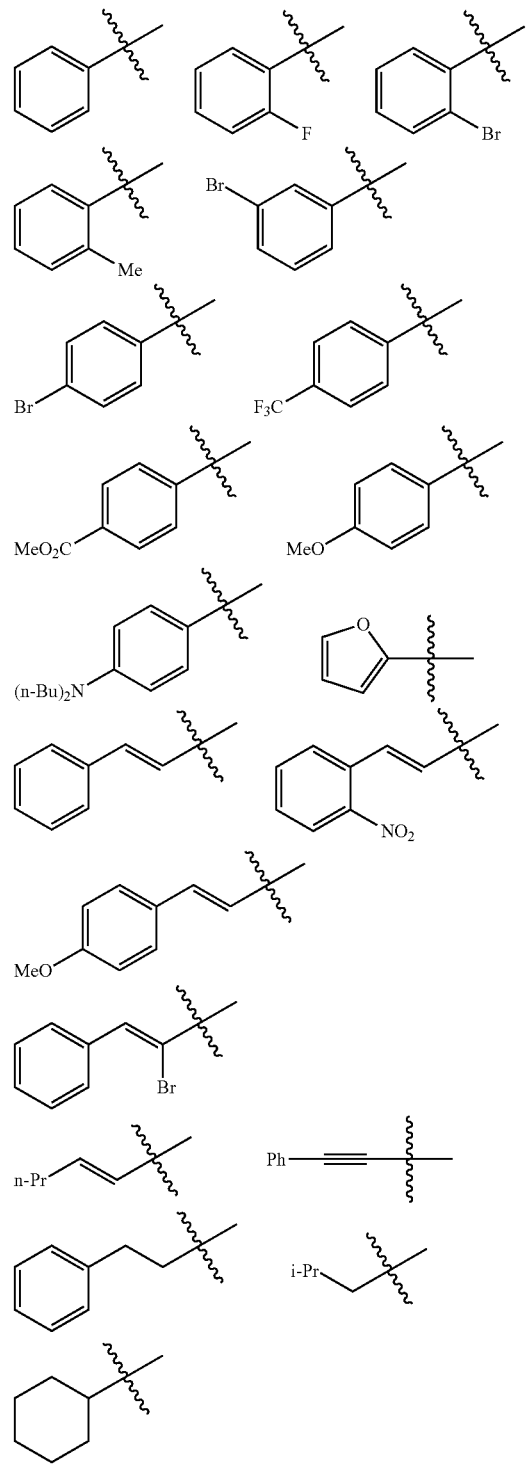

In some embodiments, $R^8$ is optionally substituted phenyl. In some embodiments, each $R^8$ is unsubstituted phenyl.

In some embodiments, the present invention provides a method for synthesis of a homoallylic amine or alcohol comprising reacting an allylboron reagent and an imine or carbonyl compound with a compound of formula I:

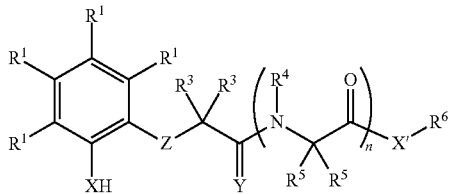

wherein the allylboron reagent has the formula of B(ORh(C(R)$_2$—CR=C(R)$_2$) or B(R$^{13}$)$_2$(C(R)$_2$—CR=C(R)$_2$), and wherein each of R$^1$, X, Z, R$^3$, R$^4$, R$^5$, n, X', R$^6$ and R' is independently as defined above and described herein. In some embodiments, the present invention provides a method for synthesis of a homoallylic amine or alcohol comprising reacting an allylboron reagent and an imine or carbonyl compound with a compound of formula I having the structure of:

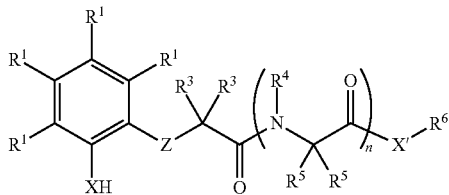

wherein the allylboron reagent has the formula of B(OR)$_2$(C(R)$_2$—CR=C(R)$_2$) or B(R$^{13}$)$_2$(C(R)$_2$—CR=C(R)$_2$), and wherein each of R$^1$, X, Z, R$^3$, R$^4$, R$^5$, n, X', R$^6$ and R' is independently as defined above and described herein.

In some embodiments, the present invention provides a method for synthesis of a homoallylic amine or alcohol comprising reacting an allylboron reagent and an imine or carbonyl compound with a compound of formula I:

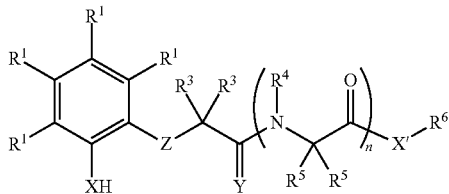

wherein the allylboron reagent is B(OR)$_2$(C(R)$_2$—CR=C(R)$_2$), and wherein each of R$^1$, X, Z, R$^3$, R$^4$, R$^5$, n, X', R$^6$ and R' is independently as defined above and described herein. In some embodiments, the present invention provides a method for synthesis of a homoallylic amine or alcohol comprising reacting an allylboron reagent and an imine or carbonyl compound with a compound of formula I having the structure of:

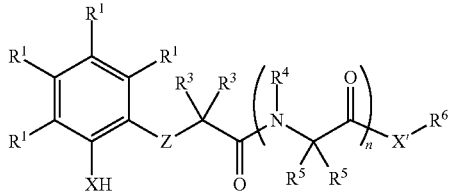

wherein the allylboron reagent is B(ORh(C(R)$_2$—CR=C(R)$_2$), and wherein each of R$^1$, X, Z, R$^3$, R$^4$, R$^5$, n, X', R$^6$ and R' is independently as defined above and described herein.

In some embodiments, the two allylic R group of B(OR)$_2$(C(R)$_2$—CR=C(R)$_2$) are the same. In some embodiments, the two allylic R group of B(OR)$_2$(C(R)$_2$—CR=C(R)$_2$) are different.

In some embodiments, the allylboron reagent in the provided method is

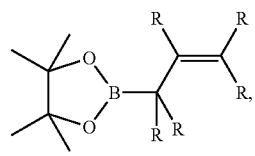

wherein each R is independently as defined above and described herein.

Exemplary allylboron reagents are depicted below:

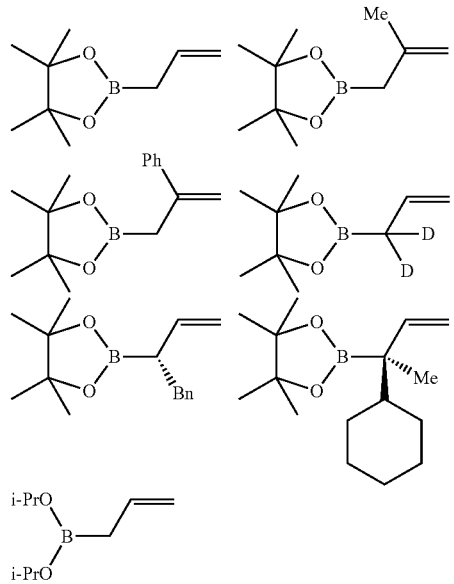

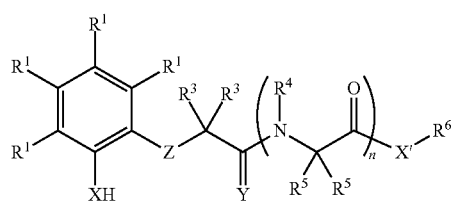

In some embodiments, a provided method further comprises the use of a base and/or an alcohol. In some embodiments, a provided method further comprises the use of a base and an alcohol. In some embodiments, the present invention provides a method for synthesis of an amine or alcohol comprising reacting an allylboron reagent with an imine or carbonyl compound with a base, an alcohol, and a compound of formula I:

I wherein each variable is independently as defined above and described herein. In some embodiments, the present invention provides a method for synthesis of a homoallylic, homoallenyl, or homopropargyl amine or alcohol comprising reacting an allylboron reagent with an imine or carbonyl compound with a base, an alcohol, and a compound of formula I:

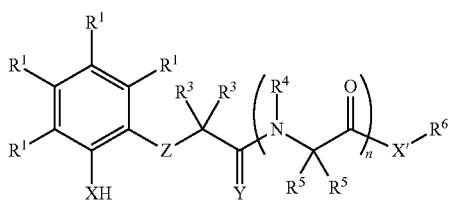

wherein each variable is independently as defined above and described herein. In some embodiments, the present invention provides a method for synthesis of a homoallylic amine or alcohol comprising reacting an allylboron reagent with an imine or carbonyl compound with a base, an alcohol, and a compound of formula I:

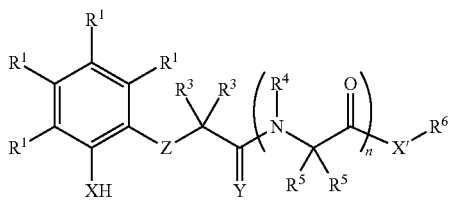

wherein each variable is independently as defined above and described herein. In some embodiments, the compound of formula I has the structure of:

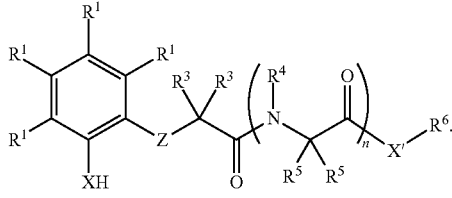

In some embodiments, a base used in a provide method is a metal hydroxide or alkoxide. In some embodiments, a base has the formula of $M(OR)_m$, wherein M is a metal, m is 1-6, and each R is independently as defined above and described herein. It is understood by a person of ordinary skill in the art that, in some embodiments, m equals the number of the positive charges the metal ion bears. In some embodiments, m is 1. In some embodiments, m is 2. In some embodiments, R is H. In some embodiments, R is R', wherein R' is as defined above and described herein. In some embodiments, R is optionally substituted $C_{1-12}$ aliphatic. In some embodiments, R is methyl. In some embodiments, M is t-butyl. In some embodiments, M is an alkali metal. In some embodiments, M is Na. In some embodiments, M is Zn. In some embodiments, the base in the provided method is metal hydroxide. In some embodiments, the base in the provided method is alkali hydroxide. In some embodiments, the base in the provided method is NaOH. In some embodiments, the base in the provided method is metal alkoxide. In some embodiments, the base in the provided method is metal t-butyloxide. In some embodiments, the base in the provided method is NaOt-Bu. In some embodiments, the base in the provided method is Zn(Ot-Bu)$_2$. In some embodiments, the base is Zn(OMe)$_2$. In some embodiments, a base is an amine, for example, 1,8-diazabicycloundec-7-ene, dbu. In some embodiments, a base is an organic base. In some embodiments, a base is an organic amine.

In some embodiment, the alcohol used in a provided method has the structure of ROH, wherein R is as defined above and described herein. In some embodiment, the alcohol used in a provided method has the structure of R'OH, wherein R' is as defined above and described herein. In some embodiment, the alcohol used in a provided method is a linear or branched $C_{1-6}$ alkyl alcohol. In some embodiment, the alcohol used in the provided method is methanol.

Exemplary transformations in the provided methods are depicted below:

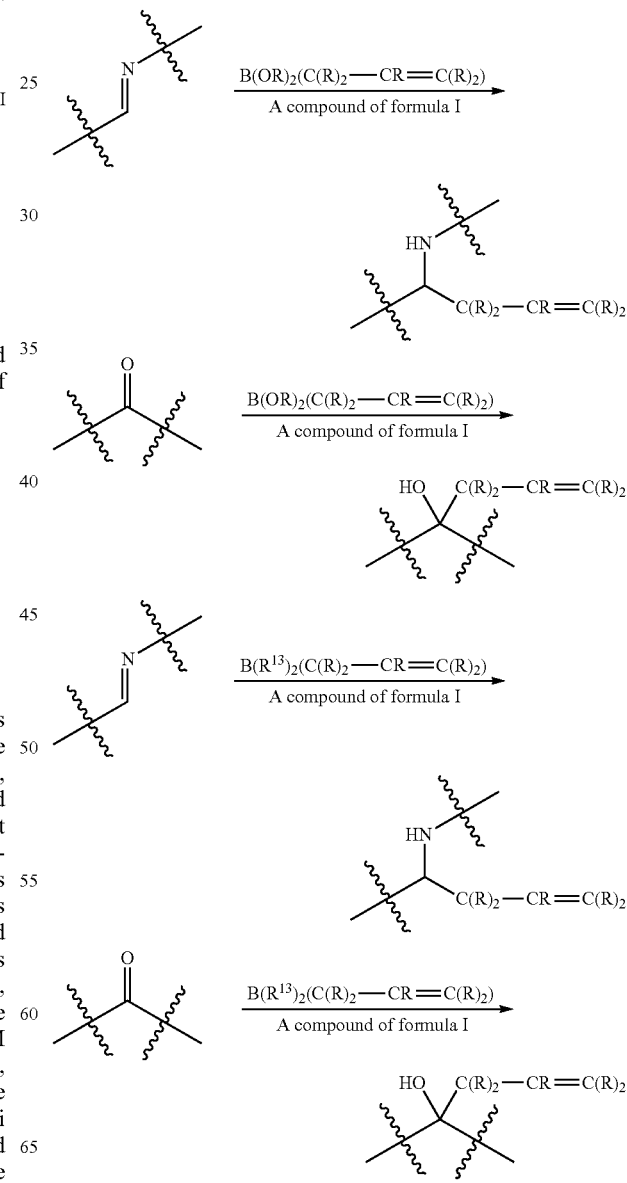

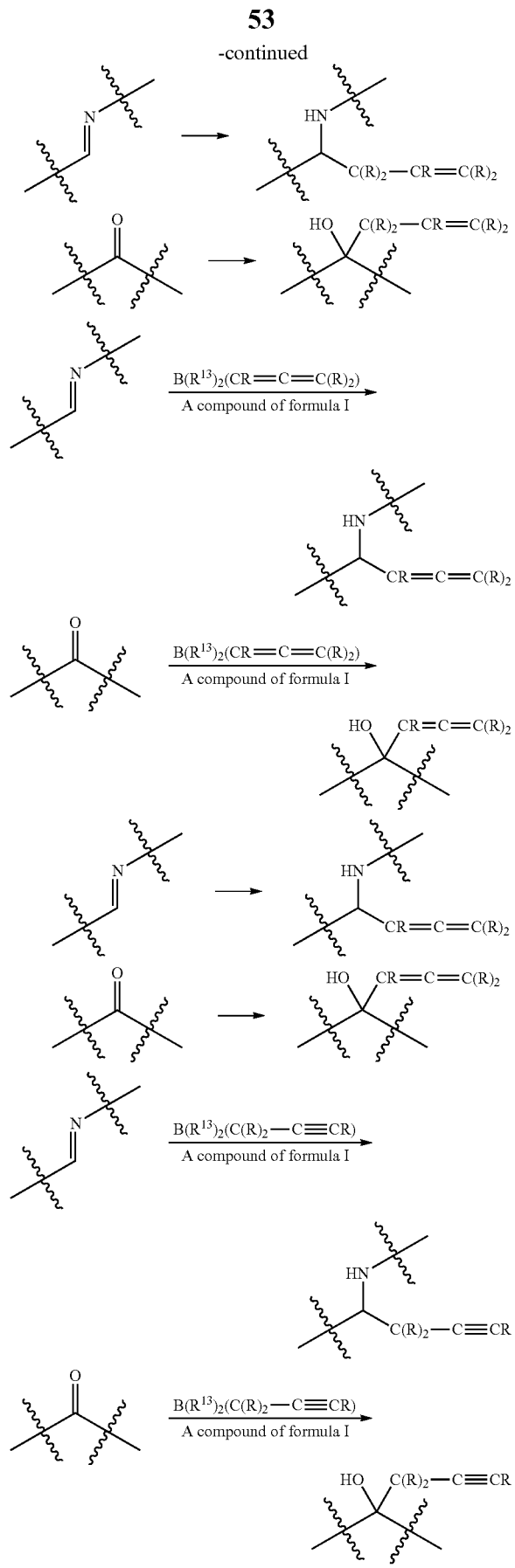
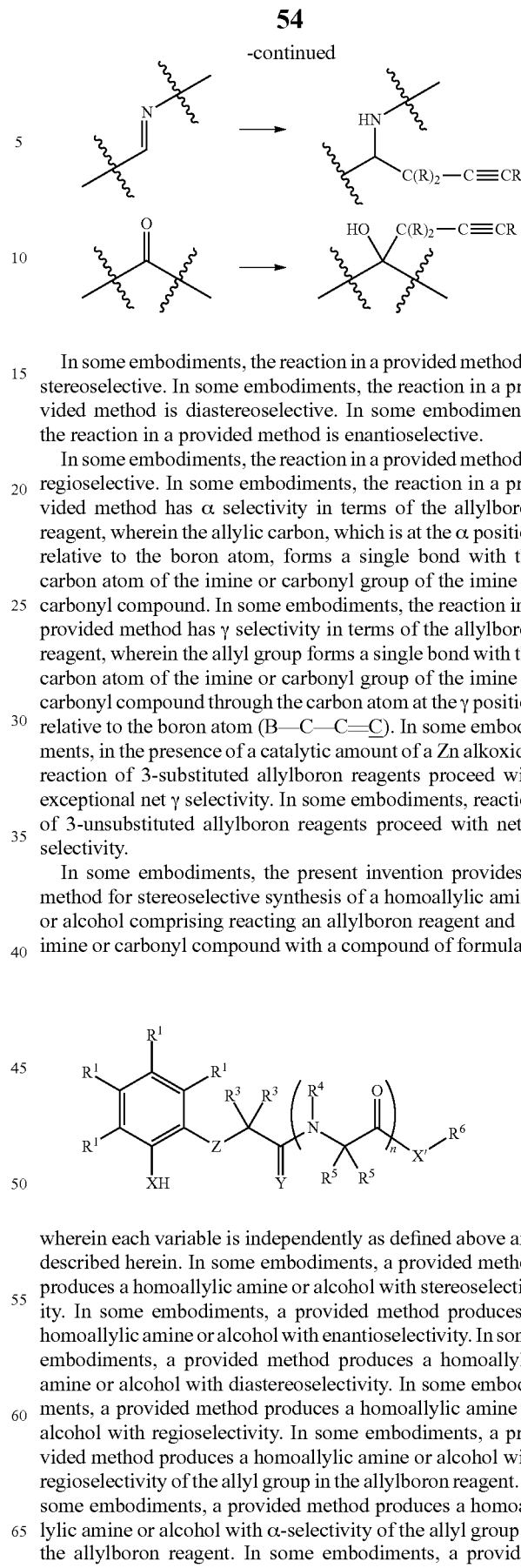

In some embodiments, the reaction in a provided method is stereoselective. In some embodiments, the reaction in a provided method is diastereoselective. In some embodiments, the reaction in a provided method is enantioselective.

In some embodiments, the reaction in a provided method is regioselective. In some embodiments, the reaction in a provided method has α selectivity in terms of the allylboron reagent, wherein the allylic carbon, which is at the α position relative to the boron atom, forms a single bond with the carbon atom of the imine or carbonyl group of the imine or carbonyl compound. In some embodiments, the reaction in a provided method has γ selectivity in terms of the allylboron reagent, wherein the allyl group forms a single bond with the carbon atom of the imine or carbonyl group of the imine or carbonyl compound through the carbon atom at the γ position relative to the boron atom (B—C—C=$\underline{C}$). In some embodiments, in the presence of a catalytic amount of a Zn alkoxide, reaction of 3-substituted allylboron reagents proceed with exceptional net γ selectivity. In some embodiments, reaction of 3-unsubstituted allylboron reagents proceed with net α selectivity.

In some embodiments, the present invention provides a method for stereoselective synthesis of a homoallylic amine or alcohol comprising reacting an allylboron reagent and an imine or carbonyl compound with a compound of formula I:

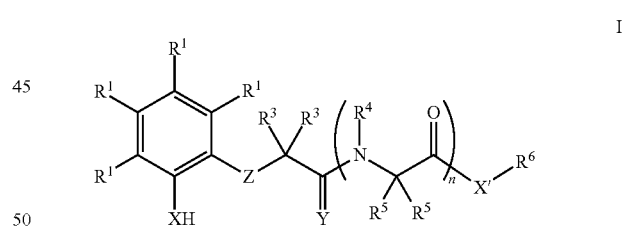

wherein each variable is independently as defined above and described herein. In some embodiments, a provided method produces a homoallylic amine or alcohol with stereoselectivity. In some embodiments, a provided method produces a homoallylic amine or alcohol with enantioselectivity. In some embodiments, a provided method produces a homoallylic amine or alcohol with diastereoselectivity. In some embodiments, a provided method produces a homoallylic amine or alcohol with regioselectivity. In some embodiments, a provided method produces a homoallylic amine or alcohol with regioselectivity of the allyl group in the allylboron reagent. In some embodiments, a provided method produces a homoallylic amine or alcohol with α-selectivity of the allyl group in the allylboron reagent. In some embodiments, a provided method produces a homoallylic amine or alcohol with enantioselectivity, diastereoselectivity and regioselectivity. In some embodiments, the compound of formula I has the structure of:

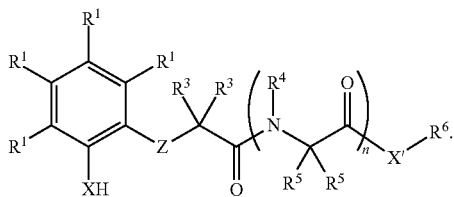

In some embodiments, an allenylboron reagent in a provided method reacts selectively through allene addition. In some embodiments, the ratio of product from allene addition to that from propargyl addition is greater than about 1:1, 2:1, 3:1, 5:1, 10:1, 20:1, 40:1, 50:1, 90:1, 95:1, 96:1, 97:1, 98:1 or 99:1. In some embodiments, the ratio is greater than about 2:1. In some embodiments, the ratio is greater than about 5:1. In some embodiments, the ratio is greater than about 10:1. In some embodiments, the ratio is greater than about 20:1. In some embodiments, the ratio is greater than about 40:1. In some embodiments, the ratio is greater than about 50:1. In some embodiments, a method of the present invention provides >98% allene addition product and <2% propargyl addition product. In some embodiments, the ratio is greater than about 90:1. In some embodiments, the ratio is greater than about 95:1. In some embodiments, the ratio is greater than about 96:1. In some embodiments, the ratio is greater than about 97:1. In some embodiments, the ratio is greater than about 98:1. In some embodiments, the ratio is greater than about 99:1.

Conditions

In some embodiments, a provided method requires an amount of a compound of formula I such that the loading is from about 0.01 mol % to about 20 mol % of the compound of formula I relative to substrate (i.e., an imine or a carbonyl compound). In certain embodiments, the compound of formula I is used in an amount of between about 0.01 mol % to about 10 mol %. In certain embodiments, the compound of formula I is used in an amount of between about 0.01 mol % to about 6 mol %. In certain embodiments, the compound of formula I is used in an amount of between about 0.01 mol % to about 5 mol %. In certain embodiments, the compound of formula I is used in an amount of between about 0.01 mol % to about 3 mol %. In certain embodiments, the compound of formula I is used in an amount of between about 0.01 mol % to about 1 mol %. In certain embodiments, the compound of formula I is used in an amount of between about 0.01 mol % to about 0.5 mol %. In certain embodiments, the compound of formula I is used in an amount of between about 0.01 mol % to about 0.2 mol %. In certain embodiments, the compound of formula I is used in an amount of about 0.05 mol %, 0.1 mol %, 0.2 mol %, 0.5 mol %, 1 mol %, 2 mol %, 3 mol %, 4 mol %, 5 mol %, 6 mol %, 7 mol %, 8 mol %, 9 mol %, or 10 mol %. In certain embodiments, the compound of formula I is used in an amount of about 0.05 mol %. In certain embodiments, the compound of formula I is used in an amount of about 0.1 mol %. In certain embodiments, the compound of formula I is used in an amount of about 0.2 mol %. In certain embodiments, the compound of formula I is used in an amount of about 0.5 mol %. In certain embodiments, the compound of formula I is used in an amount of about 1 mol %. In certain embodiments, the compound of formula I is used in an amount of about 2 mol %. In certain embodiments, the compound of formula I is used in an amount of about 3 mol %. In certain embodiments, the compound of formula I is used in an amount of about 4 mol %. In certain embodiments, the compound of formula I is used in an amount of about 5 mol %. In certain embodiments, the compound of formula I is used in an amount of about 6 mol %. In certain embodiments, the compound of formula I is used in an amount of about 7 mol %. In certain embodiments, the compound of formula I is used in an amount of about 8 mol %. In certain embodiments, the compound of formula I is used in an amount of about 9 mol %. In certain embodiments, the compound of formula I is used in an amount of about 10 mol %.

In some embodiments, a provided method requires an amount of a base such that the loading is from about 0.01 mol % to about 20 mol % of the base relative to substrate (i.e., an imine or a carbonyl compound). In certain embodiments, the base is used in an amount of between about 0.1 mol % to about 10 mol %. In certain embodiments, the base is used in an amount of between about 0.1 mol % to about 6 mol %. In certain embodiments, the base is used in an amount of between about 0.1 mol % to about 5 mol %. In certain embodiments, the base is used in an amount of between about 0.1 mol % to about 3 mol %. In certain embodiments, the base is used in an amount of between about 0.1 mol % to about 1 mol %. In certain embodiments, the base is used in an amount of between about 0.1 mol % to about 0.5 mol %. In certain embodiments, the base is used in an amount of between about 0.1 mol % to about 0.2 mol %. In certain embodiments, the base is used in an amount of about 0.1 mol %, 0.2 mol %, 0.3 mol %, 0.4 mol %, 0.5 mol %, 1 mol %, 2 mol %, 3 mol %, 4 mol %, 5 mol %, 6 mol %, 7 mol %, 8 mol %, 9 mol %, 10 mol %, 11 mol %, 12 mol %, 13 mol %, 14 mol %, 15 mol %, 16 mol %, 17 mol %, 18 mol %, 19 mol %, or 20 mol %. In some embodiments, the base is used in an amount of about 0.1 mol %. In some embodiments, the base is used in an amount of about 0.3 mol %. In some embodiments, the base is used in an amount of about 0.4 mol %. In some embodiments, the base is used in an amount of about 0.5 mol %. In some embodiments, the base is used in an amount of about 1 mol %. In some embodiments, the base is used in an amount of about 2.5 mol %. In some embodiments, the base is used in an amount of about 3 mol %. In some embodiments, the base is used in an amount of about 5 mol %. In some embodiments, the base is used in an amount of about 7.5 mol %. In some embodiments, the base is used in an amount of about 8.5 mol %. In some embodiments, the base is used in an amount of about 10 mol %. In some embodiments, the base is used in an amount of about 15 mol %. In some embodiments, the base is used in an amount of about 20 mol %. In some embodiments, the base is used in an amount of about 30 mol %. In some embodiments, the base is used in an amount of about 50 mol %.

In some embodiments, a provided method requires an amount of an organoboron reagent, e.g., an allylboron, allenylboron, or propargylboron reagent, such that the loading is from about 100 mol % of the allylboron reagent relative to substrate (i.e., the compound comprising the double bond, such as an imine or a carbonyl compound). In some embodiments, a provided method requires an amount of an allylboron reagent such that the loading is from about 100 mol % of the allylboron reagent relative to substrate (e.g., an imine or a carbonyl compound). In certain embodiments, the organoboron reagent is used in an amount of greater than 100 mol %. In certain embodiments, the organoboron reagent is used in an amount of less than 100 mol %. In certain embodiments, the organoboron reagent is used in an amount of about 100 mol % to about 200 mol %. In certain embodiments, the organoboron reagent is used in an amount of about 100 mol % to about 300 mol %. In certain embodiments, the organoboron reagent is used in an amount of about 100 mol % to about 500 mol %. In certain embodiments, the organoboron reagent is used in an amount of about 100 mol % to about 1000 mol %. In certain embodiments, the organoboron reagent is used in an amount of about 105 mol %. In certain embodiments, the organoboron reagent is used in an amount of about 140 mol %. In certain embodiments, the organoboron reagent is used in an amount of about 150 mol %.

In some embodiments, a provided method requires an amount of alcohol such that the loading is from about 100 mol % of the alcohol relative to substrate (i.e., an imine or a carbonyl compound). In certain embodiments, the alcohol is used in an amount of greater than 100 mol %. In certain embodiments, the alcohol is used in an amount of less than 100 mol %. In certain embodiments, the alcohol is used in an amount of about 100 mol % to about 200 mol %. In certain embodiments, the alcohol is used in an amount of about 100 mol % to about 300 mol %. In certain embodiments, the alcohol is used in an amount of about 100 mol % to about 500 mol %. In certain embodiments, the alcohol is used in an amount of about 100 mol % to about 1000 mol %. In some embodiments, the alcohol is used in an amount of 150 mol %. In some embodiments, the alcohol is used in an amount of 200 mol %. In some embodiments, the alcohol is used in an amount of 250 mol %.

Suitable conditions for performing a provided method generally employ one or more solvents. In certain embodiments, one or more organic solvents are used. Examples of such organic solvents include, but are not limited to, hydrocarbons such as benzene, toluene, and pentane, halogenated hydrocarbons such as dichloromethane, or polar aprotic solvents, such as ethereal solvents including ether, tetrahydrofuran (THF), or dioxanes, or mixtures thereof. In certain embodiments, one or more solvents are deuterated. In some embodiments, a single solvent is used. In certain embodiments, the solvent is benzene or toluene. In certain embodiments, the solvent is toluene. In certain embodiments, the solvent is dichloromethane.

In some embodiments, mixtures of two or more solvents are used, and in some cases may be preferred to a single solvent. Solvent mixtures may be comprised of equal volumes of each solvent or may contain one solvent in excess of the other solvent or solvents. In certain embodiments wherein a solvent mixture is comprised of two solvents, the solvents may be present in a ratio of about 20:1, about 10:1, about 9:1, about 8:1, about 7:1, about 6:1, about 5:1, about 4:1, about 3:1, about 2:1, or about 1:1. One of skill in the art would appreciate that other solvent mixtures and/or ratios are contemplated herein, that the selection of such other solvent mixtures and/or ratios will depend on the solubility of species present in the reaction (e.g., substrates, additives, etc.), and that experimentation required to optimized the solvent mixture and/or ratio would be routine in the art and not undue.

Methods of the present invention typically employ ambient reaction temperatures. In some embodiments, a suitable reaction temperature is about 15° C., about 20° C., about 22° C., about 25° C., or about 30° C. In some embodiments, a suitable reaction temperature is from about 15° C. to about 25° C. In certain embodiments, a suitable reaction temperature is about 20° C., 21° C., 22° C., 23° C., 24° C., or 25° C. In some embodiments, a suitable reaction temperature is about 22° C.

In certain embodiments, a provided method is performed at elevated temperature. In some embodiments, a suitable reaction temperature is from about 25° C. to about 110° C. In certain embodiments, a suitable reaction temperature is from about 40° C. to about 100° C., from about 40° C. to about 90° C., from about 40° C. to about 80° C., from about 40° C. to about 70° C., from about 40° C. to about 60° C., or from about 40° C. to about 50° C. In some embodiments, a suitable reaction temperature is about 50° C.

In some embodiments, a method of the present invention is performed at ambient pressure. In some embodiments, a method of the present invention is performed at reduced pressure. In some embodiments, a method of the present invention is performed at a pressure of less than about 20 torr. In some embodiments, a method of the present invention is performed at a pressure of less than about 15 torr. In some embodiments, a method of the present invention is performed at a pressure of less than about 10 torr. In some embodiments, a method of the present invention is performed at a pressure of about 9, 8, 7, 6, 5, 4, 3, 2, or 1 torr. In certain embodiments, a method of the present invention is performed at a pressure of about 7 torr. In certain embodiments, a method of the present invention is performed at a pressure of about 1 torr.

In some embodiments, a method of the present invention requires an amount of solvent such that the concentration of the reaction is between about 0.01 M and about 1 M. In some embodiments, the concentration of the reaction is between about 0.01 M and about 0.1 M. In some embodiments, the concentration of the reaction is between about 0.01 M and about 0.05 M. In some embodiments, the concentration of the reaction is about 0.01 M. In some embodiments, the concentration of the reaction is about 0.05 M. In some embodiments, the concentration of the reaction is about 0.1 M.

In some embodiments, a method of the present invention requires a reaction time of about 1 minute to about 1 day. In some embodiments, the reaction time ranges from about 0.5 hour to about 20 hours. In some embodiments, the reaction time ranges from about 0.5 hour to about 15 hours. In some embodiments, the reaction time ranges from about 1.0 hour to about 12 hours. In some embodiments, the reaction time ranges from about 1 hour to about 10 hours. In some embodiments, the reaction time ranges from about 1 hour to about 8 hours. In some embodiments, the reaction time ranges from about 1 hour to about 6 hours. In some embodiments, the reaction time ranges from about 1 hour to about 4 hours. In some embodiments, the reaction time ranges from about 1 hour to about 2 hours. In some embodiments, the reaction time ranges from about 2 hours to about 8 hours. In some embodiments, the reaction time ranges from about 2 hours to about 4 hours. In some embodiments, the reaction time ranges from about 2 hours to about 3 hours. In certain embodiments, the reaction time is about 1 hour. In certain embodiments, the reaction time is about 2, 3, 4, 5, 6, 7, 8, 9, 10, 11, or 12 hours. In some embodiments, the reaction time is about 12 hours. In certain embodiments, the reaction time is less than about 2 minutes. In certain embodiments, the reaction time is less than about 5 minutes. In certain embodiments, the reaction time is less than about 10 minutes. In certain embodiments, the reaction time is less than about 20 minutes. In certain embodiments, the reaction time is less than about 40 minutes. In certain embodiments, the reaction time is less than about 1 hour. In certain embodiments, the reaction time is about 5, 10, 15, 20, 25, 30, 35, 40, 45, 50, or 55 minutes. In some embodiments, the reaction time is about 30 minutes. In some embodiments, the reaction time is about 1, 1.5, 2, 2.5, or 3 hours. In certain embodiments, the reaction time is about 4 hours. In certain embodiments, the reaction time is about 6 hours. In certain embodiments, the reaction time is within about 6 hours. In certain embodiments, the reaction time is about 18 hours.

In some embodiments, a method of the present invention produces a chiral product. In some embodiments, a method of the present invention produces a chiral homoallylic, homoallenyl, or homopropargyl amine or alcohol. In some embodiments, a method of the present invention produces a chiral homoallylic amine or alcohol. In some embodiments, a method of the present invention produces a chiral homoallylic amine. In some embodiments, a method of the present invention produces a chiral homoallylic alcohol. In some embodiments, a method of the present invention produces a chiral homoallenyl amine. In some embodiments, a method of the present invention produces a chiral homoallenyl alcohol. In some embodiments, a method of the present invention produces a chiral homopropargyl amine. In some embodiments, a method of the present invention produces a chiral homopropargyl alcohol. In some embodiments, a method of the present invention produces a chiral product, wherein the product comprises a carbon atom from the double bond of the compound comprising a double bond, e.g., the carbon atom of the imine or carbonyl group of the imine or carbonyl compound, and the said carbon atom is chiral. In some embodiments, a method of the present invention produces a chiral homoallylic, homoallenyl, or homopropargyl amine or alcohol, wherein the homoallylic, homoallenyl, or homopropargyl carbon is chiral. In some embodiments, a method of the present invention produces a chiral homoallylic amine or alcohol, wherein the homoallylic carbon is chiral. In some embodiments, a method of the present invention produces a chiral homoallenyl amine or alcohol, wherein the homoallenyl carbon is chiral. In some embodiments, a method of the present invention produces a chiral homopropargyl amine or alcohol, wherein the homopropargyl carbon is chiral. In some embodiments, a method of the present invention produces a chiral product in an enantiomeric ratio greater than 50:50. In some embodiments, a method of the present invention produces a chiral homoallylic, homoallenyl or homopropargyl amine or alcohol in an enantiomeric ratio greater than 50:50. In some embodiments, a method of the present invention produces a chiral homoallylic amine or alcohol in an enantiomeric ratio greater than 50:50. In some embodiments, a method of the present invention produces a chiral product in an enantiomeric ratio greater than 60:40. In some embodiments, a method of the present invention produces a chiral homoallylic, homoallenyl or homopropargyl amine or alcohol in an enantiomeric ratio greater than 60:40. In some embodiments, a method of the present invention produces a chiral homoallylic amine or alcohol in an enantiomeric ratio greater than 60:40. In some embodiments, a method of the present invention produces a chiral product in an enantiomeric ratio greater than 70:30. In some embodiments, a method of the present invention produces a chiral homoallylic, homoallenyl or homopropargyl amine or alcohol in an enantiomeric ratio greater than 70:30. In some embodiments, a method of the present invention produces a chiral homoallylic amine or alcohol in an enantiomeric ratio greater than 70:30. In some embodiments, a method of the present invention produces a chiral product in an enantiomeric ratio greater than 80:20. In some embodiments, a method of the present invention produces a chiral homoallylic, homoallenyl or homopropargyl amine or alcohol in an enantiomeric ratio greater than 80:20. In some embodiments, a method of the present invention produces a chiral homoallylic amine or alcohol in an enantiomeric ratio greater than 80:20. In some embodiments, a method of the present invention produces a chiral product in an enantiomeric ratio greater than 90:10. In some embodiments, a method of the present invention produces a chiral homoallylic, homoallenyl or homopropargyl amine or alcohol in an enantiomeric ratio greater than 90:10. In some embodiments, a method of the present invention produces a chiral homoallylic amine or alcohol in an enantiomeric ratio greater than 90:10. In some embodiments, a method of the present invention produces a chiral product in an enantiomeric ratio greater than 95:5. In some embodiments, a method of the present invention produces a chiral homoallylic, homoallenyl or homopropargyl amine or alcohol in an enantiomeric ratio greater than 95:5. In some embodiments, a method of the present invention produces a chiral homoallylic amine or alcohol in an enantiomeric ratio greater than 95:5. In some embodiments, a method of the present invention produces a chiral product in an enantiomeric ratio greater than 96:4. In some embodiments, a method of the present invention produces a chiral homoallylic, homoallenyl or homopropargyl amine or alcohol in an enantiomeric ratio greater than 96:4. In some embodiments, a method of the present invention produces a chiral homoallylic amine or alcohol in an enantiomeric ratio greater than 96:4. In some embodiments, a method of the present invention produces a chiral product in an enantiomeric ratio greater than 97:3. In some embodiments, a method of the present invention produces a chiral homoallylic, homoallenyl or homopropargyl amine or alcohol in an enantiomeric ratio greater than 97:3. In some embodiments, a method of the present invention produces a chiral homoallylic amine or alcohol in an enantiomeric ratio greater than 97:3. In some embodiments, a method of the present invention produces a chiral product in an enantiomeric ratio greater than 98:2. In some embodiments, a method of the present invention produces a chiral homoallylic, homoallenyl or homopropargyl amine or alcohol in an enantiomeric ratio greater than 98:2. In some embodiments, a method of the present invention produces a chiral homoallylic amine or alcohol in an enantiomeric ratio greater than 98:2. In some embodiments, a method of the present invention produces a chiral product in an enantiomeric ratio greater than 99:1. In some embodiments, a method of the present invention produces a chiral homoallylic, homoallenyl or homopropargyl amine or alcohol in an enantiomeric ratio greater than 99:1. In some embodiments, a method of the present invention produces a chiral homoallylic amine or alcohol in an enantiomeric ratio greater than 99:1.

As understood by a person of ordinary skill in the art, when the organoboron reagent has a chiral center, diastereoisomers may be produced. In some embodiment, the allylic carbon in the allylboron reagent is chiral. In some embodiments, the allenyl group is the allenylboron reagent is chiral. In some embodiments, the propargyl carbon in the propargylboron reagent is chiral. In some embodiments, a method of the present invention produces a product, e.g., a homoallylic, homoallenyl or homopropargyl amine or alcohol, in a diastereomeric ratio greater than 50:50. In some embodiments, a method of the present invention produces a homoallylic amine or alcohol in a diastereomeric ratio greater than 50:50. In some embodiments, a method of the present invention produces a product, e.g., a homoallylic, homoallenyl or homopropargyl amine or alcohol, in a diastereomeric ratio greater than 60:40. In some embodiments, a method of the present invention produces a homoallylic amine or alcohol in a diastereomeric ratio greater than 60:40. In some embodiments, a method of the present invention produces a product, e.g., a homoallylic, homoallenyl or homopropargyl amine or alcohol, in a diastereomeric ratio greater than 70:30. In some embodiments, a method of the present invention produces a homoallylic amine or alcohol in a diastereomeric ratio greater than 70:30. In some embodiments, a method of the present invention produces a product, e.g., a homoallylic, homoallenyl or homopropargyl amine or alcohol, in a diastereomeric ratio greater than 80:20. In some embodiments, a method of the present invention produces a homoallylic amine or alcohol in a diastereomeric ratio greater than 80:20. In some embodiments, a method of the present invention produces a product, e.g., a homoallylic, homoallenyl or homopropargyl amine or alcohol, in a diastereomeric ratio greater than 85:15. In some embodiments, a method of the present invention produces a homoallylic amine or alcohol in a diastereomeric ratio greater than 85:15. In some embodiments, a method of the present invention produces a product, e.g., a homoallylic, homoallenyl or homopropargyl amine or alcohol, in a diastereomeric ratio greater than 90:10. In some embodiments, a method of the present invention produces a homoallylic amine or alcohol in a diastereomeric ratio greater than 90:10. In some embodiments, a method of the present invention produces a product, e.g., a homoallylic, homoallenyl or homopropargyl amine or alcohol, in a diastereomeric ratio greater than 95:5. In some embodiments, a method of the present invention produces a homoallylic amine or alcohol in a diastereomeric ratio greater than 95:5. In some embodiments, a method of the present invention produces a product, e.g., a homoallylic, homoallenyl or homopropargyl amine or alcohol, in a diastereomeric ratio greater than 96:4. In some embodiments, a method of the present invention produces a homoallylic amine or alcohol in a diastereomeric ratio greater than 96:4. In some embodiments, a method of the present invention produces a product, e.g., a homoallylic, homoallenyl or homopropargyl amine or alcohol, in a diastereomeric ratio greater than 97:3. In some embodiments, a method of the present invention produces a homoallylic amine or alcohol in a diastereomeric ratio greater than 97:3. In some embodiments, a method of the present invention produces a product, e.g., a homoallylic, homoallenyl or homopropargyl amine or alcohol, in a diastereomeric ratio greater than 98:2. In some embodiments, a method of the present invention produces a homoallylic amine or alcohol in a diastereomeric ratio greater than 98:2. In some embodiments, a method of the present invention produces a product, e.g., a homoallylic, homoallenyl or homopropargyl amine or alcohol, in a diastereomeric ratio greater than 99:1. In some embodiments, a method of the present invention produces a homoallylic amine or alcohol in a diastereomeric ratio greater than 99:1.

In some embodiments, the allyl group of the allylboron reagent can be added to the double bond, e.g., imine or carbonyl group of the imine or carbonyl compound, through the α-, β-, or γ-position (the allylic carbon being α). In some embodiments, the allyl group of the allylboron reagent can be added to the imine or carbonyl compounds through the α-, β-, or γ-position (the allylic carbon being α). In some embodiments, a method of the present application provides regioselectivity. In some embodiments, a method of the present invention produces a homoallylic amine or alcohol with α-selectivity. In some embodiments, a method of the present invention produces a homoallylic amine or alcohol with α-selectivity, wherein the γ position is unsubstituted. In some embodiments, a method of the present invention produces a homoallylic amine or alcohol with about 100% α-selectivity. In some embodiments, a method of the present invention produces a homoallylic amine or alcohol with greater than 99% α-selectivity. In some embodiments, a method of the present invention produces a homoallylic amine or alcohol with greater than 98% α-selectivity. In some embodiments, a method of the present invention produces a homoallylic amine or alcohol with greater than 97% α-selectivity. In some embodiments, a method of the present invention produces a homoallylic amine or alcohol with greater than 95% α-selectivity. In some embodiments, a method of the present invention produces a homoallylic amine or alcohol with greater than 90% α-selectivity. In some embodiments, a method of the present invention produces a homoallylic amine or alcohol with greater than 80% α-selectivity. In some embodiments, a method of the present invention produces a homoallylic amine or alcohol with greater than 70% α-selectivity. In some embodiments, a method of the present invention produces a homoallylic amine or alcohol with greater than 60% α-selectivity. In some embodiments, a method of the present invention produces a homoallylic amine or alcohol with greater than 50% α-selectivity. In some embodiments, a method of the present invention produces a homoallylic amine or alcohol with about 100% γ-selectivity. In some embodiments, a method of the present invention produces a homoallylic amine or alcohol with greater than 99% γ-selectivity. In some embodiments, a method of the present invention produces a homoallylic amine or alcohol with greater than 98% γ-selectivity. In some embodiments, a method of the present invention produces a homoallylic amine or alcohol with greater than 97% γ-selectivity. In some embodiments, a method of the present invention produces a homoallylic amine or alcohol with greater than 95% γ-selectivity. In some embodiments, a method of the present invention produces a homoallylic amine or alcohol with greater than 90% γ-selectivity. In some embodiments, a method of the present invention produces a homoallylic amine or alcohol with greater than 80% γ-selectivity. In some embodiments, a method of the present invention produces a homoallylic amine or alcohol with greater than 70% γ-selectivity. In some embodiments, a method of the present invention produces a homoallylic amine or alcohol with greater than 60% γ-selectivity. In some embodiments, a method of the present invention produces a homoallylic amine or alcohol with greater than 50% γ-selectivity. In some embodiments, the allyl group of the allylboron reagent is γ-substituted, and a provided method produces a homoallylic amine or alcohol with greater than 50%, 60%, 70%, 80%, 90%, 95%, 96%, 97%, 98% or 99% γ-selectivity. In some embodiments, the allyl group of the allylboron reagent is γ-substituted, and a provided method produces a homoallylic amine or alcohol with greater than 50%, 60%, 70%, 80%, 90%, 95%, 96%, 97%, 98% or 99% γ-selectivity, wherein one of the γ substituents is bonded to the allyl group through a carbon atom. In some embodiments, one of the γ substituents is R'. In some embodiments, one of the γ substituents is R', and the configuration of the double bond in the allyl group is trans. In some embodiments, one of the γ substituents is optionally substituted $C_{1-12}$ aliphatic, and the configuration of the double bond in the allyl group is trans. In some embodiments, one of the γ substituents is optionally substituted $C_{1-12}$ alkyl, and the configuration of the double bond in the allyl group is trans. In some embodiments, the allyl group of the allylboron reagent is γ-substituted (or 3-substituted), and a provided method produces a homoallylic amine or alcohol with greater than 60% γ-selectivity. In some embodiments, the allyl group of the allylboron reagent is γ-substituted, and a provided method produces a homoallylic amine or alcohol with greater than 70% γ-selectivity. In some embodiments, the allyl group of the allylboron reagent is γ-substituted, and a provided method produces a homoallylic amine or alcohol with greater than 80% γ-selectivity. In some embodiments, the allyl group of the allylboron reagent is γ-substituted, and a provided method produces a homoallylic amine or alcohol with greater than 90% γ-selectivity. In some embodiments, the allyl group of the allylboron reagent is γ-substituted, and a provided method produces a homoallylic amine or alcohol with greater than 95% γ-selectivity. In some embodiments, the allyl group of the allylboron reagent is γ-substituted, and a provided method produces a homoallylic amine or alcohol with greater than 96% γ-selectivity. In some embodiments, the allyl group of the allylboron reagent is γ-substituted, and a provided method produces a homoallylic amine or alcohol with greater than 97% γ-selectivity. In some embodiments, the allyl group of the allylboron reagent is γ-substituted, and a provided method produces a homoallylic amine or alcohol with greater than 98% γ-selectivity. In some embodiments, the allyl group of the allylboron reagent is γ-substituted, and a provided method produces a homoallylic amine or alcohol with greater than 99% γ-selectivity.

In some embodiments, a provided method comprises the use of a zinc-containing compound, and produces a homoallylic amine or alcohol with greater than 50%, 60%, 70%, 80%, 90%, 95%, 96%, 97%, 98% or 99% γ-selectivity. In some embodiments, a provided method comprises the use of a zinc-containing compound and a γ-substituted allylboron reagent, and produces a homoallylic amine or alcohol with greater than 50%, 60%, 70%, 80%, 90%, 95%, 96%, 97%, 98% or 99% γ-selectivity. In some embodiments, the γ-selectivity is greater than 60%. In some embodiments, the γ-selectivity is greater than 70%. In some embodiments, the γ-selectivity is greater than 80%. In some embodiments, the γ-selectivity is greater than 90%. In some embodiments, the γ-selectivity is greater than 95%. In some embodiments, the γ-selectivity is greater than 96%. In some embodiments, the γ-selectivity is greater than 97%. In some embodiments, the γ-selectivity is greater than 98%. In some embodiments, the γ-selectivity is greater than 99%. Exemplary γ substituents are extensively described above and herein. In some embodiments, a γ substituent is R'. Exemplary Zn-containing compounds are extensively described in the art, including but not limited to zinc alkoxide. In some embodiments, a zinc containing compound has the structure of $Zn(R^{13})_2$, wherein each $R^{13}$ is independently as defined above and described herein. In some embodiments, a zinc containing compound has the structure of $Zn(OR)_2$, wherein each R is independently as defined above and described herein. In some embodiments, a zinc containing compound has the structure of $Zn(OR')_2$, wherein each R' is independently as defined above and described herein. In some embodiments, a zinc containing compound has the structure of $Zn(OR')_2$, wherein each R' is independently optionally substituted $C_{1-12}$ aliphatic. In some embodiments, a zinc containing compound has the structure of $Zn(OR')_2$, wherein each R' is independently optionally substituted $C_{1-6}$ alkyl. In some embodiments, a zinc containing compound has the structure of $Zn(OR')_2$, wherein each R' is independently optionally substituted $C_{1-4}$ alkyl. In some embodiments, the zinc-containing compound is $Zn(OMe)_2$. The zinc-containing compound can be used in various amounts, such as those described for the base. In some embodiments, the zinc-containing compound is the base.

In some embodiments, it is surprisingly found that a provided method in this invention does not require precious elements, high catalyst loadings (for example, >10%), and/or organotin or organoindium reagents, and can bring the reaction to completion in a few hours through operationally simple procedures. In some embodiments, a provided method does not require moisture-sensitive reagents. In some embodiments, a provided method does not require flame-dried vessel. In some embodiments, a provided method does not require flame-dried vessel. In some embodiments, a provided method can directly use commercially available solvent and reagents, without further purification. In some embodiments, the organoboron reagent used in a provided method is a (pinacolato)organoboron reagent, which is more stable to moisture than many other organoboron reagents. In some embodiments, the (pinacolato)organoboron reagent is a (pinacolato)allylboron, (pinacolato)allenylboron, or (pinacolato)propargylboron reagent. In some embodiments, a provided method is scalable. In some embodiments, a provided method does not demand stringent conditions. In some embodiments, a provided method can be practiced at ambient temperature, without the need of low temperature. In some embodiments, the product of a provide method can be purified without chromatography. In some embodiments, the imine compound is an N-phosphinoylimine, which can be prepared efficiently and robust, and generate products that are easy to purify with crystallization. There are inexpensive and efficient mildly acidic methods for removal of the phosphorous-based protecting group and generation of the parent amines (Vieira, E. M., Haeffner, F., Snapper, M. L. & Hoveyda, A. H. A robust, efficient and highly enantioselective method for synthesis of homopropargyl amines. *Angew. Chem. Int. Edn* 51, 6618-6621 (2012); Weinreb, S. M. & Orr, R. K. N-Phosphinoylimines: an emerging class of reactive intermediates for stereoselective organic synthesis. *Synthesis* 8, 1205-1227 (2005)). It is noted that such protocols tolerate many commonly used functional groups and do not require strongly reductive conditions, or costly metal salts, and/or alkyllithium reagents. In some embodiments, a provided method has one or more of the features described above.

EXEMPLIFICATION

Here, we introduce a class of compound of formula I defined above and described herein that can be employed to catalyze the addition of an organoboron reagent to a double bond with high efficiency and stereoselectivity. In some embodiments, a compound of formula I catalyzes the addition of an organoboron reagent to a C=N or C=O double bond with high efficiency and stereoselectivity. In some embodiments, a compound of formula I catalyzes the addition of an organoboron reagent to a C=N or C=O double bond with high efficiency, stereoselectivity, and/or regioselectivity. In some embodiments, a compound of formula I catalyzes the addition of an organoboron reagent to an imine or carbonyl with high efficiency, providing an amine or alcohol with high stereoselectivity and/or regioselectivity. In some embodiments, a class of compound of formula I defined above and described herein can be employed to catalyze efficient and enantioselective formation of homoallylic, homoallenyl or homopropargyl amines and alcohols, entities used in the preparation of biologically active molecules, through allyl, allenyl or propargyl additions to C=N (e.g., imines) and C=O (e.g., carbonyls) double bond.

Catalytic and Enantioselective Additions to Aldimines.

We began by selecting a limited number of readily accessible amino alcohols (2a-2h) for reactions with commercially available pinacolatoallylboron (1a) and phenyl-substituted diphenylphosphinoylimine 3a (Scheme 1). A variety of phosphinoyl imines, aryl- or alkyl-containing, can be prepared in high yield; such entities are relatively robust and generate products that are easy to purify. There are several mild single-step methods for removal of the P-based group and generation of the parent amine (Weinreb, S. M. & Orr, R. K. N-Phosphinoylimines: An emerging class of reactive intermediates for stereoselective organic synthesis. *Synthesis* 8, 1205-1227 (2005)); such protocols are tolerant of most commonly used functional groups and do not expose the products to strongly oxidative (e.g., IBX; Wada, R.; Shibuguchi, T.; Makino, S.; Oisaki, K.; Kanai, M. & Shibasaki, M. Catalytic enantioselective allylation of ketoimines. *J. Am. Chem. Soc.* 126, 7687-7691 (2006)) or reductive conditions (e.g., diisobutylaluminum hydride; Lou, S.; Moquist, P. N. & Schaus, S. E.

Asymmetric allylboration of acyl imines catalyzed by chiral diols. *J. Am. Chem. Soc.* 129, 15398-15404 (2007)), nor demand costly metal salts (e.g., stoichiometric or larger quantities of $SmI_2$, Pd-catalyzed hydrogenation) that can promote undesirable side reactions. The results are listed in Table 1, below.

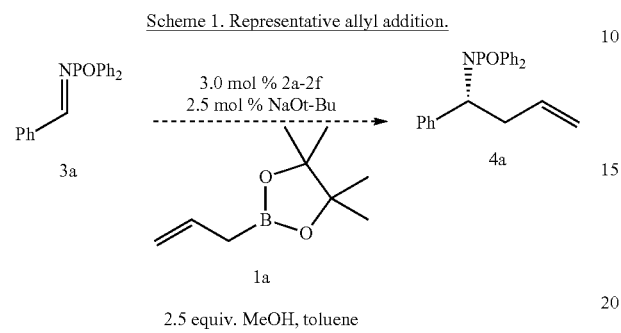

Scheme 1. Representative allyl addition.

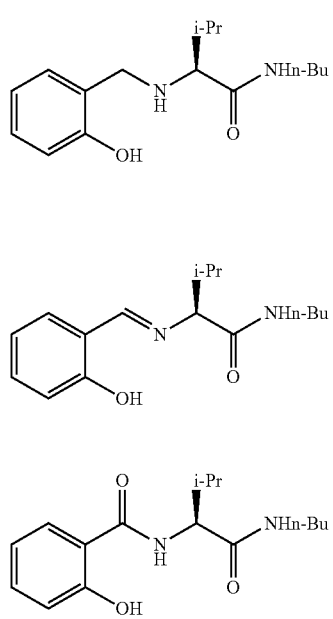

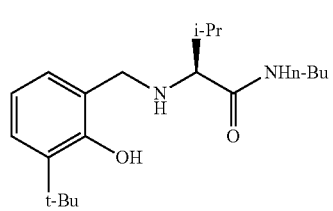

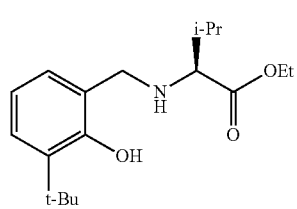

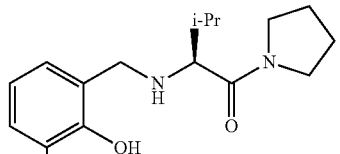

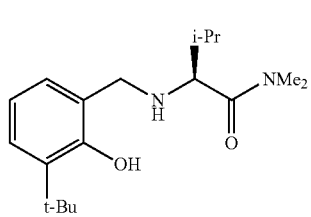

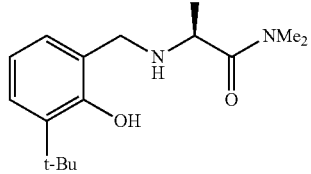

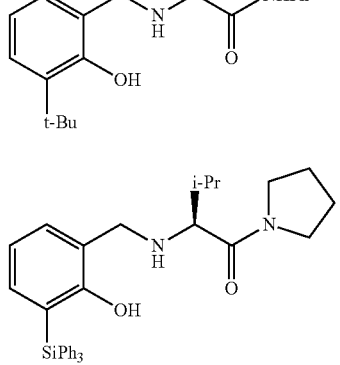

TABLE 1

Examination of various amino alcohols.*

| Entry Number | Amino alcohol; (mol %) | Time (H); T (° C.) | Conversion (%)[§] | Enantiomeric ratio[†] |
|---|---|---|---|---|
| 1 | 2a; 3.0 | 4.0; 22 | 71 | 74.5:25.5 |
| 2 | 2b; 3.0 | 4.0; 22 | <2 | ND |
| 3 | 2c; 3.0 | 4.0; 22 | <10 | ND |
| 4 | 2d; 3.0 | 4.0; 22 | >98 | 91:9 |
| 5 | 2e; 3.0 | 4.0; 22 | 47 | 80:20 |
| 6 | 2f; 3.0 | 4.0; 22 | >98 | 96:4 |
| 7 | 2g; 3.0 | 4.0; 22 | >98 | 96.5:3.5 |
| 8 | 2h; 3.0 | 4.0; 22 | 97 | 98:2 |
| 9 | 2i; 3.0 | 4.0; 22 | >98 | 88.5:11.5 |

*The reactions were carried out in purified toluene under an atmosphere of nitrogen gas. ND, not determined.
[§]Conversion to the desired product as measured by analysis of 400 MHz $^1$H NMR spectra of unpurified mixtures versus an internal standard of 9-methylanthracene; the variance of values are estimated to be <±2% for entries 1-4 and 6-9, and <±5% for entry 5.
[§§]Yield of isolated product after purification; the variance of values are estimated to be <±2%.
[†]Enantiomeric ratios were determined by HPLC analysis.

When imine 3a and allylboron 1a are treated with 3.0 mol % amino alcohol 2a (Table 1, entry 1), 2.5 mol % NaOt-Bu and 2.0 equivalents of MeOH, 71% conversion to enantiomerically enriched homoallylamide 4a is observed in four hours (74.5:25.5 enantiomeric ratio (e.r.)). When the corresponding Schiff base 2b or amide 2c are used (Table 1, entries 2-3), there is minimal transformation. Placement of a sizeable t-butyl group adjacent to the phenol group in 2d (Table 1, entry 4) led to improved efficiency (>98% conv.) and stereoselectivity (91:9 e.r.); not wishing to be limited by any theory, the higher e.r. value is likely reflective of a more competitive addition initiated by the amino alcohol-derived catalyst, as control experiments indicate that allyl addition can be promoted by the metal alkoxide, albeit at a much slower rate. 2e and 2f delivered lower e.r. The reaction performed with 2g (Table 1, entry 7), containing a dimethylamide, proceeds readily to completion to deliver the desired product in 96.5: 3.5 e.r. Reaction with and 2l (Table 1, entry 9) provides the desired product in 96:4 e.r. and >98 conversion. Reaction with 2h (entry 8) is more selective (98:2 e.r.). Similar efficiency and enantioselectivity is attained when organic amines are used as base (for example, 1,8-diazabicycloundec-7-ene, dbu).

The observations summarized in Table 2, below, underline the efficiency of the catalytic system: appreciable conversion to the homoallyl amide and high enantioselectivities are afforded with as little as 0.3-0.05 mol % of the chiral amino alcohol and 2.5 mol % of NaOt-Bu (entries 1-5). In some embodiments, if the amount of the base is reduced along with catalyst loading, as the findings in entries 6-8 of Table 2 illustrate, reaction efficiency may decrease. With 2.5 mol % base present, 0.1 mol % 2g gives 87% conversion within 4.0 hours at 22° C. (Table 2, entry 4), whereas if 0.1 mol % of both components are available, reaction rate suffers considerably (<10% conv., entry 8).

TABLE 2

Minimization of catalyst loading.*

| Entry | Mol % 2 g | NaOt-Bu mol % | Time (h); T (° C.) | Conv. (%)§; Yield (%)§§ | e.r.† |
|---|---|---|---|---|---|
| 1 | 2.5 | 2.5 | 4.0; 22 | >98; >98 | 96:4 |
| 2 | 1.0 | 2.5 | 4.0; 22 | >98; >98 | 95.5:4.5 |
| 3 | 0.3 | 2.5 | 4.0; 22 | 98; 96 | 94:6 |
| 4 | 0.1 | 2.5 | 4.0; 22 | 87; 87 | 92:8 |
| 5 | 0.05 | 2.5 | 4.0; 22 | 83; 80 | 90:10 |
| 6 | 1.0 | 1.0 | 4.0; 22 | >98; >98 | 94.5:5.5 |
| 7 | 0.3 | 0.3 | 4.0; 22 | 83; 80 | 87:13 |
| 8 | 0.1 | 0.1 | 4.0; 22 | <10; ND | ND |

*The reactions were carried out in purified toluene under an atmosphere of nitrogen gas.
§Conversion to the desired product as measured by analysis of 400 MHz 1H NMR spectra of unpurified mixtures versus an internal standard of 9-methylanthracene; the variance of values are estimated to be <±5%.
§§Yield of isolated product after purification; the variance of values are estimated to be <±2%.
†Enantiomeric ratios were determined by HPLC analysis.

A range of phosphinoyl imines, prepared from commercially available and inexpensive starting material, undergo allyl additions in the presence of 3.0 mol % of amino alcohol 2g and 1.5 equivalents of allylboron 1a within three to six hours at ambient temperature (Tables 3-4). The desired homoallylamides are typically isolated in >85% yield and >95:5 e.r. Aryl-substituted substrates, whether containing a large (e.g., Table 3, entries 3-4), an electron-deficient (e.g., entries 7-8), an electron-donating (e.g., entries 9-10), or a heterocyclic furyl moiety (entry 11), react with high efficiency and enantioselectivity. As the syntheses of 4m and 4n illustrate, use of 2-substituted allylborons, results in equally high efficiency and enantioselectivity. The catalytic method can be extended to additions with alkenyl-substituted aldimines (Table 4, entries 1-5); as before, after only four hours, regardless of the substrate's electronic attributes, products are isolated in 84-98% yield and 97.5:2.5 to >99:1 e.r. The findings summarized in entry 6 of Table 4 involve the reaction of an alkyne-substituted phosphinoyl imine, a process that generates 88:12 e.r. When alkyl-substituted imines are utilized, good yields (50-71%) and high enantioselectivities (97.5:2.5 to >99:1 e.r.) are obtained.

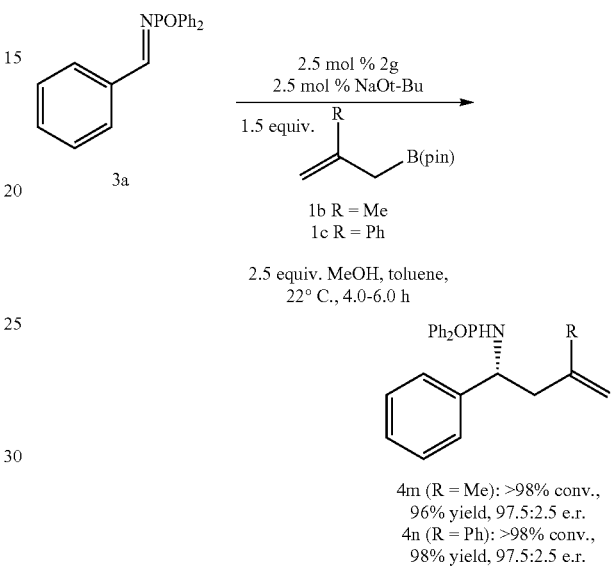

4m (R = Me): >98% conv., 96% yield, 97.5:2.5 e.r.
4n (R = Ph): >98% conv., 98% yield, 97.5:2.5 e.r.

TABLE 3

Catalytic enantioselective allyl additions to aryl-substituted imines.

| Entry number | Ar | Time (h) | Conversion (%)*; yield (%)† | Enantiomeric ratio‡ |
|---|---|---|---|---|
| 1 | Ph; 3a | 4.0 | >98; 95 | 96.5:3.5 |
| 2 | o-FC$_6$H$_4$; 3b | 4.0 | >98; 91 | 98:2 |
| 3 | o-BrC$_6$H$_4$; 3c | 4.0 | >98; 86 | 97.5:2.5 |
| 4 | o-MeC$_6$H$_4$; 3d | 6.0 | >98; 91 | 93.5:6.5 |
| 5 | m-BrC$_6$H$_4$; 3e | 4.0 | >98; 95 | 98:2 |
| 6 | p-BrC$_6$H$_4$; 3f | 6.0 | >98; 91 | 97:3 |
| 7 | p-CF$_3$C$_6$H$_4$; 3g | 4.0 | >98; 93 | 98:2 |
| 8 | p-MeO$_2$CC$_6$H$_4$; 3h | 4.0 | >98; 92 | 98:2 |
| 9 | p-MeOC$_6$H$_4$; 3i | 4.0 | >98; 98 | 96.5:3.5 |
| 10 | p-(n-Bu)$_2$C$_6$H$_4$; 3j | 4.0 | 95; 93 | 92:8 |
| 11 | 2-furyl; 3k | 6.0 | >98; 93 | 98:2 |
| 12 | 3-pyridyl; 3l | 4.0 | 90; 75 | 98:2 |

Reactions were carried out in toluene under an atmosphere of nitrogen gas.
*Conversion to the desired products as measured by analysis of 400 MHz $^1$H NMR spectra of unpurified mixtures versus an internal standard of 9-methylanthracene; the variance of values is estimated to be <±2%.
†Yield of isolated product after purification; the variance of values is estimated to be ±2%.
‡Enantiomeric ratios were determined by HPLC analysis; the variance of values is estimated to be <±2%.

TABLE 4
Catalytic enantioselective allyl additions to alkenyl-, alkynyl- and alkyl-substituted imines.
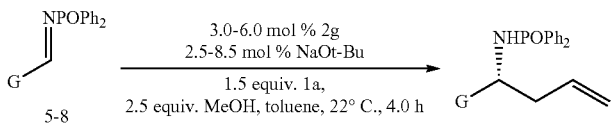
| Entry number | G | 2g (mol %); NaOt-Bu (mol %) | Conversion (%)*; Yield (%)† | Enantiomeric ratio‡ |
|---|---|---|---|---|
| 1 | 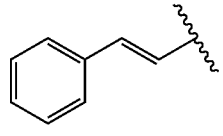 5a | 3.0; 2.5 | >98; 84 | >99:1 |
| 2 | 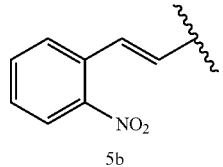 [SMILES: */C=C/c1ccccc1[N+](=O)[O-]] 5b | 3.0; 2.5 | >98; 95 | >99:1 |
| 3 | 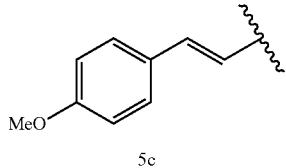 [SMILES: */C=C/c1ccc(OC)cc1] 5c | 3.0; 2.5 | >98; 98 | >99:1 |
| 4 | 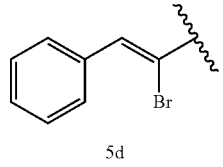 [SMILES: */C(Br)=C/c1ccccc1] 5d | 3.0; 2.5 | >98; 96 | 98:2 |
| 5 | 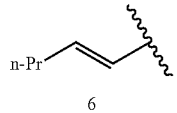 6 | 2.5; 2.5 | >98; 96 | 98:2 |
| 6 | 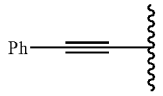 7 | 3.0; 2.5 | >98; 95 | 88:12 |

TABLE 4-continued

Catalytic enantioselective allyl additions to alkenyl-, alkynyl- and alkyl-substituted imines.

| Entry number | G | 2g (mol %); NaOt-Bu (mol %) | Conversion (%)*; Yield (%)† | Enantiomeric ratio‡ |
|---|---|---|---|---|
| 7 | Ph–CH₂CH₂– (8a) | 6.0; 5.0 | 66; 50 | >99:1 |
| 8 | i-Pr–CH₂– (8b) | 6.0; 5.0 | 70; 51 | >99:1 |
| 9 | cyclohexyl (8c) | 6.0; 8.5 | 90; 71 | 97.5:2.5 |

Reactions were carried out in toluene under an atmosphere of nitrogen gas.
*Conversion to the desired products as measured by analysis of 400 MHz ¹H NMR spectra of unpurified mixtures versus an internal standard of 9-methylanthracene; the variance of values is estimated to be <±2%.
†Yield of isolated product after purification; the variance of values is estimated to be ±2%.
‡Enantiomeric ratios were determined by HPLC analysis; the variance of values is estimated to be <±2%.

As shown in Scheme 2 below, 2-substituted allylboronates 1b and 1c also gave very high yields (96% and 98%) and enantioselectivities (97.5:2.5 e.r.). The reactions were carried out in toluene under an atmosphere of nitrogen gas. Conversion measured by analysis of 400 MHz ¹H NMR spectra of unpurified mixtures; the variance of values estimated to be ≤±5%. Yield of isolated product after purification; the variance of values estimated to be <±5%. Enantiomeric ratios were determined by HPLC analysis.

Scheme 2. Reactions with 2-substituted allylboronates.

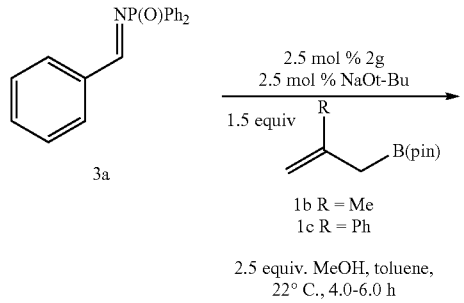

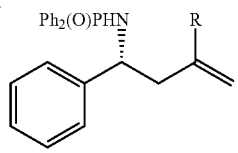

4l (R = Me): >98% conv, 96% yield, 97.5:2.5 e.r.
4m (R = Ph): >98% conv, 98% yield, 97.5:2.5 e.r.

Several distinguishing attributes of the method are illustrated. In some embodiments, compounds of formula I, for example, 2g, can be can be easily performed on multi-gram scale by a simple four-step sequence that requires valine and other inexpensive commercially available materials. Purification of 2g, which is stable to air and moisture, involves a simple filtration without the need for elaborate distillation apparatus or costly silica gel or other chromatography procedures. Enantioselective additions are scalable; for example, an enantioselective allyl addition can be easily carried out on gram-scale, as the representative case in Scheme 3 illustrates. Reaction work-up is no more than solvent evaporation (analytically pure homoallylamine is obtained by trituration)—distillation or silica gel chromatograph is, again, not needed. In some embodiments, such a simple and cost effective product isolation procedure (no need for expensive chromatography solvents) is largely due to the diphenylphosphinoyl unit.

Scheme 3. A practical catalytic protocol.

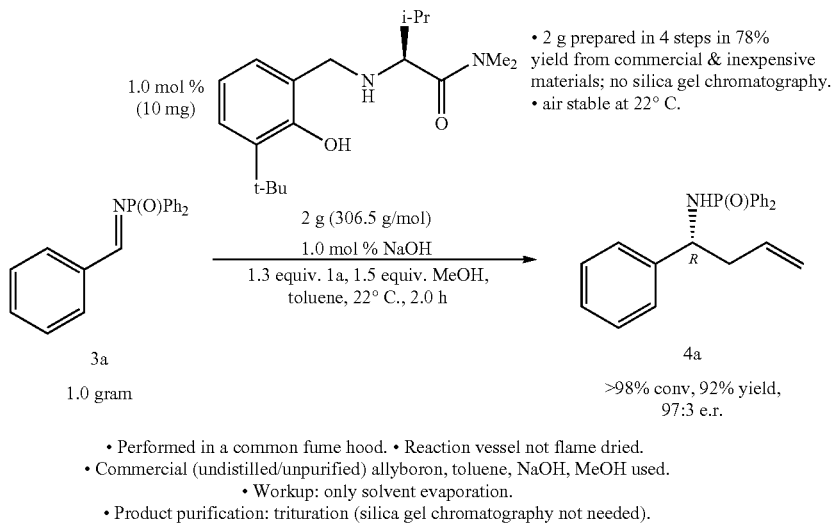

- 2 g prepared in 4 steps in 78% yield from commercial & inexpensive materials; no silica gel chromatography.
- air stable at 22° C.

>98% conv, 92% yield, 97:3 e.r.

- Performed in a common fume hood. • Reaction vessel not flame dried.
- Commercial (undistilled/unpurified) allyboron, toluene, NaOH, MeOH used.
- Workup: only solvent evaporation.
- Product purification: trituration (silica gel chromatography not needed).

The molecular weight of 2g is 306.5 g/mol, only 10 mg of the chiral amino alcohol is needed (1.0 mol % loading) for the reaction to proceed to complete conversion within two hours at room temperature, affording 4a in 92% yield and 97:3 e.r. It can be prepared on a multi-gram scale by an uncomplicated four-step sequence involving valine, inexpensively available as either enantiomer. The catalytic enantioselective process, which requires ordinary NaOH pellets as base (1.0 mol %), is readily performed in a regular fume hood, in vessels that are not flame-dried, with reagent (1a), base and alcohol additive obtained directly from bottles purchased from a vendor. Work-up is no more than evaporation of the solvent (toluene), and product purification to obtain the analytically pure homoallylamine consists of simple trituration; distillation or silica gel chromatography is, again, not needed.

As the reaction with $d_2$-1a in Scheme 4 illustrates, the overall transformation takes place with net α-selectivity ($d_2$-4a formed with >95% selectivity). The method's ability to cause the conversion of the C—B bond of an allylboron to a C—C bond, while generating a new N-substituted stereogenic center is significant, as illustrated by syntheses of 11 and 13 (Scheme 4). When enantiomerically enriched allylboron 10, accessed in 95:5 e.r. by Cu-catalyzed protocols (Ito, H.; Ito, S.; Sasaki, Y.; Matsuura, K. & Sawamura, M. Copper-catalyzed enantioselective substitution of allylic carbonates with diboron: An efficient route to optically active a-chiral allylboronates. *J. Am. Chem. Soc.* 129, 14856-14857 (2007); Guzman-Martinez, A. & Hoveyda, A. H. Enantioselective synthesis of allylboronates bearing a tertiary or quaternary B-substituted carbon by NHC—Cu-catalyzed substitution reactions. *J. Am. Chem. Soc.* 132, 10634-10636 (2010)), is used, homoallyl amide 11 is obtained in 93% yield, 84:16 diastereomeric ratio (d.r.) and 93.5:6.5 e.r. (for the major diastereomer). Similarly, reaction with allylboron 12 (Guzman-Martinez, A. & Hoveyda, A. H. Enantioselective synthesis of allylboronates bearing a tertiary or quaternary B-substituted carbon by NHC—Cu-catalyzed substitution reactions. *J. Am. Chem. Soc.* 132, 10634-10636 (2010)), bearing a boron-substituted quaternary carbon stereogenic center (95:5 e.r.), delivers 13 in 70% yield, 89:11 d.r. and 94:6 e.r. (for the major diastereomer). In both instances, addition occurs with complete α-selectivity (>98%). It is important to note that: (1) the alternative diastereomeric products can be synthesized simply through the use of the alternative enantiomer of a chiral allylboron; reaction with S-10 affords the corresponding diastereomer of 11 with virtually identical efficiency and selectivity; (2) A portion of the minor product diastereomer arises from minor enantiomer the allylborons 10 and 11; reagents of higher enantiomeric purity, which might become available through future advances, should translate to improved stereochemical purity; and (3) Reaction with the sterically demanding 12 (Cy is cyclohexyl) proceeds more readily when performed at 50° C. and with $Zn(Ot-Bu)_2$, without the intention to be limited by any theory, probably because generation of the chiral allylboron is otherwise less efficient.

The α-selectivity is also confirmed by the reaction between 3m and $d_2$-1a, which provides dr-4-o with 95% selectivity. Homoallylic amide 4o can be used in enantioselective synthesis of anti-cancer agents aza-epothilones. The ability to convert the C—B of an allylboron entity to a C—C bond, while generating a N-substituted stereogenic center, has critical implications in stereoselective synthesis. With allylboron S-9 or its enantiomer R-9, accessed in 94:6 e.r. by a Cu-catalyzed protocol (Guzman-Martinez, A. & Hoveyda, A. H. Enantioselective synthesis of allylboronates bearing a tertiary or quaternary B-substituted stereogenic carbon by NHC—Cu-catalyzed substitution reactions. *J. Am. Chem. Soc.* 132, 10634-10637 (2010)), homoallylamides 10b and 11b are obtained in 84% and 93% yield, 84:16 and 83:17 diastereomeric ratio (d.r.), respectively, and 95:5 e.r. (for the major diastereomer); reaction with allylboron 12b, bearing a quaternary carbon stereogenic center (95:5 e.r.), delivers 13 in 7-% yield (pure diastereomer), 89:11 d.r. and 95:5 e.r. (major isomer) (Scheme 4). Alternative diastereomeric products can be synthesized through the use of the other enantiomer of a chiral allylboron (10b versus 11b, Scheme 4). There is complete α selectivity in all instances. Reaction with sterically demanding 12b proceeds more readily when performed with $Zn(Ot-Bu)_2$.

Scheme 4. More examples - α-selectivity.

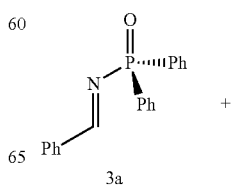

3a

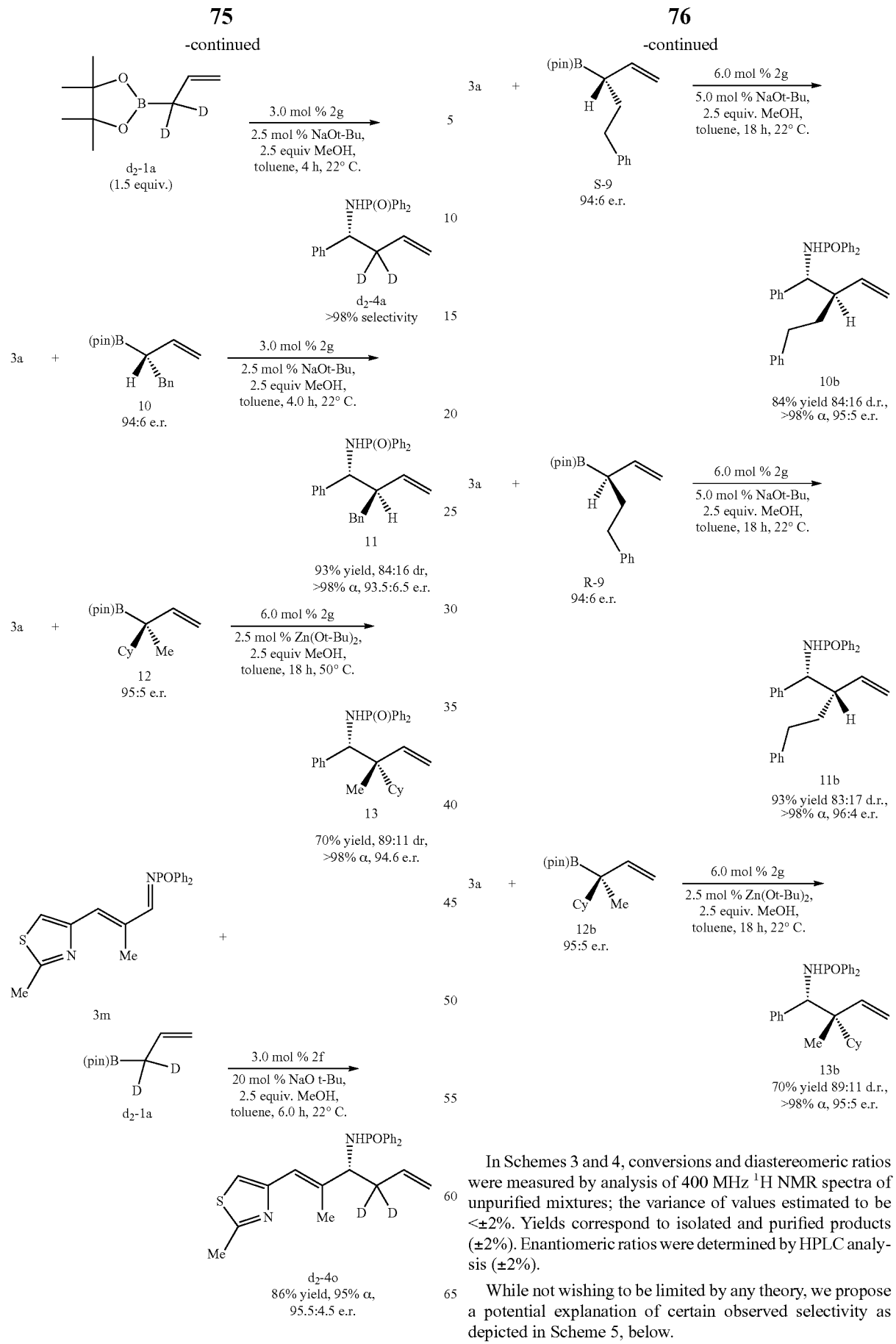

In Schemes 3 and 4, conversions and diastereomeric ratios were measured by analysis of 400 MHz $^1$H NMR spectra of unpurified mixtures; the variance of values estimated to be <±2%. Yields correspond to isolated and purified products (±2%). Enantiomeric ratios were determined by HPLC analysis (±2%).

While not wishing to be limited by any theory, we propose a potential explanation of certain observed selectivity as depicted in Scheme 5, below.

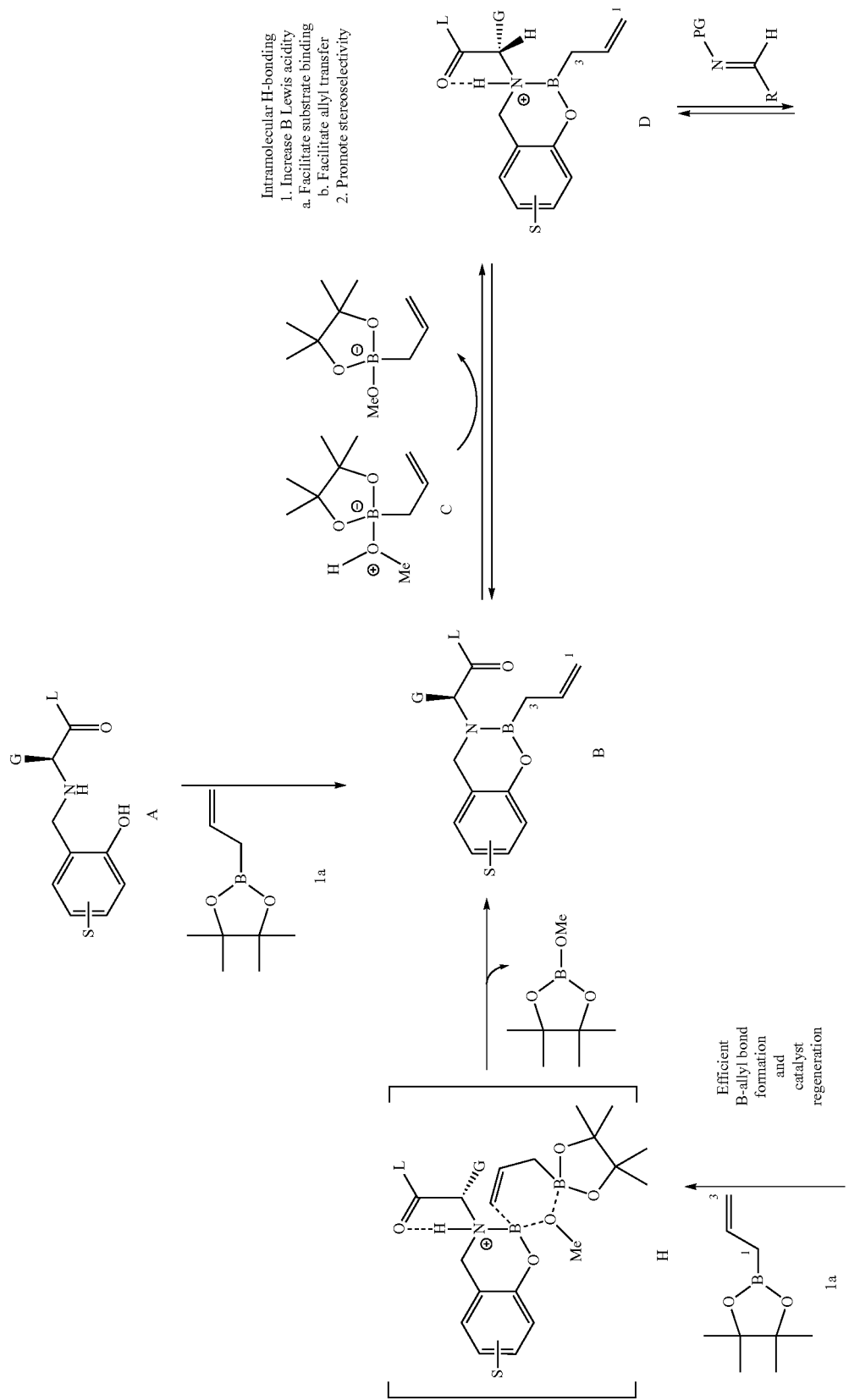
Scheme 5. Potential mechanistic model for certain selectivity.

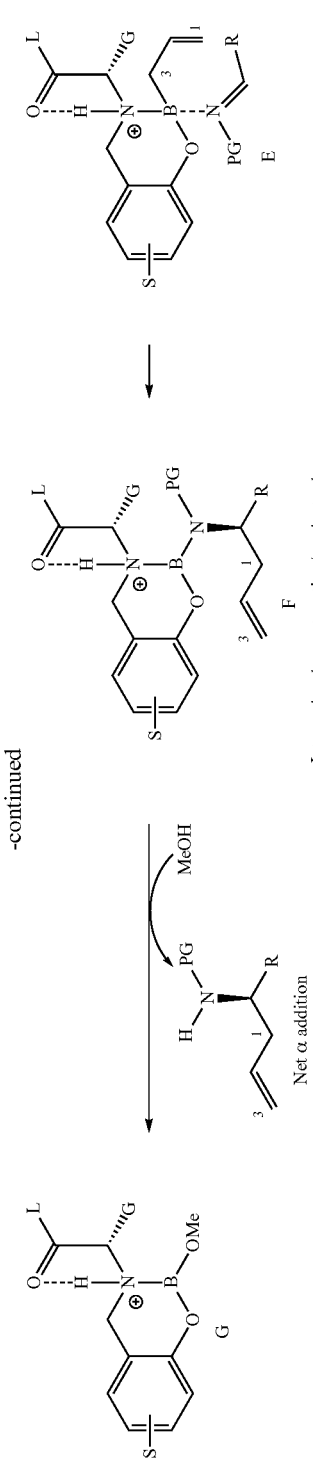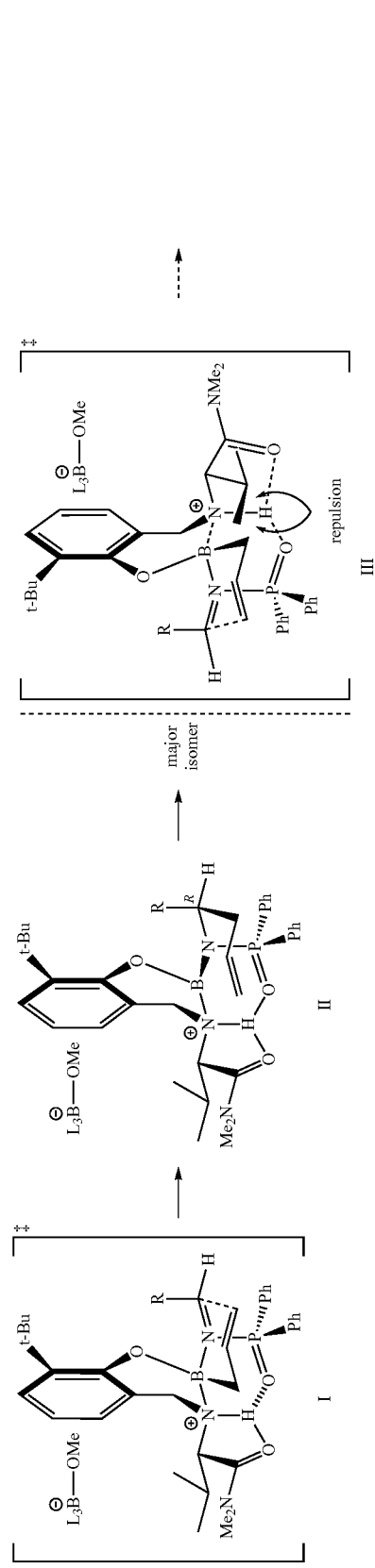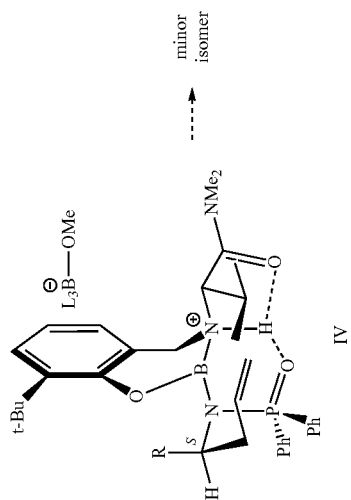

-continued
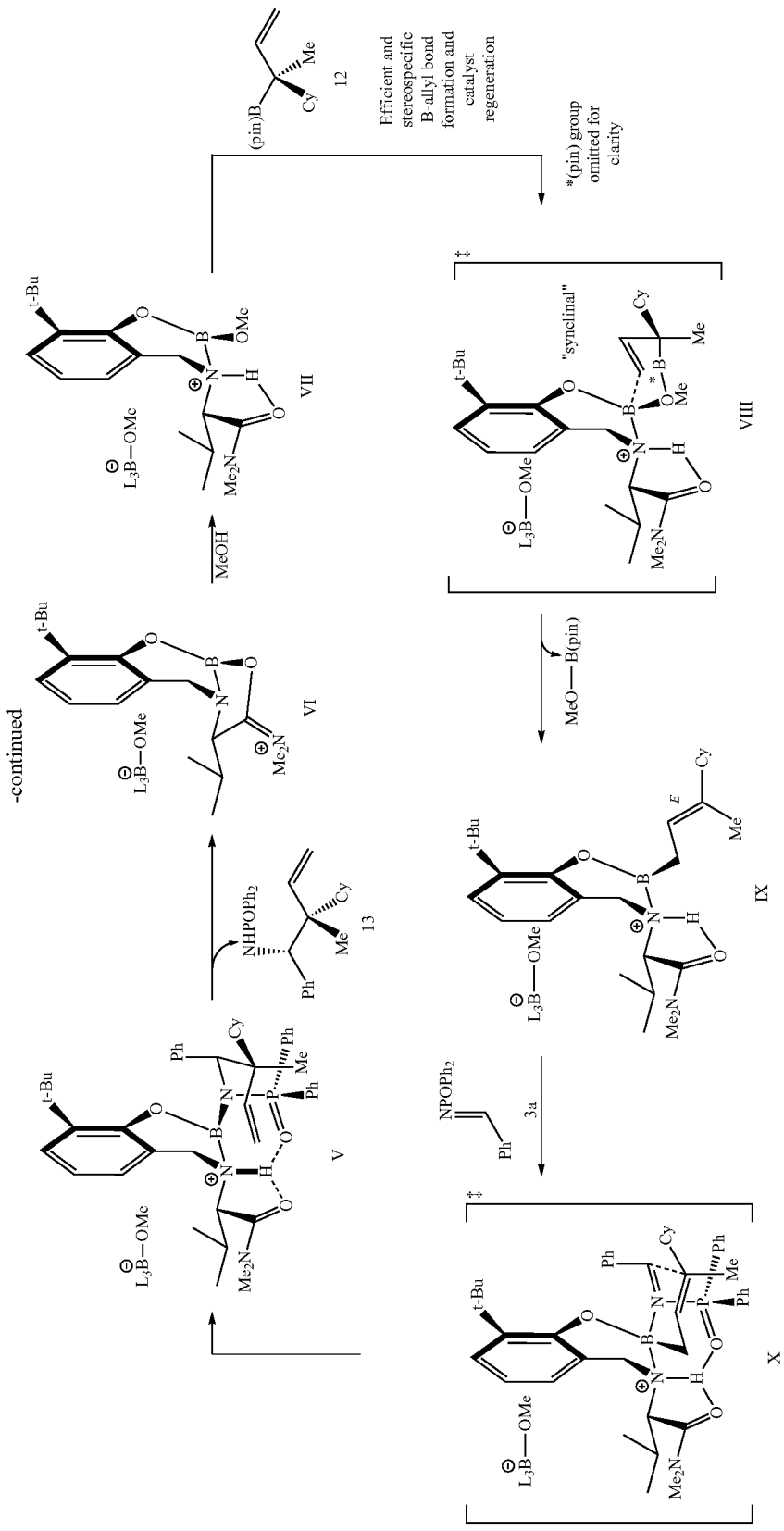

Catalytic and Enantioselective Additions to Isatins

The provided method comprising using a compound of formula I can be applied to reactions with carbonyl-containing substrates, entities that do not readily lend themselves to chiral auxiliary approaches. The chiral catalyst derived from compound 2g promoted efficient and enantioselective additions to isatins, potential precursors to chiral tertiary alcohols that can be used in synthesis of biologically significant molecules and drug development. As the data summarized in Table 5 illustrate, in the presence of 0.5-2.0 mol % 2g and 1.5 equivalents of an allylboron reagent, reaction is complete at 22° C. within 30 minutes to two hours, affording the desired enantiomerically pure homoallylic alcohols in 91-98% yield and 91.5:8.5-98.5:1.5 e.r. Similar to aryl-substituted aldimines, transformations with 2-substituted allylborons (Table 5, entry 5) as well as sterically demanding (entry 2), electron-rich (entry 3) or electron-deficient (entry 4) substrates are equally suitable. Without wishing to be limited by any theory, a stereochemical model was offered in Scheme 7. Allyl addition to acetophenone under the same conditions proceeded efficiently with 75:25 e.r.

TABLE 5

Catalytic enantioselective allyl additions to isatins.*

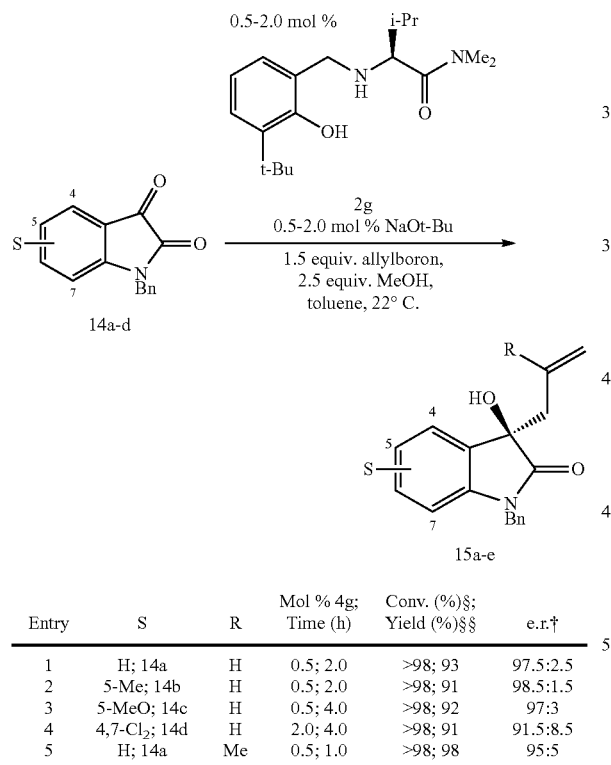

| Entry | S | R | Mol % 4g; Time (h) | Conv. (%)§; Yield (%)§§ | e.r.† |
|---|---|---|---|---|---|
| 1 | H; 14a | H | 0.5; 2.0 | >98; 93 | 97.5:2.5 |
| 2 | 5-Me; 14b | H | 0.5; 2.0 | >98; 91 | 98.5:1.5 |
| 3 | 5-MeO; 14c | H | 0.5; 4.0 | >98; 92 | 97:3 |
| 4 | 4,7-Cl$_2$; 14d | H | 2.0; 4.0 | >98; 91 | 91.5:8.5 |
| 5 | H; 14a | Me | 0.5; 1.0 | >98; 98 | 95:5 |

*The reactions were carried out in toluene under an atmosphere of nitrogen gas.
§Conversion measured by analysis of 400 MHz $^1$H NMR spectra of unpurified mixtures; the variance of values estimated to be <±5%.
§§Yield of isolated product after purification; the variance of values estimated to be <±2%.
†Enantiomeric ratios were determined by HPLC analysis.

More results are presented in Scheme 6, below. With 0.5-2.0 mol % 2g and 1.5 equiv. of the allylboron reagent, addition to N-protected isatins is complete at 22° C. within two hours; homoallylic alcohols are obtained in 84-98% yield and 91.5:8.5-98.5:1.5 e.r. As the syntheses of 15a' and 15b' exemplify, enantioselective allyl addition/amide deprotection can be carried out in a single vessel easily and with exceptional efficiency. Homoallyl carbinol 15a' is applicable to the synthesis of madindoline A[29] and 15b' is a potential intermediate en route to different convolutamydines. Allyl addition to acetophenone under the same conditions proceeds with high efficiency (3.0 mol % 2g, >98% conversion in 4.0 h) but in 70:30 e.r. Without wishing to be limited by any theory, a stereochemical model was offered in Scheme 6b.

Another readily accessible organoboron reagent may be used in the present set of catalytic transformations: in the presence of 0.5 mol % 2g, reaction of benzyl amide 14c' or p-methoxybenzyl amide 14d' with commercially available (pinacolato)allenylboron 19 is complete within four hours at ambient temperature, affording allenyl carbinols 20a and 20b in 98:2 and 96:4 e.r. and 91% and 90% yield, respectively. Similar to the reaction with 14d', addition to silylamide 14a' can be performed on the gram scale in a standard fume hood with 0.25 mol % 2g and 1.05 equiv. of 19, C—C bond formation is complete within two minutes and the silyl group is removed through mild acidic workup to afford 21, which can be isolated in high purity without chromatography, in 90% overall yield and >99:1 e.r. The enantioselective synthesis of α-hydroxy alcohol 22 further demonstrate utility; the enantiomerically pure diol, not easily accessed by an alternative protocol, can serve as precursor to various derivatives. All allene additions proceed with complete α selectivity (<2% of propargyl products detected).

Scheme 6. Examples of provided methods.

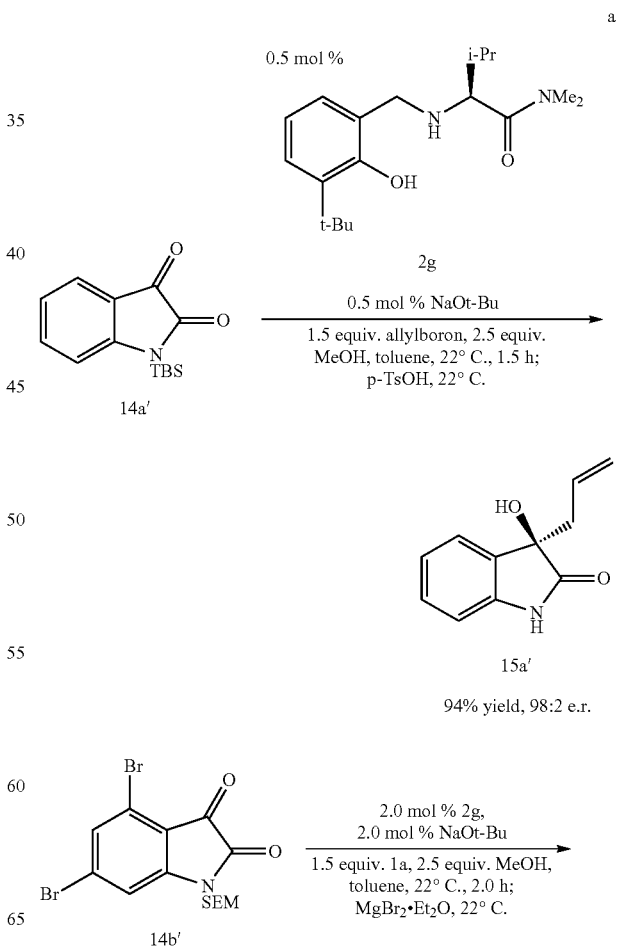

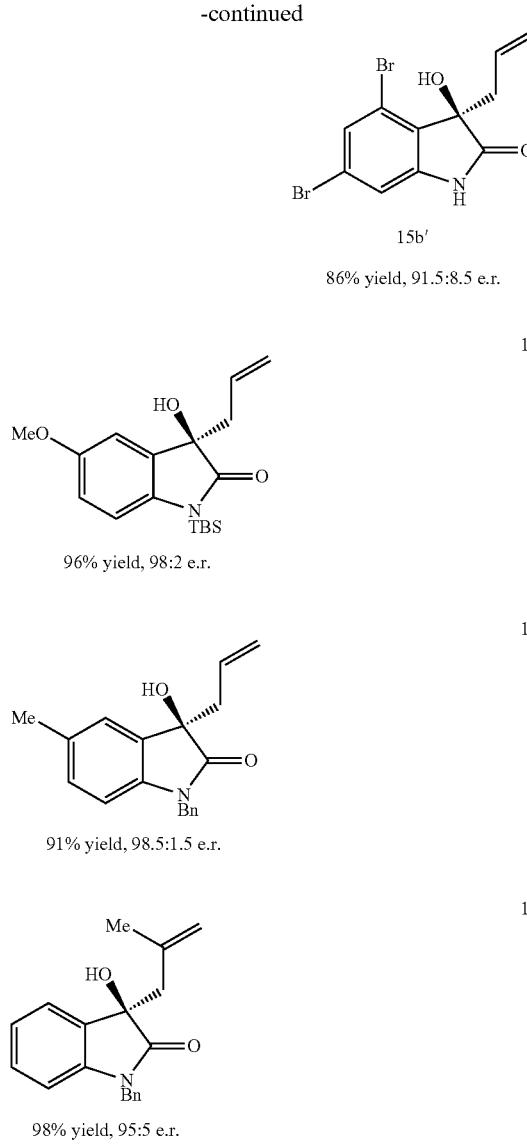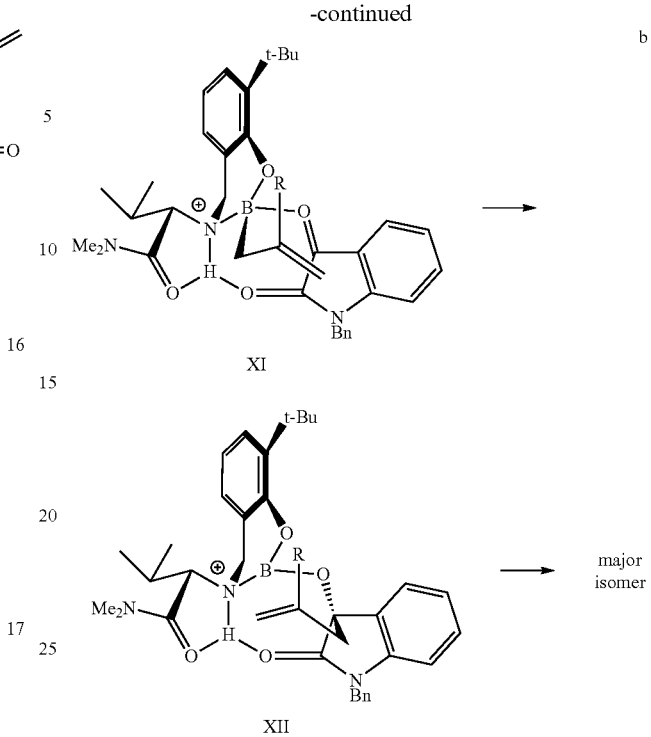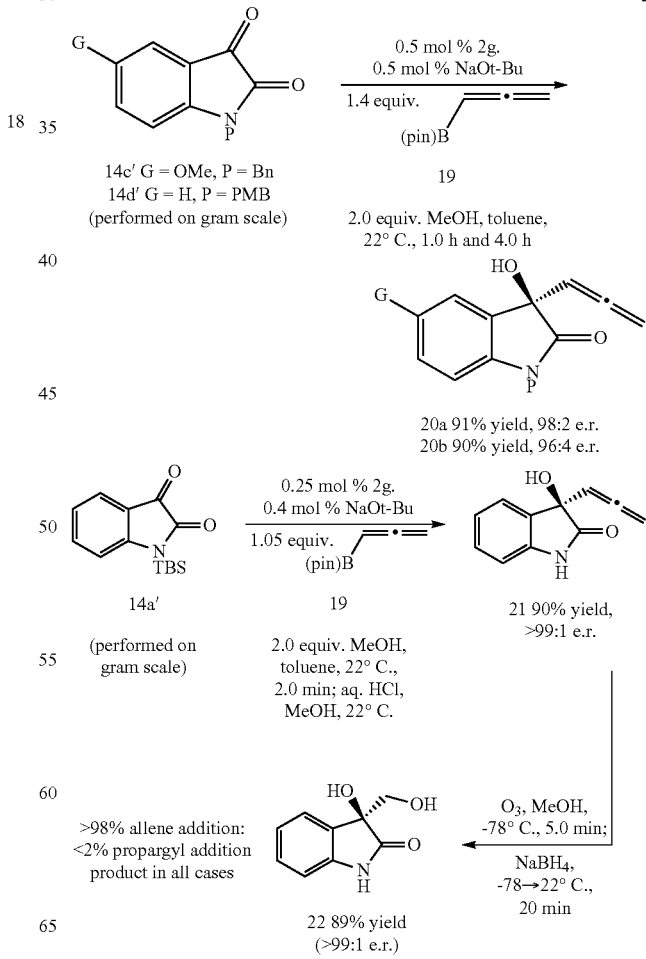

Scheme 7. Proposed model for allyl addition to isatins.

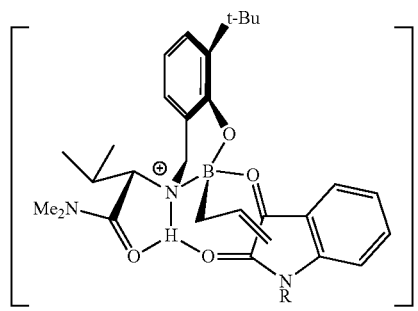

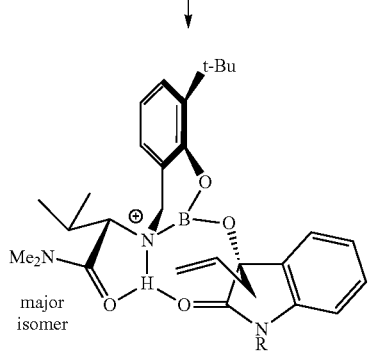

Catalytic and Enantioselective Addition to Imines Other than Phosphinoyl Imines

Besides phosphinoyl amine, highly enantioselective additions were achieved with other imines. In some embodiments, the imine is N-arylimines. A representative example is illustrated below:

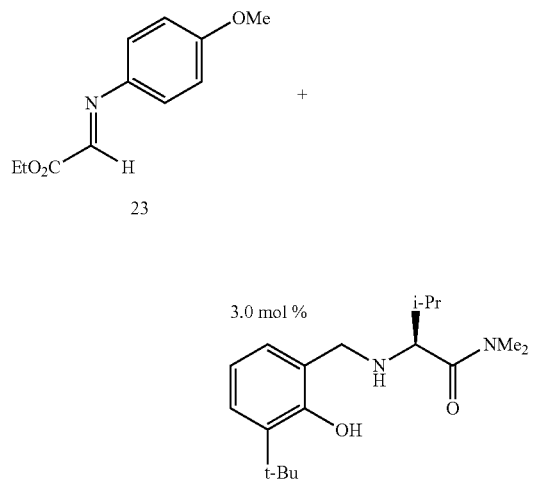

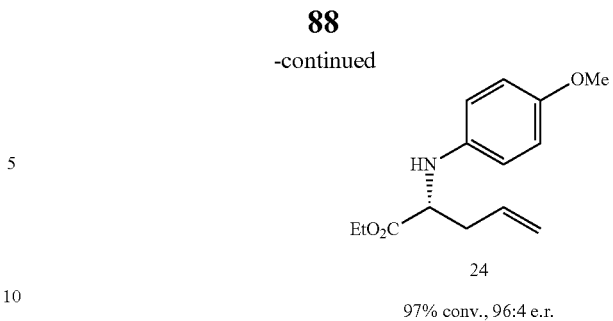

97% conv., 96:4 e.r.

The N-aryl imine 23 reacted with the allylboron reagents in the presence of 3.0 mol % catalyst 2g to afford the product 24 with 97% conversion and 96:4 e.r.

Reversal of Site Selectivity in the Catalytic Allyl Additions (from Net α- to Net γ-Selective)

As described above, in many embodiments, the reaction between allylboron and an imine or carbonyl group proceeds with α-selectivity. It is surprising found that in the presence of catalytic amounts of a Zn alkoxide, reactions of 3-substituted allylboron reagents proceed with exceptional net γ selectivity (vs. α selectivity with the unsubstituted allylboronates) to afford the desired products with exceptional efficiency as well as enantio- and diastereoselectivity. An example is depicted below:

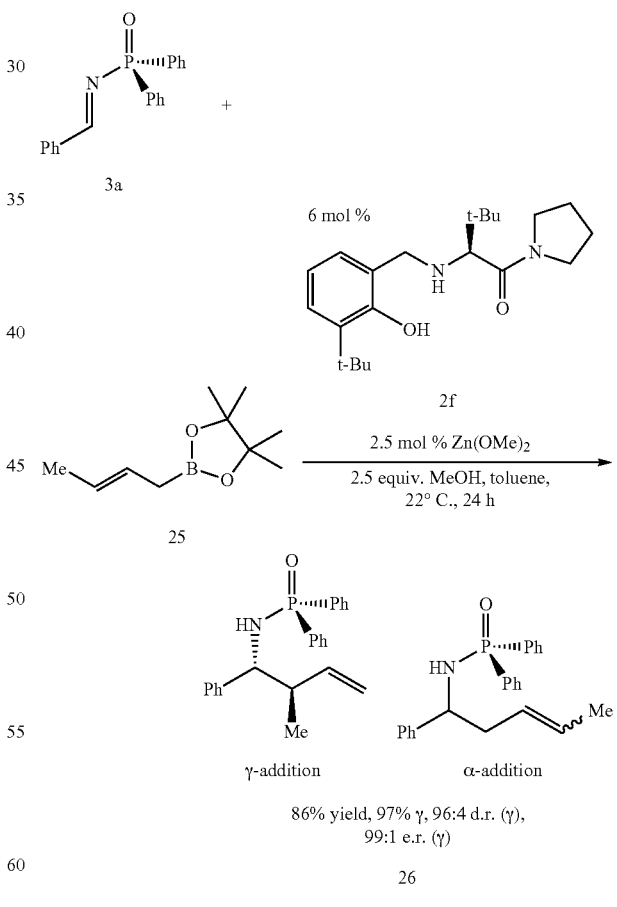

Phosphinoyl imine 3a reacted with 3-methylallylboron reagent 25 in the presence of 6 mol % 2f and 2.5 mol % Zn(OMe)$_2$ to afford product 26 with high the γ-selectivity (97%), d.r. (96:4 for the γ-addition product) and e.r. (99:1 for the γ-addition product).

Provided Methods have Broad Substrate Scope

In some embodiments, the present invention provide a method for catalytic and enantioselective addition of an allyl group to a carbonyl group. As a non-limiting example, chiral catalyst 2j allowed for efficient and highly enantioselective addition of ally groups to ketones, as depicted below:

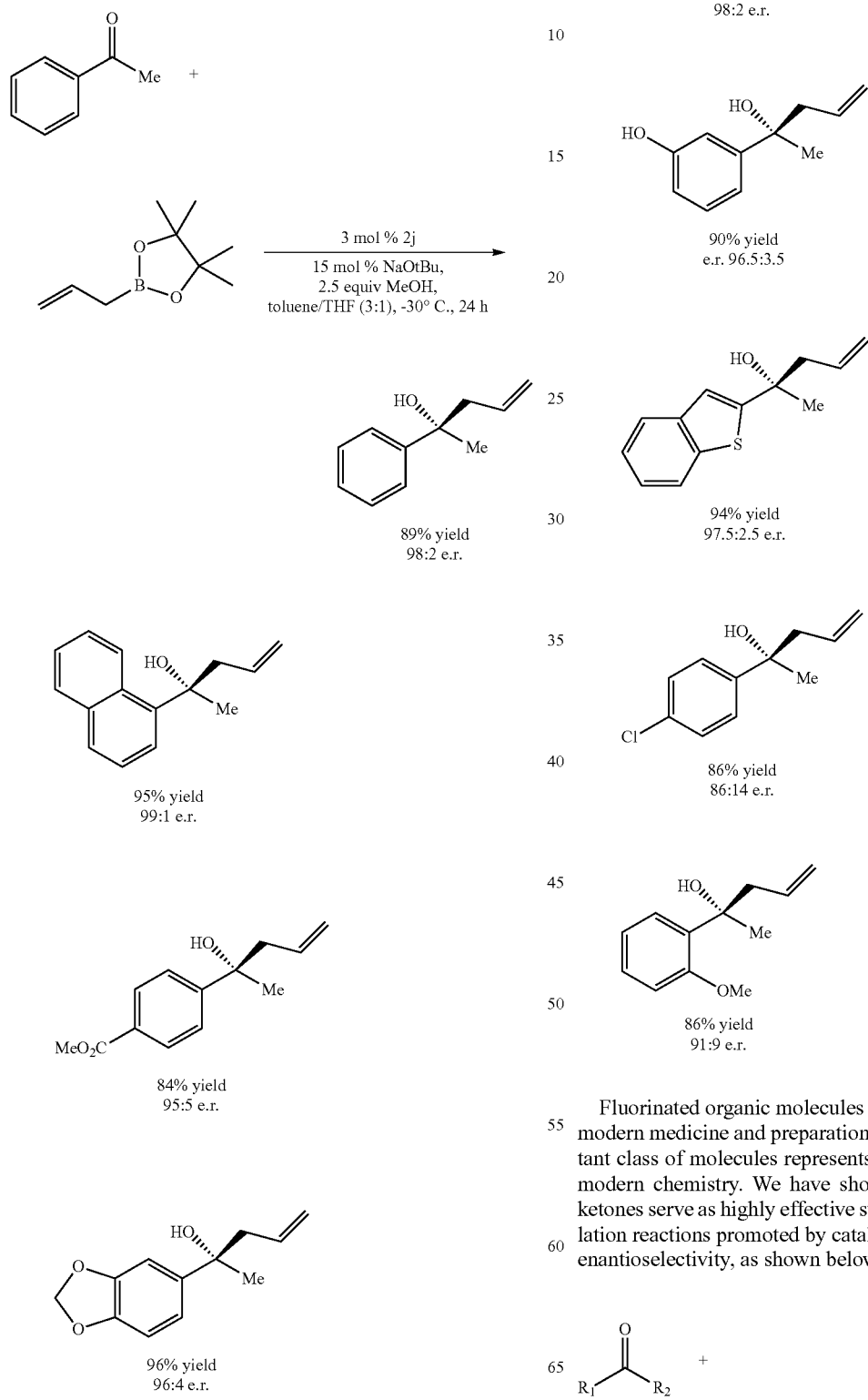

Fluorinated organic molecules are of great significance to modern medicine and preparation of members of this important class of molecules represents a compelling objective in modern chemistry. We have shown that fluoro-substituted ketones serve as highly effective substrates that undergo allylation reactions promoted by catalyst 2g with unprecedented enantioselectivity, as shown below:

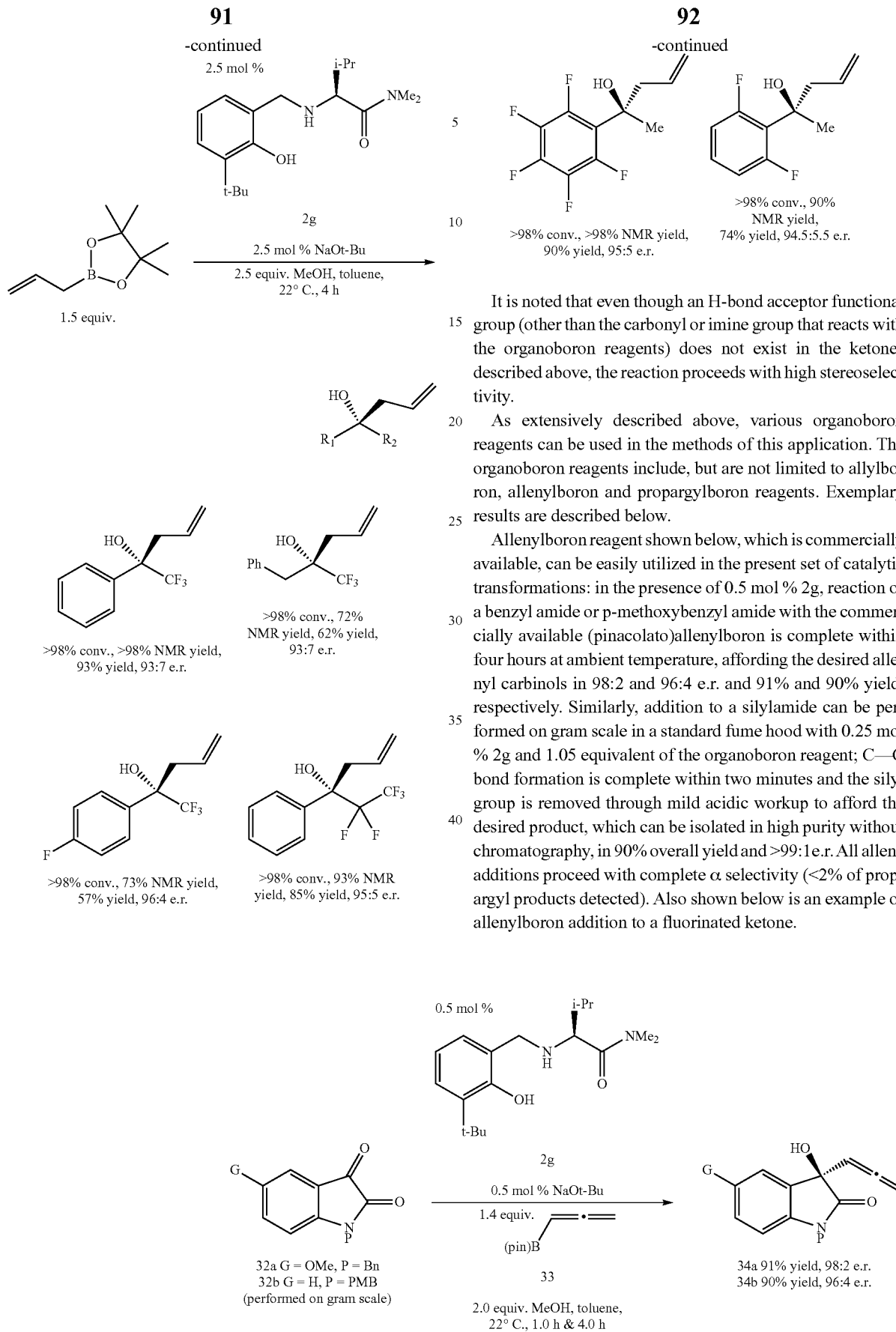

It is noted that even though an H-bond acceptor functional group (other than the carbonyl or imine group that reacts with the organoboron reagents) does not exist in the ketones described above, the reaction proceeds with high stereoselectivity.

As extensively described above, various organoboron reagents can be used in the methods of this application. The organoboron reagents include, but are not limited to allylboron, allenylboron and propargylboron reagents. Exemplary results are described below.

Allenylboron reagent shown below, which is commercially available, can be easily utilized in the present set of catalytic transformations: in the presence of 0.5 mol % 2g, reaction of a benzyl amide or p-methoxybenzyl amide with the commercially available (pinacolato)allenylboron is complete within four hours at ambient temperature, affording the desired allenyl carbinols in 98:2 and 96:4 e.r. and 91% and 90% yield, respectively. Similarly, addition to a silylamide can be performed on gram scale in a standard fume hood with 0.25 mol % 2g and 1.05 equivalent of the organoboron reagent; C—C bond formation is complete within two minutes and the silyl group is removed through mild acidic workup to afford the desired product, which can be isolated in high purity without chromatography, in 90% overall yield and >99:1 e.r. All allene additions proceed with complete α selectivity (<2% of propargyl products detected). Also shown below is an example of allenylboron addition to a fluorinated ketone.

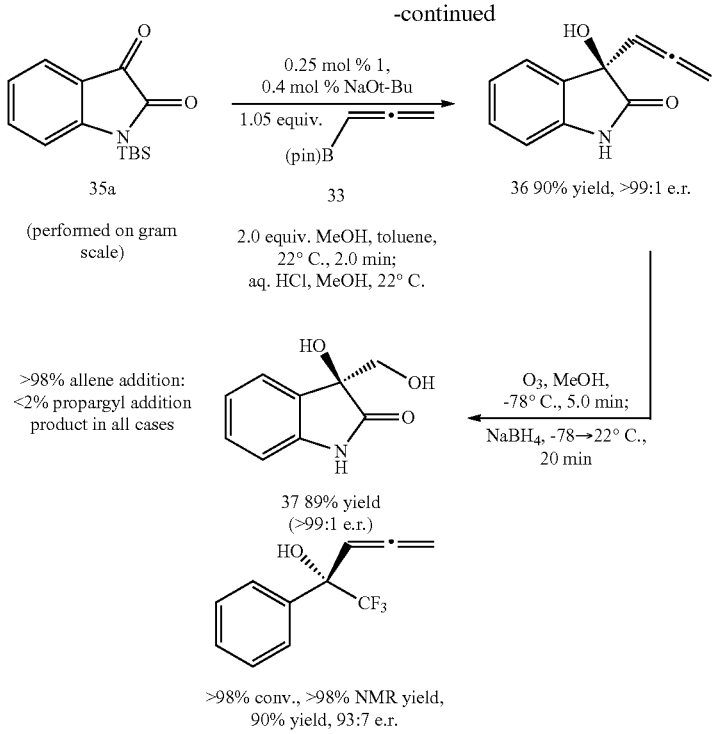

36 90% yield, >99:1 e.r.

37 89% yield (>99:1 e.r.)

>98% allene addition:
<2% propargyl addition product in all cases

>98% conv., >98% NMR yield, 90% yield, 93:7 e.r.

As demonstrated below, propargylboron reagents can be utilized as well to afford homopropargyl alcohol enantioselectively. All substrate classes mentioned thus far can be used in conjunction with any of these readily accessible organoboron reagents.

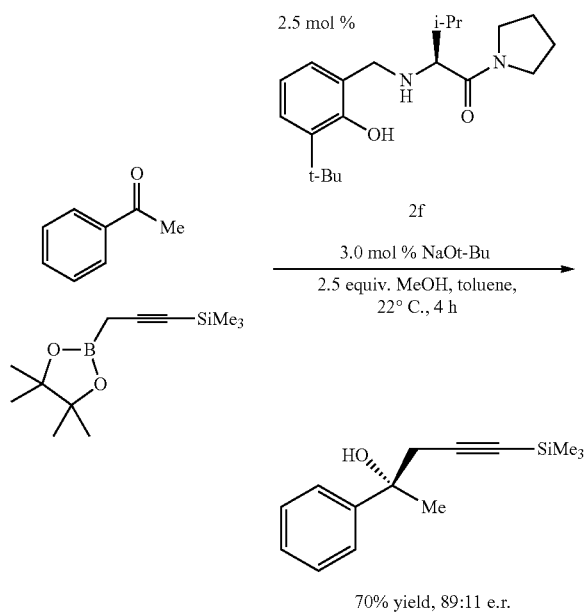

70% yield, 89:11 e.r.

Summary.

We have designed a new class of compounds of formula I and provided a new method that promotes transfer of an organic group, such as an allyl, allenyl or propargyl unit, from an organoboron reagent to a double bond, for example, an imine or a carbonyl group. In some embodiments, the transfer is performed under mild conditions and with exceptional efficiency and enantioselectivity. The new method, remarkably simple to perform on a significant variety of substrates and with a number of different allylborons, satisfies nearly every requirement that characterizes a truly valuable catalytic process. There is a range of available organoborons that can be catalytically reacted with a large assortment of imine- and carbonyl-based substrates; such transformations can afford an enormous variety of valuable products, many otherwise difficult to obtain, in high enantiomeric purity. The above attributes, the fundamental importance of amines and alcohols to the preparation of biologically active molecules, as well as the ease, economy and selectivity with which this class of catalytic transformations proceed, makes this invention very important and useful in chemical synthesis. The ease of accessing the present class of catalysts, the importance of amines and alcohols to the preparation of biologically active molecules, as well as the simplicity, economy and selectivity with which the catalytic transformations proceed, foreshadow a lasting impact on future efforts in catalyst development and chemical synthesis.

Exemplary Procedures

Preparation of Catalyst Solution:

Aminophenol 2g (15.0 mg, 0.049 mmol) is weighed out in a 4 ml vial to which is added 263 ml of a solution of sodium hydroxide (1.95 mg, 0.049 mmol) in reagent grade methanol [a 111 mg NaOH pellet (Fisher) is dissolved in 15 ml solvent]. After evaporation of the solvent, 0.5 ml of technical grade anhydrous toluene is added and concentrated in vacuo to remove residual methanol and water. The obtained white solid is dried at 0.5 Torr for 30 min and the vial sealed with a cap containing a teflon septum. Toluene (1.0 ml) is added to yield a suspension.

Gram-Scale Procedure for Allyl Addition:

A round bottom flask (50 ml, not flame dried, equipped with a magnetic stirring bar) is charged with imine 3a (1.0 g, 3.28 mmol) and subjected to 0.5 Torr for 30 min, purged with dry nitrogen and sealed with a rubber septum. Toluene (30 ml) is added, followed by allylboronic acid pinacol ester (800 ml, 4.26 mmol, 1.3 equiv.) from a septum sealed bottle (Frontier Scientific, used as received) and methanol (200 ml, 4.92 mmol, 1.5 equiv.) from a septum-sealed bottle (Acros, grade: 99.9% ExtraDry, used as received). A suspension of the catalyst containing aminophenol 2g (10.1 mg, 0.033 mmol, 0.01 equiv.) and sodium hydroxide (1.31 mg, 0.033 mmol, 0.01 equiv.) in 0.67 ml toluene is added with a syringe to the reaction mixture. After 2 hours the solvent is evaporated and the residue is taken up in 30 ml technical grade hexanes. The suspension is sonicated for 2 min, filtered and washed 4 times with 3 ml hexanes. The product is dried at 0.5 Torr and obtained in 92% yield (1.04 g, 3.01 mmol, er=97.5/2.5). Elemental analysis for C22H22NOP: Calcd: C, 76.06; H, 6.38; N, 4.03. Found: C, 75.77; H, 6.43; N, 3.98. Characterization data match those previously reported for this compound (Kim, S. J. & Jang, D. O. Indium-mediated catalytic enantioselective allylation of N-benzohydrazones using a protonated chiral amine. J. Am. Chem. Soc. 132, 12168-12169 (2010)).

General.

Infrared (IR) spectra were recorded on a Bruker alpha spectrophotometer, $\lambda_{max}$ in $cm^{-1}$. Bands are characterized as broad (br), strong (s), medium (m), and weak (w). $^1$H NMR spectra were recorded on a Varian Unity INOVA 400 (400 MHz) spectrometer. Chemical shifts are reported in ppm from tetramethylsilane with the solvent resonance as the internal standard (CDCl$_3$: δ 7.26 ppm, CD$_3$OD: δ 3.34 ppm). Data are reported as follows: chemical shift, integration, multiplicity (s=singlet, d=doublet, t=triplet, q=quartet, sept=septet, br=broad, m=multiplet), and coupling constants (Hz). $^{13}$C NMR spectra were recorded on a Varian Unity INOVA 400 (100 MHz) or a Varian Unity INOVA 500 (125 MHz) spectrometer with complete proton decoupling. Chemical shifts are reported in ppm from tetramethylsilane with the solvent resonance as the internal standard (CDCl$_3$: δ 77.16 ppm). Data are reported as follows: chemical shift, multiplicity (singlet unless otherwise noted), and coupling constants (Hz). $^2$H NMR spectra were recorded on a Varian Unity INOVA 500 (76 MHz) tuned to the lock channel. High-resolution mass spectrometry was performed on a JEOL AccuTOF-DART (positive mode) at the Mass Spectrometry Facility, Boston College. Enantiomer ratios (er) values were determined by HPLC analysis using either a Shimadzu LC-2010AHT or SCL-10AVP chromatograph (Chiral Technologies Chiralcel OD (4.6×250 mm), Chiral Technologies Chiralcel OD-H (4.6×250 mm), Chiral Technologies Chiralcel OJ-H (4.6×250 mm), Chiral Technologies Chiralpak AD-H (4.6×250 mm), Chiral Technologies Chiralcel AZ-H (4.6×250 mm) columns), or GLPC (gas-liquid partition chromatography) with an Agilent chromatograph (Alltech Associated Chiraldex CD-BDM column (30 m×0.25 mm) or a Hewlett Packard 5890 Series II chromatograph (Alltech Associated Betadex 120 column (30 m×0.25 m). Specific rotations were measured on a Rudolph Research Analytical Autopol IV Polarimeter. Melting points were determined using a Thomas Hoover Unimelt capillary melting point apparatus.

Solvents:

Unless otherwise noted, solvents were purged with Ar and purified under a positive pressure of dry Ar by a modified Innovative Technologies purification system. Toluene (Fisher, ACS Grade) was passed successively through activated copper and alumina columns. Dichloromethane (Fisher, ACS Grade) and diethyl ether (Aldrich, Chromasolv®) were passed successively through two activated alumina columns. Tetrahydrofuran was purified by distillation from sodium benzophenone ketyl immediately prior to use. Dimethyl Sulfoxide (anhydrous, 99.9+%) was purchased from Alfa Aesar and used as received. CDCl$_3$ was purchased from Cambridge Isotope Laboratories and stored over activated 4 Å molecular sieves prior to use. CD$_3$OD was purchased from Cambridge Isotope Laboratories and used as received. CD$_3$C6D$_5$ (d$_8$-toluene) was purchased from Cambridge Isotope Laboratories and distilled from sodium metal onto activated 4 Å molecular sieves prior to use. All work-up and purification procedures were carried out in air with reagent grade solvents (purchased from Fisher).

Reagents:

Allenylboronic Acid Pinacol Ester (19) was obtained from Frontier Scientific and used as received.

Allylboronates:

Allylboronic acid pinacol ester (1a) was purchased from Aldrich or obtained as a gift from Frontier Scientific, Inc and distilled prior to use. 1,1-Di-deuterioallylboronic acid pinacol ester (d$_2$-1a) was synthesized and purified in accordance with a procedure in the literature. (2-Methylallyl)boronic acid pinacol ester (1b) was synthesized and purified in accordance with a procedure in the literature. (2-Phenylallyl)boronic acid pinacol ester (1c) was synthesized and purified in accordance with a procedure in the literature. Enantiomerically enriched α-substituted allylboronates S-9, R-9, and 12b were synthesized and purified in accordance with a procedure in with the literature.

Benzyl Chloride was purchased from Aldrich and distilled from CaCl$_2$ prior to use.

Boc-Val-OH was purchased from Advanced ChemTech and used as received.

tert-Butanol was purchased from Aldrich and distilled from sodium metal before use.

n-Butylamine was purchased from Aldrich and used as received.

tert-Butyldimethylsilyl Chloride was purchased from Strem and used as received.

3-tert-Butyl-2-hydroxybenzaldehyde was purchased from Aldrich and used as received.

1,8-Diazabicycloundec-7-ene (DBU) was purchased from Aldrich and distilled from CaH$_2$ prior to use.

Diethylzinc was purchased from Aldrich and used as received.

Dimethylamine (40 wt % in H$_2$O) was purchased from Aldrich and used as received.

1-Ethyl-3-(3-dimethylaminopropyl)carbodiimide Hydrochloride (EDC.HCl) was purchased from Advanced ChemTech and used as received.

Hydrochloric Acid (4.0 M in 1,4-dioxane) was purchased from Aldrich and used as received.

Hydrochloric Acid (12 M, 36.5-38.0 wt %) was purchased from Alfa Aesar and used as received.

1-Hydroxy-benzotriazole Hydrate (HOBt.H$_2$O) was purchased from Advanced ChemTech and used as received.

Isatins. Isatin and 5-methylisatin were purchased from Aldrich and used as received. 5-methoxyisatin was purchased from Oakwood and used as received. 4,6-Dibromoisatin was purchased from D-L Chiral Chemicals and was dissolved in methanol and copious purple solid impurities were removed by filtration.

L-tert-Leucine was purchased from Chem-Impex and Boc protected prior to use.

Magnesium Sulfate was purchased from Fisher and flame-dried under vacuum prior to use.

Magnesium Bromide Diethyl Etherate (MgBr$_2$ Et$_2$O) was purchased from Aldrich and used as received.

Methanol was purchased from Acros (99.8% anhydrous) and distilled at 1 atm from sodium metal prior to use or used as received.
Potassium Carbonate was purchased from Fisher and dried at 80° C. under vacuum for 12 h prior to use.
Pyrroidine was purchased from Aldrich and used as received.
Sodium Borohydride was purchased from Aldrich and used as received.
Sodium tert-Butoxide was purchased from Strem and used as received.
Sodium Hydride (60 wt % in oil) was purchased from Strem and used as received.
Sodium Periodate was purchased from Acros and used as received.
Titanium Tetrachloride (TiCl$_4$) was purchased from Aldrich and used as received.
Triethylamine was purchased from Aldrich and distilled from CaH$_2$ prior to use.
2-(Trimethylsilyl)ethoxymethyl Chloride, technical grade (SEM-Cl) was purchased from Aldrich and used as received.
p-Toluenesulfonic Acid Monohydrate was purchased from Aldrich and used as received.
L-Valine Ethyl Ester Hydrochloride was purchased from Aldrich and used as received.
Zinc tert-Butoxide was prepared by reaction of tert-butanol with diethylzinc. A flame-dried round bottom flask is purged with nitrogen, sealed with a septum and electrical tape, and charged with toluene (100 mL) and tert-butanol (1.8 mL, 19 mmol) by syringe. The solution is cooled to −78° C. and diethylzinc (Caution Pyrophoric! 1.5 mL, 15 mmol) is added dropwise by syringe over 10 minutes. The reaction is allowed to warm to 22° C. and to stir for 18 h. The toluene is removed by distillation under nitrogen at 1 atm. and the resulting solid is dried under vacuum for 12 h. The solid is removed from the flask in a nitrogen-filled glovebox to afford 1.5 g (7.1 mmol, 46% yield) of a white powder.

Synthesis, Purification, and Analytical Data for Amino Acid-Based Aminophenols 2a-2h %, 80 mL) is then added and the mixture is allowed to stir for 0.5 h during which time a white precipitate is formed. The precipitate is removed by filtration and the resulting two layers are separated. The organic layer is washed sequentially with an aqueous solution of citric acid (10 wt %, 80 mL), a saturated aqueous solution of NaHCO$_3$ (80 mL), and brine (80 mL) and is dried over Na$_2$SO$_4$ to give (S)-tert-butyl(1-(dimethylamino)-3-methyl-1-oxobutan-2-yl)carbamate (S2) as pale yellow oil, which is employed without purification in the subsequent deprotection.

In a 100 mL round bottom flask, (S)-tert-butyl(1-(dimethylamino)-3-methyl-1-oxobutan-2-yl)carbamate S2 (4.65 g, 19.3 mmol, 1.00 equiv.) is allowed to stir with a 4.0 M solution of hydrochloric acid in dioxane (28.9 mL, 116 mmol, 6.00 equiv.) for 1.5 h at 22° C. under air, after which the solution is purged with nitrogen for 30 min (removal of HCl gas) and the solvent is removed under reduced pressure to yield (S)-2-amino-N,N,3-trimethylbutanamide as HCl salt S3, which is used without purification in the subsequent condensation.

To the same flask (purged with nitrogen) is added 3-(tert-butyl)-2-hydroxybenzaldehyde (3.43 g, 19.3 mmol, 1.00 equiv.) and MgSO$_4$ (6.93 g, 57.8 mmol, 3.00 equiv.), followed by the addition of dichloromethane (70 mL) and triethylamine (8.11 mL, 57.8 mmol, 3.00 equiv.) through a syringe. The mixture is allowed to stir overnight at 22° C. under nitrogen during which time the solution becomes bright yellow. The mixture is filtered through a small plug of silica gel to remove both MgSO$_4$ and triethylamine hydrochloride (which inhibits the following reduction) and silica plug is eluted with hexanes:ethyl acetate (2:1) until the solution becomes colorless. After evaporation of the volatiles, the remaining yellow oil is washed several times with hexanes (to remove residual triethylamine hydrochloride salt) and the combined filtrates are concentrated to afford (S,E)-2-((3-(tert-butyl)-2-hydroxybenzylidene)amino)-N,N,3-trimethylbutanamide (S4) as yellow oil, which is utilized without purification in the follow-up reduction procedure.

Figure 2A:
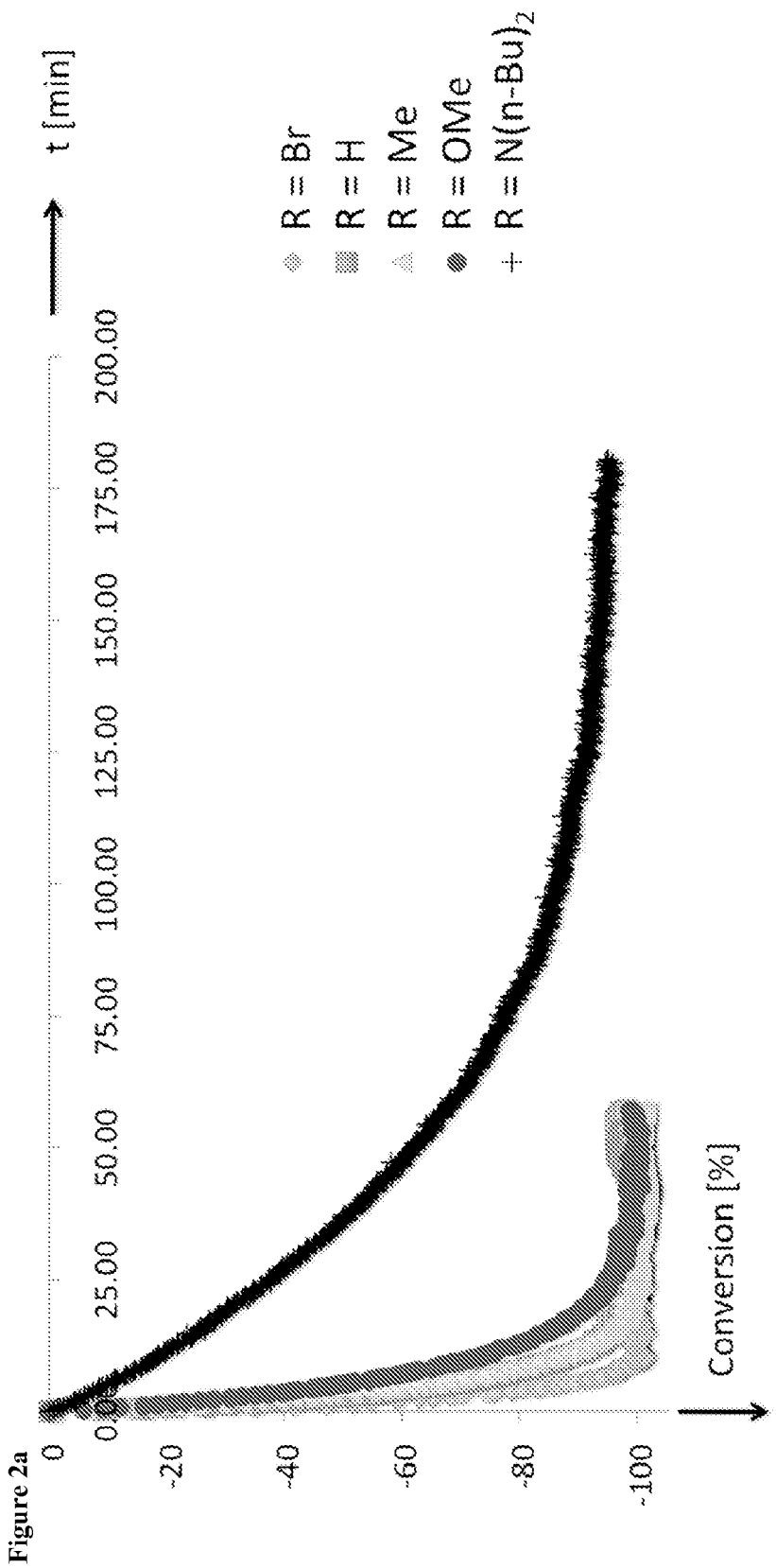
FIG. 2. (a) Conversion of Imine [%] vs Time [min]; (b) Conversion of Imine [%] vs Time [min] (Zoomed in Region); and (c) Plot of Conversion of Imine [%] vs Time [min] Including $6^{th}$-order Polymomial Fits.

Scheme S1: Representative Experimental Procedure for Synthesis of Aminophenol 2g (FIG. 2a)

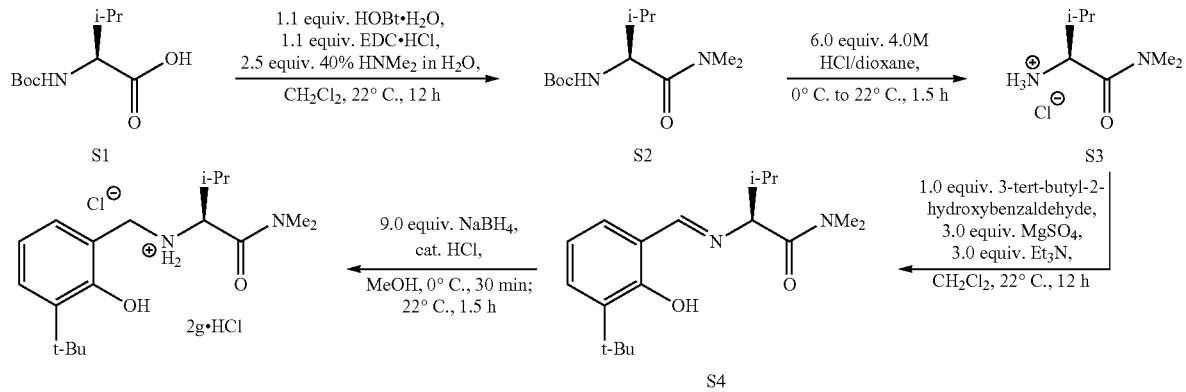

EDC.HCl (4.22 g, 22.0 mmol), reagent grade CH$_2$Cl$_2$ (80 mL), HOBt.H$_2$O (3.36 g, 22.0 mmol), and Boc-Val-OH (4.34 g, 20.0 mmol) are added successively at 22° C. under air to a 250 mL round bottom flask equipped with a stir bar. The light yellow solution is allowed to stir for five minutes and dimethylamine (40 wt % in H$_2$O, 5.3 mL, 50 mmol) is added drop-wise over one minute. The flask with the resulting light yellow solution is sealed with a rubber septum and allowed to stir for 12 h at 22° C. An aqueous solution of citric acid (10 wt To a 500 mL round bottom flask containing a solution of imine S4 in 50 mL MeOH cooled to 0° C., NaBH$_4$ is added (5.83 g, 154 mmol, 8.00 equiv.) followed by a drop of 12 M aqueous hydrochloric acid. There is vigorous gas evolution upon addition of the acid and the yellow color of the solution disappears immediately. After the solution is allowed to stir for 30 min, the excess reducing agent is quenched through slow addition of a 2.0 M solution of aqueous HCl until the pH is less than one. The aqueous phase is then washed with dichloromethane (4×50 mL) and the combined organic layers are dried over anhydrous sodium sulfate, filtered and concentrated under reduced pressure. The white solid is purified by trituration from 10 mL dichloromethane and 80 mL hexanes to afford (S)—N-(3-(tert-butyl)-2-hydroxybenzyl)-1-(dimethylamino)-3-methyl-1-oxobutan-2-aminium chloride 2g·HCl as a white solid (5.30 g, 15.5 mmol, 78% yield based on Boc-Val-NMe$_2$ S1). Crystals suitable for X-ray crystallography were grown by vapor diffusion from a dichloromethane/toluene solvent system. See Part D of the Supplementary Information for the X-ray crystal structure.

(S)—N-(3-(tert-Butyl)-2-hydroxybenzyl)-1-(dimethylamino)-3-methyl-1-oxobutan-2-aminium (2g·HCl; see above)

M.p.=182-183° C. IR (neat): 2952 (br, s), 2821 (m), 2733 (m), 1664 (s), 1649 (s), 1548 (m), 1438 (s), 1396 (s), 1373 (m), 1360 (m), 1323 (m), 1285 (m), 1209 (s), 1176 (s), 1139 (m), 1097 (m), 874 (m), 792 (m), 756 (s), 484 (m) cm$^{-1}$; $^1$H NMR (400 MHz, CDCl$_3$): δ 10.62 (1H, br s), 8.24 (1H, br s), 7.61 (1H, br s), 7.30 (1H, app dd, J=7.6, 1.6 Hz), 7.04 (1H, app dd, J=7.6, 1.6 Hz), 6.85 (1H, t, J=7.6 Hz), 4.44-4.38 (1H, m), 4.29-4.21 (2H, m), 2.95 (3H, s), 2.86 (3H, s), 2.50-2.44 (1H, m), 1.40 (9H, s), 1.13 (6H, app d, J=7.2 Hz); $^{13}$C NMR (100 MHz, CDCl$_3$): δ 166.9, 155.3, 141.3, 130.1, 129.1, 121.0, 119.9, 61.0, 47.9, 37.6, 36.2, 35.2, 30.3, 30.0, 18.7, 18.5.

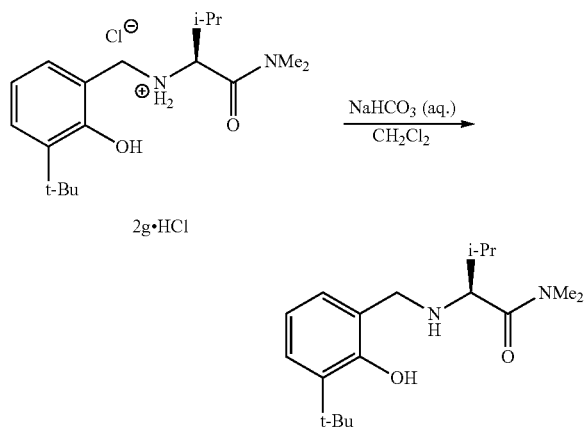

(S)-2-((3-(tert-Butyl)-2-hydroxybenzyl)amino)-N,N,3-trimethylbutanamide (2 g)

The salt 2g·HCl (5.30 g, 15.5 mmol) is dissolved in 100 mL dichloromethane and deprotonated with 200 mL of a saturated aqueous solution of NaHCO$_3$. The layers are separated and the aqueous phase is washed twice with 50 mL dichloromethane. The combined organic phases are dried over anhydrous sodium sulfate, filtered and concentrated under reduced pressure to afford 2g as white solid (4.45 g, 14.5 mmol, 73% yield based on Boc-Val-NMe$_2$ S1). Crystals suitable for X-ray crystallography were grown by slow evaporation of ethyl acetate. See Part D of the Supplementary Information for the X-ray crystal structure. M.p.=97-99° C. IR (neat): 3310 (w), 2943 (w, br), 2872 (w, br), 1638 (s), 1589 (w), 1485 (m), 1459 (m), 1241 (m), 1183 (m), 929 (m), 870 (w), 855 (w), 841(w), 753 (s), 648 (w) cm$^{-1}$; $^1$H NMR (400 MHz, CDCl$_3$): δ 11.03 (1H, br s), 7.19 (1H, app dd, J=7.0, 1.2 Hz), 6.80-6.75 (1H, m), 6.70 (1H, t, J=7.6 Hz), 4.10 and 3.46 (2H, ABq, J$_{AB}$=13.6 Hz), 3.28 (1H, br s), 3.04 (3H, s), 2.89 (3H, s), 2.65 (1H, br s), 1.90-1.84 (1H, m), 1.42 (9H, s), 0.97 (3H, d, J=6.8 Hz), 0.94 (3H, d, J=6.9 Hz); $^{13}$C NMR (100 MHz, CDCl$_3$): δ 173.6, 157.1, 137.1, 126.9, 126.2, 122.9, 118.5, 61.2, 51.5, 37.1, 35.8, 34.8, 31.3, 29.6, 20.1, 18.0; HRMS Calcd for C$_{18}$H$_{31}$N$_2$O$_2$ [M+H]$^+$: 307.23855. Found: 307.23736. [α]$^{20}$$_D$=−37 (c=0.68, CHCl$_3$).

(S)—N-Butyl-2-((2-hydroxybenzyl)amino)-3-methylbutanamide (2a)

The title compound is prepared according to the representative synthesis of aminophenol 2g except for the following changes: 1) For the amide formation (step 1), 2.5 equiv. of neat n-butylamine is used instead of dimethylamine. 2) For the imine formation (step 3) salicylaldehyde is utilized. 3) The product from the reduction is quenched with a saturated solution of aqueous NaHCO$_3$ (formation of the HCl salt is omitted) and the aminophenol is then purified by silica gel chromatography (100% dichloromethane to 98:2 dichloromethane:methanol) to afford 2a as an off-white solid. M.p.=50-52° C. IR (neat): 3318 (w), 3294 (w, br), 3255 (w), 2958 (w), 2930 (w, br), 2872 (w), 1628 (s), 1560 (m), 1469 (m), 1387 (w), 1253 (s), 1101 (w), 970 (w), 750 (s), 682 (w, br) cm$^{-1}$; $^1$H NMR (400 MHz, CDCl$_3$): δ 10.58 (1H, br s), 7.18 (1H, app dt, J=7.9, 1.4 Hz), 6.93 (1H, d, J=7.6 Hz), 6.85 (1H, d, J=8.1 Hz), 6.77 (1H, t, J=7.1 Hz), 5.46 (1H, br s), 4.10 and 3.64 (2H, ABq, J$_{AB}$=13.9 Hz), 3.34 (2H, app. dd, J=13.0, 7.1 Hz), 2.66 (1H, d, J=7.0 Hz), 2.41 (1H, br s), 1.94-1.85 (1H, m), 1.56-1.49 (2H, m), 1.42-1.33 (2H, m), 1.01 (3H, d, J=6.8 Hz), 0.97-0.93 (6H, m); $^{13}$C NMR (100 MHz, CDCl$_3$): δ 172.6, 158.1, 129.1, 128.8, 122.4, 119.3, 116.5, 67.5, 51.0, 39.4, 31.9, 31.7, 20.2, 19.8, 19.2, 13.9; HRMS Calcd for C$_{16}$H$_{27}$N$_2$O$_2$ [M+H]$^+$: 279.20725. Found: 279.20754. [α]$^{20}$$_D$=−33 (c=0.55, CHCl$_3$).

(S,E)-N-Butyl-2-((2-hydroxybenzylidene)amino)-3-methylbutanamide (2b)

This material is synthesized in a manner analogous to aminophenol 2a except the final reduction step is not performed. The analytical data are fully consistent with those reported previously.

(S)—N-(1-(Butylamino)-3-methyl-1-oxobutan-2-yl)-2-hydroxybenzamide (2c)

The title compound is prepared according to the representative synthesis of aminophenol 2a except after the second step; H$_2$N-Val-NHn-Bu is treated with salicylic acid under the standard amide formation conditions outlined in the first step. The resulting off-white solid is purified by silica gel chromatography (5:1 hexanes:ethyl acetate) to afford 2c as a white solid. M.p.=123-125° C. IR (neat): 3279 (w), 3090 (w, br), 2930 (m), 1620 (s), 1605 (s), 1547 (s), 1530 (s), 1454 (s), 1371 (m, br), 1229 (m), 756 (s), 643 (m) cm$^{-1}$; $^1$H NMR (400 MHz, CDCl$_3$): δ 12.07 (1H, s), 7.51 (1H, d, J=8.0 Hz), 7.40-7.36 (1H, m), 7.29 (1H, br s), 6.97 (1H, dd, J=8.4, 0.9 Hz), 6.85-6.81 (1H, m), 6.00 (1H, br s), 4.36 (1H, t, J=7.7 Hz), 3.39-3.30 (1H, m), 3.27-3.19 (1H, m), 2.25-2.17 (1H, m), 1.54-1.47 (2H, m), 1.39-1.30 (2H, m), 1.03 (3H, d, J=3.3 Hz), 1.01 (3H, d, J=3.2 Hz), 0.91 (3H, t, J=7.3 Hz); $^{13}$C NMR (100 MHz, CDCl$_3$): δ 170.8, 169.8, 161.4, 134.5, 126.3, 119.0, 118.5, 114.4, 58.9, 39.6, 31.7, 31.6, 20.2, 19.3, 18.7, 13.8;

(S)—N-Butyl-2-((3-(tert-butyl)-2-hydroxybenzyl)amino)-3-methylbutanamide (2d)

The title compound is prepared according to the representative synthesis of aminophenol 2g except for the following changes: 1) For the first amide formation, 2.5 equiv. of neat n-butylamine is used instead of dimethylamine. 2) The reduction is quenched with a saturated solution of aqueous NaHCO$_3$ (formation of the HCl salt is omitted) and the desired product is purified by silica gel chromatography (100% dichloromethane to 98:2 dichloromethane:methanol) to afford 2d as a white solid. M.p.=97-99° C. IR (neat): 3268 (w, br), 3084 (w, br), 2957 (m), 2871 (w), 1644 (s), 1561 (m), 1435 (s), 1259 (s), 835 (m), 784 (m), 750 (s) cm$^{-1}$; $^1$H NMR (400 MHz, CDCl$_3$): δ 10.83 (1H, br s), 7.21 (1H, app dd, J=7.8, 1.6 Hz), 6.80 (1H, dd, J=7.3, 1.6 Hz), 6.71 (1H, t, J=7.6 Hz), 5.52 (1H, br s), 4.13 and 3.59 (2H, ABq, J$_{AB}$=13.8 Hz), 3.37-3.29 (2H, m), 2.59 (1H, d, J=7.3 Hz), 1.90-1.81 (1H, m), 1.58-1.46 (2H, m), 1.43-1.33 (11H, m), 1.00 (3H, d, J=6.8 Hz), 0.95 (3H, t, J=7.3 Hz), 0.91 (3H, d, J=6.8 Hz); $^{13}$C NMR (100 MHz, CDCl$_3$): δ 172.9, 157.1, 137.1, 127.0, 126.3, 122.6, 118.5, 67.0, 51.2, 39.3, 34.8, 31.9, 31.7, 29.6, 20.2, 20.0, 19.1, 13.8; HRMS Calcd for C$_{20}$H$_{35}$N$_2$O$_2$ [M+H]$^+$: 335.26985. Found: 335.27112. [α]$^{20}_D$=−68 (c=0.63, CHCl$_3$).

(S)-Ethyl 2-((3-(tert-butyl)-2-hydroxybenzyl)amino)-3-methylbutanoate (2e)

The title compound is prepared according to the representative synthesis of aminophenol 2g except for the following changes: 1) Initial amide formation carried out with L-Valine methyl ester hydrochloride instead of Boc-Val-OH. 2) The reduction is quenched with a saturated solution of aqueous NaHCO$_3$ (formation of the HCl salt is omitted) and the desired product is purified by silica gel chromatography (100% hexanes to 30:1 hexanes:diethyl ether) to afford 2e as a yellow oil. IR (neat): 2960 (m, br), 1728 (s), 1459 (s), 1237 (m), 1186 (s), 1140 (s), 1023 (m), 747 (s) cm$^{-1}$; $^1$H NMR (400 MHz, CDCl$_3$): δ 10.57 (1H, br s), 7.21 (1H, app dd, J=7.8, 1.7 Hz), 6.84-6.82 (1H, m), 6.72 (1H, t, J=7.6 Hz), 4.28-4.21 (2H, m), 4.08 and 3.66 (2H, ABq, J$_{AB}$=13.3 Hz), 3.08 (1H, d, J=4.9 Hz), 2.27 (1H, br s), 2.04-1.96 (1H, m), 1.41 (9H, s), 1.31 (3H, t, J=7.1 Hz), 0.99 (6H, app dd, J=10.5, 6.9 Hz); $^{13}$C NMR (100 MHz, CDCl$_3$): δ 174.0, 156.9, 137.1, 127.1, 126.4, 122.8, 118.6, 65.6, 61.0, 51.9, 34.8, 31.5, 29.7, 19.7, 18.3, 14.5; HRMS Calcd for C$_{18}$H$_{30}$NO$_3$[M+H]$^+$: 308.22257. Found: 308.22291. [α]$^{20}_D$=−42 (c=0.73, CHCl$_3$).

(S)-2-((3-(tert-Butyl)-2-hydroxybenzyl)amino)-3-methyl-1-(pyrrolidin-1-yl)butan-1-one (2f)

The title compound is prepared according to the representative synthesis of aminophenol 2g except for the following changes: 1) For the first step, 2.5 equiv. of neat pyrrolidine is used instead of dimethylamine. 2) For the reduction of the imine in the last step of the synthesis, 20.0 equiv. NaBH$_4$ is used. 3) The reduction is quenched with a saturated solution of aqueous NaHCO$_3$ (formation of the HCl salt is omitted) and the desired product is purified by silica gel chromatography (hexanes to 5:1 hexanes:ethyl acetate to 3:1 hexanes:ethyl acetate) to afford 2f as a clear, colorless oil. IR (neat): 3279 (w, br), 2956 (w, br), 2873 (w), 1632 (s), 1424 (s), 1356 (w), 1239 (m), 1184 (w), 1141 (w), 1085 (w), 880 (m), 748 (s), 529 (w); $^1$H NMR (400 MHz, CDCl$_3$): δ 11.06 (1H, br s), 7.19 (1H, app dd, J=7.0, 1.2 Hz), 6.77 (1H, app dd, J=7.3, 1.5 Hz), 6.69 (1H, t, J=7.5 Hz), 4.13 (1H, app d, J=13.6 Hz), 3.66-3.60 (1H, m), 3.53-3.45 (2H, m), 3.28-3.14 (2H, m), 3.05 (1H, d, J=6.7 Hz), 2.60 (1H, br s), 1.91-1.81 (5H, m), 1.42 (9H, s), 1.00 (3H, d, J=6.7 Hz), 0.93 (3H, d, J=6.8 Hz); $^{13}$C NMR (100 MHz, CDCl$_3$): δ 172.1, 157.2, 137.1, 126.8, 126.2, 122.9, 118.4, 63.4, 51.3, 46.5, 45.8, 34.8, 31.4, 29.6, 26.2, 24.3, 20.1, 18.5; HRMS Calcd for C$_{20}$H$_{33}$N$_2$O$_2$ [M+H]$^+$: 333.25420. Found: 333.25561. [α]$^{20}_D$=−58 (c=0.58, CHCl$_3$).

(S)-2-((3-(tert-Butyl)-2-hydroxybenzyl)amino)-N,N,3,3-tetramethylbutanamide (2h)

The title compound is prepared according to the representative synthesis of aminophenol 2g except for the following changes: 1) Initial amide formation carried out with Boc-Tle-OH instead of Boc-Val-OH. 2) The product from the reduction process is quenched with a saturated solution of aqueous NaHCO$_3$ (formation of the HCl salt is omitted) and the desired product is purified by silica gel chromatography (9:1 hexanes:ethyl acetate to 6:1 hexanes:ethyl acetate to 4:1 hexanes:ethyl acetate) to afford 2h as a white solid. M.p.=96-98° C. IR (neat): 2948 (w, br), 1639 (s), 1460 (m), 1433 (m), 1352 (m), 1240 (m), 1135 (m), 878 (m), 782 (m), 751 (s) cm$^{-1}$; $^1$H NMR (400 MHz, CDCl$_3$): δ 10.87 (1H, br s), 7.19 (1H, d, J=7.3 Hz), 6.77 (1H, d, J=7.3 Hz), 6.70 (1H, t, J=7.5), 4.09 and 3.40 (2H, ABq, J$_{AB}$=13.6 Hz), 3.31 (1H, d, J=11.3 Hz), 3.03 (3H, s), 2.89 (3H, s), 2.71 (1H, br s), 1.40 (9H, s), 0.96 (9H, s); $^{13}$C NMR (100 MHz, CDCl$_3$): δ 173.3, 157.0, 137.2, 126.9, 126.3, 122.9, 118.5, 62.4, 51.3, 38.0, 35.8, 34.8, 34.7, 29.6, 27.0; HRMS Calcd for C$_{19}$H$_{33}$N$_2$O$_2$ [M+H]$^+$: 321.25420. Found: 321.25442. [α]$^{20}_D$=−33 (c=0.93, CHCl$_3$).

Chart S1. Numbering for Aldimine Precursors, Isatins, Homoallylamides, 3-Allyl-3-hydroxy Oxindoles, 3-Allenyl-3-hydroxy Oxindoles, and Homoallylamines

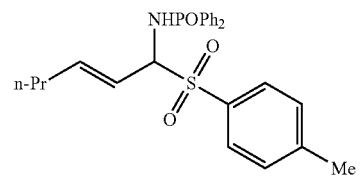

S5

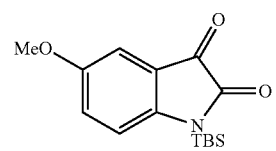

S6

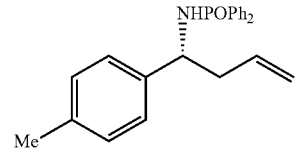

S7

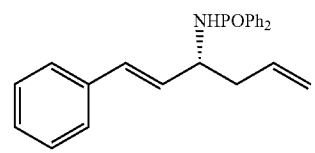

S8

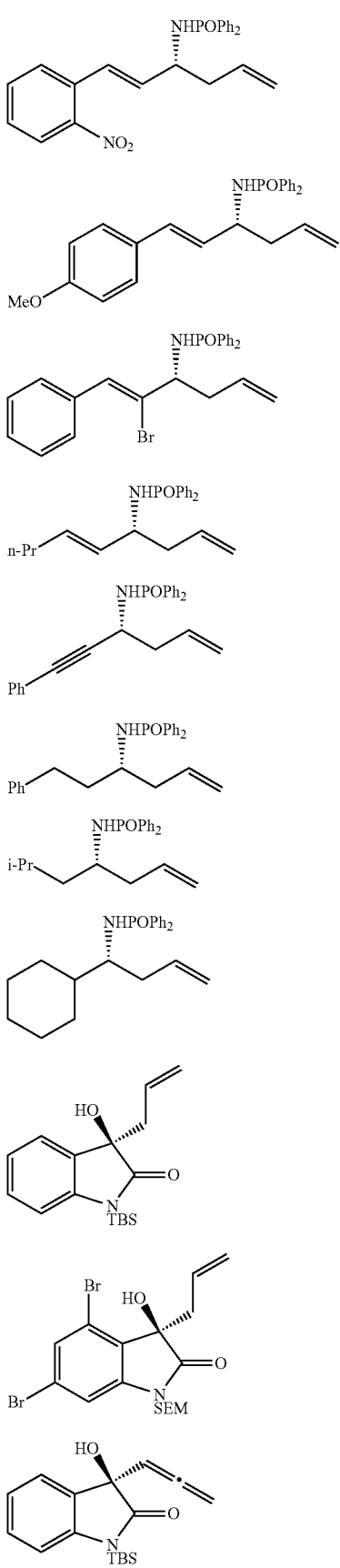

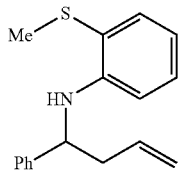

Preparation, Purification, and Analytical Data for Aldimine Substrates:

Aryl-, heteroaryl-, alkenyl-, and alkynyl-substituted N-diphenylphosphinoyl imines were synthesized through a $TiCl_4$-promoted reaction between P,P-diphenylphosphinic amide and the corresponding aldehyde. Alkyl-substituted aldimines as well as aldimines 3e, 3g, 3h and 6 were synthesized through the intermediacy of the corresponding sulfinyl adducts according to previously disclosed methods. Occasionally, for optimal results, aryl-, heteroaryl-, alkenyl-, and alkynyl-substituted aldimines should be purified by silica gel chromatography (5% triethylamine in the slurry packed bed of silica) shortly before to their use.

General Procedure for Preparation of Aryl-, Heteroaryl-, Alkenyl-, and Alkynyl Aldimines (3j):

Aldimine 3j was prepared following a modified reported procedure. A flame-dried 100 mL round-bottom flask, purged with nitrogen, is charged with 4-(dibutylamino)benzaldehyde (5.51 g, 23.6 mmol, 1.25 equiv.), P,P-diphenylphosphinic amide (4.10 g, 18.9 mmol, 1.00 equiv.), triethylamine (10.6 mL, 75.6 mmol, 4.00 equiv.), and dichloromethane (60 mL). The resulting mixture is allowed to cool to −78° C., followed by the drop-wise addition of neat $TiCl_4$ (1.14 mL, 10.4 mmol, 0.55 equiv.). The solution is allowed to stir for 12 h at 22° C. and is then filtered through a plug of Celite. The resulting yellow solid is purified by silica gel column chromatography (ethyl acetate:hexanes 2:1 followed by 100% ethyl acetate as eluent) and recrystallized from dichloromethane/hexanes to afford 3j as pale yellow solid (6.40 g, 14.8 mmol, 78% yield).

(E)-N-(4-(dibutylamino)benzylidene)-P,P-diphenylphosphinic amide (3j)

M.p.=113-115° C. IR (neat): 2951 (w), 2928 (w), 2869 (w), 1579 (m), 1525 (m), 1435 (m), 1364 (m), 1203 (m), 1173 (m), 1104 (m), 831 (s), 807 (m), 725 (m), 695 (s), 580 (m), 545 (s), 522 (s), 510 (s) $cm^{-1}$; $^1H$ NMR (400 MHz, $CDCl_3$): δ 9.08 (1H, d, J=32.0 Hz), 7.95-7.89 (4H, m), 7.85 (2H, d, J=8.8 Hz), 7.48-7.38 (6H, m), 6.65 (2H, d, J=9.2 Hz), 3.34 (4H, dd, J=7.6, 7.2 Hz), 1.63-1.56 (4H, m), 1.37 (4H, app sextet, J=7.6 Hz), 0.97 (6H, t, J=7.2 Hz); $^{13}C$ NMR (100 MHz, $CDCl_3$): δ 172.1 (d, J=6.9 Hz), 152.3, 134.4 (d, J=126.0 Hz), 132.7 (br peak as the result of hindered rotation around the (Ar)—(C=NR) bond), 131.7 (d, J=9.1 Hz), 131.4 (d, J=2.7 Hz), 128.4 (d, J=12.3 Hz), 123.5 (d, J=26.2 Hz), 111.0, 51.0, 29.4, 20.4, 14.1; HRMS Calcd for $C_{27}H_{34}N2OP$ $[M+H]^+$: 433.24087. Found: 433.23945.

(E)-N-((E)-3-(2-Nitrophenyl)allylidene)-P,P-diphenylphosphinic amide (5b)

White solid. M.p.=148-149° C. IR (neat): 3076 (w), 3041 (w), 2856 (w), 1625 (m), 1608 (m), 1591 (m), 1520 (m), 1437 (w), 1344 (m), 1205 (s), 1157 (w), 1124 (m), 1108 (m), 966 (w), 874 (m), 845 (m), 798 (s), 784 (m), 752 (w), 741 (w), 725 (s), 693 (s), 676 (m), 577 (w), 547 (s) $cm^{-1}$; $^1H$ NMR (400

MHz, CDCl$_3$): δ 9.09 (1H, dd, J=31.6, 8.8 Hz), 8.06 (1H, d, J=8.4 Hz), 7.94-7.86 (5H, m), 7.70 (1H, t, J=8.0 Hz), 7.67 (1H, t, J=7.6 Hz), 7.58-7.42 (7H, m), 7.02 (1H, ddd, J=15.6, 8.8, 1.6 Hz); $^{13}$C NMR (100 MHz, CDCl$_3$): δ 174.1 (d, J=7.9 Hz), 148.1, 145.0, 133.8, 133.0 (d, J=28.6 Hz), 132.5 (d, J=126.0 Hz), 132.1 (d, J=2.8 Hz), 131.7 (d, J=9.3 Hz), 130.8, 130.7 (d, J=1.4 Hz), 129.0, 128.7 (d, J=12.6 Hz), 125.3; HRMS Calcd for C$_{21}$H$_{18}$N$_2$O$_3$P [M+H]$^+$: 377.10550. Found: 377.10545.

(E)-N-((E)-3-(4-Methoxyphenyl)allylidene)-P,P-diphenylphosphinic amide (5c)

Pale yellow solid. M.p.=150-151° C. IR (neat): 3064 (w), 3053 (w), 3014 (w), 2939 (w), 2844 (w), 1619 (m), 1586 (s), 1568 (s), 1513 (m), 1436 (m), 1311 (m), 1258 (s), 1203 (s), 1180 (m), 1160 (m), 1123 (m), 1106 (m), 1023 (m), 875 (m), 818 (s), 753 (m), 723 (m), 696 (s), 595 (m), 546 (s) cm$^{-1}$; $^1$H NMR (400 MHz, CDCl$_3$): δ 9.01 (1H, dd, J=31.6, 8.8 Hz), 7.91-7.86 (4H, m), 7.53-7.42 (8H, m), 7.33 (1H, d, J=15.6 Hz), 7.00 (1H, ddd, J=15.6, 9.2, 2.0 Hz), 6.93 (2H, d, J=8.4 Hz), 3.85 (3H, s); $^{13}$C NMR (100 MHz, CDCl$_3$): δ 175.1 (d, J=7.7 Hz), 162.0, 150.7, 133.3 (d, J=126.0 Hz), 131.8 (d, J=2.8 Hz), 131.7 (d, J=9.1 Hz), 130.2, 128.6 (d, J=12.5 Hz), 127.6 (d, J=1.2 Hz), 126.7 (d, J=28.5 Hz), 114.6, 55.6; HRMS Calcd for C$_{22}$H$_{21}$NO$_2$P [M+H]$^+$: 362.13099. Found: 362.12964.

(E)-N-((Z)-2-Bromo-3-phenylallylidene)-P,P-diphenylphosphinic amide (5d)

White solid. M.p.=144-145° C. IR (neat): 3074 (w), 3061 (w), 3025 (w), 3012 (w), 2958 (w), 1620 (m), 1593 (s), 1569 (m), 1438 (m), 1199 (s), 1160 (w), 1134 (m), 1122 (s), 1106 (m), 1070 (w), 877 (s), 808 (m), 752 (m), 726 (s), 702 (s), 684 (s), 659 (m), 587 (m), 550 (s), 517 (m), 501 (s), 468 (m) cm$^{-1}$; $^1$H NMR (400 MHz, CDCl$_3$): δ 8.86 (1H, d, J=29.2 Hz), 7.99-7.93 (6H, m), 7.78 (1H, s), 7.53-7.43 (9H, m); $^{13}$C NMR (100 MHz, CDCl$_3$): δ 171.3 (d, J=5.2 Hz), 148.2, 133.8, 132.9 (d, J=127.0 Hz), 132.0 (d, J=2.8 Hz), 131.7 (d, J=9.3 Hz), 131.1, 130.9, 128.7, 128.7 (d, J=11.5 Hz), 124.1 (d, J=31.6 Hz); HRMS Calcd for C$_{21}$H$_{18}$BrNOP [M+H]$^+$: 410.03094. Found: 410.02999.

(E)-P,P-Diphenyl-N-(1-tosylhex-2-en-1-yl)phosphinic amide (S5)

The title compound is synthesized following a previously reported procedure[7] from P,P-diphenylphosphinic amide (2.17 g, 10.0 mmol, 1.00 equiv.), (E)-hex-2-enal (2.31 mL, 20.0 mmol, 2.00 equiv.), and p-toluenesulfinic acid (2.34 g, 15.0 mmol, 1.50 equiv.) to obtain S5 as white solid (3.22 g, 7.10 mmol, 71% yield). M.p.=138-139° C. IR (neat): 3177 (w, br), 2959 (w), 2933 (w), 2870 (w), 1661 (m), 1596 (w), 1437 (m), 1300 (m), 1281 (m), 1214 (m), 1185 (s), 1170 (m), 1138 (m), 1125 (s), 1106 (m), 1083 (m), 955 (m), 894 (m), 752 (m), 726 (s), 693 (s), 662 (m), 583 (m), 568 (m), 536 (s) cm$^{-1}$; $^1$H NMR (400 MHz, CDCl$_3$): δ 7.79-7.71 (4H, m), 7.59 (2H, d, J=8.4 Hz), 7.59-7.54 (2H, m), 7.50-7.43 (4H, m), 7.23 (2H, d, J=8.0 Hz), 5.90 (1H, ddd, J=13.6, 11.6, 9.6 Hz), 5.31 (1H, t, J=10.0 Hz), 4.73 (1H, dd, J=14.0, 10.4 Hz), 3.28 (1H, app td, J=10.8, 3.6 Hz), 2.42 (3H, s), 1.97-1.88 (1H, m), 1.52-1.32 (2H, m), 1.20-1.10 (1H, m), 0.82 (3H, t, J=7.2 Hz); $^{13}$C NMR (100 MHz, CDCl$_3$): δ 144.3, 134.7, 132.8, 132.6 (d, J=2.9 Hz), 132.5 (d, J=2.9 Hz), 132.2 (d, J=10.1 Hz), 131.9 (d, J=10.1 Hz), 131.4 (d, J=128.0 Hz), 131.0 (d, J=128.0 Hz), 129.6, 129.2, 128.9 (d, J=12.9 Hz), 128.9 (d, J=13.0 Hz), 101.9 (d, J=9.9 Hz), 67.6, 29.7, 21.8, 20.0, 13.7.

(E)-N-((E)-Hex-2-en-1-ylidene)-P,P-diphenylphosphinic amide (6)

Following a modification to a previously reported procedure,[7b] 6 is synthesized through vigorous stirring of a suspension of sulfinic adduct S5 (see above, 150 mg, 0.330 mmol) in 5 mL of diethyl ether and 5 mL of an aqueous saturated solution of Na$_2$CO$_3$ until the white solid dissolves completely (~8 h). The layers are separated and the aqueous phase is washed with diethyl ether. The combined organic phases are dried with anhydrous sodium sulfate and the filtrate is concentrated to dryness. The residue is dissolved again in dichloromethane, filtered, and the solvent is evaporated to afford 6 as colorless viscous oil (97.7 mg, 0.328 mmol, 99% yield). IR (neat): 3056 (w), 2959 (w), 2930 (w), 2871 (w), 1637 (m), 1596 (s), 1203 (s), 1122 (m), 1106 (m), 826 (s), 724 (s), 693 (s), 571 (m), 544 (s) cm$^{-1}$; $^1$H NMR (400 MHz, CDCl$_3$): δ 8.86 (1H, dd, J=32.4, 8.8 Hz), 7.89-7.83 (4H, m), 7.50-7.41 (6H, m), 6.73 (1H, dt, J=15.6, 6.8 Hz), 6.50-6.42 (1H, m), 2.30 (2H, app quartet, J=7.2 Hz), 1.53 (2H, app sextet, J=7.2 Hz), 0.95 (3H, t, J=7.2 Hz); $^{13}$C NMR (100 MHz, CDCl$_3$): δ 175.5 (d, J=8.0 Hz), 156.7, 133.1 (d, J=126.0 Hz), 132.3 (d, J=26.8 Hz), 131.8 (d, J=2.8 Hz), 131.6 (d, J=9.1 Hz), 128.5 (d, J=12.4 Hz), 35.2, 21.4, 13.8; HRMS Calcd for C$_{18}$H$_{21}$NOP [M+H]$^+$: 298.13608. Found: 298.13599.

Preparation, Purification, and Analytical Data for Isatin Substrates

General Procedure for Preparation of N-tert-Butyldimethylsilyl Isatins:

In a 250 mL flame dried round bottom flask equipped with a stir bar, tert-butyldimethylsilyl chloride (4.5 g, 30 mmol) is dissolved in 150 mL dichloromethane. To this solution, in a single portion, isatin (2.2 g, 15 mmol) and 4-dimethylaminopyridine (0.18 g, 1.5 mmol) are added. The flask is sealed with a rubber septum and purged with nitrogen. Triethylamine (6.3 mL, 45 mmol) is added in one portion through a syringe and mixture is allowed to stir for 24 h at 22° C. The volatiles are removed in vacuo and the resultant dark orange solid is purified by silica gel chromatography (hexanes to 1:1 hexanes:dichloromethane to dichloromethane) to afford an orange solid, which is recrystallized from hot EtOH (details below) to afford 14a (2.6 g, 9.9 mmol, 67% yield) as an orange crystalline solid. Please note that for long-term storage, N-tert-butyldimethylsilyl protected isatins should be kept under an inert atmosphere at −15° C. 1-(tert-Butyldimethylsilyl)indoline-2,3-dione (14a): M.p.=123-124° C. IR (neat): 2929 (w), 2853 (w), 1731 (s), 1603 (m), 1589 (m), 1463 (m), 1325 (m), 1252 (m), 1170 (m), 1139 (m), 927 (m), 835 (s), 796 (m), 752 (s), 686 (m), 466 (m), 424 (m) cm$^{-1}$; $^1$H NMR (400 MHz, CDCl$_3$): δ 7.63-7.61 (1H, m), 7.53-7.49 (1H, m), 7.10-7.03 (2H, m), 1.02 (9H, s), 0.56 (6H, s); $^{13}$C NMR (100 MHz, CDCl$_3$): δ 184.2, 164.9, 155.4, 138.3, 125.6, 123.4, 120.0, 115.1, 26.4, 19.7, −3.3; HRMS Calcd for C$_{14}$H$_{20}$NO$_2$Si [M+H]$^+$: 262.12633. Found: 262.12608.

1-(tert-Butyldimethylsilyl)-5-methoxyindoline-2,3-dione (S6)

Crimson crystalline solid. M.p.=169-171° C. IR (neat): 2929 (w, br), 2859 (w), 1731 (s), 1625 (w), 1589 (w), 1492 (m), 1310 (m), 1270 (m), 1142 (m), 942 (m), 847 (m) cm$^{-1}$; $^1$H NMR (400 MHz, CDCl$_3$): δ 7.12-7.07 (2H, m), 6.96 (1H, d, J=9.0 Hz), 3.79 (3H, s), 1.01 (9H, s), 0.54 (6H, s); $^{13}$C NMR (100 MHz, CDCl$_3$): δ 184.7, 165.3, 156.0, 149.5, 125.6, 120.4, 116.0, 108.8, 56.0, 26.5, 19.8, −3.3; HRMS Calcd for $C_{15}H_{22}NO_3Si$ [M+H]$^+$: 292.13689. Found: 292.13766.

4,6-Dibromo-1-((2-(trimethylsilyl)ethoxy)methyl) indoline-2,3-dione (14b)

Amide protection performed in accordance to a previously disclosed procedure. Yellow crystalline solid, M.p.=142-143° C. IR (neat): 3077 (w), 2896 (w), 1742 (m), 1595 (s), 1562 (m), 1419 (w), 1244 (m), 1073 (s), 1024 (m), 839 (s), 733 (m), 456 (m) cm$^{-1}$; $^1$H NMR (400 MHz, CDCl$_3$): δ 7.51 (1H, d, J=1.6 Hz), 7.28 (1H, d, J=1.2 Hz), 5.16 (2H, s), 3.85 (2H, m), 0.94 (2H, m), −0.01 (9H, s); $^{13}$C NMR (100 MHz, CDCl$_3$): δ 179.5, 157.2, 152.2, 133.5, 131.5, 122.1, 115.3, 114.3, 70.0, 67.1, 17.9, −1.3; HRMS Calcd for $C_{14}H_{21}Br_2N_2O_3Si$ [M+NH$_4$]$^+$: 450.96882. Found: 450.96873.

Synthesis of N-Bn Isatins:

Synthesized in accordance to a published procedure with the following modification: After isolation of the unpurified N-protected isatin, a small portion (~10 mg) of the solid is passed through a small plug of silica gel using dichloromethane as the elutant. If a dark (usually maroon) residue remains on the silica gel after the N-protected isatin is eluted, then the entire unpurified N-Bn isatin is dissolved in dichloromethane and passed through a short plug of silica gel using dichloromethane as an elutant. After concentration in vacuo, the isatin is purified as described below.

Purification of N-Bn, N-SEM, and N-TBS Isatins:

With hot EtOH as the solvent, ~95% of the resulting solid is dissolved and filtered while hot through a fritted glass funnel (this initial filtration is critical to obtain N-protected isatins of sufficient purity). The filtered solids are discarded. The filtrate is allowed to cool to room temperature during which time the desired product crystallizes from solution. The desired product is collected by filtration through a fritted glass funnel. Concentrating the mother liquor in vacuo and recrystallization of the resultant solids from hot EtOH yields additional product. The products are then dried azeotropically with anhydrous benzene prior to use.

Procedure for Gram-Scale Catalytic Enantioselective Allyl Addition to Aldimine 3a to Afford Homoallylamide 4a:

Preparation of the Catalyst Suspension:

Aminophenol 2g (15.0 mg, 0.0490 mmol) is weighed out in air into a 4 mL vial to which is added 263 L of a solution of sodium hydroxide (1.95 mg, 0.0490 mmol) in reagent-grade methanol [111 mg NaOH pellet (Fisher) is dissolved in 15 ml methanol]). After removal of the solvent in vacuo, the resultant white oil is azeotropically dried with reagent grade toluene. The obtained white solid is allowed to dry at 0.5 Torr for 30 min and the vial is sealed with a cap containing a teflon septum. Toluene (1.0 mL) is added to yield a suspension after sonication (2 min).

A round bottom flask (50 mL, equipped with a magnetic stirring bar) is charged with imine 3a (1.00 g, 3.28 mmol) and dried at 0.5 Torr for 30 min, purged with nitrogen and sealed with a rubber septum. Toluene (30 mL) is added, followed by allylboronic acid pinacol ester 1a (800 μl, 4.26 mmol) from a septum-sealed bottle (Frontier Scientific, Inc., as received) and methanol (200 μL, 4.92 mmol) from a septum-sealed bottle (Acros, grade: 99.9% ExtraDry, as received). A suspension of the catalyst containing aminophenol 2g (10.1 mg, 33 mol, 0.0100 equiv.) and sodium hydroxide (1.31 mg, 33 mol, 0.0100 equiv.) in 0.67 mL toluene is added with a syringe to the mixture (see below). After two h, the solvent is evaporated and the residue is taken up in 30 mL hexanes. The suspension is allowed to sonicate for two min, filtered and washed with hexanes (4×3 mL). The desired product, dried under vacuum, is obtained in 97.5:2.5 er (1.04 g, 3.01 mmol, 92% yield). Elemental analysis for $C_{22}H_{22}NOP$: Calcd: C, 76.06; H, 6.38; N, 4.03. Found: C, 75.77; H, 6.43; N, 3.98.

(R)—P,P-Diphenyl-N-(1-phenylbut-3-en-1-yl)phosphinic amide (4a)

The analytical data are fully consistent with those reported previously. $^1$H NMR (400 MHz, CDCl$_3$): δ 7.89-7.84 (2H, m), 7.79-7.74 (2H, m), 7.51-7.47 (1H, m), 7.45-7.41 (3H, m), 7.34-7.18 (7H, m), 5.61 (1H, dddd, J=17.2, 10.0, 7.2, 7.2 Hz), 5.11-5.03 (2H, m), 4.47 (1H, dddd, J=10.4, 10.4, 6.4, 6.4 Hz), 3.35 (1H, br dd, J=9.6, 6.0 Hz), 2.74-2.60 (2H, m); HRMS Calcd for $C_{22}H_{23}NOP$ [M+H]$^+$: 348.15173. Found: 348.15251; $[α]^{20}_D$=+52 (c=0.40, CHCl$_3$) for a 96:4 er sample. The enantiomeric purity was determined by HPLC analysis in comparison with authentic racemic material (Chiracel OD, 92:8 hexanes:i-PrOH, 0.5 mL/min, 220 nm): $t_R$ of 4a:

| Peak # | Ret. Time | Area % | Peak # | Ret. Time | Area % |
|---|---|---|---|---|---|
| 1 | 16.5 min | 50.660 | 1 | 15.5 min | 96.036 |
| 2 | 22.8 min | 49.340 | 2 | 20.9 min | 3.964 |

Representative Procedure for Small Scale Catalytic Enantioselective Allyl Additions to Aryl-, Heteroaryl-, Alkenyl-, and Alkynyl N-Diphenylphosphinoyl Imines:

In a nitrogen-filled glovebox (not needed for gram scale; only used when reactions are performed at mg scale to achieve highly reproducible data), aminophenol 2g (6.9 mg, 0.023 mmol) is added to an oven-dried two dram vial equipped with a stir bar followed by 1.5 mL of a stock solution of NaOt-Bu in toluene (9.6 mg, 0.10 mmol/8.0 mL) and the solution is allowed to stir at 22° C. for ~10 minutes. A separate vial equipped with a stir bar is charged sequentially with aldimine 3b (32.3 mg, 0.100 mmol), 800 μL of toluene, MeOH (10. μL, 0.25 mmol), and allylboronic acid pinacol ester 1a (28 μL, 0.15 mmol) under nitrogen. To this mixture is added 200. μL of the 2g/NaOt-Bu solution and a cap is attached to the vial and sealed (electrical tape). The clear and colorless solution is allowed to stir at 22° C. for four hours during which time the solution becomes cloudy and white. The cap is removed and 3 mL of a solution of saturated aqueous NaIO$_4$ is added and the biphasic mixture is allowed to stir for 20 minutes. The aqueous layer is washed with ethyl acetate (4×4 mL), dried over Na$_2$SO$_4$, and concentrated in vacuo to yield a pale yellow solid. The homoallylamide product is purified by silica gel chromatography (10 mm diameter column slurry packed with 2.5 g of silica gel in 95:5 hexanes: triethylamine and eluted with 10 mL hexanes, 10 mL 3:1 hexanes:ethyl acetate, 10 mL 1:1 hexanes:ethyl acetate, 10 mL 1:3 hexanes:ethyl acetate, and 15 mL ethyl acetate) to afford 4b (35.2 mg, 0.0960 mmol, 96% yield) as a white solid.

(R)—N-(1-(2-Fluorophenyl)but-3-en-1-yl)-P,P-diphenylphosphinic amide (4b)

The analytical data are fully consistent with those reported previously.[13] $^1$H NMR (400 MHz, CDCl$_3$): δ 7.87-7.82 (2H, m), 7.78-7.72 (2H, m), 7.51-7.47 (1H, m), 7.44-7.39 (3H, m), 7.34-7.29 (2H, m), 7.23-7.18 (1H, m), 7.15 (1H, ddd, J=7.6, 7.6, 1.6 Hz), 7.05 (1H, ddd, J=7.6, 7.6, 1.2 Hz), 6.97 (1H, ddd, J=10.8, 8.0, 0.8 Hz), 5.61 (1H, dddd, J=17.2, 10.0, 7.2, 7.2 Hz), 5.09-5.01 (2H, m), 4.47 (1H, dddd, J=10.4, 10.4, 6.4, 6.4 Hz), 3.56 (1H, br dd, J=10.4, 6.8 Hz), 2.78-2.60 (2H, m);

HRMS Calcd for $C_{22}H_{21}FNOP$ [M+H]$^+$: 366.14230. Found: 366.14250. [α]$^{20}_D$=+34 (c=0.39, CHCl$_3$) for a 98.5:1.5 er sample. The enantiomeric purity was determined by HPLC analysis in comparison to authentic racemic material (Chiracel OD, 92:8 hexanes:i-PrOH, 0.5 mL/min, 220 nm) t$_R$ of 4b: 17 min (major) and 21 min (minor).

| Peak # | Ret. Time | Area % | Peak # | Ret. Time | Area % |
|---|---|---|---|---|---|
| 1 | 17.9 | 49.348 | 1 | 17.4 | 98.321 |
| 2 | 20.8 | 50.652 | 2 | 21.0 | 1.679 |

(R)—N-(1-(2-Bromophenyl)but-3-en-1-yl)-PP-diphenylphosphinic amide(4c)

The title compound is purified in a manner identical to 4b affording 4c (38.0 mg, 0.0891 mmol, 89% yield) as a white solid. The analytical data are fully consistent with those reported previously.[13] $^1$H NMR (400 MHz, CDCl$_3$): δ 7.87-7.82 (2H, m), 7.75-7.70 (2H, m), 7.51-7.47 (1H, m), 7.44-7.39 (4H, m), 7.35-7.27 (4H, m), 7.07 (1H, ddd, J=8.8, 8.0, 2.0 Hz), 5.64 (1H, dddd, J=17.4, 10.4, 7.2, 7.2 Hz), 5.14-5.10 (2H, m), 4.71 (1H, dddd, J=10.4, 10.4, 6.0, 6.0 Hz), 3.56 (1H, br dd, J=9.6, 6.0 Hz), 2.64 (2H, app t, J=6.4 Hz); HRMS Calcd for $C_{22}H_{22}BrNOP$ [M+H]$^+$: 426.06224. Found: 426.06229. [α]$^{20}_D$=+2.30 (c=1.00, CHCl$_3$) for a 98.0:2.0 er sample. The enantiomeric purity was determined by HPLC analysis in comparison to authentic racemic material (Chiracel AD-H, 87:13 hexanes:i-PrOH, 0.5 mL/min, 220 nm) t$_R$ of 4c: 26 min (minor) and 45 min (major).

| Peak # | Ret. Time | Area % | Peak # | Ret. Time | Area % |
|---|---|---|---|---|---|
| 1 | 25.0 | 49.745 | 1 | 25.9 | 1.985 |
| 2 | 43.0 | 50.255 | 2 | 45.1 | 98.015 |

(R)—P,P-Diphenyl-N-(1-(o-tolyl)but-3-en-1-yl) phosphinic amide (4d)

The title compound is synthesized and purified analogously to 4b (six h reaction time) affording 4d (34.3 mg, 0.0949 mmol, 95% yield) as a white solid. The analytical data are fully consistent with those reported previously.[13] $^1$H NMR (400 MHz, CDCl$_3$): δ 7.88-7.83 (2H, m), 7.72-7.67 (2H, m), 7.50-7.46 (1H, m), 7.44-7.38 (3H, m), 7.33 (1H, d, J=7.7 Hz), 7.29-7.21 (3H, m), 7.12 (1H, ddd, J=8.4, 7.6, 1.6 Hz), 7.00 (1H, d, J=7.5 Hz), 5.61 (1H, dddd, J=17.2, 10.0, 7.2, 7.2 Hz), 5.11-5.03 (2H, m), 4.54 (1H, dddd, J=10.0, 10.0, 6.4, 6.4 Hz), 3.43 (1H, br dd, J=9.6, 6.4 Hz), 2.65-2.52 (2H, m), 1.91 (3H, s); HRMS Calcd for $C_{23}H_{25}NOP$ [M+H]$^+$: 362.16738. Found: 362.16744. [α]$^{20}_D$=+7.20 (c=1.00, CHCl$_3$) for a 94:6 er sample. The enantiomeric purity was determined by HPLC analysis in comparison to authentic racemic material (Chiracel AD-H, 87:13 hexanes:i-PrOH, 0.5 mL/min, 220 nm) t$_R$ of 4d: 25 min (major) and 31 min (minor).

| Peak # | Ret. Time | Area % | Peak # | Ret. Time | Area % |
|---|---|---|---|---|---|
| 1 | 23.8 | 49.425 | 1 | 24.9 | 93.155 |
| 2 | 28.7 | 50.575 | 2 | 30.9 | 6.845 |

(R)—N-(1-(3-Bromophenyl)but-3-en-1-yl)-PP-diphenylphosphinic amide (4e)

The title compound is purified identically to 4b affording 4e (39.5 mg, 0.0927 mmol, 93% yield) as a white solid. The analytical data are fully consistent with those reported previously.[13] $^1$H NMR (400 MHz, CDCl$_3$): δ 7.87-7.82 (2H, m), 7.77-7.71 (2H, m), 7.53-7.47 (1H, m), 7.45-7.40 (3H, m), 7.35-7.30 (4H, m), 7.13-7.11 (2H, m), 5.58 (1H, dddd, J=17.2, 10.0, 7.2, 7.2 Hz), 5.13-5.07 (2H, m), 4.31 (1H, dddd, J=10.0, 10.0, 6.4, 6.4 Hz), 3.42 (1H, br dd, J=9.4, 6.0 Hz), 2.67-2.58 (2H, m); HRMS Calcd for $C_{22}H_{22}BrNOP$ [M+H]$^+$: 426.06224. Found: 426.06326. [α]$^{20}_D$=+59 (c=0.57, CHCl$_3$) for a 97.5:2.5 er sample. The enantiomeric purity was determined by HPLC analysis in comparison with authentic racemic material (Chiracel OD, 92:8 hexanes:i-PrOH, 0.5 mL/min, 220 nm): t$_R$ of 4e: 17 min (major) and 20 min (minor).

| Peak # | Ret. Time | Area % | Peak # | Ret. Time | Area % |
|---|---|---|---|---|---|
| 1 | 16.8 | 49.640 | 1 | 16.6 | 97.673 |
| 2 | 20.1 | 50.360 | 2 | 20.4 | 2.327 |

(R)—N-(1-(4-Bromophenyl)but-3-en-1-yl)-PP-diphenylphosphinic amide (4f)

The title compound is purified identically to 4b affording 4f (39.2 mg, 0.0920 mmol, 92% yield) as a white solid. The analytical data are fully consistent with those reported previously.[13] $^1$H NMR (400 MHz, CDCl$_3$): δ 7.87-7.82 (2H, m), 7.78-7.72 (2H, m), 7.51-7.47 (1H, m), 7.45-7.37 (5H, m), 7.35-7.30 (2H, m), 7.08-7.05 (2H, m), 5.57 (1H, dddd, J=16.8, 10.0, 7.2, 7.2 Hz), 5.13-5.06 (2H, m), 4.31 (1H, dddd, J=10.0, 10.0, 6.4, 6.4 Hz), 3.30 (1H, br dd, J=9.6, 5.6 Hz), 2.69-2.55 (2H, m); HRMS Calcd for $C_{22}H_{22}BrNOP$ [M+H]$^+$: 426.0622; HRMS Calcd for $C_{22}H_{22}BrNOP$ [M+H]$^+$: 426.06224. Found: 426.06197. [α]$^{20}_D$=+73 (c=1.0, CHCl$_3$) for a 97:3 er sample. The enantiomeric purity was determined by HPLC analysis in comparison with authentic racemic material (Chiracel AD-H, 97:3 hexanes:i-PrOH, 0.5 mL/min, 220 nm): t$_R$ of 4f: 36 min (minor) and 44 min (major).

| Peak # | Ret. Time | Area % | Peak # | Ret. Time | Area % |
|---|---|---|---|---|---|
| 1 | 35.5 | 49.744 | 1 | 35.6 | 2.763 |
| 2 | 44.3 | 50.256 | 2 | 44.4 | 97.237 |

(R)—P,P-Diphenyl-N-(1-(4-(trifluoromethyl)phenyl) but-3-en-1-yl)phosphinic amide (4g)

The title compound is purified identically to 4b affording 4g (38.8 mg, 0.0934 mmol, 93% yield) as a white solid. The analytical data are fully consistent with those reported previously.[13] $^1$H NMR (400 MHz, CDCl$_3$): δ 7.88-7.83 (2H, m) 7.75-7.70 (2H, m), 7.52-7.48 (3H, m), 7.45-7.40 (3H, m), 7.32-7.28 (4H, m), 5.58 (1H, dddd, J=17.2, 10.0, 7.2, 7.2 Hz), 5.14-5.08 (2H, m), 4.41 (1H, dddd, J=9.6, 9.6, 6.4, 6.4 Hz), 3.49 (1H, br dd, J=8.8, 6.2 Hz), 2.71-2.58 (2H, m); HRMS Calcd for $C_{23}H_{22}F_3NOP$ [M+H]$^+$: 416.13911. Found: 416.13996. [α]$^{20}_D$=+57 (c=0.45, CHCl$_3$) for a 98:2 er sample. The enantiomeric purity was determined by HPLC analysis in comparison with authentic racemic material (Chiracel OD, 92:8 hexanes:i-PrOH, 0.5 mL/min, 220 nm): $t_R$ of 4g: 17 min (major) and 19 min (minor).

| Peak # | Ret. Time | Area % | Peak # | Ret. Time | Area % |
|---|---|---|---|---|---|
| 1 | 17.9 | 48.582 | 1 | 16.6 | 98.108 |
| 2 | 20.4 | 51.418 | 2 | 19.3 | 1.892 |

(R)-Methyl-4-(1-((diphenylphosphoryl)amino)but-3-en-1-yl)benzoate (4h)

The title compound is synthesized and purified analogously to 4b except for the following changes: 1) 2.5 mol % aminophenol 2g (instead of 3 mol % 2g) 2) 1.5 equiv. MeOH (instead of 2.5 equiv.). Homoallylamide 4h (74.4 mg, 0.183 mmol, 92% yield) is obtained as a white solid. M.p.=128° C. IR (neat): 3144 (w, br), 3055 (w), 3006 (w), 2948 (w), 2872 (w), 1720 (s), 1610 (w), 1435 (m), 1277 (s), 1193 (s), 1181 (s), 1106 (s), 1067 (m), 926 (m), 907 (m), 721 (s), 694 (s), 561 (m), 527 (s) cm$^{-1}$; $^1$H NMR (400 MHz, CDCl$_3$): δ 7.93 (2H, d, J=8.4 Hz), 7.86-7.80 (2H, m), 7.74-7.68 (2H, m), 7.47-7.37 (4H, m), 7.30-7.25 (2H, m), 7.25 (2H, d, J=8.0 Hz), 5.55 (1H, dddd, J=17.2, 10.0, 7.6, 6.8 Hz), 5.09-5.03 (2H, m), 4.38 (1H, app tt, J=10.1, 6.2 Hz), 3.88 (3H, s), 3.52 (1H, br dd, J=9.9, 5.9 Hz), 2.70-2.56 (2H, m); $^{13}$C NMR (100 MHz, CDCl$_3$): δ 166.9, 148.4 (d, J=5.0 Hz), 133.2, 132.9 (d, J=127.0 Hz), 132.5 (d, J=9.7 Hz), 132.0 (d, J=2.7 Hz), 131.9 (d, J=130.0 Hz), 131.9 (d, J=3.9 Hz, one peak is overlapping with the other d at 131.9), 131.9 (d, J=9.5 Hz), 129.8, 129.0, 128.6 (d, J=12.5 Hz), 128.4 (d, J=12.6 Hz), 126.6, 119.4, 54.3, 52.2, 43.6 (d, J=4.2 Hz); HRMS Calcd for C$_{24}$H$_{25}$NO$_3$P [M+H]$^+$: 406.15720. Found: 406.15720. $[\alpha]^{20}_D$=+75.5 (c=2.40, CHCl$_3$) for a 98:2 er sample. The enantiomeric purity of this compound was determined by HPLC analysis in comparison with authentic racemic material (Chiracel AD-H, 80:20 hexanes:i-PrOH, 0.8 mL/min, 220 nm): $t_R$ of 4h: 30 min (major) and 38 min (minor).

| Peak # | Ret. Time | Area % | Peak # | Ret. Time | Area % |
|---|---|---|---|---|---|
| 1 | 29.9 | 50.019 | 1 | 30.0 | 98.190 |
| 2 | 38.2 | 49.981 | 2 | 38.5 | 1.810 |

(R)—N-(1-(4-Methoxyphenyl)but-3-en-1-yl)-PP-diphenylphosphinic amide (4i)

The title compound is synthesized and purified analogously to 4b except for the following changes: 1) 2.5 mol % aminophenol 2g (instead of 3 mol % 2g) 2) 1.5 equiv. MeOH (instead of 2.5 equiv.). Homoallylamide 4l (74.1 mg, 0.196 mmol, 98% yield) is afforded as a white solid. The analytical data are fully consistent with those reported previously.[13] M.p.=116-117° C. $^1$H NMR (400 MHz, CDCl$_3$): δ 7.88-7.83 (2H, m), 7.80-7.75 (2H, m), 7.49-7.38 (3H, m), 7.35-7.30 (2H, m), 7.14-7.10 (2H, m), 6.83-6.79 (2H, m), 5.56 (1H, dddd, J=17.2, 10.4, 6.8, 6.8 Hz), 5.10-5.02 (2H, m), 4.30 (1H, dddd, J=9.6, 9.6, 6.4, 6.4 Hz), 3.79 (3H, s), 3.28 (1H, br dd, J=9.6, 6.0 Hz), 2.72-2.57 (2H, m); HRMS Calcd for C$_{23}$H$_{25}$NO$_2$P [M+H]$^+$: 378.16229. Found: 378.16236. $[\alpha]^{20}_D$=+54.7 (c=1.99, CHCl$_3$) for a 96.5:3.5 er sample. The enantiomeric purity of this compound was determined by HPLC analysis in comparison with authentic racemic material (Chiracel OJ-H, 92:8 hexanes:i-PrOH, 0.8 mL/min, 220 nm): $t_R$ of 4i: 12 min (minor) and 19 min (major).

| Peak # | Ret. Time | Area % | Peak # | Ret. Time | Area % |
|---|---|---|---|---|---|
| 1 | 11.7 | 50.058 | 1 | 11.7 | 3.416 |
| 2 | 17.9 | 49.942 | 2 | 19.2 | 96.584 |

(R)—N-(1-(4-(Dibutylamino)phenyl)but-3-en-1-yl)-P,P-diphenylphosphinic amide (4j)

The title compound is synthesized analogously to 4b except for the following changes: 1) 2.5 mol % aminophenol 2g (instead of 3 mol % 2g) 2) 1.5 equiv. MeOH (instead of 2.5 equiv.). 3) Reaction time is six h. 4) After NaIO$_4$ workup (see representative procedure above), the unpurified mixture is treated for 12 h while allowing it to stir with ~1 g basic aluminum oxide in 4 mL dichloromethane:diethyl ether (1:1) to hydrolyze unreacted 3j, after which the aluminum oxide is filtered off and washed with dichloromethane and ethyl acetate (20 mL). The product is purified as described for 4b, affording 4j (44.2 mg, 0.0931 mmol, 93% yield) as a white solid. M.p.=83-84° C. IR (neat): 3154 (w, br), 3071 (w), 2955 (m), 2930 (m), 2870 (m), 1614 (m), 1519 (m), 1455 (m), 1436 (m), 1368 (w), 1283 (w), 1181 (s), 1107 (s), 1066 (m), 925 (m), 900 (m), 752 (w), 722 (s), 693 (s), 553 (s), 521 (s) cm$^{-1}$; $^1$H NMR (400 MHz, CDCl$_3$): δ 7.89-7.79 (4H, m), 7.49-7.32 (6H, m), 7.03 (2H, d, J=8.8 Hz), 6.54 (2H, d, J=8.8 Hz), 5.63 (1H, app ddt, J=17.2, 10.0, 7.2 Hz), 5.10-4.99 (2H, m), 4.26-4.19 (1H, m), 3.23 (4H, app dd, J=7.8, 7.2 Hz), 3.26-3.21 (1H, m, overlapping with the dd at 3.23), 2.75-2.58 (2H, m), 1.59-1.52 (4H, m), 1.40-1.30 (4H, app sextet, J=7.6 Hz), 0.96 (6H, t, J=7.6 Hz); $^{13}$C NMR (100 MHz, CDCl$_3$): δ 147.3, 134.6, 133.6 (d, J=127.0 Hz), 132.6 (d, J=9.5 Hz), 132.4 (d, J=130.0 Hz), 131.9 (d, J=9.3 Hz), 131.7 (d, J=2.7 Hz), 131.6 (d, J=2.7 Hz), 129.2 (d, J=6.3 Hz), 128.4 (d, J=12.3 Hz), 128.3 (d, J=12.4 Hz), 127.6, 118.1, 111.5, 54.3, 50.9, 43.5 (d, J=3.7 Hz), 29.5, 20.4, 14.1; HRMS Calcd for C$_{30}$H$_{40}$N$_2$OP [M+H]$^+$: 475.28782. Found: 475.28783. $[\alpha]^{20}_D$=+61.6 (c=1.33, CHCl$_3$) for a 92:8 er sample. The enantiomeric purity of this compound was determined by HPLC analysis in comparison with authentic racemic material (Chiracel OD-H, 92:8 hexanes:i-PrOH, 0.5 mL/min, 220 nm): $t_R$ of 4j: 12 min (major) and 14 min (minor).

| Peak # | Ret. Time | Area % | Peak # | Ret. Time | Area % |
|---|---|---|---|---|---|
| 1 | 12.6 | 50.161 | 1 | 12.1 | 91.817 |
| 2 | 14.7 | 49.839 | 2 | 13.9 | 8.183 |

(R)—N-(1-(Furan-2-yl)but-3-en-1-yl)-P,P-diphenylphosphinic amide (4k)

The title compound is synthesized and purified analogously to 4b (only with a six h reaction time) affording 4k (32.2 mg, 0.0955 mmol, 96% yield) as a light tan solid. The analytical data are fully consistent with those reported previously.[13] $^1$H NMR (400 MHz, CDCl$_3$): δ 7.89-7.82 (4H, m), 7.50-7.37 (6H, m), 7.32-7.31 (1H, m), 6.25-6.24 (1H, m), 6.12-6.11 (1H, m), 5.63 (1H, dddd, J=17.6, 10.0, 7.6, 7.6 Hz), 5.14-5.05 (2H, m), 4.37 (1H, dddd, J=10.0, 10.0, 6.4, 6.4 Hz), 3.34 (1H, br dd, J=10.4, 7.2 Hz), 2.79-2.61 (2H, m); HRMS Calcd for C$_{20}$H$_{21}$NO$_2$P [M+H]$^+$: 338.13099. Found: 338.13157. $[\alpha]^{20}_D$=+53.3 (c=1.00, CHCl$_3$) for a 98:2 er sample. The enantiomeric purity was determined by HPLC analysis in comparison with authentic racemic material

(R)—P,P-diphenyl-N-(1-(pyridin-3-yl)but-3-en-1-yl) phosphinic amide (4l)

The title compound is synthesized analogously to 4b and purified analogously to 4o (see below). M.p.=133-134° C. IR (neat): 3169 (w, br), 1438 (m), 1184 (s), 1123 (m), 1109 (m), 1071 (m), 921 (w), 754 (w), 725 (m), 698 (m), 533 (m) cm$^{-1}$; $^1$H NMR (400 MHz, CDCl$_3$): δ 8.39 (2H, br dd, J=4.8, 1.6 Hz), 8.36 (1H, br d, J=2.4 Hz), 7.82-7.77 (2H, m), 7.70-7.65 (2H, m), 7.419-7.42 (2H, m), 7.40-7.34 (3H, m), 7.28-7.23 (2H, m), 7.15-7.11 (1H, m), 5.53 (1H, dddd, J=16.8, 10.4, 7.2, 7.2 Hz), 5.08-5.03 (2H, m), 4.35 (1H, dddd, J=9.6, 9.6, 6.4, 6.4 Hz), 3.33 (1H, br dd, J=8.0, 5.6 Hz), 2.65-2.55 (2H, m); $^{13}$C NMR (125 MHz, CDCl$_3$): δ 148.6 (d, J=15.6 Hz), 138.5 (d, J=4.5 Hz), 134.4, 132.9, 132.7 (d, J=127 Hz, peak overlaps with doublet at 132.06), 132.5 (d, J=9.7 Hz), 132.2 (d, J=2.2 Hz), 132.1 (d, J=2.9 Hz), 131.9 (d, J=8.9 Hz), 131.8 (d, J=127 Hz, peak overlaps with doublet at 132.5), 128.7 (d, J=12.6 Hz), 128.5 (d, J=12.7 Hz), 123.4, 119.9, 52.5, 43.4 (d, J=4.5 Hz); HRMS Calcd for C$_{21}$H$_{22}$N2OP [M+H]$^+$: 349.14697. Found: 349.14651. [α]$^{25}$D=+45.2 (c=1.00, CHCl$_3$) for a 98:2 er sample. The enantiomeric purity of this compound was determined by HPLC analysis in comparison with authentic racemic material (Chiralpak AD-H, 86:14 hexanes:i-PrOH, 0.6 mL/min, 220 nm): t$_R$ of 4l: 38 min (major) and 43 min (minor).

| Peak # | Ret. Time | Area % | Peak # | Ret. Time | Area % |
|---|---|---|---|---|---|
| 1 | 36.2 min | 49.809 | 1 | 39.1 min | 98.360 |
| 2 | 40.8 min | 50.191 | 2 | 43.1 min | 1.640 |

(R)—P,P-Diphenyl-N-(1-(p-4-methylphenyl)but-3-en-1-yl)phosphinic amide (S7, see Chart S1)

This compound is not listed in Table 2 of the publication, but has been used for determination of the absolute stereochemistry through X-ray analysis. It was synthesized and purified analogously to 4b except for the following changes: 1) 2.5 mol % aminophenol 2g (instead of 3 mol % 2g) 2) 1.5 equiv. MeOH (instead of 2.5 equiv.). Homoallylamide S7 (70.8 mg, 0.196 mmol, 98% yield) is obtained as a white solid. Crystals suitable for X-ray crystallography were obtained by slow evaporation of dichloromethane (See Part D of the Supplementary Information for the X-ray crystal structure). M.p.=130-131° C. IR (neat): 3178 (w, br), 3076 (w), 3052 (w), 3007 (w), 2977 (w), 2919 (w), 2882 (w), 1454 (m), 1435 (m), 1181 (s), 1123 (m), 1108 (m), 1078 (s), 917 (m), 899 (m), 748 (m), 723 (s), 694 (s), 561 (m), 535 (s), 497 (m) cm$^{-1}$; $^1$H NMR (400 MHz, CDCl$_3$): δ 7.88-7.75 (4H, m), 7.49-7.29 (6H, m), 7.09 (4H, app s), 5.58 (1H, app ddt, J=17.2 10.0, 7.2 Hz), 5.10-5.00 (2H, m), 4.33-4.26 (1H, m), 3.40 (1H, br dd, J=10.0, 6.4 Hz), 2.74-2.58 (2H, m), 2.31 (3H, s); $^{13}$C NMR (100 MHz, CDCl$_3$): δ 140.1 (d, J=5.7 Hz), 136.6, 133.9, 133.3 (d, J=127.0 Hz, 1 peak hidden under 133.9), 132.6 (d, J=9.6 Hz), 132.2 (d, J=130.0 Hz), 131.9 (d, J=9.6 Hz), 131.8 (d, J=3 Hz, 1 peak hidden under 131.9), 131.7 (d, J=2.7 Hz), 129.1, 128.5 (d, J=12.5 Hz), 128.3 (d, J=12.6 Hz), 126.4, 118.6, 54.5, 43.7 (d, J=3.8 Hz), 21.1; HRMS Calcd for C$_{23}$H$_{25}$NOP [M+H]$^+$: 362.16738. Found: 362.16709. [α]$^{20}$$_D$=+50.8 (c=2.11, CHCl$_3$) for a 96.5:3.5 er sample. The enantiomeric purity of this compound was determined by HPLC analysis in comparison with authentic racemic material (Chiracel OD-H, 92:8 hexanes:i-PrOH, 0.5 mL/min, 220 nm): t$_R$ of S7: 16 min (major) and 18 min (minor).

| Peak # | Ret. Time | Area % | Peak # | Ret. Time | Area % |
|---|---|---|---|---|---|
| 1 | 15.8 | 49.997 | 1 | 15.8 | 96.568 |
| 2 | 17.9 | 50.003 | 2 | 18.3 | 3.432 |

(R)—N-(3-Methyl-1-phenylbut-3-en-1-yl)-P,P-diphenylphosphinic amide (4m)

The title compound is synthesized and purified analogously to 4b [except allylboronic acid pinacol ester 1b (32 µL, 0.15 mmol) is used as the nucleophile instead of 1a], affording 4m (34.4 mg, 0.0952 mmol, 95% yield) as a white solid. The analytical data are fully consistent with those reported previously.[13] $^1$H NMR (400 MHz, CDCl$_3$): δ 7.86-7.80 (2H, m), 7.76-7.70 (2H, m), 7.50-7.46 (1H, m), 7.44-7.38 (3H, m), 7.29-7.17 (7H, m), 4.78 (1H, s), 4.69 (1H, s), 4.40 (1H, dddd, J=16.4, 16.4, 8.4, 8.4 Hz), 3.32 (1H, br dd, J=8.0, 6.0 Hz), 2.62 (1H, dd, J=13.6, 7.2 Hz), 2.53 (1H, dd, J=14.0, 7.2 Hz), 1.58 (3H, s); HRMS Calcd for C$_{23}$H$_{25}$NOP [M+H]$^+$: 362.16738. Found: 362.16649. [α]$^{20}$$_D$=+39 (c=1.2, CHCl$_3$) for a 97.5:2.5 er sample. The enantiomeric purity was determined by HPLC analysis in comparison with authentic racemic material (Chiracel OD-H, 92:8 hexanes:i-PrOH, 0.8 mL/min, 220 nm): t$_R$ of 4m: 11 min (major) and 14 min (minor).

| Peak # | Ret. Time | Area % | Peak # | Ret. Time | Area % |
|---|---|---|---|---|---|
| 1 | 9.90 | 49.583 | 1 | 10.8 | 98.206 |
| 2 | 12.1 | 50.417 | 2 | 14.1 | 1.792 |

(R)—N-(1,3-Diphenylbut-3-en-1-yl)-P,P-diphenylphosphinic amide (4n)

The title compound is synthesized and purified analogously to 4b [except allylboronic acid pinacol ester 1c (37 µL, 0.15 mmol) is used as the nucleophile instead of 1a and the reaction time is 6 h] affording 4n (42.1 mg, 0.0994 mmol, >98% yield) as a white foam. The analytical data are fully consistent with those reported previously.[13] $^1$H NMR (400 MHz, CDCl$_3$): δ 7.76-7.70 (4H, m), 7.47-7.40 (2H, m), 7.37-7.30 (4H, m), 7.27-7.16 (8H, m), 7.07-7.00 (2H, m), 5.21 (1H, d, J=1.2 Hz), 4.87 (1H, d, J=1.2 Hz), 4.27 (1H, dddd, J=8.4, 8.4, 6.4, 6.4 Hz), 3.29 (1H, br dd, J=8.8, 5.6 Hz), 3.25 (1H, dd, J=14.0, 6.0 Hz), 2.99 (1H, dd, J=14.0, 8.0 Hz); HRMS Calcd for C$_{28}$H$_{27}$NOP [M+H]$^+$: 424.18303. Found: 424.18255. [α]$^{20}$$_D$=+26 (c=1.7, CHCl$_3$) for a 98:2 er sample. The enantiomeric purity was determined by HPLC analysis in comparison with authentic racemic material (Chiracel OD-H, 92:8 hexanes:i-PrOH, 0.8 mL/min, 220 nm): t$_R$ of 4n: 15 min (minor) and 16 min (major).

| Peak # | Ret. Time | Area % | Peak # | Ret. Time | Area % |
|---|---|---|---|---|---|
| 1 | 13.3 | 50.107 | 1 | 14.5 | 3.286 |
| 2 | 15.5 | 49.893 | 2 | 16.4 | 96.714 |

(R,E)-P,P-Diphenyl-N-(1-phenylhexa-1,5-dien-3-yl)
phosphinic amide (S8, see Chart S1)

The title compound is purified in the manner identical to that used for 4b to afford S8 (31.3 mg, 0.0838 mmol, 84% yield) as a white solid. The analytical data are fully consistent with those reported previously.[13] $^1$H NMR (400 MHz, CDCl$_3$): δ 7.96-7.87 (4H, m), 7.51-7.39 (6H, m), 7.31-7.26 (4H, m), 7.24-7.21 (1H, m), 6.46-6.42 (1H, m), 6.15 (1H, ddd, J=15.9, 6.3, 2.4 Hz), 5.78 (1H, dddd, J=14.4, 7.6, 6.8, 6.8 Hz), 5.20-5.12 (2H, m), 4.01-3.92 (1H, m), 3.09 (1H, br dd, J=9.6, 6.0 Hz), 2.59-2.45 (2H, m); HRMS Calcd for C$_{24}$H$_{25}$NOP [M+H]$^+$: 374.16738. Found: 374.16756. [α]$^{20}_D$=+89 (c=0.65, CHCl$_3$) for a 99:1 er sample. The enantiomeric purity was determined by HPLC analysis in comparison with authentic racemic material (Chiracel OD, 92:8 hexanes:i-PrOH, 0.6 mL/min, 220 nm): t$_R$ of S8: 17 min (major) and 21 min (minor).

| Peak # | Ret. Time | Area % | Peak # | Ret. Time | Area % |
|---|---|---|---|---|---|
| 1 | 16.3 | 49.181 | 1 | 16.8 | 99.084 |
| 2 | 19.5 | 50.819 | 2 | 20.7 | 0.916 |

(R,E)-N-(1-(2-Nitrophenyl)hexa-1,5-dien-3-yl)-P,P-
diphenylphosphinic amide (S9, see Chart S1)

The title compound is purified identically to 4b affording S9 (39.6 mg, 0.095 mmol, 95% yield) as a white solid. M.p.=135° C. IR (neat): 3149 (m, br), 3067 (w), 2857 (w), 1641 (w), 1605 (w), 1571 (w), 1520 (s), 1436 (m), 1350 (m), 1178 (s), 1123 (m), 1106 (m), 1067 (m), 952 (m), 918 (m), 745 (m), 724 (s), 691 (s), 541 (s) cm$^{-1}$; $^1$H NMR (400 MHz, CDCl$_3$): δ 8.00-7.88 (5H, m), 7.55-7.35 (9H, m), 7.01 (1H, dd, J=16.0, 1.6 Hz), 6.17 (1H, dd, J=15.6, 5.6 Hz), 5.80 (1H, dddd, J=16.8, 10.0, 7.6, 6.4 Hz), 5.22-5.14 (2H, m), 4.02-3.96 (1H, m), 3.16 (1H, br dd, J=9.6, 5.6 Hz), 2.62-2.49 (2H, m); $^{13}$C NMR (100 MHz, CDCl$_3$): δ 147.7, 137.0 (d, J=6.0 Hz), 133.3, 133.3, 132.9, 132.9 (d, J=128.0 Hz), 132.5 (d, J=9.4 Hz), 132.4 (d, J=130.0 Hz), 132.0 (2 d peaks exactly overlapping, J=3 Hz), 132.0 (d, J=9.3 Hz), 129.2, 128.7 (2 d peaks exactly overlapping, J=12.6 Hz), 128.2, 125.9, 124.6, 119.5, 52.5, 42.0 (d, J=4.2 Hz); HRMS Calcd for C$_{24}$H$_{24}$N$_2$O$_3$P [M+H]$^+$: 419.15245. Found: 419.15207. [α]$^{20}_D$=+ 94.4 (c=1.00, CHCl$_3$) for a 99.5:0.5 er sample. The enantiomeric purity of this compound was determined by HPLC analysis in comparison with authentic racemic material (Chiracel OD-H, 92:8 hexanes:i-PrOH, 0.5 mL/min, 220 nm): t$_R$ of S9 30 min (minor) and 32 min (major).

| Peak # | Ret. Time | Area % | Peak # | Ret. Time | Area % |
|---|---|---|---|---|---|
| 1 | 29.6 | 49.698 | 1 | 30.0 | 0.321 |
| 2 | 32.7 | 50.302 | 2 | 32.2 | 99.679 |

(R,E)-N-(1-(4-Methoxyphenyl)hexa-1,5-dien-3-yl)-
P,P-diphenylphosphinic amide (S10)

The title compound is purified in the manner identical to that used for 4b to generate S10 (39.4 mg, 0.098 mmol, 98% yield) as a white solid. M.p.=134° C. IR (neat): 3180 (w, br), 3059 (w), 2929 (w), 2837 (w), 1607 (w), 1509 (m), 1433 (m), 1248 (m), 1185 (s), 1124 (m), 1108 (m), 1069 (m), 1031 (m), 976 (m), 912 (w), 811 (m), 745 (m), 725 (s), 693 (s), 541 (s), 516 (m) cm$^{-1}$; $^1$H NMR (400 MHz, CDCl$_3$): δ 7.96-7.86 (4H, m), 7.51-7.37 (6H, m), 7.22 (2H, d, J=8.8 Hz), 6.82 (2H, d, J=8.4 Hz), 6.37 (1H, d, J=15.6 Hz), 6.01 (1H, dd, J=16.0, 6.4 Hz), 5.79 (1H, dddd, J=17.2, 10.4, 7.6, 7.2 Hz), 5.19-5.10 (2H, m), 3.94 (1H, m), 3.80 (3H, s), 3.08 (1H, br dd, J=9.6, 6.0 Hz), 2.58-2.43 (2H, m); $^{13}$C NMR (100 MHz, CDCl$_3$): δ 159.3, 133.9, 133.3 (d, J=127.0 Hz), 132.7 (d, J=130.0 Hz), 132.6 (d, J=9.4 Hz), 132.0 (d, J=9.5 Hz), 131.9 (d, J=2.8 Hz), 131.8 (d, J=2.8 Hz), 129.9, 129.6, 129.3 (d, J=5.7 Hz), 128.6 (d, J=12.4 Hz), 128.5 (d, J=12.6 Hz), 127.7, 119.0, 114.0, 55.4, 52.9, 42.4 (d, J=4.5 Hz); HRMS Calcd for C$_{25}$H$_{27}$NO$_2$P [M+H]$^+$: 404.17794. Found: 404.17730. [α]$^{20}_D$=+128.2 (c=1.00, CHCl$_3$) for a 99:1 er sample.

| Peak # | Ret. Time | Area % | Peak # | Ret. Time | Area % |
|---|---|---|---|---|---|
| 1 | 98.4 | 48.621 | 1 | 98.0 | 99.431 |
| 2 | 105.9 | 51.379 | 2 | 108.1 | 0.569 |

The enantiomeric purity of this compound was determined by HPLC analysis in comparison with authentic racemic material (Chiracel OD-H, 95:5 hexanes:i-PrOH, 0.2 mL/min, 220 nm): t$_R$ of S10: 98 min (major) and 108 min (minor).

(R,Z)-N-(2-Bromo-1-phenylhexa-1,5-dien-3-yl)-P,P-
diphenylphosphinic amide (S11)

The title compound is purified identically to 4b affording S11 (43.4 mg, 0.096 mmol, 96% yield) as a white solid. M.p.=123° C. IR (neat): 3133 (m, br), 3077 (w), 3056 (w), 2910 (w), 2861 (w), 1643 (w), 1591 (w), 1458 (w), 1434 (m), 1182 (s), 1123 (m), 1105 (m), 1088 (m), 984 (m), 952 (m), 916 (m), 865 (m), 746 (m), 723 (s), 691 (s), 594 (m), 568 (m), 536 (s) cm$^{-1}$; $^1$H NMR (400 MHz, CDCl$_3$): δ 7.95-7.85 (4H, m), 7.54-7.28 (11H, m), 6.56 (1H, s), 5.74 (1H, app ddt, J=17.2, 10.0, 7.2 Hz), 5.19-5.08 (2H, m), 4.04-3.95 (1H, m), 3.40 (1H, br dd, J=9.6, 8.4 Hz), 2.68-2.51 (2H, m); $^{13}$C NMR (100 MHz, CDCl$_3$): δ 135.1, 133.3, 133.0 (d, J=127.0 Hz), 132.8 (d, J=9.8 Hz), 132.2 (d, J=2.7 Hz), 132.1 (d, J=2.9 Hz), 131.9 (d, J=130.0 Hz), 131.8 (d, J=9.6 Hz), 129.7 (d, J=5.4 Hz), 129.4, 129.1, 128.7 (d, J=12.5 Hz), 128.5 (d, J=12.8 Hz), 128.2, 128.1, 118.6, 58.8, 41.3 (d, J=4.3 Hz); HRMS Calcd for C$_{24}$H$_{24}$BrNOP [M+H]$^+$: 452.07789. Found: 452.07908. [α]$^{20}_D$=+7.5 (c=1.00, CHCl$_3$) for a 98:2 er sample. The enantiomeric purity of this compound was determined by HPLC analysis in comparison with authentic racemic material (Chiracel OD-H, 92:8 hexanes:i-PrOH, 0.5 mL/min, 220 nm): t$_R$ of S11: 14 min (major) and 19 min (minor).

| Peak # | Ret. Time | Area % | Peak # | Ret. Time | Area % |
|---|---|---|---|---|---|
| 1 | 13.8 | 49.618 | 1 | 13.9 | 98.297 |
| 2 | 19.1 | 50.382 | 2 | 19.5 | 1.703 |

(R,E)-N-(Nona-1,5-dien-4-yl)-P,P-diphenylphosphinic amide (S12)

The title compound is prepared and purified analogously to 4b from freshly prepared 6 (except 2.5 mol % aminophenol 2g used in the reaction instead of 3.0 mol %) affording S12 (32.7 mg, 0.096 mmol, 96% yield) as a white solid. Crystals suitable for x-ray crystallography were obtained by vapor diffusion from a dichloromethane/hexane solvent system at 22° C. See Part D of the Supplementary Information for the X-ray crystal structure. M.p.=87° C. IR (neat): 3121 (m, br), 3057 (w), 2953 (w), 2928 (w), 2868 (w), 1639 (w), 1590 (w), 1458 (m), 1436 (m), 1198 (m), 1182 (m), 1107 (m), 1065 (m), 966 (m), 909 (m), 753 (w), 719 (s), 691 (s), 565 (m), 524 (s) cm$^{-1}$; $^1$H NMR (400 MHz, CDCl$_3$): δ 7.94-7.83 (4H, m), 7.50-7.38 (6H, m), 5.74 (1H, dddd, J=17.2, 10.4, 8.0, 6.8 Hz), 5.50 (1H, app dtd, J=15.2, 6.4, 0.8 Hz), 5.39 (1H, app ddt, J=15.6, 6.0, 1.0 Hz), 5.15-5.07 (2H, m), 3.78-3.68 (1H, m), 2.93 (1H, br dd, J=9.6, 6.0 Hz), 2.47-2.31 (2H, m), 1.94 (2H, quartet, J=6.8 Hz), 1.33 (2H, app sextet, J=7.2 Hz), 0.86 (3H, t, J=7.2 Hz); $^{13}$C NMR (100 MHz, CDCl$_3$): δ 134.1, 133.4 (d, J=127.0 Hz), 132.9 (d, J=130.0 Hz), 132.6 (d, J=9.4 Hz), 132.0 (d, J=9.5 Hz), 131.8 (2 d exactly overlapping, J=2.5 Hz), 131.7 (d, J=5.7 Hz), 131.5, 128.5 (d, J=12.5 Hz), 128.5 (d, J=12.5 Hz), 118.4, 52.6, 42.7 (d, J=4.5 Hz), 34.4, 22.4, 13.8; HRMS Calcd for C$_{21}$H$_{27}$NOP [M+H]$^+$: 340.18303. Found: 340.18359. [α]$^{20}_D$=+7.40 (c=1.00, CHCl$_3$) for a 98:2 er sample. The enantiomeric purity of this compound was determined by HPLC analysis in comparison with authentic racemic material (Chiracel OD-H, 98.5:1.5 hexanes:i-PrOH, 0.15 mL/min, 220 nm): t$_R$ of S12: 175 min (major) and 193 min (minor).

| Peak # | Ret. Time | Area % | Peak # | Ret. Time | Area % |
|---|---|---|---|---|---|
| 1 | 170.6 | 49.503 | 1 | 175.0 | 98.210 |
| 2 | 181.4 | 50.497 | 2 | 193.4 | 1.790 |

(R)—P,P-Diphenyl-N-(1-phenylhex-5-en-1-yn-3-yl) phosphinic amide (S13)

The title compound is purified identically to 4b affording S13 (33.9 mg, 0.0913 mmol, 91% yield) as a yellow solid. M.p.=105-107° C. IR (neat): 3132 (m, br), 3076 (w), 3055 (w), 2913 (w), 2857 (w), 1641 (w), 1591 (w), 1488 (m), 1312 (m), 1181 (s), 1125 (s), 1107 (s), 1070 (m), 945 (m), 747 (s), 725 (s), 690 (s), 530 (s) cm$^{-1}$; $^1$H NMR (400 MHz, CDCl$_3$): δ 8.04-7.99 (2H, m), 7.89-7.84 (2H, m), 7.52-7.40 (6H, m), 7.35-7.32 (2H, m), 7.32-7.24 (3H, m) 5.97 (1H, dddd, J=17.0, 10.0, 7.6, 6.9 Hz), 5.29-5.19 (2H, m), 4.31-4.23 (1H, m), 3.37 (1H, dd, J=10.1, 8.3 Hz), 2.70-2.53 (2H, m); $^{13}$C NMR (100 MHz, CDCl$_3$): δ 133.2, 133.0 (d, J=127.6 Hz), 132.9 (d, J=9.8 Hz), 132.1 (d, J=2.7 Hz), 132.0 (d, J=130.4 Hz), 131.8 (d, J=9.8 Hz, only the peak at 131.9 is visible, the other is overlapping), 131.8, 128.8 (d, J=12.6 Hz), 128.8 (d, J=12.9 Hz), 128.4 (d, J=5.5 Hz, only the peak at 128.4 is visible, the other is overlapping), 122.9, 119.7, 89.7 (d, J=8.0 Hz), 84.1, 43.4, 42.9 (d, J=3.5 Hz); HRMS Calcd for C$_{24}$H$_{23}$NOP [M+H]$^+$: 372.15173. Found: 372.15177. [α]$^{20}_D$=-100 (c=0.85, CHCl$_3$) for a 88:12 er sample. The enantiomeric purity was determined by HPLC analysis in comparison with authentic racemic material (Chiracel OD, 97:3 hexanes:i-PrOH, 0.8 mL/min, 220 nm): t$_R$ of S13: 27 min (minor) and 30 min (major).

| Peak # | Ret. Time | Area % | Peak # | Ret. Time | Area % |
|---|---|---|---|---|---|
| 1 | 26.5 | 48.389 | 1 | 27.0 | 11.961 |
| 2 | 30.1 | 51.611 | 2 | 29.5 | 88.039 |

Representative Procedure for Enantioselective Allyl Additions to Alkyl-Substituted N-Diphenylphosphinoyl Imines

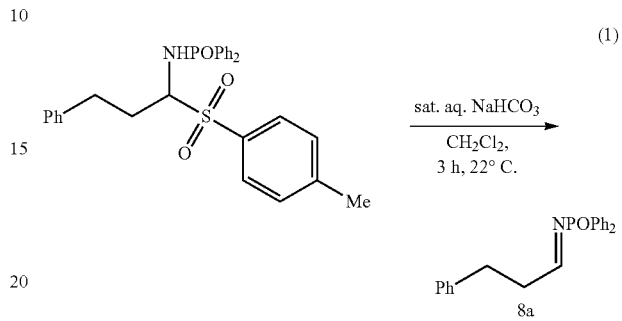

Preparation of the Alkyl-Substituted Aldimine:

A six-dram vial equipped with an 11×4 mm stir bar is charged with sulfinyl adduct (eq. 1, 0.4 mmol) to which is added CH$_2$Cl$_2$ (8.0 mL) and a saturated aqueous solution of NaHCO$_3$ (8.0 mL) consecutively. The biphasic mixture is allowed to stir vigorously enough for the solution to be homogeneous for 3 h at 22° C. The organic layer is separated and the aqueous phase is washed with CH$_2$Cl$_2$ (3×5 mL). The combined organic layers are dried over MgSO$_4$. The volatiles are removed under reduced pressure and the unpurified imine is azeotropically dried under vacuum with anhydrous benzene to afford aldimine 8a as light yellow oil (>98% conversion and yield are assumed). The vessel containing 8a is sealed with a rubber septum and anhydrous toluene (2 mL) is added to prepare a stock solution of 0.1 mmol 8a/500. μL toluene.

Preparation of Catalyst Solution (Small Scale):

In a nitrogen-filled glovebox (not needed for gram scale; only used when reactions are performed at mg scale to achieve highly reproducible data), aminophenol 2g (6.9 mg, 0.023 mmol) is added to an oven-dried two-dram vial equipped with a stir bar followed by 1.5 mL of a stock solution of NaOt-Bu in toluene (9.6 mg, 0.10 mmol/8.0 mL). The vial is sealed with a cap (phenolic open top cap with a red PFTE/white silicone septa) and electrical tape and allowed to stir under nitrogen at 22° C. for ~10 minutes.

An oven-dried two-dram vial equipped with a stir bar and sealed with a cap (phenolic open top cap with a red PFTE/white silicone septa) and electrical tape is charged with toluene (100. μL), methanol (10. μL, 0.25 mmol), and allylboronic acid pinacol ester (28 μL, 0.15 mmol). To this mixture is added 500. μL of the stock solution of aldimine 8a (described above), followed by 400. μL of the catalyst solution (described above) of [2g (1.82 mg, 6.00 mol) and NaOt-Bu (0.48 mg, 5.0 mol)]. The clear and colorless solution is allowed to stir at 22° C. for four h during which time no visible change occurs. The cap is removed and 3 mL of saturated aqueous NaIO$_4$ is added and the biphasic mixture is allowed to stir for 20 minutes. The aqueous layer is washed with ethyl acetate (4×4 mL), and the combined organic layers are dried over Na$_2$SO$_4$ and concentrated in vacuo. The resulting yellow oil was purified by silica gel chromatography (10 mm diameter column slurry packed with 2.5 g of silica gel in 95:5 hexanes:triethylamine and eluted with 10 mL hexanes, 10 mL 3:1 hexanes:ethyl acetate, 10 mL 2:1 hexanes:ethyl acetate, 10 mL 1:1 hexanes:ethyl acetate, and 10 mL ethyl acetate) to afford S14 (19.2 mg, 0.0511 mmol, 51% yield) as a white solid.

(S)—P,P-Diphenyl-N-(1-phenylhex-5-en-3-yl)phosphinic amide (S14)

The analytical data are fully consistent with those reported previously.[13] $^1$H NMR (400 MHz, CDCl$_3$): δ 7.91-7.84 (4H, m), 7.49-7.39 (6H, m), 7.24-7.19 (2H, m), 7.15-7.10 (3H, m), 5.78 (1H, dddd, J=17.2, 10.4, 7.6, 7.6 Hz), 5.14-5.09 (2H, m), 3.25-3.16 (1H, m), 2.82 (1H, br dd, J=10.8, 6.4 Hz), 2.73-2.57 (2H, m), 2.39-2.35 (2H, m), 1.86-1.80 (2H, m); HRMS Calcd for C$_{24}$H$_{27}$NOP [M+H]$^+$: 376.18303. Found: 376.18135. [α]$^{20}_D$=−2.6 (c=0.43, CHCl$_3$) for a>99:1 er sample. The enantiomeric purity of this compound was determined by HPLC analysis in comparison with authentic racemic material (Chiracel OD-H, 95:5 hexanes:i-PrOH, 0.6 mL/min, 220 nm): t$_R$ of S14: 22 min (major) and 28 min (minor).

| Peak # | Ret. Time | Area % | Peak # | Ret. Time | Area % |
|---|---|---|---|---|---|
| 1 | 22.9 | 50.002 | 1 | 22.3 | 99.421 |
| 2 | 27.8 | 49.998 | 2 | 28.1 | 0.579 |

(S)—N-(6-Methylhept-1-en-4-yl)-P,P-diphenylphosphinic amide (S15)

The title compound is purified identically to S14, affording S15 (17.7 mg, 0.0540 mmol, 54% yield) as a white solid. The analytical data are fully consistent with those reported previously.[13] $^1$H NMR (400 MHz, CDCl$_3$): δ 7.93-7.87 (4H, m), 7.51-7.41 (6H, m), 5.79 (1H, dddd, J=17.6, 10.4, 7.6, 7.6 Hz), 5.14-5.10 (2H, m), 3.25-3.14 (1H, m), 2.75 (1H, br dd, J=10.8, 6.0 Hz), 2.39-2.28 (2H, m), 1.84-1.70 (1H, m), 1.42-1.29 (2H, m), 0.80 (3H, d, J=6.6 Hz), 0.76 (3H, d, J=6.5 Hz); HRMS Calcd for C$_{20}$H$_{27}$NOP [M+H]$^+$: 328.18303. Found: 328.18398. [α]$^{20}_D$=−38 (c=0.73, CHCl$_3$) for a 98.5:1.5 er sample. The enantiomeric purity of this compound was determined by HPLC analysis in comparison with authentic racemic material (Chiracel OD-H, 95:5 hexanes:i-PrOH, 0.6 mL/min, 220 nm): t$_R$ of 515: 13 min (minor) and 14 min (major).

| Peak # | Ret. Time | Area % | Peak # | Ret. Time | Area % |
|---|---|---|---|---|---|
| 1 | 12.7 | 48.675 | 1 | 13.3 | 0.875 |
| 2 | 13.4 | 51.325 | 2 | 14.1 | 99.125 |

(R)—N-(1-Cyclohexylbut-3-en-1-yl)-P,P-diphenylphosphinic amide (S16)

The title compound is synthesized and purified identically to S14 (except 8.5 mol % of NaOt-Bu is used in the reaction instead of 5 mol %) affording S16 (27.2 mg, 0.0769 mmol, 77% yield) as a white solid. M.p.=120-122° C. IR (neat): 3207 (w, br), 3075 (w), 3057 (w), 2921 (m), 2850 (m), 1639 (w), 1436 (s), 1187 (s), 1123 (s), 1108 (s), 1067 (m), 994 (w), 909 (m), 722 (s), 694 (s), 533 (s) cm$^{-1}$; $^1$H NMR (400 MHz, CDCl$_3$): δ 7.93-7.87 (4H, m), 7.50-7.42 (6H, m), 5.77 (1H, dddd, J=17.3, 10.1, 7.3, 7.3 Hz), 5.12-5.06 (2H, m), 3.02-2.87 (1H, m), 2.77 (1H, br dd, J=10.7, 6.1 Hz), 2.09 (2H, app t, J=6.5 Hz), 1.82-1.61 (5H, m), 1.46-1.41 (1H, m), 1.24-1.15 (4H, m), 0.98-0.92 (1H, m); $^{13}$C NMR (100 MHz, CDCl$_3$): δ 135.1, 133.3 (d, J=128.7 Hz), 133.2 (d, J=129.8 Hz, only peak at 132.8 is visible, the other is overlapping), 132.5 (d, J=9.3 Hz), 132.3 (d, J=9.3 Hz), 131.80 (d, J=1.4 Hz), 131.78 (d, J=1.4 Hz), 127.50 (d, J=12.5 Hz), 127.48 (d, J=12.5 Hz), 117.8, 55.9 (d, J=2.2 Hz), 42.1 (d, J=5.1 Hz), 38.5 (d, J=4.2 Hz), 29.5, 28.8, 26.6, 26.5, 26.4; HRMS Calcd for C$_2$H$_{29}$NOP [M+H]$^+$: 354.19868. Found: 354.19835. [α]$^{20}_D$=−21 (c=0.78, CHCl$_3$) for a 97.5:2.5 er sample. The enantiomeric purity of this compound was determined by HPLC analysis in comparison with authentic racemic material (Chiracel OD-H, 95:5 hexanes:i-PrOH, 0.6 mL/min, 220 nm): t$_R$ of S16: 11 min (minor) and 14 min (major).

| Peak # | Ret. Time | Area % | Peak # | Ret. Time | Area % |
|---|---|---|---|---|---|
| 1 | 11.3 | 50.004 | 1 | 10.8 | 2.631 |
| 2 | 15.5 | 49.996 | 2 | 14.3 | 97.369 |

(R,E)-N-(2-Methyl-1-(2-methylthiazol-4-yl)hexa-1,5-dien-3-yl)-P,P-diphenylphosphinic amide (4o)

Please note that the data (reaction conditions/stoichiometries, yield, e.r.) refer to the reaction with 1a as the nucleophile instead of dr-1a. The title compound is synthesized analogously to 4o except for the following changes: 1) The aminophenol catalyst 2f is employed as a catalyst instead of 2g. 2) 20 mol % of NaOt-Bu is used in the reaction instead of 3 mol %. 3) Reaction time is six h. The product is purified by silica gel chromatography (10 mm diameter column slurry packed with 2.5 g of silica gel in 95:5 hexanes:triethylamine and eluted with 10 mL hexanes, 10 mL 1:1 hexanes:ethyl acetate, 15 mL diethyl ether, 6 mL ethyl acetate and 16 mL 5:1 ethyl acetate:MeOH) to afford 4o (37.7 mg, 0.0923 mmol, 92% yield) as a pale yellow oil. IR (neat): 3357 (w, br), 3193 (w, br), 3076 (w), 3058 (w), 2966 (w), 2926 (w), 2871 (w), 1574 (w), 1437 (m), 1184 (s), 1121(m), 1108 (m), 952 (m), 910 (m), 723 (s), 694 (s), 525 (s) cm$^{-1}$; $^1$H NMR (400 MHz, CDCl$_3$): δ 7.92-7.84 (4H, m), 7.40-7.37 (6H, m), 6.83 (1H, s), 6.30 (1H, s), 5.70 (1H, dddd, J=17.1, 9.9, 7.2, 7.2 Hz), 5.14-5.06 (2H, m), 3.81 (1H, dddd, J=9.4, 9.4, 6.6, 6.6 Hz), 3.16 (1H, dd, J=9.5, 5.6 Hz), 2.69 (3H, s), 2.60-2.53 (1H, m), 2.50-2.43 (1H, m), 2.00 (3H, s); $^{13}$C NMR (100 MHz, CDCl$_3$): δ 164.5, 152.9, 139.9 (d, J=5.0 Hz), 133.9, 133.1 (d, J=127.6 Hz), 132.6 (d, J=9.5 Hz), 132.4 (d, J=131.1 Hz), 131.9 (d, J=9.5 Hz), 131.9 (d, J=2.8 Hz), 131.8 (d, J=2.8 Hz), 128.6 (d, J=12.6 Hz), 128.5 (d, J=12.7 Hz), 120.2, 118.6, 115.7, 58.0, 40.4 (d, J=4.3 Hz), 19.3, 15.5; HRMS Calcd for C$_{24}$H$_{26}$N2OPS$_1$ [M+H]$^+$: 409.15034. Found: 409.15018. [α]$^{20}_D$=+94 (c=0.45, CHCl$_3$) for a 95:5 er sample. The enantiomeric purity was determined by HPLC analysis in comparison with authentic racemic material (Chiracel AD, 86:14 hexanes:i-PrOH, 0.5 mL/min, 220 nm): t$_R$ of 40: 25 min (minor) and 35 min (major).

| Peak # | Ret. Time | Area % | Peak # | Ret. Time | Area % |
|---|---|---|---|---|---|
| 1 | 25.4 | 49.688 | 1 | 25.3 | 4.741 |
| 2 | 35.7 | 50.312 | 2 | 35.3 | 95.259 |

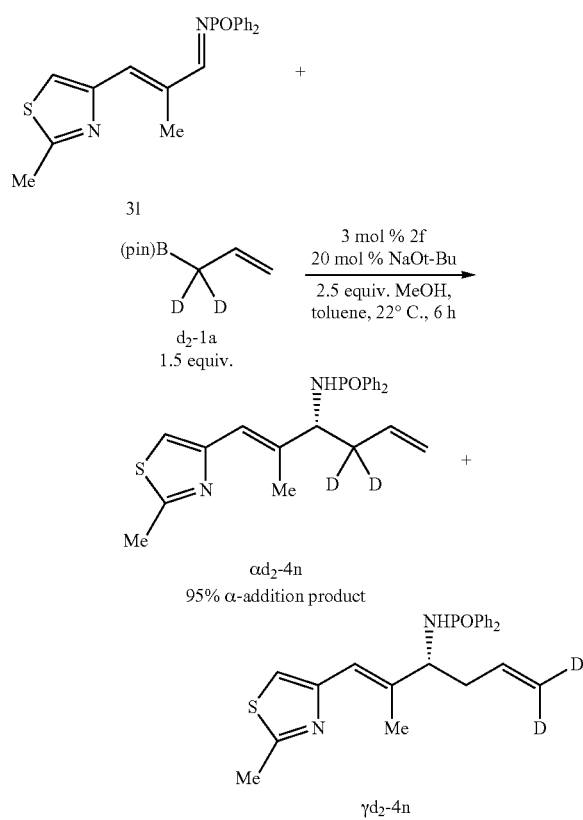

(R,E)-N-(4,4-Dideuterio-2-methyl-1-(2-methylthiazol-4-yl)hexa-1,5-dien-3-yl)-P,P-diphenylphosphinic amide (d₂-4o)

The title compound is synthesized and purified analogously to 4o, except 1,1-dideuterioallylboronic acid pinacol ester (d₂-1a) is used as the nucleophile (contaminated with ~50% vinylboronic acid pinacol ester). The reaction proceeded to 85% conversion (based on 400 MHz $^1$H NMR analysis and affords d₂-4-o (24.5 mg, 0.0597 mmol, 60% yield) in 95:5 α:γ addition products (see above; determined by $^2$H NMR) as yellow oil. The following analytical data is for a addition product α-d₂-4o, unless otherwise noted. IR (neat): 3357 (w, br), 3193 (w, br), 3076 (w), 3058 (w), 2966 (w), 2926 (w), 2871 (w), 1574 (w), 1437 (m), 1184 (s), 1121(m) 1108 (m), 910 (m), 723 (s), 694 (s), 525 (s) cm$^{-1}$; $^1$H NMR (400 MHz, CDCl₃): δ 7.95-7.85 (4H, m), 7.51-7.36 (6H, m), 6.84 (1H, s), 6.31 (1H, s), 5.70 (1H, dd, J=17.1, 10.1 Hz), 5.15-5.07 (2H, m), 3.79 (1H, app t, J=9.6 Hz), 3.16 (1H, dd, J=9.8, 5.6 Hz), 2.70 (3H, s), 2.60-2.53 (1H, m), 2.50-2.43 (γ-addition product; 0.17 H, m), 2.00 (3H, s); $^{13}$C NMR (100 MHz, CDCl₃): δ 164.6, 152.9, 139.9 (d, J=5.1 Hz), 133.8, 133.0 (d, J=127.7 Hz), 132.6 (d, J=9.5 Hz), 132.4 (d, J=131.1 Hz), 132.0 (d, J=9.5 Hz), 132.0 (d, J=2.9 Hz), 131.9 (d, J=2.6 Hz), 128.6 (d, J=12.6 Hz), 128.5 (d, J=12.7 Hz), 120.2, 118.7, 115.7, 57.9, 40.4-39.2 (m), 19.4, 15.5; $^2$H NMR (76 MHz, 9:1 CHCl₃:CDCl₃): δ 5.22-5.08 (γ-addition product; 0.09H, m), 2.51 (α-addition product; 2H, d, J=6.1 Hz); HRMS Calcd for C₂₄H₂₄D2N₂OPS [M+H]$^+$: 411.16290. Found: 411.16232. [α]$^{20}_D$=+47 (c=0.73, CHCl₃) for a 95:5 er sample. The enantiomeric purity was determined by HPLC analysis in comparison with authentic racemic material (Chiracel AD-H, 86:14 hexanes:i-PrOH, 0.5 mL/min, 254 nm): $t_R$ of d₂-4o: 25 min (minor) and 35 min (major).

| Peak # | Ret. Time | Area % | Peak # | Ret. Time | Area % |
|---|---|---|---|---|---|
| 1 | 24.6 | 49.354 | 1 | 24.2 | 4.425 |
| 2 | 34.5 | 50.646 | 2 | 33.7 | 95.575 |

Representative Procedure for Enantioselective Allyl Additions with Enantiomerically Enriched Allylboronates Preparation of catalyst solution and allylboronate Solution:

Under an atmosphere of nitrogen, aminophenol 2g (6.1 mg, 0.02 mmol) is added to an oven-dried two-dram vial equipped with a stir bar followed by 1.0 mL of a stock solution of NaOt-Bu in toluene (9.6 mg, 0.010 mmol/6.0 mL) and the solution is allowed to stir at 22° C. for ~10 minutes. In a separate oven-dried two-dram vial, allylboronate S-9 (70.8 mg, 0.260. mmol) and MeOH (17.5 L, 0.690. mmol) are dissolved in 700. μL of toluene to make a stock solution of S-9 and MeOH.

An oven-dried one-dram vial equipped with a stir bar is charged with phenyl-substituted aldimine 3a (15.3 mg, 50.0 mol), 150. μL of toluene, and 200. μL of the prenominate stock solution of S-9 (20 mg, 74 mol) and MeOH (4.0 mg, 13 mol). To this mixture is added 150. μL of the catalyst solution (described above) of 2g (0.92 mg, 3.0 mol) and NaOt-Bu (0.24 mg, 2.5 mol) and a cap is attached to the vial and sealed with electrical tape. The clear and colorless solution is allowed to stir at 22° C. for 18 hours during which time it becomes cloudy and white. The cap is removed and 3 mL of a saturated aqueous solution of NaIO₄ is added and the biphasic mixture is allowed to stir for 20 minutes. The aqueous layer is washed with ethyl acetate (4×4 mL), dried over Na₂SO₄, and concentrated in vacuo to provide a yellow solid. The homoallylamine product was purified by silica gel chromatography (10 mm diameter column slurry packed with 2.5 g of silica gel in 95:5 hexanes:triethylamine and eluted with 10 mL hexanes, 10 mL 1:1 hexanes:diethyl ether, 30 mL 1:3 hexanes:diethyl ether, 35 mL diethyl ether, 30 mL 4:1 diethyl ether:ethyl acetate) to afford 10b (19.3 mg, 0.0427 mmol, 85% yield of a 85:15 ratio of diastereomers) as an off white solid, which is re-crystallized from CH₂Cl₂/hexanes (vapor diffusion, 22° C.) to give 6.4 mg (0.014 mmol, 28% yield) of 10b as clear, colorless, needles suitable for X-ray crystallography in >20:1 dr and >99:1 er (See Part D of the Supplementary Information for the X-ray crystal structure). This diastereo- and enantiomerically enriched product was used to obtain the data given below (excluding the HPLC chromatographs). The HPLC chromatograph of the authentic racemic material was obtained from a 60:40 ratio of anti:syn diastereomers (enriched by silica gel chromatography). The excess of the anti diastereomer allowed assignment of which peak corresponds to which diastereomer. The identity and absolute stereochemistry of the major enantiomer of the major diastereomer is determined by X-Ray crystallography.

N-((1R,2R)-2-Phenethyl-1-phenylbut-3-en-1-yl)-P,P-diphenylphosphinic

M.p.=156-158° C. IR (neat): 3228 (w, br), 3059 (w), 3027 (w), 2916 (w), 2857 (w), 1437 (w), 1187 (m), 1125 (m), 1109 (m), 1069 (m), 917 (m), 745 (m), 723 (m), 692 (s), 534 (s) cm$^{-1}$; $^1$H NMR (400 MHz, CDCl₃): δ 7.82-7.77 (2H, m), 7.64-7.59 (2H, m), 7.50-7.46 (1H, m), 7.40-7.33 (3H, m), 7.21-7.12 (8H, m), 7.04-7.02 (4H, m), 5.73 (1H, ddd, J=17.5, 10.1, 9.1 Hz), 5.28 (1H, d, J=10.3 Hz), 5.11 (1H, d, J=17.1 Hz), 4.17 (1H, app dd, J=18.2, 8.0 Hz), 3.37 (1H, app t, J=7.1 Hz), 2.62 (1H, ddd, J=14.2, 9.4, 5.3 Hz), 2.50-2.43 (1H, m), 2.40-2.33 (1H, m), 1.76-1.68 (1H, m), 1.63-1.53 (1H, m); $^{13}$C NMR (100 MHz, CDCl$_3$): δ 142.6 (d, J=3.1 Hz), 142.0, 138.8, 133.5 (d, J=127.2 Hz), 132.7 (d, J=9.7 Hz, only peak at 132.6 is visible, the other is overlapping), 132.1 (d, J=130.7 Hz, only peak at 131.4 is visible, the other is overlapping), 131.9 (d, J=2.6 Hz), 131.8 (d, J=9.6 Hz), 131.6 (d, J=2.8 Hz), 128.6 (d, J=12.5 Hz), 128.6, 128.4, 128.2, 128.1 (d, J=12.8 Hz), 127.4, 127.1, 125.8, 118.8, 58.1, 51.1 (d, J=5.5 Hz), 33.3, 32.1; HRMS Calcd for C$_{30}$H$_{31}$NOP [M+H]$^+$: 452.21433. Found: 452.21249. [α]$^{20}$$_D$=+12 (c=0.43, CHCl$_3$) for a >20:1 dr, >99:1 er sample. The enantiomeric purity of this compound was determined by HPLC analysis in comparison with authentic racemic material (Chiracel AZ-H, 90:10 hexanes:i-PrOH, 0.8 mL/min, 220 nm): t$_R$ of 10b (anti diastereomer): 37 min (major) and 41 min (minor); t$_R$ of 10b (syn diastereomer): 26 min (major) and 45 min (minor).

| Peak # | Ret. Time | Area % | Peak # | Ret. Time | Area % |
|---|---|---|---|---|---|
| 1 (syn) | 25.9 | 18.157 | 1 (syn) | 25.8 | 7.653 |
| 2 (anti) | 36.9 | 30.657 | 2 (anti) | 36.6 | 87.094 |
| 3 (anti) | 41.3 | 31.716 | 3 (anti) | 41.0 | 4.572 |
| 4 (syn) | 45.4 | 19.470 | 4 (syn) | 45.0 | 0.681 |
| 1 (anti) | 36.6 | 95.012 | 1 (syn) | 25.8 | 91.828 |
| 2 (anti) | 41.0 | 4.988 | 2 (syn) | 45.0 | 8.172 |

To measure the enantiomeric purity of S-9, allylboronate S-9 was oxidized by hydrogen peroxide to the corresponding alcohol. The enantiomeric purity of allylboronate S-9 was determined by GLPC analysis in comparison with authentic racemic material (Betadex 120 column, 110° C., 15 psi).

| # | Time | Area | Area % | # | Time | Area | Area % |
|---|---|---|---|---|---|---|---|
| 1 | 114.54 | 59663 | 49.690 | 1 | 111.769 | 5814.6 | 6.057 |
| 2 | 118.40 | 66041 | 50.310 | 2 | 114.434 | 90180.3 | 93.943 |

N-((1R,2S)-2-Phenethyl-1-phenylbut-3-en-1-yl)-P,P-diphenylphosphinic amide (11)

The title compound is purified analogously to 10 affording 11 (22.5 mg, 0.0498 mmol, >98% yield of a 85:15 ratio of diastereomers) as a white solid. The resulting solid was recrystallized from CH$_2$Cl$_2$/hexanes (vapor diffusion, 22° C.) to give 7.4 mg (0.016 mmol, 32% yield) of 11 as clear, colorless needles suitable for x-ray crystallography in >20:1 dr and >99:1 er. This diastereo- and enantiomerically enriched product was used to obtain the data given below (excluding the HPLC chromatographs). The identity (and absolute stereochemistry of the major enantiomer) of the major diastereomer is determined by X-Ray crystallography (see Part D of the Supplementary Information). M.p.=161-163° C. IR (neat): 3215 (w, br), 3056 (w), 3027 (w), 2912 (w), 2855 (w), 1494 (m), 1184 (m), 1122 (m), 1106 (m), 1083 (m), 912 (m), 749 (m), 691 (s), 531 (s) cm$^{-1}$; $^1$H NMR (400 MHz, CDCl$_3$): δ 7.84-7.79 (2H, m), 7.67-7.62 (2H, m), 7.51-7.47 (1H, m), 7.42-7.36 (3H, m), 7.26-7.20 (7H, m), 7.15-7.12 (1H, m), 7.07-7.00 (4H, m), 5.49 (1H, ddd, J=17.3, 10.0, 10.0 Hz), 5.30-5.26 (2H, m), 4.22 (1H, ddd, J=11.1, 11.1, 4.7 Hz), 3.67 (1H, dd, J=10.7, 6.4 Hz), 2.68-2.61 (1H, m), 2.58-2.42 (2H, m), 1.76 (1H, dddd, J=13.5, 9.9, 6.3, 3.6 Hz), 1.29-1.19 (1H, m); $^{13}$C NMR (100 MHz, CDCl$_3$): δ 142.3, 140.9 (d, J=5.4 Hz), 137.6, 133.5 (d, J=127.5 Hz, only peak at 134.1 is visible, the other is overlapping), 132.8 (d, J=9.8 Hz, only peak at 132.7 is visible, the other is overlapping), 132.0 (d, J=2.7 Hz), 131.9 (d, J=131.7 Hz), 131.77 (d, J=9.6 Hz), 131.78 (d, J=2.8 Hz), 128.6 (d, J=12.5 Hz), 128.5, 128.4, 128.3 (d, J=12.8 Hz), 128.0, 127.8, 127.2, 125.9, 120.0, 58.0, 52.1 (d, J=3.1 Hz), 34.2, 33.9; HRMS Calcd for C$_{30}$H$_{31}$NOP [M+H]$^+$: 452.21433. Found: 452.21376. [α]$^{20}$$_D$=−16 (c=0.20) for a >20:1 dr and >99:1 er sample. The enantiomeric purity of this compound was determined by HPLC analysis in comparison with authentic racemic material; see explanation of peak assignment in the analytical data for compound 10 (Chiracel AZ-H, 90:10 hexanes:i-PrOH, 0.8 mL/min, 220 nm): t$_R$ of 11 (major diastereomer): 25 min (major) and 42 min (minor); t$_R$ of 11 (minor diastereomer): 35 min (major) and 38 min (minor).

| Peak # | Ret. Time | Area % | Peak # | Ret. Time | Area % |
|---|---|---|---|---|---|
| 1 (syn) | 25.9 | 18.157 | 1 (syn) | 24.5 | 87.752 |
| 2 (anti) | 36.9 | 30.657 | 2 (anti) | 34.9 | 8.135 |
| 3 (anti) | 41.3 | 31.716 | 3 (anti) | 38.3 | 0.574 |
| 4 (syn) | 45.4 | 19.470 | 4 (syn) | 41.7 | 3.539 |
| 1 (syn) | 24.5 | 96.123 | 1 (anti) | 34.9 | 93.411 |
| 2 (syn) | 41.7 | 3.877 | 2 (anti) | 38.3 | 6.589 |

To measure the enantiomeric purity of R-9, allylboronate R-9 was oxidized by hydrogen peroxide to the corresponding alcohol. The enantiomeric purity of allylboronate R-9 was determined by GLPC analysis in comparison with authentic racemic material (Betadex 120 column, 110° C., 15 psi).

| # | Time | Area | Area % | # | Time | Area | Area % |
|---|---|---|---|---|---|---|---|
| 1 | 114.54 | 59663 | 49.690 | 1 | 113.517 | 93000 | 95.398 |
| 2 | 118.40 | 66041 | 50.310 | 2 | 118.245 | 4486.1 | 4.60 |

N-((1S,2R)-2-Cyclohexyl-2-methyl-1-phenylbut-3-en-1-yl)-P,P-diphenylphosphinic amide (13)

The title compound is synthesized in the manner identical to that used for the preparation of 10 (except when utilizing Zn(Ot-Bu)$_2$ instead of NaOt-Bu). The homoallylamide 13 is purified by silica gel chromatography (10 mm diameter column slurry packed with 2.5 g of silica gel in 95:5 hexanes:triethylamine and eluted with 10 mL hexanes, 10 mL 1:1 hexanes:diethyl ether, 30 mL 1:3 hexanes:diethyl ether, 60 mL diethyl ether) to afford 13 (17.0 mg, 0.038 mmol, 76% yield of isolated major diastereomer) as a white solid. Crystals suitable for X-ray crystallography were obtained by vapor diffusion from a diethyl ether/hexane solvent system at 22° C. The identity (and absolute stereochemistry of the major enantiomer) of the major diastereomer is determined by X-ray crystallography (see Part D of the Supplementary Information). M.p.=137-139° C. IR (neat): 3221 (w, br), 3058 (w), 2924 (s), 2851 (m), 1452 (m), 1184 (s), 1123 (s), 1108 (s), 1064 (m), 912 (m), 723 (s), 698 (s), 530 (s) cm$^{-1}$; $^1$H NMR (400 MHz, CDCl$_3$): δ 7.79-7.74 (2H, m), 7.51-7.45 (3H, m), 7.41-7.38 (2H, m), 7.34-7.30 (1H, m), 7.23-7.20 (3H, m), 7.15 (2H, app ddd, J=7.7, 7.7, 3.2 Hz), 7.00-6.98 (2H, m), 5.70 (1H, dd, J=17.7, 11.0 Hz), 5.27 (1H, dd, J=10.9, 1.4 Hz), 5.13 (1H, dd, J=17.7, 1.4 Hz), 4.17 (1H, app t, J=11.2 Hz), 3.56 (1H, app t, J=9.8 Hz), 1.81 (1H, d, J=12.9 Hz), 1.67 (1H, d, J=10.8 Hz), 1.60-1.53 (2H, m), 1.36 (1H, d, J=6.9 Hz), 1.22 (3H, s), 1.10-0.67 (6H, m); $^{13}$C NMR (100 MHz, CDCl$_3$): δ 143.0, 141.9 (d, J=3.3 Hz) 133.7 (d, J=128.3 Hz), 132.8 (d, J=9.9 Hz), 132.0 (d, J=131.8 Hz), 131.83 (d, J=3.1 Hz, only peak at 131.81 is visible, the other is overlapping), 131.79 (d, J=9.4 Hz, only peak at 131.74 is visible, the other is overlapping), 131.5 (d, J=2.8 Hz), 128.6 (d, J=12.4 Hz), 128.4, 128.0 (d, J=12.8 Hz), 127.7, 126.9, 115.9, 59.4, 48.5 (d, J=3.8 Hz), 42.8, 29.1, 27.9, 27.1, 26.9, 26.6, 15.8; HRMS Calcd for C$_{29}$H$_{35}$NOP [M+H]$^+$: 444.24563. Found: 444.24499. [α]$^{20}_D$=+8.9 (c=0.87, CHCl$_3$) for a 95:5 er sample. The enantiomeric purity of this compound was determined by HPLC analysis in comparison with authentic racemic material (Chiracel AD-H, 90:10 hexanes:i-PrOH, 1.0 mL/min, 220 nm): t$_R$ of 13: 7.0 min (major) and 20 min (minor).

| Peak # | Ret. Time | Area % | Peak # | Ret. Time | Area % |
|---|---|---|---|---|---|
| 1 | 7.0 | 50.073 | 1 | 6.9 | 94.953 |
| 2 | 19.9 | 49.927 | 2 | 19.5 | 5.047 |

To measure the enantiomeric purity of 12, allylboronate 12 was oxidized by hydrogen peroxide to the corresponding alcohol. The enantiomeric purity of allylboronate 12 was determined by GLPC analysis in comparison with authentic racemic material (Chiral dex CD-BDM column, 140° C., 15 psi).

| # | Time | Area | Area % | # | Time | Area | Area % |
|---|---|---|---|---|---|---|---|
| 1 | 19.929 | 276.1 | 49.861 | 1 | 20.266 | 51.1 | 94.727 |
| 2 | 20.779 | 277.7 | 50.139 | 2 | 21.133 | 2.8 | 5.273 |

Representative Procedure for Small Scale Catalytic Enantioselective Allyl Additions to Isatins:

Under an atmosphere of N$_2$, aminophenol 2g (6.1 mg, 0.020 mmol) is added to an oven-dried two dram vial equipped with a stir bar followed by 2.0 mL of a stock solution of NaOt-Bu in toluene (7.7 mg, 0.080 mmol/8.0 mL). The vial is sealed with a cap (phenolic open top cap with a red PFTE/white silicone septa) and electrical tape, removed from the glovebox and allowed to stir under nitrogen at 22° C. for ~10 minutes.

A separate vial equipped with a stir bar is charged with N-TBS-isatin 14a' (26.2 mg, 0.100 mmol), sealed with a cap (phenolic open top cap with a red PFTE/white silicone septa) and electrical tape and purged with N$_2$. To this sealed vial under nitrogen is added toluene (0.95 mL), 50. uL of a catalyst solution [described above; 2g (0.16 mg, 0.50 mmol) and NaOt-Bu (0.048 mg, 0.50 mmol)], MeOH (10 µL, 0.25 mmol) and allylboronic acid pinacol ester 1a (28 µL, 0.15 mmol) by syringe in the stated order. The clear yellow solution is allowed to stir at 22° C. for 1.5 h during which time it becomes colorless, which signifies complete consumption of the highly pigmented starting material 14a'.

Removal of the TBS Group:

The cap is removed and the mixture is concentrated in vacuo. The resultant pale yellow oil is then dissolved in a solution of p-toluenesulfonic acid monohydrate (22.8 mg, 0.120 mmol) in methanol (0.5 mL, Fisher ACS grade). The mixture is allowed to stir at 22° C. for 3 h after which time 1 mL of a saturated solution of aqueous NaHCO$_3$ is added drop-wise over one minute. Ethyl acetate (1 mL) is subsequently added, the organic and the aqueous layers are separated, which are then washed with ethyl acetate (3×1 mL). The combined organic layers are dried over Na$_2$SO$_4$ and concentrated in vacuo to provide a white solid that is purified by silica gel chromatography (10 mm diameter column slurry packed with 2.5 g of silica gel in hexanes. The off-white solid residue is dry loaded on silica gel and eluted with 10 mL 4:1 hexanes:ethyl acetate, 20 mL 2:1 hexanes:ethyl acetate, 20 mL 1:1 hexanes:ethyl acetate) to afford 15a' (17.5 mg, 0.0925 mmol, 98% yield) as a white solid. Crystals suitable for X-ray crystallography (see Part D of the Supplementary Information) were grown by slow evaporation from methanol at 22° C.

(R)-3-Allyl-3-hydroxyindolin-2-one (15a')

The analytical data are fully consistent with those reported previously. $^1$H NMR (400 MHz, CD$_3$OD): δ 7.36 (1H, d, J=7.2 Hz), 7.26 (1H, t, J=8.5 Hz), 7.07 (1H, t, J=7.4 Hz), 6.89 (1H, d, J=7.7 Hz) 5.54 (1H, app dq, J=16.7, 8.1 Hz), 5.05-4.98 (2H, m), 2.76-2.59 (2H, m); HRMS Calcd for C$_1$H$_{12}$NO$_{12}$ [M+H]$^+$: 190.08680. Found: 190.08650. [α]$^{20}_D$=+11 (c=1.3, CHCl$_3$) for a 98:2 er sample. The enantiomeric purity of this compound was determined by HPLC analysis in comparison with authentic racemic material (Chiracel OD-H, 90:10 hexanes:i-PrOH, 0.8 mL/min, 220 nm): t$_R$ of 15a': 12 min (minor) and 15 min (major).

| Peak # | Ret. Time | Area % | Peak # | Ret. Time | Area % |
|---|---|---|---|---|---|
| 1 | 12.3 | 47.660 | 1 | 12.0 | 1.303 |
| 2 | 16.0 | 52.340 | 2 | 15.1 | 98.697 |

(R)-3-Allyl-(tert-butyldimethylsilyl)-3-hydroxyindolin-2-one (S17)

To obtain the N-TBS protected hydroxyl-oxindole, after concentration in vacuo, the resultant pale yellow oil can be purified by silica gel chromatography (10 mm diameter column slurry packed with 2.5 g of silica gel in dichloromethane and eluted with 10 mL dichloromethane followed by 30 mL 20:1 dichloromethane:diethyl ether) to afford S17 (30.4 mg, 0.100 mmol, >98% yield) as pale yellow oil. IR (neat): 3401 (w, br), 2953 (w), 2929 (w), 2858 (w), 1701 (s), 1613 (m), 1465 (s), 1255 (s), 1171 (s), 1105 (m), 945 (m), 824 (s), 732 (s) cm$^{-1}$; $^1$H NMR (400 MHz, CDCl$_3$): δ 7.36 (1H, dd, J=7.4, 1.4 Hz), 7.22 (1H, td, J=7.8, 1.5 Hz), 7.05 (1H, td, J=7.5, 0.8 Hz), 6.99 (1H, d, J=8.0 Hz), 5.54 (1H, dddd, J=16.9, 10.1, 8.5, 6.2 Hz), 5.10-5.04 (2H, m), 2.96 (1H, s), 2.72-2.57 (2H, m), 0.99 (9H, s), 0.51 (3H, s), 0.50 (3H, s); $^{13}$C NMR (100 MHz, CDCl$_3$): δ 185.3, 145.8, 131.6, 130.9, 129.4, 124.4, 122.7, 120.3, 113.2, 76.3, 43.9, 26.6, 19.8, −3.1, −3.3; HRMS Calcd for C$_{17}$H$_{26}$NO$_2$Si [M+H]$^+$: 304.17328. Found: 304.17280. [α]$^{20}_D$=+24.2 (c=1.5, CHCl$_3$) for a 94:6 er sample. The enantiomeric purity of this compound was determined by HPLC analysis in comparison with authentic racemic material (Chiracel AD-H, 90:10 hexanes:i-PrOH, 0.8 mL/min, 220 nm): t$_R$ of S17: 7 min (major) and 9 min (minor).

| Peak # | Ret. Time | Area % | Peak # | Ret. Time | Area % |
|---|---|---|---|---|---|
| 1 | 7.2 | 50.070 | 1 | 7.2 | 98.043 |
| 2 | 9.1 | 49.930 | 2 | 9.1 | 1.957 |

(R)-3-Allyl-4,6-dibromo-3-hydroxyindolin-2-one (15b')

The enantioselective allyl addition to SEM-isatin 14b' is carried out following the representative procedure for aminophenol catalyzed enantioselective allyl additions to isatins. The procedure for removal of SEM group is as follows. After 2.0 h, the mixture of the enantioselective allyl addition turns from yellow to colorless (signifying complete consumption of highly pigmented 14b'), the cap is removed and the reaction mixture is concentrated in vacuo. The resultant pale yellow oil is transferred to a two-dram vial, sealed with a septum and purged with nitrogen. A separate oven dried one-dram vial equipped with a stir bar is charged with $MgBr_2 \cdot Et_2O$ (96.8 mg, 0.375 mmol), sealed with a cap (phenolic open top cap with a red PFTE/white silicone septa) and electrical tape, and removed from the glovebox. The unpurified 3-allyl-3-hydroxy oxindole S18 is transferred through a syringe to the vial containing $MgBr_2 \cdot Et_2O$ using 3×300 uL of dichloromethane. The mixture is allowed to stir under nitrogen at 22° C. for 60 h during which time it becomes a tan slurry. The cap is removed and the tan slurry is dissolved in methanol and passed through a short plug of Celite®; the plug is washed with methanol (15 mL) and the combined solution is concentrated in vacuo to afford a tan solid. The resulting solid is dissolved in 1 mL of methanol and 2 mL of a solution of saturated aqueous $NaHCO_3$, and the cloudy light pink solution is allowed to stir open to the air at 22° C. for five h. Ethyl acetate (2 mL) is added and the layers separate. The aqueous layer is extracted with 3×2 mL of ethyl acetate and the combined organic layers are dried over $Na_2SO_4$ and concentrated in vacuo to afford a light tan solid. The hydroxyoxindole product is purified by silica gel chromatography (10 mm diameter column slurry packed with 2.5 g of silica gel in dichloromethane and eluted with 15 mL dichloromethane followed by 10 mL 9:1 dichloromethane:diethyl ether, 10 mL 8:1 dichloromethane:diethyl ether, and 30 mL 4:1 dichloromethane:diethyl ether), affording 15b' (14.9 mg, 0.0429 mmol, 86% yield) as a white solid. The analytical data are fully consistent with those reported previously. IR (neat): 3368 (m, br), 3169 (w, br), 2923 (w, br), 1703 (s), 1605 (s), 1572 (s), 1429 (m), 1364 (m), 1334 (m), 1300 (m), 1175 (m), 1086 (m), 1074 (m), 944 (m), 928 (m), 840 (s), 785 (m), 738 (m), 673 (s) cm$^{-1}$; $^1$H NMR (400 MHz, CD$_3$OD): δ 7.38 (1H, s), 7.02 (1H, s), 5.39-5.28 (1H, m), 5.09-5.05 (1H, m), 4.97-4.94 (1H, m), 3.26-3.21 (1H, m), 2.72-2.67 (1H, m), 3.24-3.19 (1H, m), 2.92 (1H, br s), 2.84-2.79 (1H, m), 0.91 (2H, t, J=8.0 Hz), −0.02 (9H, s); HRMS Calcd for $C_{11}H_{10}NO_2Br_2$ [M+H]$^+$: 347.90578. Found: 347.90587. $[\alpha]^{20}_D$=−10 (c=0.64, CH$_3$OH) for a 91.5:8.5 er sample. The enantiomeric purity of this compound was determined by HPLC analysis in comparison with authentic racemic material (Chiracel AD-H, 86:14 hexanes:i-PrOH, 0.5 mL/min, 220 nm): $t_R$ of 15b': 16 min (minor) and 21 min (major).

| Peak # | Ret. Time | Area % | Peak # | Ret. Time | Area % |
|---|---|---|---|---|---|
| 1 | 16.3 | 49.912 | 1 | 16.1 | 8.704 |
| 2 | 21.7 | 50.088 | 2 | 21.2 | 91.296 |

(R)-3-Allyl-4,6-dibromo-3-hydroxy-1-((2-(trimethylsilyl)ethoxy)methyl)indolin-2-one (S18, Chart S1)

If one wishes to obtain the N-SEM-protected hydroxyloxindole, then after concentration in vacuo, purify the resultant yellow oil by silica gel chromatography (10 mm diameter column slurry packed with 2.5 g of silica gel in dichloromethane and eluted with 40 mL dichloromethane) to afford S18 (23.0 mg, 0.0481 mmol, 96% yield) as a clear, colorless oil. IR (neat): 3400 (w, br), 3082 (w), 2953 (w), 2923 (w), 2895 (w), 1723 (m), 1597 (s), 1571 (m), 1249 (m), 1077 (s, br), 1010 (m), 922 (m), 857 (m), 831 (s) cm$^{-1}$; $^1$H NMR (400 MHz, CDCl$_3$): δ 7.41 (1H, s), 7.16 (1H, s), 5.34 (1H, dddd, J=17.0, 17.0, 8.4, 8.4 Hz), 5.16-5.10 (2H, m), 5.00-4.97 (2H, m), 3.56-3.46 (2H, m), 3.24-3.19 (1H, m), 2.92 (1H, br s), 2.84-2.79 (1H, m), 0.91 (2H, t, J=8.0 Hz), −0.02 (9H, s); $^{13}$C NMR (100 MHz, CDCl$_3$): δ 176.6, 145.0, 129.9, 129.6, 126.2, 124.2, 121.0, 120.0, 112.9, 78.1, 70.0, 66.6, 40.1, 17.9, −1.3; HRMS Calcd for $C_{18}H_{24}NO_3NaSiBr_2$ [M+Na]$^+$: 497.97062. Found: 497.97090. $[\alpha]^{20}_D$=+5.6 (c=1.1, CHCl$_3$) for a 91.5:8.5 er sample. The enantiomeric purity of this compound was determined by HPLC analysis in comparison with authentic racemic material (Chiracel OJ-H, 95:5 hexanes:i-PrOH, 0.5 mL/min, 220 nm): $t_R$ of S18: 9 min (major) and 20 min (minor).

| Peak # | Ret. Time | Area % | Peak # | Ret. Time | Area % |
|---|---|---|---|---|---|
| 1 | 9.1 | 49.485 | 1 | 9.1 | 91.606 |
| 2 | 19.6 | 50.515 | 2 | 19.2 | 8.394 |

(R)-3-Allyl-(tert-butyldimethylsilyl)-3-hydroxy-5-methoxyindolin-2-one (16)

The title compound is synthesized in the same manner as described for S17 (except reaction time is four h) and purified by silica gel chromatography (10 mm diameter column slurry packed with 2.5 g of silica gel in dichloromethane and eluted with 10 mL dichloromethane, 15 mL 30:1 dichloromethane:diethyl ether, 30 mL 20:1 dichloromethane:diethyl ether), affording N-TBS-protected hydroxyoxindole 16 (31.2 mg, 0.0932 mmol, 93% yield) as a pale orange oil. IR (neat): 3400 (w, br), 2953 (w), 2930 (w), 2858 (w), 1699 (s), 1594 (m), 1482 (s), 1255 (s), 1197 (s), 1120 (w), 1081 (m), 911 (m), 840 (s), 790 (m), 730 (s) cm$^{-1}$; $^1$H NMR (400 MHz, CDCl$_3$): δ 6.96 (1H, d, J=2.8 Hz), 6.89 (1H, d, J=8.7 Hz), 6.75 (1H, app dd, J=8.7, 2.7 Hz), 5.54 (1H, dddd, J=16.9, 10.1, 9.0, 6.1 Hz), 5.11-5.07 (2H, m), 3.79 (3H, s), 2.99 (1H, s), 2.70-2.56 (2H, m), 0.98 (9H, s), 0.50 (3H, s), 0.48 (3H, s); $^{13}$C NMR (100 MHz, CDCl$_3$): δ 185.2, 155.8, 138.9, 132.8, 130.8, 120.3, 114.5, 113.7, 110.7, 76.7, 55.9, 44.0, 26.6, 19.8, −3.2, −3.4; HRMS Calcd for $C_{15}H_{28}NO_3Si$ [M+H]$^+$: 334.18384. Found: 334.18318. $[\alpha]^{20}_D$=+11 (c=1.3, CHCl$_3$) for a 98:2 er sample. The enantiomeric purity of this compound was determined by HPLC analysis in comparison with authentic racemic material (Chiracel AD-H, 90:10 hexanes:i-PrOH, 0.8 mL/min, 254 nm): $t_R$ of 16: 9 min (major) and 12 min (minor).

| Peak # | Ret. Time | Area % | Peak # | Ret. Time | Area % |
|---|---|---|---|---|---|
| 1 | 8.7 | 49.828 | 1 | 8.9 | 97.966 |
| 2 | 12.0 | 50.172 | 2 | 12.0 | 2.034 |

(R)-3-Allyl-1-benzyl-3-hydroxy-5-methylindolin-2-one (17)

The title compound is synthesized in the same manner as that described for S17 except for the following changes: 1) Reaction time is two h. 2) The catalytic enantioselective allyl addition is quenched with 3 mL of a solution of saturated aqueous NaIO$_4$ (to remove excess pinacol) and allowed to stir for 14 h at 22° C. The aqueous layer is washed with ethyl acetate (4×4 mL) and the combined organic layers are dried over Na$_2$SO$_4$ and concentrated in vacuo to provide yellow oil.

The product 17 is purified by silica gel chromatography (10 mm diameter column slurry packed with 2.5 g of silica gel in hexanes and eluted with 10 mL hexanes, 10 mL 6:1 hexanes: ethyl acetate, and 20 mL 4:1 hexanes:ethyl acetate), affording 17 (24.5 mg, 0.084 mmol, 84% yield) as an off-white solid. The analytical data are fully consistent with those reported previously. $^1$H NMR (400 MHz, CDCl$_3$): δ 7.31-7.22 (6H, m), 6.99 (1H, d, J=7.9 Hz), 6.57 (1H, d, J=8.0 Hz), 5.69-5.58 (1H, m), 5.18-5.09 (2H, m), 4.99 and 4.70 (2H, ABq, J$_{AB}$=15.7 Hz), 3.18 (1H, br s), 2.83-2.78 (1H, m), 2.73-2.68 (1H, m), 2.31 (3H, s); HRMS Calcd for C$_{19}$H$_{20}$NO$_2$ [M+H]$^+$: 294.14940. Found: 294.14905. [α]$^{20}$$_D$=+5.1 (c=0.95, CHCl$_3$) for a 98.5:1.5 er sample. The enantiomeric purity of this compound was determined by HPLC analysis in comparison with authentic racemic material (Chiracel OJ-H, 90:10 hexanes:i-PrOH, 0.8 mL/min, 220 nm): t$_R$ of

| Peak # | Ret. Time | Area % | Peak # | Ret. Time | Area % |
|---|---|---|---|---|---|
| 1 | 13.4 | 49.524 | 1 | 13.3 | 98.654 |
| 2 | 16.2 | 50.476 | 2 | 16.1 | 1.346 |

(R)-1-Benzyl-3-hydroxy-3-(2-methylallyl)indolin-2-one (18)

The title compound is synthesized in the same manner as described for S17 except for the following changes: 1) Reaction time is one h. 2) Allylboronate 1b is employed as the nucleophile instead of allylboronate 1a. 3) The catalytic enantioselective allyl addition process is quenched with 3 mL of a solution of saturated aqueous NaIO$_4$ (to remove excess pinacol) and allowed to stir for 14 h at 22° C. The aqueous layer is washed with ethyl acetate (4×4 mL), dried over Na$_2$SO$_4$, and concentrated in vacuo to provide yellow oil. The product is purified by silica gel chromatography (10 mm diameter column slurry packed with 2.5 g of silica gel in dichloromethane and eluted with 34 mL dichloromethane followed by 26 mL 9:1 dichloromethane:ethyl acetate), affording 18 (28.7 mg, 0.0976 mmol, 98% yield) as a white solid. M.p.=52-54° C. IR (neat): 3399 (w, br), 3366 (w, br), 1692 (s), 1614 (m), 1466 (m), 1350 (m), 1196 (m), 991 (m), 756 (s), 727 (s) cm$^{-1}$; $^1$H NMR (400 MHz, CDCl$_3$): δ 7.41 (1H, d, J=7.3 Hz), 7.31-7.22 (5H, m), 7.20 (1H, t, J=7.7 Hz), 7.06 (1H, t, J=7.5 Hz), 6.69 (1H, d, J=7.7 Hz), 5.02 and 4.72 (2H, ABq, J$_{AB}$=15.7 Hz), 4.79 (1H, s), 4.68 (1H, s), 2.93 (1H, s), 2.77 (2H, s), 1.50 (3H, s); $^{13}$C NMR (100 MHz, CDCl$_3$): δ 178.0, 142.9, 139.1, 135.5, 129.9, 129.8, 128.9, 127.8, 127.4, 124.6, 123.1, 116.5, 109.6, 76.5, 46.3, 44.0, 24.1; HRMS Calcd for C$_{19}$H$_{20}$NO$_2$ [M+H]$^+$: 294.14940. Found: 294.14930. [α]$^{20}$$_D$=+22 (c=1.3, CHCl$_3$) for a 96:4 er sample. The enantiomeric purity of this compound was determined by HPLC analysis in comparison with authentic racemic material (Chiracel OJ-H, 90:10 hexanes:i-PrOH, 0.8 mL/min, 220 nm): t$_R$ of 15e: 15 min (major) and 34 min (minor).

| Peak # | Ret. Time | Area % | Peak # | Ret. Time | Area % |
|---|---|---|---|---|---|
| 1 | 16.4 | 50.578 | 1 | 15.4 | 95.755 |
| 2 | 31.3 | 49.422 | 2 | 33.6 | 4.245 |

Representative Procedure for Small Scale Catalytic Enantioselective Allene Group Additions to Isatins:

An oven-dried vial equipped with a stir bar is charged with aminophenol 2g (6.1 mg, 20 mmol) and NaOt-Bu (1.9 mg, 20. μmol). The vial is sealed with a septum and Teflon tape and purged with N$_2$. Anhydrous toluene (2.0 mL) is added and the mixture is allowed to stir for 10 min under N$_2$ at 22° C. A separate oven-dried vial equipped with a stir bar is charged with isatin 14c' (53.4 mg, 0.200 mmol). The vial is sealed with a septum and Teflon tape and purged with N$_2$. Toluene (600. μL) and MeOH (8.1 μL, 0.20 mmol) are then transferred by syringe to the vial containing isatin 14c'. An appropriate portion of the stock solution of catalyst (100. μL) is transferred to the vial. Allenyl boron 19 (50.0 μL, 0.140 mmol) is added by syringe and the mixture was allowed to stir at 22° C. until the solution becomes colorless indicating complete consumption of the highly pigmented isatin. The mixture is diluted with AcOEt and passed through a short column of silica gel. The unpurified residue obtained as a pale yellow oil was purified by silica gel chromatography (a gradient from 100% CH$_2$Cl$_2$ to 1:1 Et$_2$O:CH$_2$Cl$_2$ to 100% Et$_2$O) to yield 56.0 mg (0.182 mmol, 91% yield) of pure 20a as a white crystalline solid in 98.5:1.5 er.

(R)-1-Benzyl-3-hydroxy-5-methoxy-3-(propa-1,2-dien-1-yl)indolin-2-one (20a)

white crystalline solid: M.p.=117-119° C. IR (neat): 3366 (m, br), 1697 (s), 1604 (w), 1490 (s), 1435 (m), 1346 (m), 1179 (m), 1017 (m), 853 (m), 730 (m), 697 (m) cm$^{-1}$; $^1$H NMR (400 MHz, CDCl$_3$): δ 7.33-7.24 (5H, m), 7.03 (1H, d, J=2.4 Hz), 6.73 (1H, dd, J=8.4, 2.8 Hz), 6.60 (1H, d, J=8.4 Hz), 5.55 (1H, t, J=6.4 Hz), 5.01 (2H, dd, J=6.4, 1.2 Hz), 4.93 and 4.72 (2H, ABq, J$_{AB}$=15.8 Hz), 3.76 (3H, s), 3.36 (1H, br s); $^{13}$C NMR (100 MHz, CDCl$_3$): δ 207.8, 176.6, 156.4, 135.5, 135.4, 130.9, 128.9, 127.8, 127.3, 114.7, 111.7, 110.3, 93.1, 80.2, 75.1, 55.9, 44.0; HRMS Calcd for C$_{19}$H$_{18}$NO$_3$ [M+H]$^+$: 308.12867. Found: 308.12935. [α]$^{20}$$_D$=−37.6 (c=1.00, CHCl$_3$) for a 98.5:1.5 er sample. The enantiomeric purity of this compound was determined by HPLC analysis in comparison with authentic racemic material (Chiracel OD, 92:8 hexanes:i-PrOH, 0.8 mL/min, 220 nm): t$_R$ of 20a: 17 min (major) and 21 min (minor), t$_R$ of corresponding propargyl adduct: 19 min (major) and 25 min (minor).

| Peak # | Ret. Time | Area % | Peak # | Ret. Time | Area % |
|---|---|---|---|---|---|
| 1 | 16.7 min | 49.606 | 1 | 16.5 min | 98.581 |
| 2 | 21.3 min | 50.394 | 2 | 21.6 min | 1.419 |

Representative Procedure for Gram Scale Catalytic Enantioselective Allene Group Additions to Isatins:

An oven-dried vial equipped with a stir bar is charged with aminophenol 2g (11.6 mg, 38. μmol) and NaOt-Bu (3.6 mg, 38 μmol). The vial is sealed with a septum and Teflon tape and purged with N$_2$. Anhydrous toluene (2.0 mL) is added and the mixture is allowed to stir for 10 min under N$_2$ at 22° C. A separate flame-dried 50 mL round bottom flask equipped with a stir bar is charged with isatin 14d' (1.015 g, 3.800 mmol). The flask is sealed with a septum and Teflon tape and purged with N$_2$. Toluene (14.0 mL) and MeOH (307 μL, 7.60 mmol) are then transferred by syringe to the flask containing isatin 14d'. An appropriate portion of the stock solution of catalyst (1.00 mL) is transferred to the flask. Allenyl boron 19 (750. μL, 4.17 mmol) is added by syringe and the mixture is allowed to stir at 22° C. until the solution becomes colorless indicating complete consumption of the highly pigmented isatin (4.0 h). The reaction mixture is concentrated and the unpurified residue obtained as pale yellow oil is purified by silica gel chromatography (a gradient from 100% CH$_2$Cl$_2$ to 1:1 Et$_2$O:CH$_2$Cl$_2$ to 100% Et$_2$O) to yield 1.056 g (3.43 mmol, 90% yield) of pure 20b as a foamy white solid in 96:4 er.

(R)-3-Hydroxy-1-(4-methoxybenzyl)-3-(propa-1,2-dien-1-yl)indolin-2-one (20b)

clear oil. IR (neat): 3367 (m, br), 1701 (s), 1612 (m), 1512 (m), 1467 (m), 1350 (m), 1246 (m), 1175 (m), 1031 (m), 810 (m), 749 (m) cm$^{-1}$; $^1$H NMR (400 MHz, CDCl$_3$): δ 7.41-7.39 (1H, m), 7.23-7.19 (3H, m), 7.08-7.04 (1H, m), 6.85-6.81 (2H, m), 6.73 (1H, d, J=7.6 Hz), 5.55 (1H, t, J=6.4 Hz), 4.98 (2H, d, J=6.8 Hz), 4.92 and 4.73 (2H, ABq, J$_{AB}$=15.6 Hz), 3.76 (3H, s), 3.43 (1H, br s); $^{13}$C NMR (100 MHz, CDCl$_3$): δ 207.8, 176.6, 159.3, 142.3, 129.9, 129.6, 128.7, 127.5, 124.8, 123.3, 114.3, 109.8, 93.0, 80.3, 74.7, 55.4, 43.5; HRMS Calcd for C$_{19}$H$_{18}$NO$_2$ [M+H]$^+$: 292.13375. Found: 292.13468. [α]$^{20}_D$=−2.92 (c=1.00, CHCl$_3$) for a 96:4 er sample. The enantiomeric purity of this compound was determined by HPLC analysis in comparison with authentic racemic material (Chiracel OD, 95:5 hexanes:i-PrOH, 0.8 mL/min, 220 nm): t$_R$ of 20b: 31 min (minor) and 38 min (major), t$_R$ of corresponding propargyl adduct: 36 min

| Peak # | Ret. Time | Area % | Peak # | Ret. Time | Area % |
|---|---|---|---|---|---|
| 1 | 30.7 min | 49.810 | 1 | 31.0 min | 3.610 |
| 2 | 38.8 min | 50.190 | 2 | 38.0 min | 96.390 |

Procedure for One-Pot Aminophenol-Catalyzed Enantioselective Allene Group Addition/Desilylation of N-TBS-protected-Isatin 14a' on Gram Scale:

On a bench-top, an oven-dried vial equipped with a stir bar is charged with aminophenol 2g (6.1 mg, 20. μmol) and NaOt-Bu (3.1 mg, 32 mmol). The vial is sealed with a septum and Teflon tape and purged with N$_2$. Anhydrous toluene (2.0 mL) is added and the mixture is allowed to stir for 10 min under N$_2$ at 22° C. A separate flame-dried 50 mL round bottom flask equipped with a stir bar is charged with isatin 14a' (1.045 g, 4.000 mmol). The flask is sealed with a septum and Teflon tape and purged with N$_2$. Toluene (9.0 mL) and MeOH (325 μL, 8.00 mmol) are then transferred by syringe to the flask containing N-TBS-protected isatin 14a'. An appropriate portion of the stock solution of catalyst (1.00 mL) is transferred to the flask. Allenylboron reagent 19 (750. μL, 4.17 mmol) is added by syringe and the mixture is allowed to stir at 22° C. until the solution becomes colorless indicating complete consumption of intensely orange 14a' (2.0 minutes). The mixture is concentrated and the unpurified residue is re-dissolved in MeOH (20.0 mL) and treated with an aqueous 1.0 M solution of HCl (5.0 mL). The solution is allowed to stir at 22° C. until TLC analysis indicated complete consumption of the silylamide (typically 2.0 h). The solution is diluted with EtOAc (20 mL) and H$_2$O (20 mL) and the organic layer is separated. The aqueous layer is further washed with EtOAc (3×20 mL), the organic layers are combined and dried over Na$_2$SO$_4$. The volatiles are removed yielding white solid which is recrystallized from EtOAc/hexanes (2 crops) to yield 675.8 mg of hydroxyindole 21 (3.61 mmol, 90% yield) as a white crystalline solid in >99:1 er.

(R)-3-Hydroxy-3-(propa-1,2-dien-1-yl)indolin-2-one (21)

white crystalline solid, M.p.=189-190° C. IR (neat): 3316 (s, br), 1955 (w), 1691 (s), 1619 (m), 1469 (m), 1377 (m), 1355 (m), 1181 (m), 1103 (m), 1068 (m), 928 (m), 852 (m), 782 (m), 731 (m), 642 (s), 559 (m), 497 (m) cm$^{-1}$; $^1$H NMR (400 MHz, CD$_3$OD): δ 7.33-7.31 (1H, m), 7.26-7.22 (1H, m), 7.05-7.01 (1H, m), 6.88-6.86 (1H, m), 5.51 (1H, t, J=6.4 Hz), 4.90-4.75 (2H, m); $^{13}$C NMR (100 MHz, CD$_3$OD): δ 209.5, 180.6, 142.5, 132.3, 130.8, 126.3, 123.7, 111.3, 93.5, 78.9, 76.3; HRMS Calcd for C$_{11}$H$_{10}$NO$_2$ [M+H]$^+$: 188.07115. Found: 188.07196. [α]$^{20}_D$=−35.2 (c=1.00, MeOH) for a >99:1 er sample. The enantiomeric purity of this compound was determined by HPLC analysis in comparison with authentic racemic material (Chiracel OD, 90:10 hexanes:i-PrOH, 0.6 mL/min, 220 nm): t$_R$ of 21: 21 min (minor) and 24 min (major).

| Peak # | Ret. Time | Area % | Peak # | Ret. Time | Area % |
|---|---|---|---|---|---|
| 1 | 20.9 min | 50.317 | 1 | 24.4 min | 100.000 |
| 2 | 24.1 min | 49.683 | | | |

If the TBS-protected hydroxyindole is desired instead, the unpurified residue, obtained as a pale yellow oil after the allene addition protocol, can be purified by silica gel chromatography directly (a gradient from 100% CH$_2$Cl$_2$ to 1:4 Et$_2$O:CH$_2$Cl$_2$ to 100% Et$_2$O) to obtain a 92% to >98% yield of (R)-1-(tert-Butyldimethylsilyl)-3-hydroxy-3-(propa-1,2-dien-1-yl)indolin-2-one (S19): pale yellow oil. IR (neat): 3398 (m, br), 2929 (w), 2858 (w), 1955 (w), 1703 (s), 1613 (m), 1464 (m), 1256 (m), 1172 (m), 1101 (m), 939 (m), 829 (s), 746 (m) cm$^{-1}$; $^1$H NMR (400 MHz, CDCl$_3$): δ 7.38-7.36 (1H, m), 7.23-7.19 (1H, ddd, J=7.6, 7.6, 1.6 Hz), 7.07-7.00 (2H, m), 5.44 (1H, t, J=6.4 Hz), 4.96 (2H, d, J=6.4 Hz), 3.13 (1H, br s), 1.00 (9H, s), 0.54 (3H, s), 0.52 (3H, s); $^{13}$C NMR (100 MHz, CDCl$_3$): δ 207.6, 183.9, 145.6, 131.5, 129.6, 125.1, 122.7, 113.2, 93.7, 79.9, 74.9, 26.6, 19.8, −3.1, −3.2; HRMS Calcd for C$_{17}$H$_{24}$NO$_2$Si [M+H]$^+$: 302.15763. Found: 302.15757. [α]$^{20}_D$=+25.9 (c=1.00, CHCl$_3$) for a 98:2 er sample. The enantiomeric purity of this compound was determined by HPLC analysis in comparison with authentic racemic material (Chiracel OD, 96:4 hexanes:i-PrOH, 0.6 mL/min, 220 nm): t$_R$ of 10 min (minor) and 13 min (major), t$_R$ of corresponding propargyl adduct: 12 and 18 min.

| Peak # | Ret. Time | Area % | Peak # | Ret. Time | Area % |
|---|---|---|---|---|---|
| 1 | 10.4 min | 49.806 | 1 | 10.1 min | 1.295 |
| 2 | 12.8 min | 50.194 | 2 | 12.4 min | 98.705 |

Procedure for Two-step Conversion of Allenic Alcohol 21 to α-Hydroxy Alcohol 22:

A vial equipped with a stir bar is charged with allenyl carbinol 21 (37.4 mg, 0.200 mmol) to which is added enough MeOH to ensure complete dissolution of the solid (~2 mL). The solution is allowed to cool to −78° C., before a flow of O$_3$ (10 mL/min) is bubbled through the solution until TLC analysis indicated complete consumption of the allene (typically between 1 and 5 minutes). Upon complete oxidative cleavage, the solution is purged with O$_2$ before the addition of NaBH$_4$ (76.0 mg, 2.00 mmol) at −78° C. The solution is allowed to warm to 22° C. and stir for 20 min during the reduction. A drop of acetyl chloride is added and the mixture is concentrated in vacuo. The residue is redissolved in MeOH and a drop of acetyl chloride is added and reconcentrated. This procedure is repeated twice more to ensure protonation to the diol with concomitant removal of B(OMe)$_3$. The maroon solid is purified by silica gel chromatography (gradient from 1:1 EtOAc:Et$_2$O to 100% EtOAc to 4:1 EtOAc:MeOH) to afford 31.8 mg of diol 22 (0.177 mmol, 89% yield) as a pale yellow solid.

(S)-3-Hydroxy-3-(hydroxymethyl)indolin-2-one (22)

sticky pale yellow solid. IR (neat): 3248 (s, br), 1701 (s), 1620 (m), 1470 (m), 1334 (w), 1184 (m), 1118 (m), 1052 (s), 810 (m), 749 (m), 670 (m), 489 (m) cm$^{-1}$; $^1$H NMR (400 MHz, CD$_3$OD): δ 7.39 (1H, ddd, J=7.6, 1.2, 0.8 Hz), 7.25 (1H, ddd, J=7.6, 7.6, 1.2 Hz), 7.25 (1H, ddd, J=7.6, 7.6, 1.2 Hz), 6.90-6.87 (1H, m), 3.83 and 3.80 (2H, ABq, J$_{AB}$=10.8 Hz), 3.35 (1H, s); $^{13}$C NMR (100 MHz, CD$_3$OD): δ 181.5, 143.7, 131.7, 130.7, 125.8, 123.7, 111.2, 78.1, 66.9; HRMS Calcd for C$_9$H$_{10}$NO$_3$ [M+H]$^+$: 180.06607. Found: 180.06614. [α]$^{20}_D$=+43.9 (c=1.00, MeOH) for a >99:1 er sample.

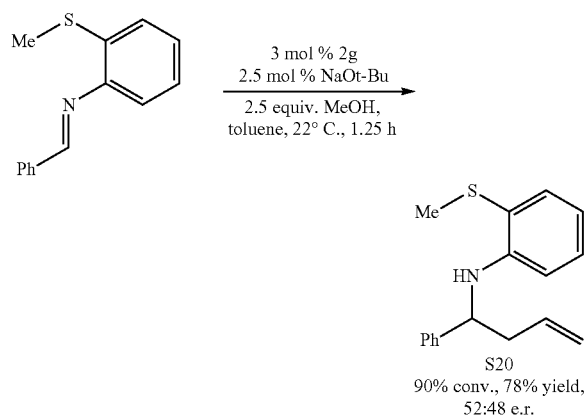

Aminophenol-Catalyzed Enantioselective Allyl Additions to o-Thiomethylaniline-derived Aldimines:

2-(methylthio)-N-(1-phenylbut-3-en-1-yl)aniline (S20) is synthesized analogously to 4b and purified by column chromatography (10 mm diameter column slurry packed with 2.5 g of silica gel in 95:5 hexanes:triethylamine and eluted with 50 mL hexanes and 20 mL 50:1 hexanes:diethyl ether) to afford 21 mg (0.078 mmol, 78% yield) of S20 as a yellow oil. The analytical data are fully consistent with those reported previously.[13] The enantiomeric purity of this compound was determined by HPLC analysis in comparison with authentic racemic material (Chiracel OD, 98:2 hexanes:i-PrOH, 0.5 mL/min, 220 nm): t$_R$ of S20:11 min (minor) and 13 min (major).

| Peak # | Ret. Time | Area % | Peak # | Ret. Time | Area % |
| --- | --- | --- | --- | --- | --- |
| 1 | 10.8 min | 50.097 | 1 | 10.6 min | 47.756 |
| 2 | 13.5 min | 49.903 | 2 | 13.4 min | 52.244 |

Representative Example of Utilization of DBU as the Base Instead of NaOt-Bu for the Enantioselective Allyl Addition to Aldimine 3a:

The reaction is performed following the representative procedure for small scale catalytic enantioselective allyl additions to aryl-, heteroaryl-, alkenyl-, and alkynyl N-diphenylphosphinoyl imines except for the following changes: 1) 2.5 mol % DBU is used (instead of 2.5 mol % NaOt-Bu) 2) Reaction time is 75 min. The conversion to desired product is 83% (judged by 400 MHz $^1$H NMR spectra of unpurified reaction mixture vs. an internal standard of 9-methylanthracene) which is lower than the >98% conversion obtained when using the same amount of NaOt-Bu. The enantiomeric purity was determined by HPLC analysis in comparison with authentic racemic material (Chiracel OD, 92:8 hexanes:i-PrOH, 0.5 mL/min, 220 nm): t$_R$ of 4a: 15 min (major) and 21 min (minor).

| Peak # | Ret. Time | Area % | Peak # | Ret. Time | Area % |
| --- | --- | --- | --- | --- | --- |
| 1 | 16.5 min | 50.660 | 1 | 15.4 min | 95.561 |
| 2 | 22.8 min | 49.340 | 2 | 20.5 min | 4.439 |

Absolute Stereochemistry of Products

Absolute configuration of homoallyamide S7 and S12 were determined by X-ray crystallographic data. For the catalytic enantioselective allyl additions to aldimines, it should be noted that the absolute stereochemical identities of the major product enantiomers are inferred from the obtained X-ray crystal structures of homoallylic amides S7 and S12. Absolute configuration of homoallylamide 10 was determined by X-ray crystallographic data. The absolute stereochemistry of the obtained crystal was further verified by HPLC analysis in comparison with authentic racemic material.

| Peak # | Ret. Time | Area % | Peak # | Ret. Time | Area % |
| --- | --- | --- | --- | --- | --- |
| 1 (syn) | 25.9 | 18.157 | 1 (syn) | 26.8 | 1.029 |
| 2 (anti) | 36.9 | 30.657 | 2 (anti) | 37.8 | 98.971 |
| 3 (anti) | 41.3 | 31.716 | 3 (anti) | — | — |
| 4 (syn) | 45.4 | 19.470 | 4 (syn) | — | — |

Absolute configuration of homoallylamide 11 was determined by X-ray crystallographic data. The absolute stereochemistry of the obtained crystal was further verified by HPLC analysis in comparison with authentic racemic material.

| Peak # | Ret. Time | Area % | Peak # | Ret. Time | Area % |
| --- | --- | --- | --- | --- | --- |
| 1 (syn) | 25.9 | 18.157 | 1 (syn) | 26.5 | 96.864 |
| 2 (anti) | 36.9 | 30.657 | 2 (anti) | 38.0 | 2.910 |
| 3 (anti) | 41.3 | 31.716 | 3 (anti) | — | — |
| 4 (syn) | 45.4 | 19.470 | 4 (syn) | 47.6 | 0.226 |
| 1 (syn) | 26.5 | 99.830 | 1 (anti) | 38.0 | 100.000 |
| 2 (syn) | 41.7 | 0.170 | 2 (anti) | — | — |

Absolute configuration of homoallylamide 13 was determined by X-ray crystallographic data. The absolute stereochemistry the obtained crystal was further verified by HPLC analysis in comparison with authentic racemic material.

| Peak # | Ret. Time | Area % | Peak # | Ret. Time | Area % |
| --- | --- | --- | --- | --- | --- |
| 1 | 7.0 | 50.073 | 1 | 7.1 | 97.460 |
| 2 | 19.9 | 49.927 | 2 | 19.6 | 2.540 |

Absolute configuration of homoallylic alcohol 15a': For the aminophenol catalyzed enantioselective allyl additions to isatin, please note that the absolute stereochemistries of the major product enantiomers are inferred from the obtained X-ray crystal of homoallylic alcohol 15a'. The absolute stereochemistry of the obtained crystal was also verified by HPLC analysis in comparison with authentic racemic material (Chiracel OD-H, 90:10 hexanes:i-PrOH, 0.8 mL/min, 220 nm): t$_R$ of 15a': 12 min (minor) and 16 min (major).

| Peak # | Ret. Time | Area % | Peak # | Ret. Time | Area % |
|---|---|---|---|---|---|
| 1 | 12.3 | 47.660 | 1 | 12.2 | 0.088 |
| 2 | 16.0 | 52.340 | 2 | 16.2 | 99.912 |

Absolute configuration of allenyl alcohol 21: For the catalytic enantioselective allene additions to isatin, please note that the absolute stereochemistries of the major product enantiomers are inferred from the obtained X-ray crystal of allenyl alcohol 21. The absolute stereochemistry of the obtained crystal was further verified by HPLC analysis in comparison with authentic racemic material (Chiracel OD, 90:10 hexanes:i-PrOH, 0.6 mL/min, 220 nm): $t_R$ of 21: 21 min (minor) and 24 min (major).

| Peak # | Ret. Time | Area % | Peak # | Ret. Time | Area % |
|---|---|---|---|---|---|
| 1 | 20.9 min | 50.317 | 1 | 22.5 min | 0.063 |
| 2 | 24.1 min | 49.683 | 2 | 24.3 min | 99.937 |

Investigation of the Level of Brønsted Acidity of the Complex Derived from Allylboron Reagent (1a) and MeOH General Information Specific to the Following.

All vials, stir bars, and NMR tubes were oven-dried (135° C.) overnight prior to use. The $^1$H NMR spectra were recorded on a Varian Unity INOVA 400 (400 MHz) spectrometer. Chemical shifts are reported in ppm from tetramethylsilane with the solvent resonance as the internal standard (d$_8$-toluene: δ 7.09 ppm).

Preparation of Samples for NMR Spectroscopy:

In a nitrogen-filled glovebox, aminophenol 2g (7.7 mg, 25 μmol) is weighed into a one-dram vial and dissolved in 700. μL of d$_8$-toluene. The solution is transferred to an NMR tube and sealed with a cap and Teflon tape; it is then used to obtain Spectrum 1 in FIG. 1a.

Spectrum 1 ($^1$H NMR, 400 MHz, d$_8$-toluene): Aminophenol 2g

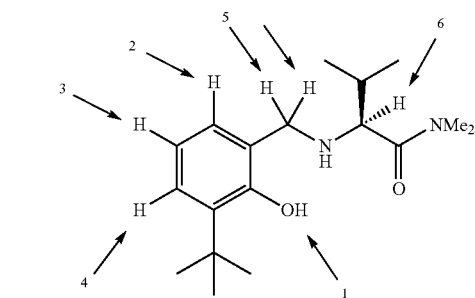

1: 11.11 ppm (1H, br s)
2: 7.27-7.24 ppm (1H, m)
3: 6.72 ppm (1H, t, J = 7.6 Hz)
4: 6.65-6.63 ppm (1H, m)
5a, 5b: 3.79, 3.26 ppm (2H, ABq, J$_{AB}$ = 13.5 Hz)
6: 3.02-2.98 ppm (1H, br m)

Figure 1B:
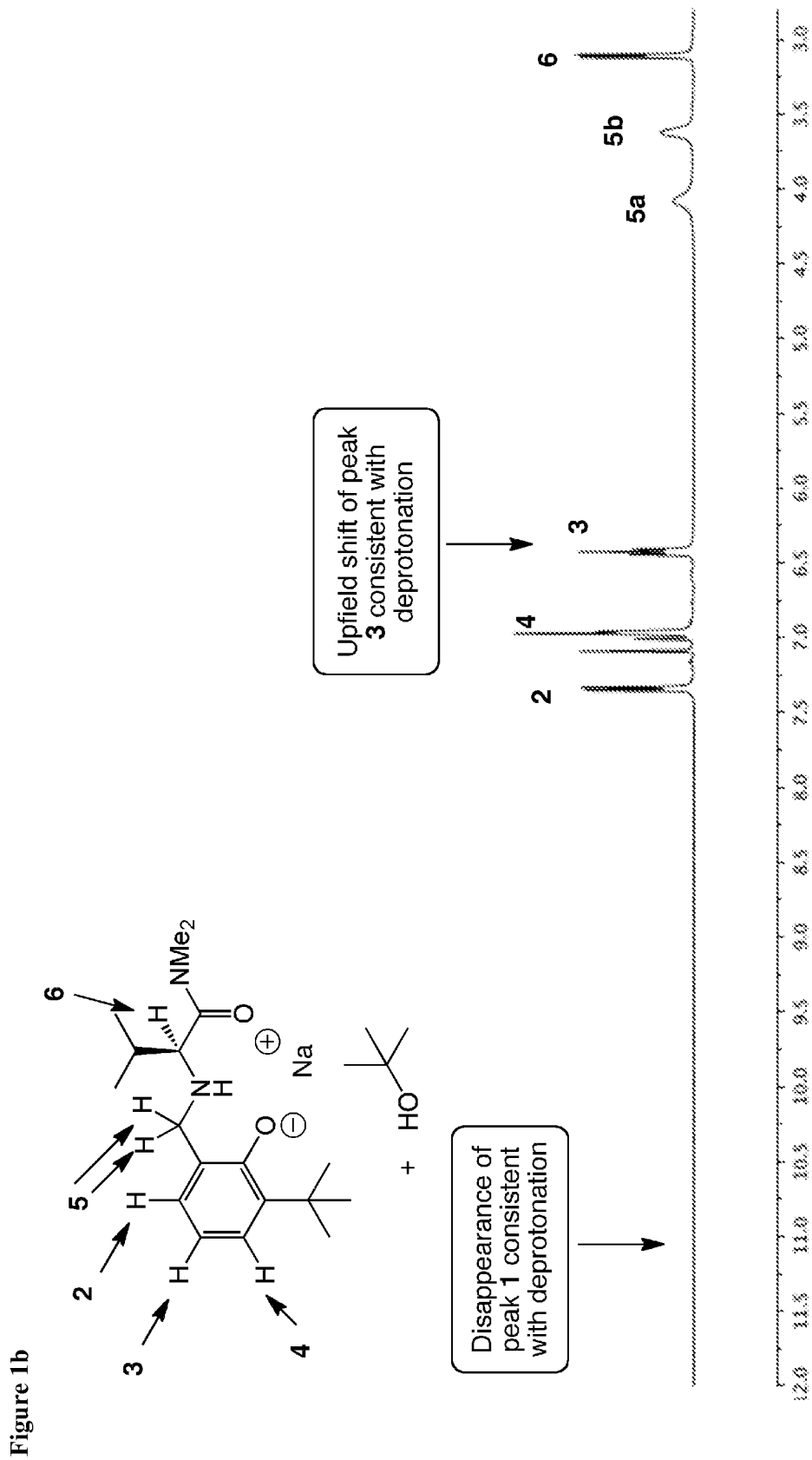

A separate one-dram vial equipped with a stir bar is charged with 2g (30.8 mg, 0.101 mmol) and 2.8 mL of a stock solution of NaOt-Bu in do-toluene (9.6 mg, 0.10 mmol NaOt-Bui2.8 ml. d-toluene) to afford a translucent solution. A 700. μL aliquot of this solution (containing NaOt-Bu [2.4 mg, 25 μmol] and aminophenol [7.7 mg, 25 μmol]) is added to an NMR tube and sealed with a cap and Teflon tape; it is then used to obtain Spectrum 2 in FIG. 1b.

Spectrum 2 ($^1$H NMR, 400 MHz, d$_8$-toluene): Aminophenol 2g (25 μmol, 1 equiv.) and NaOt-Bu (25 μmol, 1 equiv.)

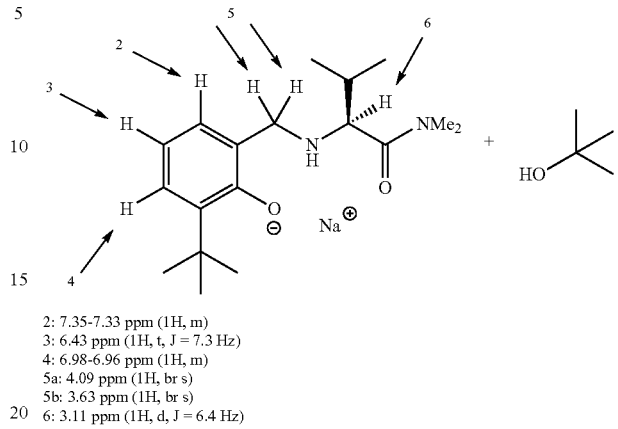

2: 7.35-7.33 ppm (1H, m)
3: 6.43 ppm (1H, t, J = 7.3 Hz)
4: 6.98-6.96 ppm (1H, m)
5a: 4.09 ppm (1H, br s)
5b: 3.63 ppm (1H, br s)
6: 3.11 ppm (1H, d, J = 6.4 Hz)

Figure 1C:
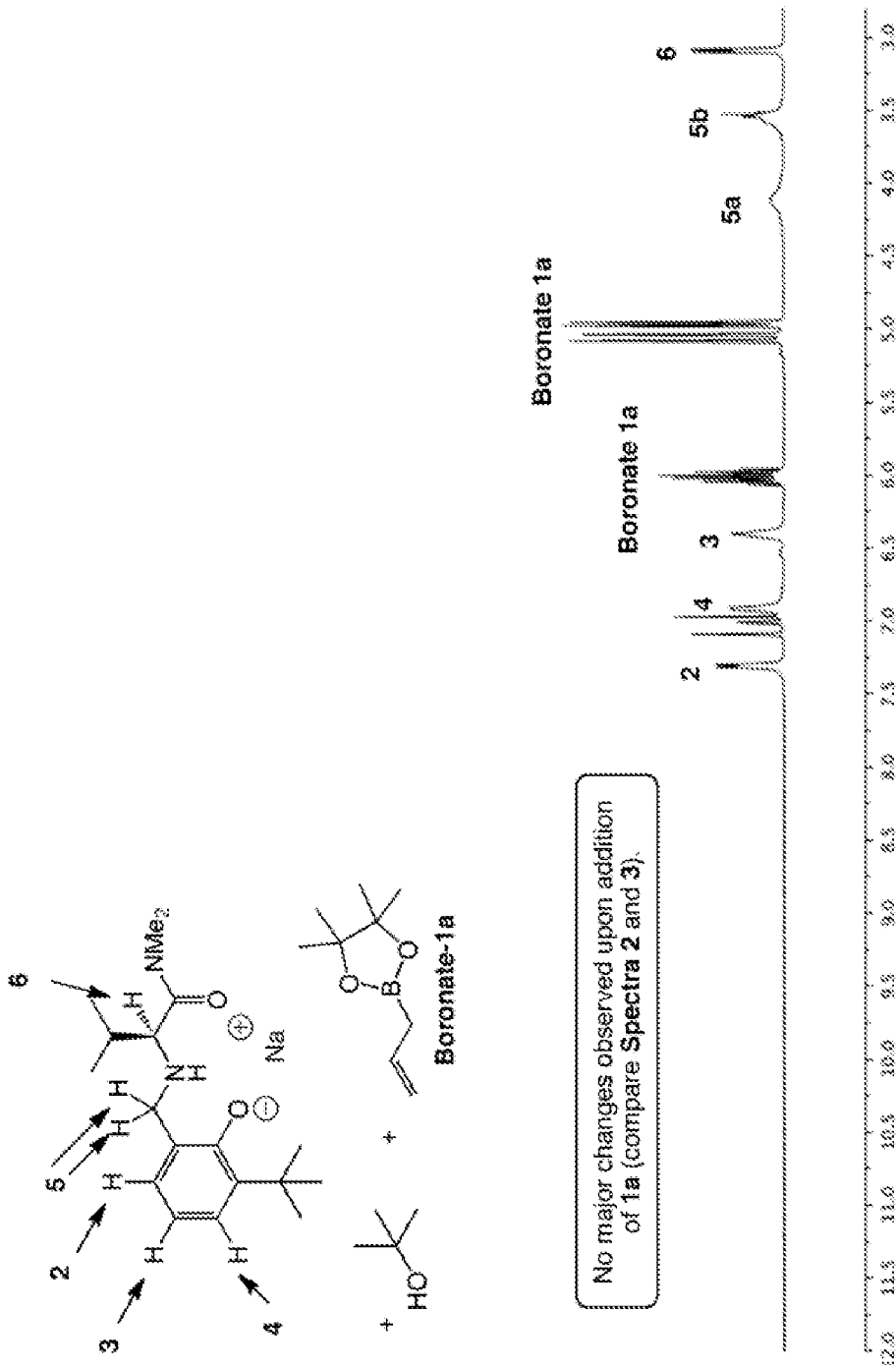

A second 700. μL aliquot is transferred to a one-dram vial containing allylboronic acid pinacol ester (10. μL, 53 μmol) 1a and this mixture is then used to obtain Spectrum 3 in FIG. 1c.

Spectrum 3 ($^1$H NMR, 400 MHz, d$_8$-toluene): Aminophenol 2g (25 μmol, 1 equiv.), NaOt-Bu (25 μmol, 1 equiv.), and Allylboronate 1a (53 μmol, 2 equiv.)

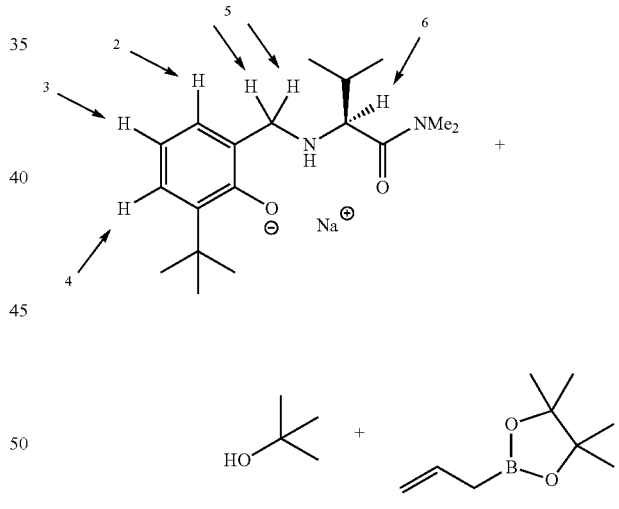

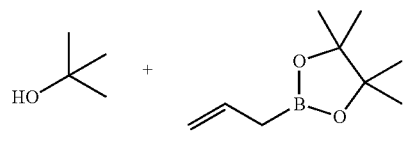

Boronate-1a

2: 7.32 ppm (1H, d, J = 7.4 Hz)
3: 6.42-6.38 ppm (1H, br m)
4: 6.92 ppm (1H, br s)
5a: 4.12 ppm (1H, br s)
5b: 3.80-3.66 ppm (1H, br m [overlaps with new unknown peak].
6: 3.09 ppm (1H, d, J = 6.3 Hz)

Figure 1D:
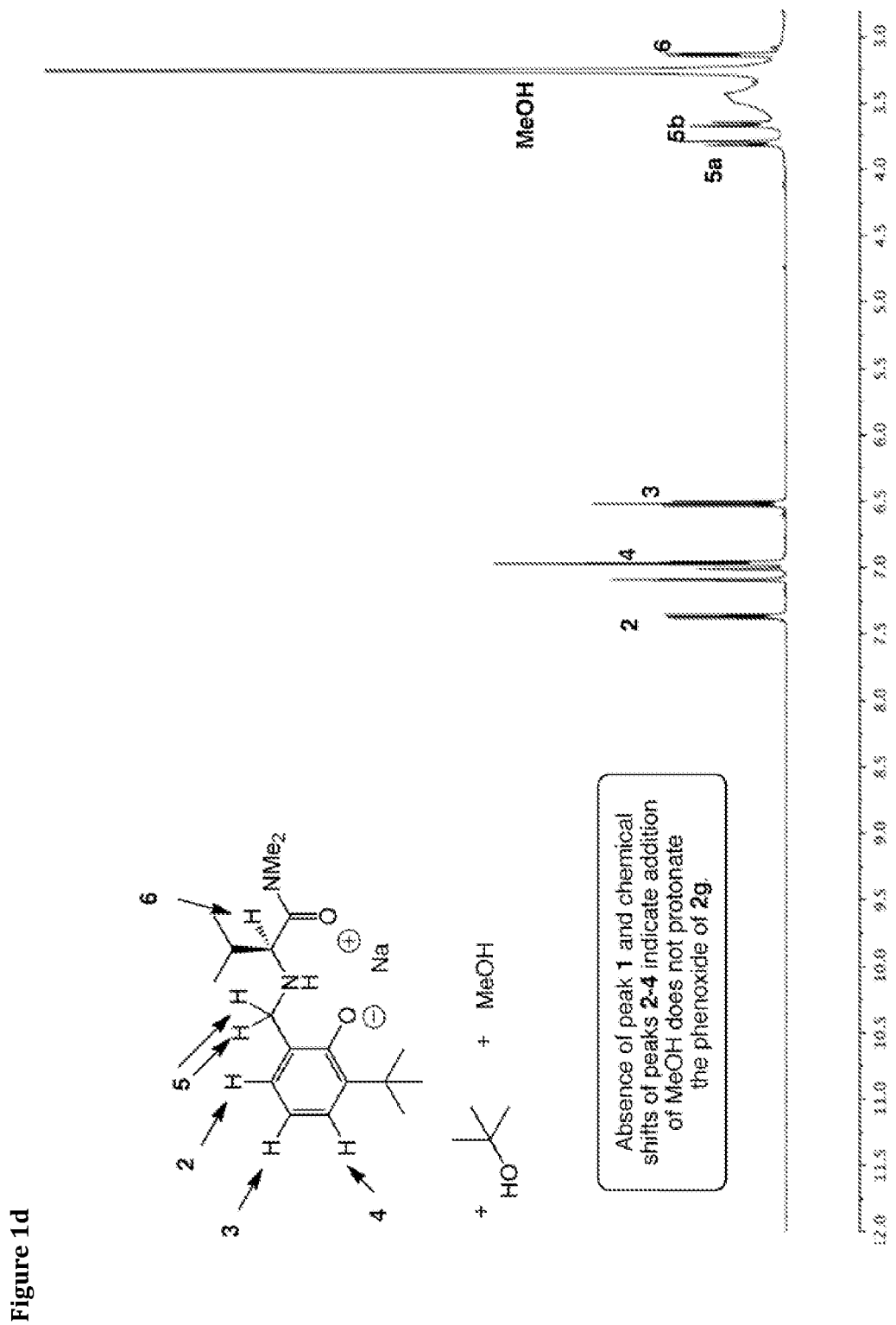

Methanol (10. μL, 250 μmol) is added to the remaining 1.4 mL of NaOt-Bu and 2$_g$ mixture and a 700. L aliquot (containing NaOt-Bu [2.4 mg, 25 μmol], aminophenol 2g [7.7 mg, 25 μmol], and methanol [5.0 L, 130 μmol]) of the resultant solution is added to an NMR tube and sealed with a cap and Teflon tape; it is then used to obtain Spectrum 4 in FIG. 1d.

Spectrum 4 ($^1$H NMR, 400 MHz, d$_8$-toluene): Aminophenol 2g (25 μmol, 1 equiv.), NaOt-Bu (25 μmol, 1 equiv.), and MeOH (130 μmol, 5 equiv.)

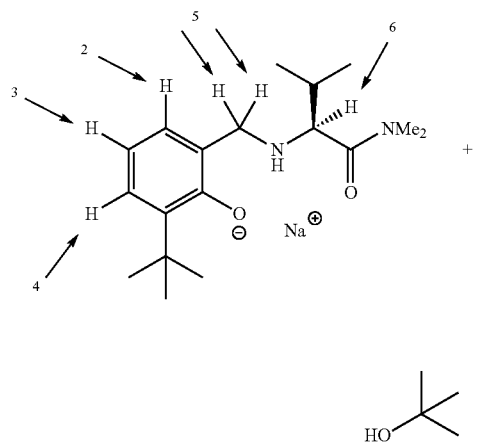

2: 7.40-7.35 ppm (1H, m)
3: 6.52 ppm (1H, t, J = 7.4 Hz)
4: 6.97-6.95 ppm (1H, m)
5a, 5b: 3.80, 3.66 ppm (2H, ABq, J$_{AB}$ = 10.9 Hz)
6: 3.14 ppm (1H, d, J = 6.5 Hz)

Figure 1E:
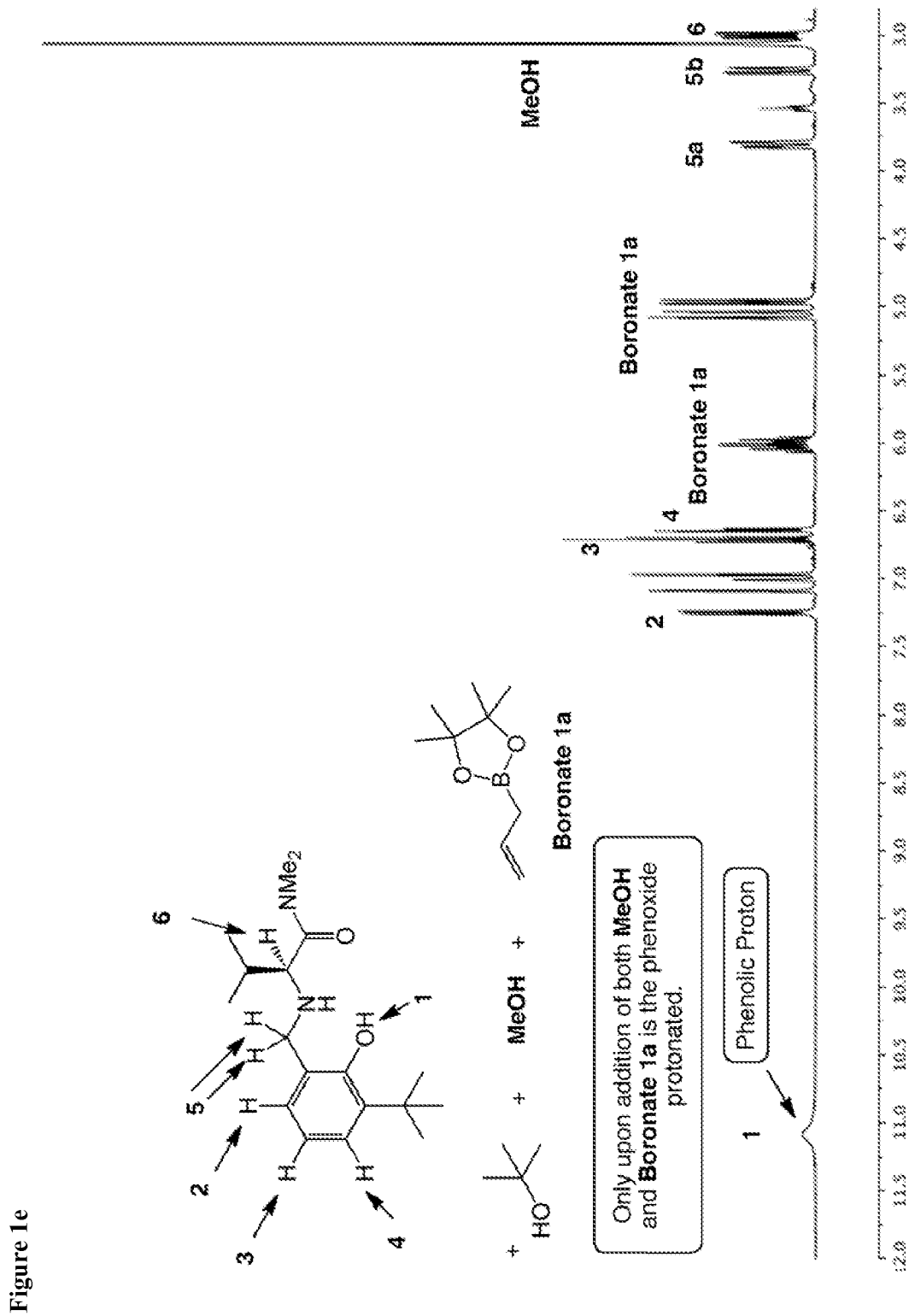

Allylboronic acid pinacol ester 1a (10. μL, 53 μmol) is added to the remaining solution (containing NaOt-Bu [2.4 mg, 25 μmol], aminophenol 2g [7.7 mg, 25 μmol], and methanol [5.0 μL, 130 μmol]), which results in formation of a white precipitate, causing the toluene solution to become cloudy. The latter solution is added to an NMR tube and sealed with a cap and Teflon tape; it is then used to obtain Spectrum 5 in FIG. 1e.

Spectrum 5 ($^1$H NMR, 400 MHz, d$_8$-toluene): Aminophenol 2g (25 μmol, 1 equiv.), NaOt-Bu (25 μmol, 1 equiv.), Allylboronate 1a (53 μmol, 2 equiv.), and MeOH (130 μmol, 5 equiv.)

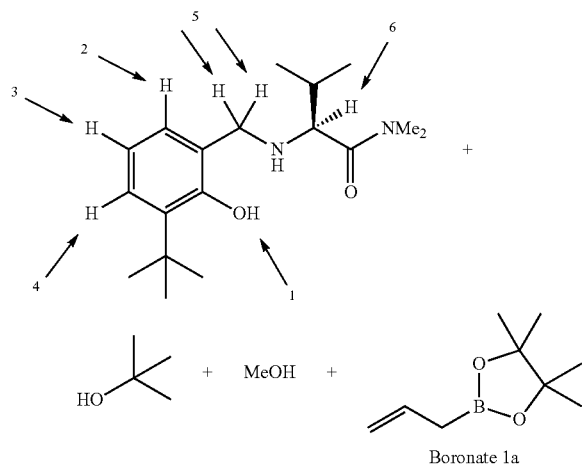

1: 11.09 ppm (1H, br s)
2: 7.26-7.24 ppm (1H, m)
3: 6.71 ppm (1H, t, J = 7.6 Hz)
4: 6.65-6.63 ppm (1H, m)
5a, 5b: 3.81, 3.26 ppm (2H, ABX, J$_{AB}$ = 13.6 Hz; J$_{BX}$ = 4.1 Hz; J$_{AX}$ = 3.9 Hz)
6: 3.00 ppm (1H, dd, J = 11.8, 5.9 Hz)

Generation of a Hammett Plot for the Aminophenol Catalyzed Enantioselective Allyl Addition to a Series of Aryl-Substituted Aldimines The electronic effect of the aryl substituent on the reaction rate of the aminophenol catalyzed enantioselective allyl addition to aryl-substituted aldimines was determined by React-IR measurements of conversion of imine [%] as a function of time [min](Scheme S1).

Scheme S1: Reaction Conditions for the Enantioselective Allylation of Imines Applied in React-IR Measurements to Generate the Hammett Plot

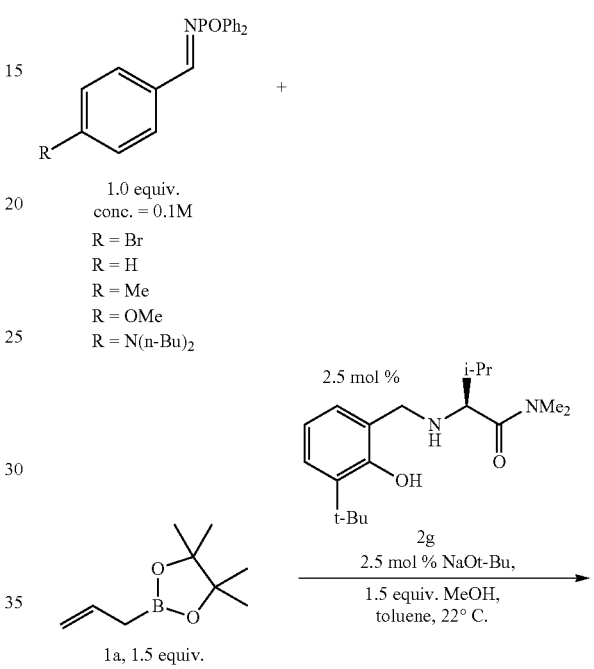

1.0 equiv.
conc. = 0.1M
R = Br
R = H
R = Me
R = OMe
R = N(n-Bu)$_2$ 1a, 1.5 equiv.

2.5 mol % NaOt-Bu,
1.5 equiv. MeOH,
toluene, 22° C.

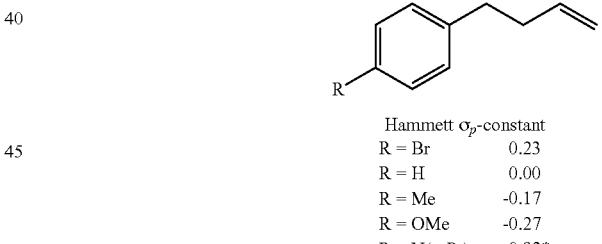

Hammett σ$_p$-constant
R = Br        0.23
R = H         0.00
R = Me       -0.17
R = OMe      -0.27
R = N(n-Pr)$_2$   -0.93*

↑ Increasing rate of reaction

*The σ$_p$-constant for ⎯⎯ N(n-Pr)$_2$ has been used for ⎯⎯ N(n-Bu)$_2$.

General Procedure:

The preparation of stock solutions of reagents (allylboronate 1a, MeOH, aminophenol 2g, and NaOt-Bu) and weighing of imines were performed in a nitrogen-filled glovebox. All vials and stir bars were oven-dried (135° C.) overnight prior to use. Rubber septa and caps were oven-dried (60° C.) overnight prior to use. An 8 mL vial equipped with a stir bar is charged with the desired aldimine (0.200 mmol) and the vial is sealed with a cap. To prepare the stock solution of allylboronate 1a, a 4 mL vial is charged with 1a (0.450 mL, 2.40 mmol) and toluene (3.55 mL) and sealed with a cap containing a teflon septum. To prepare the stock solution of MeOH, a 4 mL vial is charged with MeOH (0.120 mL, 3.00 mmol) and toluene (3.88 mL) and sealed with a cap containing a teflon septum. To prepare the stock solution of aminophenol 2g, 4 mL vial is charged with aminophenol 2g (15.3 mg, 0.0499 mmol) and toluene (4.00 mL) and sealed with a cap containing a Teflon septum. To prepare the stock solution of NaOt-Bu, a 4 mL vial is charged with NaOt-Bu (19.2 mg, 0.200 mmol) and toluene (4.00 mL). The NaOt-Bu solution is diluted further by charging a 4 mL vial with toluene (3.00 mL) and 1.00 mL of the original stock solution. The vial was sealed with a cap containing a teflon septum. The prepared solutions and vials containing the imines were taken out of the glovebox and stored in a desiccator for the duration of React-IR measurements.

React-IR Measurements:

Measurements were performed on a ReactIR iC10 instrument equipped with a 6.3 mm AgX DiComp Fiber probe. Spectra were recorded from 2000 $cm^{-1}$ to 650 $cm^{-1}$ at standard resolution (8 $cm^{-1}$) in 15 s intervals. The vial containing imine is equipped with a 14/20 rubber septum with a 4 mm diameter hole and attached to the probe, which had been dried with a heat gun ($T_{max}$=200° C.). The rubber septum is further sealed with electrical tape. Toluene (0.3 mL) is added with a syringe, followed by the addition of the stock solutions of allylboronate 1a (0.50 mL) and MeOH (0.40 mL). After 3 min, the reaction is started by the simultaneous addition of the solutions of aminophenol 2g (0.4 mL) and NaOt-Bu (0.4 mL).

Data Processing:

The decrease in concentration of imine was monitored as a function of time [min]. The following IR absorption frequencies characteristic of the imines in this study were used: 834-822 $cm^{-1}$ for R=Br, 836-824 $cm^{-1}$ for R=H, 842-830 $cm^{-1}$ for R=Me, 835-823 $cm^{-1}$ for R=OMe, and 1592-1580 $cm^{-1}$ for R=N(n-Bu)$_2$. The intensities were calibrated as following: the difference between the intensities at the start of the reaction and the intensities at the end of the reaction (i.e. when no further change was observed in the concentration of imine) was set to the conversion [%] determined by 400 MHz $^1$H NMR (100% except for 95% in the case of R=N(n-Bu)$_2$).

Figure 2B:
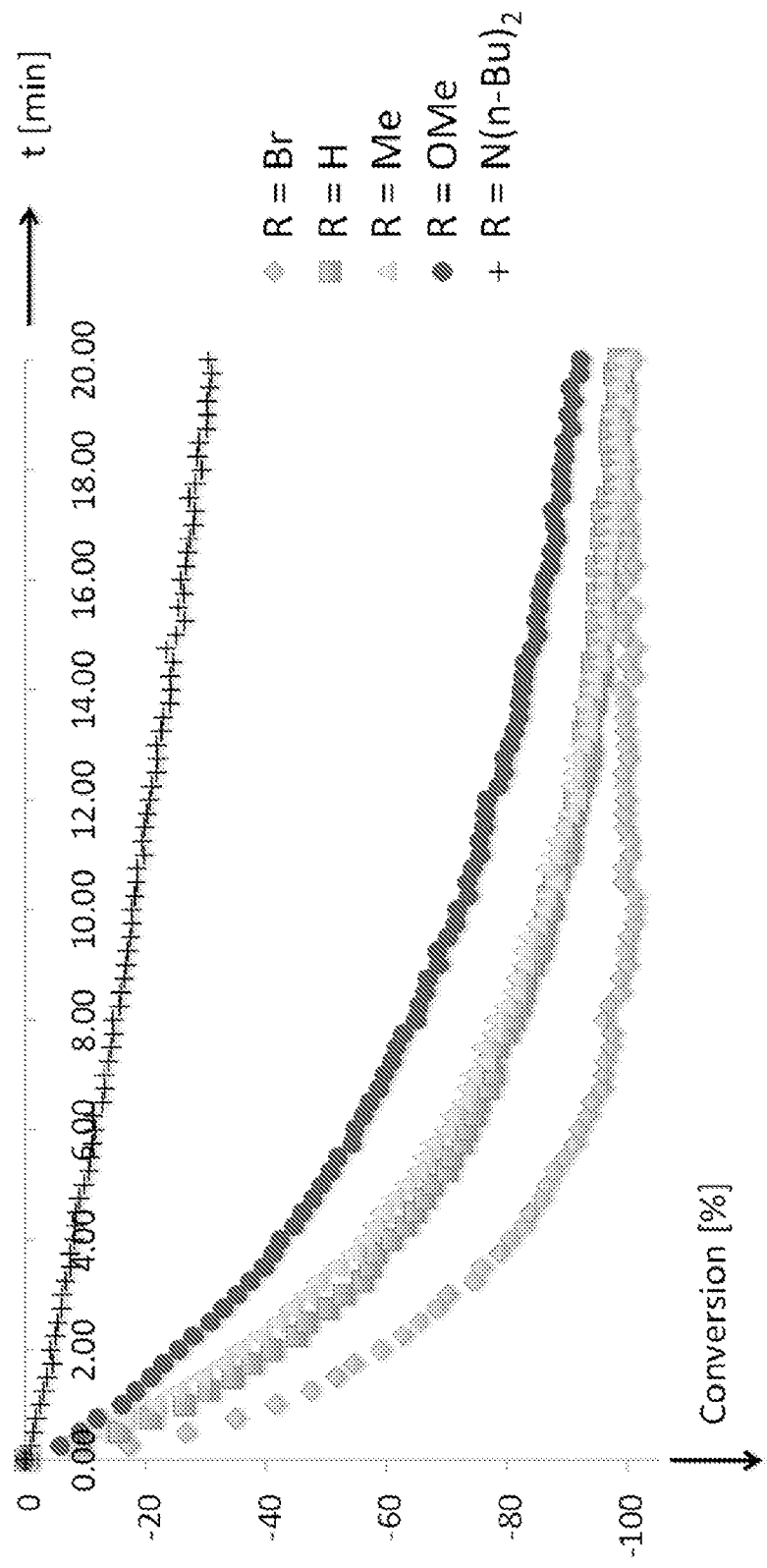
Figure 2C:
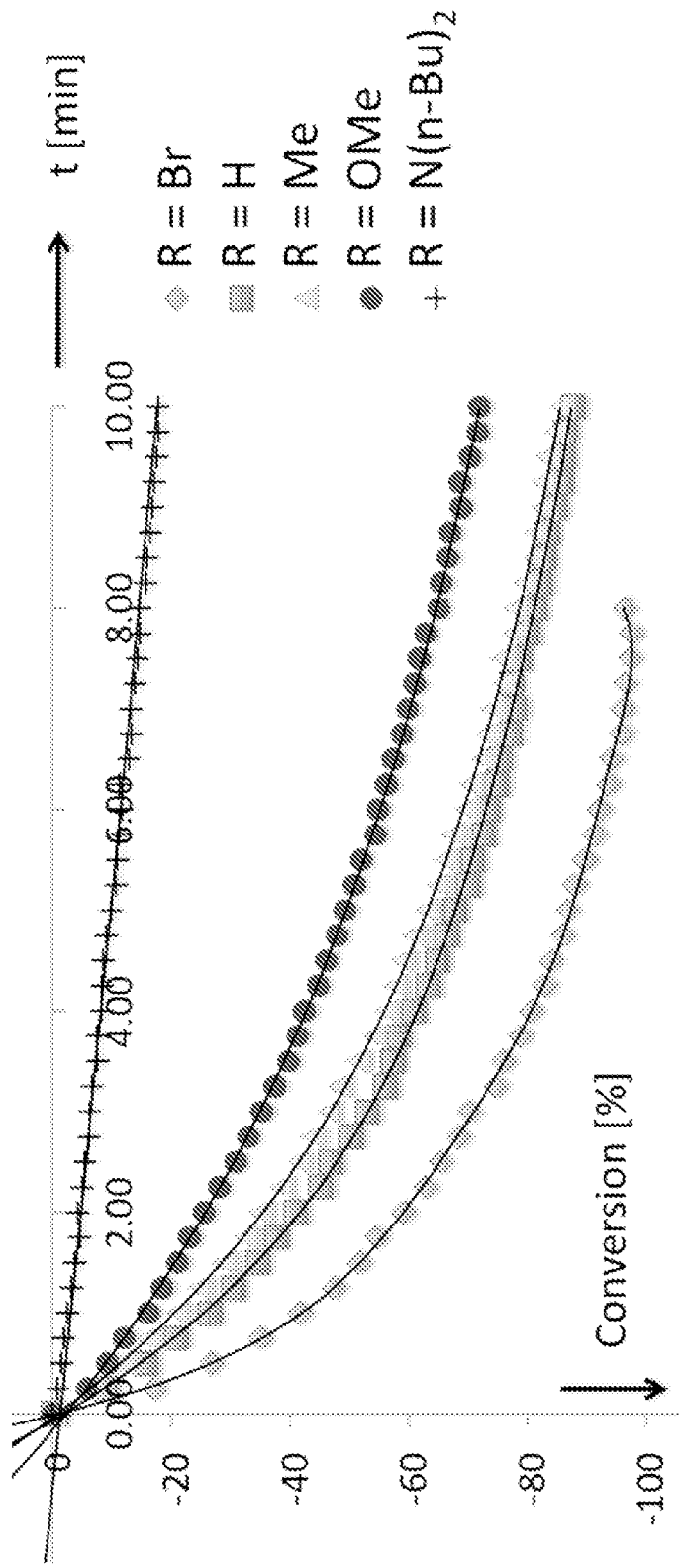
Figure 3:
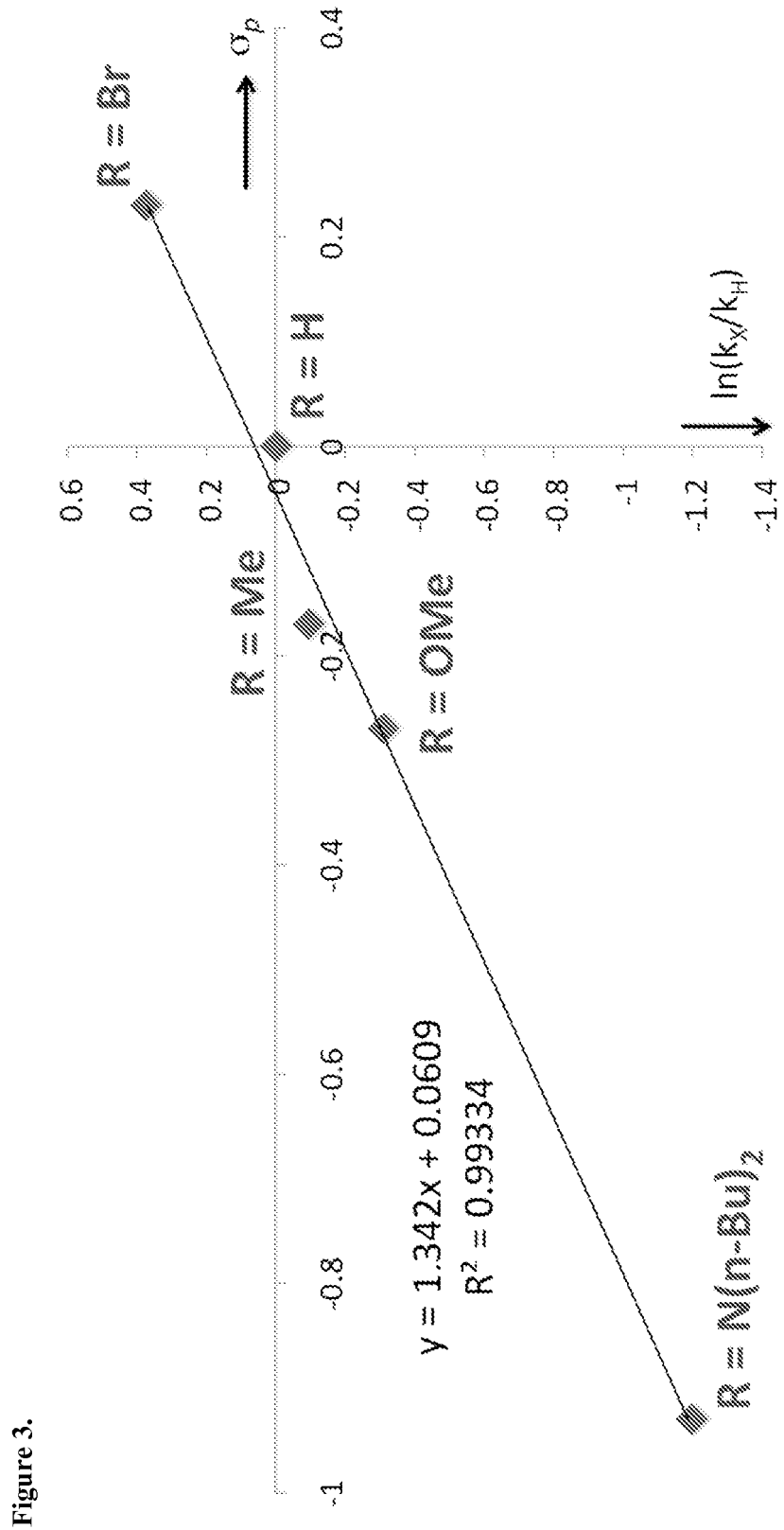
FIG. 3. Hammett Plot [$\log(k_X/k_H)$ vs $\sigma_p$-constant] Indicating the Electronic Substituent Dependence for the Enantioselective Allylation Under the Conditions Shown in Scheme S1.

The curves in FIGS. 2a and 2b were fitted with a $6^{th}$-order polynomial function through the use of Microsoft Excel (FIG. 2c). In order to obtain a reasonable fit, the curves were truncated after a maximum time (8 min for R=Br, 20 min for R=H, 20 min for R=Me, 40 min for R=OMe, and 180 min for R=N(n-Bu)$_2$). The relative rates $k_x$ (for time →0 min) can be read directly from the equations of the polynomials (values in red), which are used for the generation of the Hammett plot in FIG. 3 (plot of log($k_x/k_H$) vs $\sigma_p$-constant). Linear regression results in a ρ-value of 1.3 (slope), indicating a faster reaction with more electron deficient aryl substituted aldimines. Plot of Conversion of Imine [%] vs Time [min] include $6^{th}$-order polymomial fits:

R=Br y=0.0088x$^6$-0.23x$^5$+2.3827x$^4$-12.444x$^3$+35.757x$^2$-66.425x-0.9584

R=H y=2E-05x$^6$-0.0013x$^5$+0.0396x$^4$-0.5957x$^3$+5.1132x$^2$-28.015x-1.8831

R=Me y=9E-06x$^6$-0.0007x$^5$+0.0204x$^4$-0.3258x$^3$+3.216x$^2$-22.544x-0.8435

R=OMe y=3E-07x$^6$-4E-05x$^5$+0.0022x$^4$-0.0642x$^3$+1.1379x$^2$-13.766x-2.2367

R=N(n-Bu)$_2$ y=6E-12x$^6$-3E-09x$^4$+6E-07x$^4$-8E-05x$^3$+0.0138x$^2$-1.7579x-1.2783

Please Note: The relative rates at t=0 can be read directly from the polynomial functions (values highlighted).

DFT Calculations:

All geometry and frequency calculations of the transition states shown in Scheme S2 were carried out employing the hybrid functional B3LYP and the split-valence 6-31G** basis set. The calculations were carried out in toluene, which was simulated by the polarizable dielectric continuum solvation model PCM. Frequency calculations were carried out on the fully optimized geometries. All computed frequencies are real except for the transition state structures, which have one imaginary frequency. Free energies were computed at 298.15 K and 1.0 atm. with harmonic, unscaled frequencies. All quantum chemical calculations were carried out with the Gaussian 09 computer program.

Scheme S2a: Calculated Transition State Complex Which Leads to the R (Major) Enantiomer

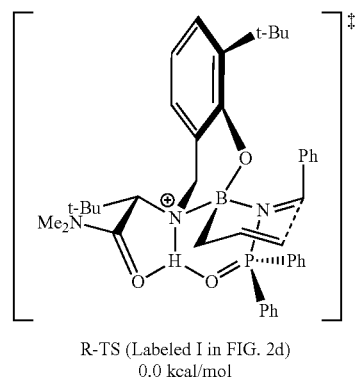

R-TS (Labeled I in FIG. 2d)
0.0 kcal/mol

Scheme S2b: Calculated Transition State Complexes Which Lead to the S (Minor) Enantiomer and their Energies Relative to R-TS

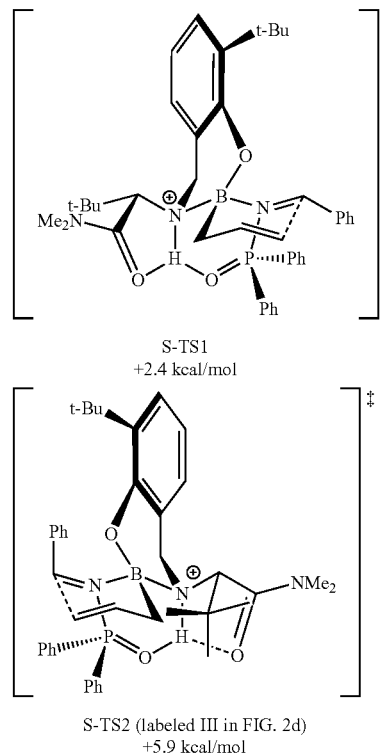

S-TS1
+2.4 kcal/mol

S-TS2 (labeled III in FIG. 2d)
+5.9 kcal/mol

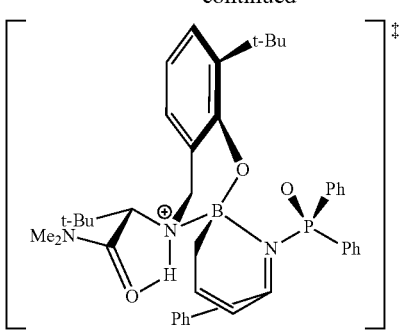

S-TS3
+7.5 kcal/mol

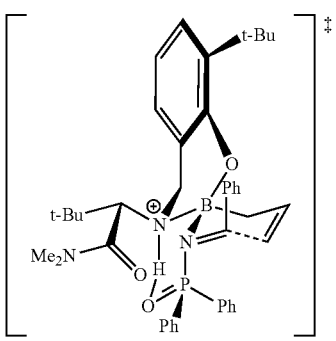

S-TS4
+10.8 kcal/mol

Please Note:

(a) The energy of complex R-TS is used as a zero point reference. (b) The aminophenol derived from L-tert-leucine 2h (Table 1) was modeled instead of 2g due to fewer possible conformers present in 2h.

The invention claimed is:

1. A compound selected from the group consisting of

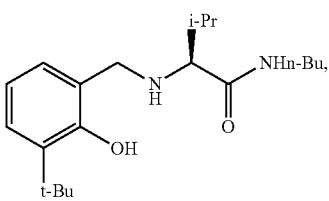

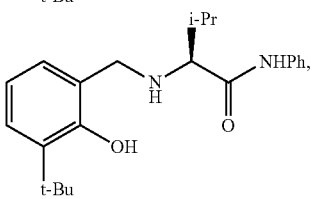

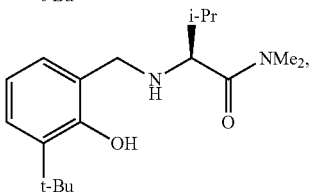

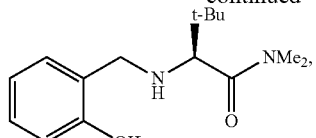

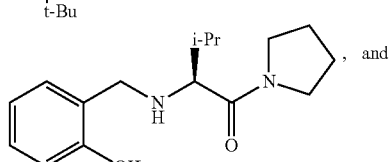

, and

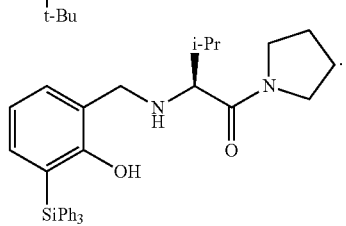

.

2. A compound having the structure of formula I-a:

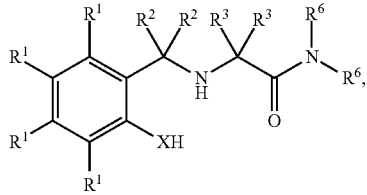

wherein:

X is —O—;

each of $R^2$, $R^3$, and $R^6$ is independently R, —OR, —N(R)$_2$, —SR, or —C(O)L;

L is R, halogen, —OR, —N(R)$_2$, or —SR;

each R is independently hydrogen or R'; and each R' is independently unsubstituted $C_{1-12}$ aliphatic or an optionally substituted group selected from the group consisting of phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, and an 8-10 membered bicyclic heteroaryl ring having 1-5 heteroatoms independently selected from nitrogen, oxygen, or sulfur, or two R' groups on the same nitrogen atom are optionally taken together with the nitrogen atom to form an optionally substituted 3-8 membered, saturated, partially unsaturated, or aryl ring having 1-4 heteroatoms independently selected from nitrogen, oxygen, or sulfur; or two R' groups on the same carbon atom are optionally taken together with their intervening atoms to form an optionally substituted 3-8 membered saturated or partially unsaturated spirocycle ring having 0-4 heteroatoms independently selected from nitrogen, oxygen, or sulfur; or two R' groups on adjacent atoms are optionally taken together with their intervening atoms form an optionally substituted 3-8 membered, saturated, partially unsaturated, or aryl ring having 0-4 heteroatoms independently selected from nitrogen, oxygen, or sulfur, wherein the $R^1$ at the o position of —XH is tert-butyl and each other $R^1$ is hydrogen.

3. A compound having the structure of formula I-a:

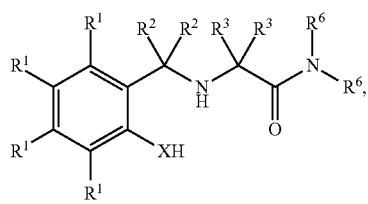

I-a wherein:

each R' is independently R, halogen, —OR, —N(R)$_2$, —SR, —NO$_2$, —SOR, —SO$_2$R, —Si(R)$_3$, or —C(O)L;

X is —O—;

independently ( . . . )—N(R)$_2$;

each R is independently hydrogen or R'; and each R' is independently unsubstituted $C_{1-12}$ aliphatic or an optionally substituted group selected from the group consisting of phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, and an 8-10 membered bicyclic heteroaryl ring having 1-5 heteroatoms independently selected from nitro en ox en or sulfur; or two R' groups on the same nitrogen atom are optionally taken together with the nitro en atom to form an optionally substituted 3-8 membered, saturated, partially unsaturated, or aryl ring having 1-4 heteroatoms independently selected from nitrogen, oxygen, or sulfur; or two R' groups on the same carbon atom are optionally taken together with their intervening atoms to form an optionally substituted 3-8 membered saturated or partially unsaturated spirocycle ring having 0-4 heteroatoms independently selected from nitrogen, oxygen, or sulfur; or two R' groups on adjacent atoms are optionally taken together with their intervening atoms form an optionally substituted 3-8 membered, saturated, partially unsaturated, or aryl ring having 0-4 heteroatoms independently selected from nitrogen, oxygen, or sulfur, wherein one $R^3$ is hydrogen and the other $R^3$ is isopropyl.

4. A compound having the structure of formula I-a:

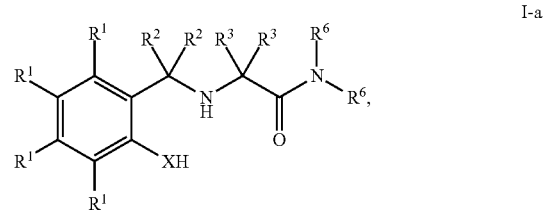

I-a wherein:

each $R^1$ is independently R, halogen, —OR, —N(R)$_2$, —SR, —NO$_2$, —SOR, —SO$_2$R, —Si(R)$_3$, or —C(O)L;

X is —O—;

independently ( . . . )—SR, or —C(O)L;

L is R, halogen, —OR, —N(R)$_2$, or —SR;

each R is independently hydrogen or R'; and each R' is independently unsubstituted $C_{1-12}$ aliphatic or an optionally substituted group selected from the group consisting of phenyl, a 3-7 membered saturated or partially unsaturated carbocyclic ring having 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, and an 8-10 membered bicyclic heteroaryl ring having 1-5 heteroatoms independently selected from nitrogen, oxygen, or sulfur; or two R' groups on the same nitrogen atom are optionally taken together with the nitrogen atom to form an optionally substituted 3-8 membered, saturated, partially unsaturated, or aryl ring having 1-4 heteroatoms independently selected from nitrogen, oxygen, or sulfur; or two R' groups on the same carbon atom are optionally taken together with their intervening atoms to form an optionally substituted 3-8 membered saturated or partially unsaturated spirocycle ring having 0-4 heteroatoms independently selected from nitrogen, oxygen, or sulfur; or two R' groups on adjacent atoms are optionally taken together with their intervening atoms form an optionally substituted 3-8 membered, saturated, partially unsaturated, or aryl ring having 0-4 heteroatoms independently selected from nitrogen, oxygen, or sulfur, wherein;

each $R^6$ is independently R', or:

one is hydrogen and the other is R', wherein R' is unsubstituted $C_{1-12}$ aliphatic, or an optionally substituted group selected from the group consisting of phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, and an 8-10 membered bicyclic heteroaryl ring having 1-5 heteroatoms independently selected from nitrogen, oxygen, or sulfur.

5. The compound of claim 4, wherein each $R^6$ is independently unsubstituted $C_{1-12}$ aliphatic.

\* \* \* \* \*